United States Patent
Bernett et al.

(10) Patent No.: US 10,626,182 B2
(45) Date of Patent: Apr. 21, 2020

(54) OPTIMIZED ANTIBODIES THAT TARGET CD19

(71) Applicant: XENCOR, INC., Monrovia, CA (US)

(72) Inventors: Matthew J. Bernett, Monrovia, CA (US); Seung Yup Chu, Cypress, CA (US); John R. Desjarlais, Pasadena, CA (US); Sher Bahadur Karki, Pomona, CA (US); Gregory Alan Lazar, Arcadia, CA (US); Erik Weiking Pong, Temple City, CA (US); John O. Richards, Duarte, CA (US); Eugene Alexander Zhukovsky, West Hollywood, CA (US)

(73) Assignee: Xencor, Inc., Monrovia, CA (US)

( * ) Notice: Subject to any disclaimer, the term of this patent is extended or adjusted under 35 U.S.C. 154(b) by 216 days.

(21) Appl. No.: 15/712,918

(22) Filed: Sep. 22, 2017

(65) Prior Publication Data
US 2018/0009900 A1 Jan. 11, 2018
US 2018/0148511 A9 May 31, 2018

Related U.S. Application Data

(62) Division of application No. 13/959,587, filed on Aug. 5, 2013, now Pat. No. 9,803,020, which is a division of application No. 12/377,251, filed as application No. PCT/US2007/075932 on Aug. 14, 2007, now Pat. No. 8,524,867.

(60) Provisional application No. 60/822,362, filed on Aug. 14, 2006.

(51) Int. Cl.
*C07H 21/02* (2006.01)
*C07H 21/04* (2006.01)
*C07K 16/28* (2006.01)
*C07K 16/00* (2006.01)

(52) U.S. Cl.
CPC ...... *C07K 16/2896* (2013.01); *C07K 16/2803* (2013.01); *C07K 2317/24* (2013.01); *C07K 2317/41* (2013.01); *C07K 2317/52* (2013.01); *C07K 2317/565* (2013.01); *C07K 2317/72* (2013.01); *C07K 2317/732* (2013.01); *C07K 2317/77* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 4,816,397 A | 3/1989 | Boss et al. |
| 5,225,348 A | 7/1993 | Nagata et al. |
| 5,266,491 A | 11/1993 | Nagata et al. |
| 5,328,987 A | 7/1994 | Maliszewski |
| 5,530,101 A | 6/1996 | Queen et al. |
| 5,541,087 A | 7/1996 | Lo et al. |
| 5,576,184 A | 11/1996 | Better et al. |
| 5,623,053 A | 4/1997 | Gastinel et al. |
| 5,624,821 A | 4/1997 | Winter et al. |
| 5,633,162 A | 5/1997 | Keen et al. |
| 5,648,237 A | 7/1997 | Carter |
| 5,648,260 A | 7/1997 | Winter et al. |
| 5,686,072 A | 11/1997 | Uhr et al. |
| 5,821,337 A | 10/1998 | Carter et al. |
| 5,834,597 A | 11/1998 | Tso et al. |
| 5,885,573 A | 3/1999 | Bluestone et al. |
| 6,030,613 A | 2/2000 | Blumberg et al. |
| 6,086,875 A | 7/2000 | Blumberg et al. |
| 6,121,022 A | 9/2000 | Presta et al. |
| 6,165,745 A | 12/2000 | Ward et al. |
| 6,188,965 B1 | 2/2001 | Mayo et al. |
| 6,194,551 B1 | 2/2001 | Idusogie et al. |
| 6,242,195 B1 | 6/2001 | Idusogie et al. |
| 6,269,312 B1 | 7/2001 | Mayo et al. |
| 6,277,375 B1 | 8/2001 | Ward |
| 6,331,415 B1 | 12/2001 | Cabilly et al. |
| 6,358,733 B1 | 3/2002 | Motwani et al. |
| 6,365,161 B1 | 4/2002 | Deo et al. |
| 6,403,312 B1 | 6/2002 | Dahiyat et al. |
| 6,444,789 B1 | 9/2002 | Luo |
| 6,485,726 B1 | 11/2002 | Blumberg et al. |
| 6,528,624 B1 | 3/2003 | Idusogie et al. |
| 6,538,124 B1 | 3/2003 | Idusogie et al. |
| 6,632,927 B2 | 10/2003 | Adair et al. |
| 6,649,165 B2 | 11/2003 | Schubert |
| 6,708,120 B1 | 3/2004 | Mayo et al. |
| 6,719,971 B1 | 4/2004 | Carter et al. |

(Continued)

FOREIGN PATENT DOCUMENTS

| | | |
|---|---|---|
| EP | 0268636 | 1/1997 |
| EP | 0481790 | 2/1999 |

(Continued)

OTHER PUBLICATIONS

Aase, A. et al. "The extended hinge region of IgG3 is not required for high phagocytic capacity mediated by Fc gamma receptors, but the heavy chains must be disulfide bonded," EurJ Immunol., 23(7):1546-1551 (Jul. 1993).

(Continued)

*Primary Examiner* — Chun W Dahle

(74) *Attorney, Agent, or Firm* — Polsinelli PC

(57) ABSTRACT

The present invention describes antibodies that target CD19, wherein the antibodies comprise at least one modification relative to a parent antibody, wherein the modification alters affinity to an FcγR or alters effector function as compared to the parent antibody. Also disclosed are methods of using the antibodies of the invention.

27 Claims, 49 Drawing Sheets

Specification includes a Sequence Listing.

(56) References Cited

U.S. PATENT DOCUMENTS

| | | |
|---|---|---|
| 6,737,056 B1 | 5/2004 | Presta et al. |
| 6,792,356 B2 | 9/2004 | Mayo et al. |
| 6,797,492 B2 | 9/2004 | Daugherty et al. |
| 6,801,861 B2 | 10/2004 | Mayo et al. |
| 6,804,611 B2 | 10/2004 | Mayo et al. |
| 6,821,505 B2 | 11/2004 | Ward et al. |
| 6,933,368 B2 | 8/2005 | Co et al. |
| 6,946,292 B2 | 9/2005 | Kanda et al. |
| 6,950,754 B2 | 9/2005 | Mayo et al. |
| 6,982,321 B2 | 1/2006 | Winter |
| 6,992,234 B2 | 1/2006 | Roopenian |
| 7,109,304 B2 | 9/2006 | Hansen et al. |
| 7,112,324 B1 | 9/2006 | Dorken et al. |
| 7,129,330 B1 | 10/2006 | Little et al. |
| 7,317,091 B2 | 1/2008 | Lazar et al. |
| 7,662,925 B2 | 2/2010 | Lazar et al. |
| 8,063,187 B2 | 11/2011 | Chu et al. |
| 9,803,020 B2 | 10/2017 | Bernett et al. |
| 2001/0036459 A1 | 11/2001 | Ravetch |
| 2002/0004587 A1 | 1/2002 | Miller et al. |
| 2002/0048772 A1 | 4/2002 | Dahiyat et al. |
| 2002/0062010 A1 | 5/2002 | Arathoon et al. |
| 2002/0090648 A1 | 7/2002 | Dahiyat et al. |
| 2002/0142374 A1 | 10/2002 | Gallo et al. |
| 2002/0155537 A1 | 10/2002 | Carter et al. |
| 2002/0164328 A1 | 11/2002 | Shinkawa et al. |
| 2002/0182208 A1 | 12/2002 | Page et al. |
| 2002/0192222 A1 | 12/2002 | Blumberg et al. |
| 2003/0012789 A1 | 1/2003 | Blumberg et al. |
| 2003/0049654 A1 | 3/2003 | Dahiyat et al. |
| 2003/0078385 A1 | 4/2003 | Arathoon et al. |
| 2003/0103971 A1 | 6/2003 | Hariharan et al. |
| 2003/0105294 A1 | 6/2003 | Gilles et al. |
| 2003/0108548 A1 | 6/2003 | Bluestone et al. |
| 2003/0118592 A1 | 6/2003 | Ledbetter et al. |
| 2003/0130827 A1 | 7/2003 | Desjarlais et al. |
| 2003/0133930 A1 | 7/2003 | Goldenberg et al. |
| 2003/0133939 A1 | 7/2003 | Ledbetter et al. |
| 2003/0143682 A1 | 7/2003 | Nicolaides et al. |
| 2003/0157108 A1 | 8/2003 | Presta et al. |
| 2003/0158289 A1 | 8/2003 | Rusin et al. |
| 2003/0158389 A1 | 8/2003 | Idusogie et al. |
| 2003/0166868 A1 | 9/2003 | Presta et al. |
| 2003/0175884 A1 | 9/2003 | Umana et al. |
| 2003/0190311 A1 | 10/2003 | Dall'Acqua et al. |
| 2003/0208054 A1 | 11/2003 | Olsen et al. |
| 2003/0224397 A1 | 12/2003 | Lowman et al. |
| 2003/0229208 A1 | 12/2003 | Queen et al. |
| 2003/0235536 A1 | 12/2003 | Blumberg et al. |
| 2004/0002587 A1 | 1/2004 | Watkins et al. |
| 2004/0043429 A1 | 3/2004 | Dahiyat et al. |
| 2004/0043430 A1 | 3/2004 | Dahiyat et al. |
| 2004/0062763 A1 | 4/2004 | Mosser et al. |
| 2004/0132101 A1 | 7/2004 | Lazar et al. |
| 2004/0136908 A1 | 7/2004 | Olson et al. |
| 2004/0185045 A1 | 9/2004 | Koenig et al. |
| 2004/0191244 A1 | 9/2004 | Presta |
| 2004/0191256 A1 | 9/2004 | Raju |
| 2004/0192897 A2 | 9/2004 | Winter |
| 2004/0219156 A1 | 11/2004 | Goldenberg et al. |
| 2004/0228856 A1 | 11/2004 | Presta |
| 2004/0258677 A1 | 12/2004 | Waldmann et al. |
| 2004/0258682 A1 | 12/2004 | Leung et al. |
| 2004/0259150 A1 | 12/2004 | Nakamura et al. |
| 2005/0014934 A1 | 1/2005 | Hinton et al. |
| 2005/0031626 A1 | 2/2005 | Stevenson |
| 2005/0032114 A1 | 2/2005 | Hinton et al. |
| 2005/0033029 A1 | 2/2005 | Lu |
| 2005/0037000 A1 | 2/2005 | Stavenhagen et al. |
| 2005/0037002 A1 | 2/2005 | Velardi et al. |
| 2005/0038610 A1 | 2/2005 | Mayo et al. |
| 2005/0054046 A1 | 3/2005 | Presta et al. |
| 2005/0064514 A1 | 3/2005 | Stavenhagen et al. |
| 2005/0070693 A1 | 3/2005 | Hansen et al. |
| 2005/0118174 A1 | 6/2005 | Presta et al. |
| 2005/0152894 A1 | 7/2005 | Krummen et al. |
| 2005/0175614 A1 | 8/2005 | Ledbetter et al. |
| 2005/0202023 A1 | 9/2005 | Ledbetter et al. |
| 2005/0202028 A1 | 9/2005 | Ledbetter et al. |
| 2005/0202534 A1 | 9/2005 | Ledbetter et al. |
| 2005/0215767 A1 | 9/2005 | Koenig et al. |
| 2005/0226864 A1 | 10/2005 | Hinton et al. |
| 2005/0233382 A1 | 10/2005 | Presta |
| 2005/0272128 A1 | 12/2005 | Umana et al. |
| 2005/0276799 A1 | 12/2005 | Hinton et al. |
| 2006/0019316 A1 | 1/2006 | Mayo et al. |
| 2006/0193852 A1 | 8/2006 | Dorken et al. |
| 2006/0233791 A1 | 10/2006 | Tedder et al. |
| 2006/0257398 A1 | 11/2006 | Hansen et al. |
| 2006/0263357 A1 | 11/2006 | Tedder et al. |
| 2006/0280738 A1 | 12/2006 | Tedder |
| 2007/0009519 A1 | 1/2007 | Hariharan et al. |
| 2007/0009541 A1 | 1/2007 | Amphlett et al. |
| 2007/0031436 A1 | 2/2007 | Little et al. |
| 2007/0123479 A1 | 5/2007 | Kufer et al. |
| 2008/0260731 A1 | 10/2008 | Bernett et al. |
| 2010/0272723 A1 | 10/2010 | Bernett et al. |
| 2012/0082664 A1 | 4/2012 | Bernett et al. |
| 2014/0112916 A1 | 4/2014 | Bernett et al. |

FOREIGN PATENT DOCUMENTS

| | | |
|---|---|---|
| EP | 1176195 | 1/2002 |
| EP | 1229125 | 8/2002 |
| EP | 1255209 | 11/2002 |
| EP | 1255826 | 11/2002 |
| EP | 0753065 | 5/2003 |
| EP | 0805628 | 5/2003 |
| EP | 1323346 | 11/2003 |
| EP | 0888125 | 5/2004 |
| EP | 0904107 | 10/2004 |
| EP | 0383799 | 2/2005 |
| JP | H11-505704 | 5/1999 |
| WO | WO 88/007089 | 9/1988 |
| WO | WO 91/006305 | 5/1991 |
| WO | WO 91/019515 | 12/1991 |
| WO | WO 92/004053 | 3/1992 |
| WO | WO 92/016562 | 10/1992 |
| WO | WO 92/022324 | 12/1992 |
| WO | WO 94/029351 | 12/1994 |
| WO | WO 95/005468 | 2/1995 |
| WO | WO 96/022024 | 7/1996 |
| WO | WO 96/036360 | 11/1996 |
| WO | WO 97/028267 | 8/1997 |
| WO | WO 97/034631 | 9/1997 |
| WO | WO 98/002462 | 1/1998 |
| WO | WO 98/005787 | 2/1998 |
| WO | WO 98/023289 | 6/1998 |
| WO | WO 98/047089 | 11/1998 |
| WO | WO 99/004813 | 2/1999 |
| WO | WO 99/051642 | 10/1999 |
| WO | WO 99/054342 | 10/1999 |
| WO | WO 99/054440 | 10/1999 |
| WO | WO 99/058572 | 11/1999 |
| WO | WO 00/009560 | 2/2000 |
| WO | WO 00/023564 | 4/2000 |
| WO | WO 00/024782 | 5/2000 |
| WO | WO 00/042072 | 7/2000 |
| WO | WO 00/061739 | 10/2000 |
| WO | WO 00/067796 | 11/2000 |
| WO | WO 01/029246 | 4/2001 |
| WO | WO 01/038490 | 5/2001 |
| WO | WO 01/057088 | 8/2001 |
| WO | WO 01/059066 | 8/2001 |
| WO | WO 01/077342 | 10/2001 |
| WO | WO 01/097843 | 12/2001 |
| WO | WO 02/030954 | 4/2002 |
| WO | WO 02/031140 | 4/2002 |
| WO | WO 02/044215 | 6/2002 |
| WO | WO 02/060919 | 8/2002 |
| WO | WO 02/061090 | 8/2002 |
| WO | WO 02/061093 | 8/2002 |
| WO | WO 02/080987 | 10/2002 |
| WO | WO 03/014325 | 2/2003 |

(56) References Cited

FOREIGN PATENT DOCUMENTS

| WO | WO 03/016470 | 2/2003 |
|---|---|---|
| WO | WO 03/025018 | 3/2003 |
| WO | WO 03/035835 | 5/2003 |
| WO | WO 03/048209 | 6/2003 |
| WO | WO 03/054213 | 7/2003 |
| WO | WO 03/074679 | 9/2003 |
| WO | WO 03/088998 | 10/2003 |
| WO | WO 03/089624 | 10/2003 |
| WO | WO 04/004662 | 1/2004 |
| WO | WO 04/004798 | 1/2004 |
| WO | WO 04/016750 | 2/2004 |
| WO | WO 04/022717 | 3/2004 |
| WO | WO 04/024871 | 3/2004 |
| WO | WO 04/024889 | 3/2004 |
| WO | WO 04/035752 | 4/2004 |
| WO | WO 04/056312 | 7/2004 |
| WO | WO 04/063351 | 7/2004 |
| WO | WO 04/074455 | 9/2004 |
| WO | WO 04/092219 | 10/2004 |
| WO | WO 04/103404 | 12/2004 |
| WO | WO 04/106381 | 12/2004 |
| WO | WO 04/110472 | 12/2004 |
| WO | WO 05/000899 | 1/2005 |
| WO | WO 05/001025 | 1/2005 |
| WO | WO 05/007809 | 1/2005 |
| WO | WO 05/011376 | 2/2005 |
| WO | WO 05/012493 | 2/2005 |
| WO | WO 05/012877 | 2/2005 |
| WO | WO 05/013090 | 2/2005 |
| WO | WO 05/012493 | 3/2005 |
| WO | WO 05/018572 | 3/2005 |
| WO | WO 05/023866 | 3/2005 |
| WO | WO 05/027966 | 3/2005 |
| WO | WO 05/037867 | 4/2005 |
| WO | WO 05/040217 | 5/2005 |
| WO | WO 05/047327 | 5/2005 |
| WO | WO 05/052004 | 6/2005 |
| WO | WO 05/060642 | 7/2005 |
| WO | WO 05/063815 | 7/2005 |
| WO | WO 05/070963 | 8/2005 |
| WO | WO 05/116078 | 12/2005 |
| WO | WO 05/123780 | 12/2005 |
| WO | WO 06/012500 | 2/2006 |
| WO | WO 06/047350 | 5/2006 |
| WO | WO 06/089133 | 8/2006 |
| WO | WO 06/121852 | 11/2006 |
| WO | WO 06/133450 | 12/2006 |
| WO | WO 07/002223 | 1/2007 |
| WO | WO 07/068354 | 6/2007 |
| WO | WO 07/076950 | 7/2007 |
| WO | WO 07/082715 | 7/2007 |
| WO | WO 07/085470 | 8/2007 |
| WO | WO 08/031056 | 3/2008 |
| WO | WO 08/131940 | 11/2008 |

OTHER PUBLICATIONS

Abadeh, S., et al., "Remodelling the oligosaccharide of human IgG antibodies: effects on biological activities," Biochem Soc Trans., 25(4):S661 (Nov. 1997).
Akewanlop, C., et al., "Phagocytosis of Breast Cancer Cells Mediated by Anti-MUG-1 Monoclonal antibody, DF3, and Its Bispecific Antibody" Cancer Research, 61 :4061-4065 (May 15, 2001).
Alegre, M., et al., "Effect of a Single Amino Acid Mutation on the Activating and Immunosuppressive Properties of a "Humanised" OKT3 Monoclonal Antibody," J. Immunology, 148:3461-3468 (Jun. 1992).
Algre, et al., "A non-activating "humanized" anti-CD3 monoclonal antibody retains immunosuppressive properties in vivo," Transplantation, 57:1537-1543 (1994).
Allen, Theresa M., et al., "Anti-CD19-Targeted Liposomal Doxorubicin Improves the Therapeutic Efficacy in Murine B-Cell Lymphoma and Ameliorates the Toxicity of Liposomes with Varying Drug Release Rates", Clin. Cancer Res., May 1, 2005, pp. 3567-3573, vol. 11, No. 9.
Amigorena, S., et al., "Fc receptors for IgG and antigen presentation on MHC class I and class II molecules" Immunology, 11:385-390 (1999).
Andreakos, E., et al., "Monoclonal antibodies in immune and inflammatory diseases," Curr. Opin. Biotech., 13:615-620 (2002).
Armour, et al., "Recombinant human IgG molecules lacking Fcgamma receptor I binding and monocyte triggering activities," Eur J Immunol, 29:2613-2624 (1999).
Armour, K. L., et al., "Differential binding to human FcγRIIa and FcγRIIb receptors by human IgG wildtype and mutant antibodies," Molecular Immunology, 40:585-593 (2003).
Ashkenazi et al., "Immunoadhesins as research tools and therapeutic agents," Curr. Opin. Immunol., 9 (1997) 195-200.
Ashkenazi, A., et al., "Mapping the CD4 binding site for human immunodeficiency virus by alanine-scanning mutagenesis,"PNAS, USA, 87:7150-7154 (Sep. 1990).
Barbin et al., "Influence of variable N-Glycosylation on the cytolytic potential of chimeric CD19 antibodies," J. Immun., 29:2 (2006) 122-133.
Bargou, R.C., et al., "MT103 (MEDI-538) Induces B-cell Depletion, Clearance of Bone Marrow Infiltration and Clinical Responses in Heavily Pre-treated NHL Patients: First Data from Phase I Dose-escalation Study MT103-104", source unknown, date unknown, 1 page.
Bolland, S. "A Newly Discovered Fc Receptor tha Explains IgG-Isotype Disparities in Effector Responses," J. Immunity, 23:2-4 (Jul. 2005).
Boruchov, A. M., et al., "Activating and inhibitory IgG Fc receptors on human DCs mediate opposing functions" J. Clin. Invest. doi :10.1172/JCI24772 (Sep. 16, 2005).
Bowles, J. A., et al., "CD16 polymorphisms and NK activation induced by monoclonal antibody-coated target cells," Journal of Immunological Methods, pp. 1-12 (2005).
Brekke, 0. H., et al., "Human IgG isotype-specific amino acid residues affecting complement-mediated cell lysis and phagocytosis," Eur J. ImmunL, 24(10) :2542-5247 (Oct. 1994).
Brekke, 0. H., et al., "Human IgG3 can adopt the disulfide bond pattern characteristic for IgG1 without resembling it in complement mediated cell lysis," Mol. Immunol. 30(16):1419-1425 (Nov. 1993).
Bruenke, Joerg, et al., "Effective lysis of lymphoma cells with a stabilized bispecific single-chain Fv antibody against CD19 and FcγRIII (CD16)", British Journal of Haematology, pp. 218-228, vol. 130.
Bruggeman, M., et al., "Comparison of the Effector Functions of Human Immunoglobulins Using a Matched Set of Chimeric Antibodies," J. Exp. Med., 166:1351-1361 (Nov. 1987).
Bruggemann, M., et al., "A matched set of raVmouse chimeric antibodies. Identification and biological properties of rat H chain constant regions mu, gamma 1, gamma 2a, gamma 2b, gamma 2c, epsilon, and alpha," J. Immunol., 142(9):3145-3150 (May 1989).
Burmeister, W. P., et al., "Crystal structure of the complex of rat neonatal Fc receptor with Fc" Nature, 372:379-383 (Nov. 24, 1994).
Callard, Robin E., et al., "CD19 Regulation of Human B Cell Responses, B Cell Proliferation and Antibody Secretion Are Inhibited or Enhanced by Ligation of the CD19 Surface Glycoprotein Depending on the Stimulating Signal Used", The Journal of Immunology, May 15, 1992, pp. 2983-2987, vol. 148, No. 10.
Canfield, S. M., et al., "The Binding Affinity of Human IgG for its High Affinity Fc Receptor is Determined by Multiple Amino Acids in the CH2 Domain and Is Modulated by the Hinge Region," J. Exp. Med., 173:1483-1491 (Jun. 1991).
Caron et al., "Engineered humanized dimeric forms of IgG are more effective antibodies," J. Exp. Med., 176 (1992) 1191-1195.
Caron, P. C., et al., "Murine and humanized constructs of monoclonal antibody M19 (anti-CD33) for the therapy of acute myelogenous leukemia," Cancer, 73(3 Supp):1049-1056 (Feb. 1994).
Carpenter, P.A., et al., "Non-Fc Receptor-Binding Humanized Anti-CD3 Antibodies Induce Apoptosis of Activated Human T Cells," Journal of Immunology, 165:6205-6213 (2000).
Carter, P., "Improving the Efficacy of Antibody-Based Cancer Therapies," Nature Reviews, 1 :118-129 (2001).

(56) References Cited

OTHER PUBLICATIONS

Carter, P., et al., "Humanization of an anti-p185$^{HER2}$ antibody for human cancer therapy" PNAS, 89:4285-4289 (May 1992).
Carter, Robert H., et al., "Signaling by the CD19/CD21 Complex on B Cells", Curr. Dir. Autoimmun. Basel, Karger, 2004, pp. 4-32, vol. 7.
Carter, Robert H., et al., "Role of CD19 Signal Transduction in B Cell Biology, Immunologic Research", 2002, pp. 45-54, vol. 26, No. 1.
Cartron et al., "Therapeutic activity of humanized anti-CD20 monoclonal antibody and polymorphism in IgG Fc receptor FcRyIIIa gene," Blood, 99:3 (2002) 754-758.
Casset, et al., "A peptide mimetic of an anti-CD4 monoclonal antibody by rational design", Biochemical and Biophysical Research Communications, vol. 307, May 20, 2003, 198-205.
Chadd, H., et al., "Therapeutic antibody expression technology," Curr. Opin. Biotech., 12:188-194 (2001).
Chamow et al., "Immunoadhesins: principles and applications," Trends in Biotechnol, 14:2 (1996) 52-60.
Chan, et al. "Variable Region Domain Exchange in Human IgGs promotes antibody complex formation with accompanying structural changes and altered effector functions" Molecular Immunology 2004, 21 :527-538.
Chapman, P. B., "T-Cell Chauvinists Versus Antibody Advocates—Can't We All Just Get Along?" J. Clin. Oncology, 22(22):4446-4448 (Nov. 15, 2004).
Chappel, M. S., et al., "Identification of a Secondary Fcγ RI Binding Site within a Genetically Engineered Human IgG Actibody," J. Bioi. Chern., 268(33):25124-25131 (Nov. 1993).
Chappel, M. S., et al., "Identification of the Fcγ receptor class I binding site in human IgG through the use of recombinant IgG1/IgG2 hybrid and point-mutated antibodies," PNAS, USA, 88:9036-9040 (Oct. 1991).
Chen, et al., "Selection and analysis of an optimized anti-VEGF antibody: crystal structure of an affinity matured Fab in complex with antigen", Journal of Molecular Biology, vol. 293, 1999, 865-881.
Cheng, W.W.K., et al., "Expression and purification of two anti-CD19 single chain Fv fragments for targeting of liposomes to CD19-expressing cells", Biochimica et Biophysica Acta 1768, 2007, pp. 21-29.
Chintalacharuvu, K. R., et al., "Hybrid IgA2/IgG1 Antibodies with Tailor-Made Effector Functions," Clinical Immunology, 101(1):21-31 (Oct. 2001).
Clark, M. "Antibody humanization: a case of the Emperor's new clothes?" Immunol. Today, 21(8):397-402 (2000).
Clark, M. R. "Chemical Immunology Antibody Engineering IgG Effector Mechanisms," Dissertation submitted to Immunology R., of Department of Pathology at Cambridge University, UK, 21 :8, pp. 397-402 (Aug. 2000).
Clynes, R. A., et al., "Inhibitory Fc receptors modulate in vivo cytoxicity against tumor targets," Nature Medicine, 6(4):443-446 (Apr. 2000).
Clynes, R. et al., "Modulation of Immune complex-induced Inflammation In Vivo by the Coordinate Expression of Activation and Inhibitory Fc Receptors," J. Exp. Med., 189(1):179-185 (Jan. 4, 1999).
Clynes, R., "Immune complexes as therapy for autoimmunity" J. Clin. Invest., 115:25-27 (2005).
Clynes, R., et al., "Fc receptors are required in passive and active immunity to melanoma," PNAS USA, 95:652-656 (Jan. 1998).
Cochlovius, Bjorn, et al., "Cure of Burkitt's Lymphoma in Severe Combined Immunodeficiency Mice by T Cells, Tetravalent CD3 X CD19 Tandem Diabody, and CD28 Costimulation", Cancer Research, Aug. 15, 2000, pp. 4336-4341, vol. 60.
Cohen-Sodal, J. FG., et al., "Review: Fc γ receptors" Immunology Lefts, 92:199-205 (2004).
Cole, M. S., et al., "Human lgG2 variants of chimeric anti-CD3 are nonmitogenic to T cells," J. Immunol., 159(7) :3613-3621 (Oct. 1, 1997).

Coloma, M. J. et al., "The hinge as a spacer contributes to convalent assembly and is required for function of IgG," J. Immunol., 158(2) :733-740 (Jan. 15, 1997).
Cooper, Laurence J.N., et al., "Development and application of CD19-specific T cells for adoptive immunotherapy of B cell malignancies", Blood Cells, Molecules and Diseases, 2004, pp. 83-89, vol. 33.
Cooper, Laurence J.N., et al., "Enhanced antilymphoma efficacy of CD19-redirected influenza MP1-specific CTLs by cotransfer ofT cells modified to present influenza MP1",Blood, Feb. 15, 2005, pp. 1622-1631, vol. 105, No. 4.
Cragg, M., et al., "Signaling antibodies in cancer therapy," Curr. Opin. Immunol, 11:541-547 (1999).
Culton, Donna A., et al., "Similar CD19 Dysregulation in Two Autoantibody-Associated Autoimmune Diseases Suggests a Shared Mechanism of B-Cell Tolerance Loss", Journal of Clinical Immunology, Jan. 2007, pp. 53-68, vol. 27, No. 1.
Da Silveira, S. A., et al., "Complement Activation Selectively Potentiates the Pathogenicity of the IgG2 b and IgG3 Isotypes of a High Affinity Anti-Erythrocyte Autoantibody," J. Exp. Med., 195(6) :665-672 (Mar. 18, 2002).
Dall'Acqua et al., "Increasing the affinity of a human IgG1 for the neonatal Fc receptor: biological consequences," Journal of Immunology, 169 (2002) 5171-5180.
Dall'Acqua, W., et al., "Antibody Engineering," Curr. Opin Structural Bioi., 8:443-450 (1998).
Daniel, Peter T., et al., "Immunotherapy of B-Cell Lymphoma With CD3x19 Bispecific Antibodies: Costimulation via CD28 Prevents 'Veto' Apoptosis of Antibody-Targeted Cytotoxic T Cells", Blood, Dec. 15, 1998, pp. 4750-4757, vol. 92, No. 12.
Dass, Shouvik, et al., "Rituximab: B-cell depletion therapy for the treatment of rheumatoid arthritis", Future Rheumatol., 2006, pp. 293-302, vol. 1, No. 3.
Davies et al. "Expression of GnTIII in a recombinant anti-CD20 CHO production cell line: Expression of antibodies with altered glycoforms leads to an increase in ADCC through higher affinity for FCyRIII," Biotechnol. Bioeng., 74:4 (2001) 288-294.
Davis et al., "Fc receptor homologs: newest members of a remarkably diverse Fc receptor gene family," Immunological Reviews, 190 (2002) 123-136.
Davis, R. S., et al., "Identification of a family of Fc receptor homologs with preferential B cell expression," PNAS, USA, 98(17):9772-9777 (Aug. 2001).
Delano, W. L., et al., "Convergent Solutions to Binding at a Protein-Protein Interface" Science, 287:1279-1283 (Feb. 18, 2000).
De Pascalis, et al., "Grafting of "Abbreviated" Complementarity-Determining Regions Containing Specificity-Determining Residues Essential for Ligand Contact to Engineer a Less Immunogenic Humanized Monoclonal Antibody", Journal of Immunology (2002) 169, 3076-3084.
Dhodapkar et al., "Selective Blockade of Inhibitory Fcy Receptor Enables Human Dendritic Cell Maturation With IL-12p70 Production and Immunity to Antibody-Coated Tumor Cells", *PNAS*, 102:8 (2005) 2910-2915.
Dhodapkar, K.M., et al., "Antitumor Monoclonal Antibodies Enhance Cross-Presentation of Cellular Antigens and the Generation of Myeloma-specific Killer T-Cells by Dendritic Cells" J. Exp Med., 195(1):125-133 (Jan. 7, 2002).
Dhodapkar, K.M., et al., "Recruiting dendritic cells to improve antibody therapy of cancer" PNAS, 102(18):6243-6244 (May 3, 2005).
Dhodapkar, M. V., et al., "T cells from the tumor microenvironment of patients with progressive myeloma can generate strong, tumor-specific cytolytic responses to autologous, tumor-loaded dendritic cells" PNAS, 99(20) :13009-13013 (Oct. 1, 2002).
Doody et al., "Activation of B lymphocytes: integrating signals from CD19, CD22 and FcyRIIb1," Curr. Opin. Immunol., 8 (1996) 378-382.
Dreier, Torsten, et al., "Extremely Potent, Rapid and Costimulation-Independent Cytotoxic T-Cell Response Against Lymphoma Cells Catalyzed by a Single-Chain Bispecific Antibody", Int. J. Cancer, 2002, pp. 690-697, vol. 100.

(56) References Cited

OTHER PUBLICATIONS

Dreier, Torsten, et al., "T Cell CostimuiUS Independent and Very Efficacious Inhibition of Tumor Growh in Mice Bearing Subcutaneous or Leukemic Human B Cell Lymphoma Xenografts by a CD19-/CD3-Bispecific Single-Chain Antibody Construct", The Journal of Immunology, 2003, pp. 4397-4402, vol. 170.
Duncan, A. R., et al., "Localization of the binding site for the human high-affinity Fc receptor on IgG," Nature, 332:563-564 (Apr. 7, 1988).
Duncan, A. R., et al., "The binding site for C1q on IgG," Nature 332:738-740 (Apr. 21, 1988).
D'Uscio, C. H., et al., "Cellular cytotoxicity mediated by isotype-switch variants of a monoclonal antibody to human neuroblastoma," Br. J. Cancer, 64(3):445-450 (Sep. 1991).
Edelman et al., "The covalent structure of an entire yG immunoglobulin molecule," Biochemistry, 63 (1969) 78-85.
Edwards, Jonathan C.W., et al., "B-cell targeting in rheumatoid arthritis and other autoimmune diseases," Nature Reviews, May 2006, pp. 394-403, vol. 6.
Ehrhardt, G. R. A., et al., "The inhibitory potential of Fc receptor homolog 4 on memory B cells," PNAS, USA, 100(23):13489-13494 (Nov. 2003).
Ellison, J. W., et al., "The nucleotide sequence of a human immunoglobulin Cy1 gene" Nucleic Acids Research, 10(13) :4071-4079(1982).
Ernst, L. K., et al., "Molecular characterization of six variant Fcγ receptor class I (CD64) transcripts," Molecular Immunology, 35:943-954 (1998).
Facchetti, F., et al., "An unusual Fc receptor-related protein expressed in human centroblasts," PNAS, USA, 99(6):3776-3781 (Mar. 19, 2002).
Fearon, Douglas T., et al., "Regulation of B Lymphocyte Responses to Foreign and Self-Antigens by the CD19/CD21 Complex", Annu. Rev. Immunol., 2000, pp. 393-422, vol. 18.
Fearon, Douglas T., et al., The CD19/CR2/TAPA-1 Complex of B Lymphocytes: Linking Natural to Acquired Immunity, Annu. Rev. Immunol., 1995, pp. 127-149, vol. 13.
Gaboriaud, C. et al., "The Crystal Structure of the Globular Head of Complement Protein C1q Provides a Basis for Its Versatile Recognition Properties," J. Bioi. Chern., 278(47):46974-46982 (2003).
Garman, S.C., et al., "Structure of the Fc fragment of human IgG bound to its high-affinity receptor Fc€Ria," Nature, 406:259-266 (2000).
Getahun, A., et al., "IgG2a-Mediated Enhancement of Antibody and T Cell Responses and Its Relation to Inhibitory and Activating Fcγ Receptors," J. of Immunology, 172:5269-5276 (2004).
Ghazizadeh, S., et al., "Physical and Functional Association of Src-related Protein Tyrosine Kinases with FcRII in Monocytic THP-1 Cells," J. Bioi. Chern., 269(12):8878-8884 (Mar. 25, 1994).
Ghetie et al., "Multiple roles for the major histocompatibility complex Class I-related receptor FcRn," Annual Rev. Immunol., 18 (2000) 739-766.
Ghetie, Maria-Ana, et al., "Anti-CD19 Antibodies Inhibit the Function of the P-gp Pump in Multidrugresistant B Lymphoma Cells", Clinical Cancer Research, Dec. 1999, pp. 3920-3927, vol. 5.
Ghetie, Maria-Ana, et al., "Anti-CD19 Inhibits the Growth of Human B-Cell Tumor Lines In Vitro and of Daudi Cells in SCID Mice by Inducing Cell Cycle Arrest", Blood, Mar. 1, 1994, pp. 1329-1336, vol. 83, No. 5.
Ghetie, Maria-Ana, et al., "An anti-CD19 antibody inhibits the interaction between P-glycoprotein (P-gp) and CD19, causes P-gp to translocate out of lipid rafts, and chemosensitizes a multidrug-resistant (MDR) lymphoma cell line", Blood, Jul. 1, 2004, pp. 178-183, vol. 104, No. 1.
Ghetie, V., et al., "FcRn: the MHC class 1-related receptor that is more than an IgG transporter" Immunology Today, 18(12):592-598 (Dec. 1997).
Ghetie, V., et al., "Increasing the serum persistence of an IgG fragment random mutagenesis," Nat. Biotechol., 15(7):637-640 (Jul. 1997).

Ginaldi, Lia, et al., "Levels of expression of CD19 and CD20 in chronic B cell leukaemias", J. Clin. Pathol., 1998, pp. 364-369, vol. 51.
Glennie, M., et al., "Clinical trials of antibody therapy," Immun. Today, 21(8):403-410 (2000).
Glennie, M., et al., "Renaissance of cancer therapeutic antibodies," Drug Discovery Today, 8(11):503-510 (2003).
Gonzales, N. R., et al., "SDR grafting of a murine antibody using multiple human germline templates to minimize its immunogenicity," Molecular Immunology, 41:863-872 (2004).
Greenwood, J. "Molecular Recognition in the Structure and Assembly of Filamentous Bacteriphages," Dissertation submitted to the University of Cambridge (Oct. 1989).
Greenwood, J. et al., "Effector functions of matched sets of recombinant human IgG subclass antibodies," Dissertation submitted to Cambridge University, CambridQe, UK (Feb. 1993).
Greenwood, J., et al. "Dual Importance of Positive Charge in the C-Terminal Region of Filamentous Bacteriophage Coat Protein for Membrane Insertion and DNA-Protein Interaction in Virus Assembly," Virology, 171 :444-452 (1989).
Greenwood, J., et al., "Engineering multiple-domain forms of the therapeutic antibody CAMPATH-1 H: effects on complement lysis," Ther Immunol, 1(5):247-255 (Oct. 1994).
Greenwood, J., et al., "Structural motifs involved in human IgG antibody effector functions," Eur. J. Immunol., 23(5) :1098-1104 (May 1993).
Groh, V., et al., "Efficient cross-priming of tumor antigen specific T cells by dendritic cells sensitized with diverse anti-MICA opsonized tumor cells" PNAS, 102(18) :6461-6466 (May 3, 2005).
Grossbard, Michael L., et al., "A Phase II Study of Adjuvant Therapy with Anti-B4-blocked Ricin after Autologous Bone Marrow Transplantation for Patients with Relapsed B-Cell Non-Hodgkin's Lymphoma", Clinical Cancer Research, Sep. 1999, pp. 2392-2398, vol. 5.
Grossbard, Michael L., et al., "Anti-B4-blocked ricin: a phase II trial of 7 day continuous infusion in patients with multiple myeloma", British Journal of Hematology, 1998, 102, pp. 509-515.
Grossbard, Michael L., et al., "Monoclonal Antibody-Based Therapies of Leukemia and Lymphoma", Blood, Aug. 15, 1992, pp. 863-878, vol. 80, No. 4.
Grossbard, Michael L., et al., "Short Analytical Review, Prospects for Immunotoxin Therapy of Non-Hodgkin's Lymphoma", Clinical Immunology and Immunopathology, Aug. 1995, pp. 107-114, vol. 76, No. 2.
Gruen, Michael, et al., "T-cell-mediated lysis of B cells induced by a CD19xCD3 bispecific single-chain antibody is perforin dependent and death receptor independent", Cancer Immunol. Immunother, 2004, pp. 625-632, vol. 53.
Harata, Masamitsu, et al., "CD19-targeting liposomes containing imatinib efficiently kill Philadelphia chromosome-positive acute lymphoblastic leukemia cells", Blood, Sep. 1, 2004, pp. 1442-1449, vol. 104, No. 5.
Harrison, P. T., et al., "Domain swap chimeras to study the binding of IgG by Fc gamm RI, the high affinity receptor for IgG," Biochem Soc Trans., 24(1):1445 (Feb. 1996).
Hayhurst et al., "High-throughput antibody isolation," Curr. Opin. in Chem. Biol., 5 (2001) 683-689.
Hazenbos, W.L., et al., "Murine IgG1 complexes Trigger Immune Effector Functions Predominately via FcγRIII (CD16)," J. of Immunology, 161 :3026-3032 (1998).
Hekman, A., et al., Initial experience with treatment of human B cell lymphoma with anti-CD19 monoclonal antibody, Cancer Immunol. Immunother, 1991, pp. 364-372, vol. 32.
Henry, A. J., et al., "Participation of theN-Terminal of CE3 in the Binding of Human IgE to Its High-Affinity Receptor Fc€RI," Biochemistry, 36:15568-15578 (1997).
Hezareh, M., et al., "Effector Function Activities of a Panel of Mutants of a Broadly Neutralizing Antibody against Human Immunodeficiency Virus Type 1," Journal of Virology, 75(24):12161-12168 (2001).
Hinton et al., "Engineered human IgG antibodies with longer serum half-lives in primates," J. Biol Chem., 279:8 (2004) 6213-6216.

(56) References Cited

OTHER PUBLICATIONS

Hoffmann, Patrick, et al., "Serial killing of tumor cells by cytotoxic T cells redirected with a CD19-/CD3-bispecific single-chain antibody construct", Int. J. Cancer, 2005, pp. 98-104, vol. 115.
Hogarth, P., "Fc receptors are major mediators of antibody based inflammation in autoimmunity," Curr. Opin. Immun., 14:798-802 (2002).
Holliger, P., et al., "Antibodies come back from the brink," Nature Biotechnology, 16:1015-1016 (1998).
Holm, et al., "Functional mapping and single chain construction of the anti-cytokeratin 8 monoclonal antibody TS1", Molecular Immunology, vol. 44, 2007, 1075-1084.
Hudson, P., "Recombinant antibody constructs in cancer therapy," Curr. Opin. Immunology, 11 :548-557 (1999).
Hudson, P., "Recombinant antibody fragments," Curr. Opin in Biotechnology, 9:395-402 (1998).
Hutchins, et al., "Improved biodistribution, tumor targeting, and reduced immunogenicity in mice with a gamma 4 variant of Cannpath-1 H," PNAS USA, 92:11980-11984 (1995).
Idusogie, E. E., et al., "Engineered Antibodies with Increased Activity to Recruit Complement," J. of Immunology, 166:2571-2575 (2001).
Idusogie, E.E., et al., "Mapping of the C1q Binding Site on Rituxan, a Chimeric Antibody with a Human IgG1 Fc," J. of Immunology, 164:4178-4184 (2000).
Isaacs, J. D., "Improving Serotherapy with Monoclonal Antibodies" dissertation submitted to the University of Cambridge (Mar. 1991).
Isaacs, J. D., et al., "From bench to bedside: discovering rules for antibody design, and improving serotherapy with monoclonal antibodies," Rheumatology, 40:724-738 (2001).
Isaacs, J. D., et al., "Therapy with Monoclonal Antibodies: an in vivo model for the assessment of therapeutic potential," J. Immunol., 148(10):3062-3071 (May 15, 1992).
Isaacs, J.D., et al., "Therapy with Monoclonal Antibodies, II. The contribution of Fcγ Receptor binding and the Influenece of CH1 and CH3 Domains on In Vivo Effector Function," J. of Immunology, 161 :3862-3869 (1998).
Jefferis, et al., Modulation of FcγR and human complement activation by IgG3-core oligosaccharide interactions, Immunol Lett, 54:101-104 (1996).
Jefferis et al., "Interaction sites on human IgG-Fc for FcγR: current models," Immunol. Letters, 82:1 (2002) 57-65.
Jefferis, R. et al., "Recognition sites on human IgG for Fc gamma receptors: the role of glycosylatin," Immunol Letters, 44(2-3):111-117 (Jan. 1995).
Jefferis, R., et al., "Modulation of FcγR and human complement activation by IgG3-core oligosaccharide interactions," Immunology Letters, 54:101-104 (1996) and errata at Immunology Letters, 58:67 (1997).
Jefferis, R., et al., "Molecular definition of interaction sites on human IgG for Fc receptors (huFc gamma R)," MolImmunol., 27(12):1237-1240 (Dec. 1990).
Jendeberg, L., et al., "Engineering of Fci and Fc3 from human immunoglobulin G to analyse subclass specificity for staphylococcal protein A, "Journal of Immunological Methods, 201 :25-34 (1997).
Johnson, G., et al., "Kabat Database and its applications: future directions," Nucleic Acids Research, 29(1):205-206 (2001).
Johnson, G., et al., "Kabat Database and its applications: 30 years after the first variability plot," Nucleic Acids Research, 28(1) :214-218 (2000).
Junghans, R. P., et al., "The protection receptor for IgG catabolism is the (32_ microglobulin-containing neonatal Intestinal transport receptor," PNAS, 93:5512-5516 (May 1996).
Kalergis, A.M., et al., "Inducing Tumor Immunity through the Selective Engagement of Activating Fcγ Receptors on Dendritic Cells" J. Exp. Med. 195(12):1653-1659 (Jun. 17, 2002).
Kan et al., "Thioether-bonded constructs of Fab'y and Fcy modules utilizing differential reduction of interchain disulfide bonds," J. Immunol., 166 (2001) 1320-1326.

Karassa, F. B., et al., "The role of FcγRIIA and lilA polymorphisms in autoimmune diseases," Biomedicine & Pharmacotherapy, 58:286-291 (2004).
Kim et al., "Analysis of FcγRIII and IgG Fc polymorphism reveals functional and evolutionary implications of protein-protein interaction," J. Mol. Evol., 53 (2001) 1-9.
Kim, J. et al., "Mapping the site on human IgG for binding of the MHC class 1-related receptor, FcRn" Eur. J. Immunol., 29:2819-2825 (1999).
Kim, J. Ketal "Localization of the site of the murine IgG1 molecule that is involved in binding to the murine intestinal Fc receptor," Eur J Immunol, 24(10):2429-2439 (Oct. 1994).
Kim, J.K. et al "Identifying amino acid residues that influence plasma clearance of murine IgG1 fragments by site-directed nnutagenesis," EurJ. Immunol., 24(3):542-548 (Mar. 1994).
Kipriyanov, Sergey M., et al., Rapid detection of recombinant antibody fragments directed against cell-surface antigens by flow cytometry, Journal of Immunological Methods, 1996, pp. 51-62, vol. 196, No. 1.
Kipriyanov, Sergey M., et al., "Bispecific CD3 X CD19 Diabody ForT Cell-Mediated Lysis of Malignant Human B Cells", Mt. J. Cancer, 1998, pp. 763-772, vol. 77.
Kipriyanov, Sergey M., eta!., "Synergistic Antitumor Effect of Bispecific CD19 X CD3 and CD19 X CD16 Diabodies in a Preclinical Model of Non-Hodgkin's Lymphoma", TheJournalofImmunology, 2002, pp. 137-144, vol. 169.
Krapp, et al., "Structural analysis of human IgG-Fc glycoforms reveals a correlation between glycosylation and structural integrity," J Mol Bioi, 325:979-989 (2003).
Kurucz, 1., et al., "Bacterially expressed human FcγRIIb is soluble and functionally active after in vitro refolding" Immunology Letts., 75:33-40 (2000).
Lang, Peter, et al., "Chimeric CD19 antibody mediates cytotoxic activity against leukemic blasts with effector cells from pediatric patients who received T-cell-depleted allografts", Blood, May 15, 2004, pp. 3982-3985, vol. 103, No. 10.
Lankester, Arjan C., et a/.,"Aiteration of B-cell Antigen Receptor Signaling by CD19 Co-ligation", The Journal of Biological Chemistry, Sep. 13, 1996, pp. 22326-22330, vol. 271, No. 37.
Le Gall, Fabrice, et al., "Effect of linker sequences between the antibody variable domains on the formation, stability and biological activity of a bispecific tandem diabody", Protein Engineering, Design & Selection, 2004, pp. 357-366, vol. 17, No. 4.
Lehrnbecher, et al., "Variant Genotypes of the Low-Affinity Fcγ Receptors in Two Control Populations and a Review of Low-Affinity Fcγ Receptor Polymorphisms in Control and Disease Populations," Blood, 94:4220-4232 (1999).
Liu, et al. "Production of a Mouse-Human Chimeric Monoclonal Antibody to CD20 with Potent Fe-Dependent Biologic Activity" The Journal of Immunology, 1998, 139-10:3521-3526.
Loftier, Anja et al., "A recombinant bispecific single-chain antibody, CD19 X CD3, induces rapid and high lymphoma-directed cytotoxicity by unstimulated T lymphocytes", Blood, Mar. 15, 2000, pp. 2098-2103, vol. 95.
Lund, et al., "Human Fc gamma RI and Fc gamma RII interact with distinct but overlapping sites on human IgG," J Immunol, 147:2657-2662 (1991).
Lund, et al., "Multiple binding sites on the CH2 domain of IgG for mouse Fc gamma R11 ," Mol. Immunol, 29:53-59 (1992).
Lund, et al., "Multiple interactions of IgG with its core oligosaccharide can modulate recognition by complement and human Fc gamma receptor I and influence the synthesis of its oligosaccharide chains," J Immunol, 154:49634969 (1996).
Lund, et al., "Oligosaccharide-protein interactions in IgG can modulate recognition by Fc gamma receptors," Faseb J, 9:115-119 (1995).
Lund, J., et al., "A protein structural change in aglycosylated IgG3 correlates with loss of huFc gamma R1 and huFc gamma R111 binding and/or activation," Mol. Immunol., 27(11) :1145-1153 (Nov. 1990).
Lund, J., et al., "Control of IgG/Fc glycosylation: a comparision of oligosaccharides from chimeric human/mouse and mouse subclass immunoglobulin Gs," Mol. Immunol., 30(8):741-748 (Jun. 1993).

(56) References Cited

OTHER PUBLICATIONS

Maccallum, et al., "Antibody antigen interactions: contact analysis and binding site topography", Journal of Molecular Biology, vol. 262, 1996, 732-745.
Maenaka, K., et al., "The Human Low Affinity Fcγ Receptors IIa, lib and III Bind IgG with Fast Kinetics and Distinct Thermodynamic Properties" J. Bioi. Chern. 276(48) :44898-44904 (2001).
Martin, Flavius, et al., "B Cell Immunobiology in Disease: Evolving Concepts from the Clinic", Annu. Rev. Immunol., 2006, pp. 467-496, vol. 24.
Martin, W. L., et al., "Characterization of the 2:1 Complex between the Class I MHC-Related Fc Receptor and Its Fc Ligand in Solution," Biochemistry, 38:12639-12647 (1999).
Martin, W. L., et al., "Crystal Structure at 2.8 A of an FcRn/Heterodimeric Fc Complex: Mechanism of pH-Dependent Binding" Molecular Cell, 7:867-877 (Apr. 2000).
Masir, N., et al., "Loss of CD19 expression in B-cell neoplasms", Histopathology, 2006, pp. 239-246, vol. 48.
Masztalerz, A., et al., "Mechanisms of macrophage cytotoxicity in IL-2 and IL-12 mediated tumor regression," Cancer ImmunolImmunother, 52:235-242 (2003).
Maxwell, K.F., et al., "Crystal structure of the human leukocyte Fc receptor, FcRIIa." Nature Structural Biology, 6(5) :437-442 (May 1999).
Mayfield, S. P., et al., "Expression and assembly of a fully active antibody algae," PNAS, 100(2):438-442 (Jan. 21, 2003).
Maynard et al., "Antibody engineering," Annu. Rev. Biomed. Eng., 2 (2000) 339-376.
Mechetina et al., "Identification of CD16-2, a novel mouse receptor homologous to CD16/FcγRIII," Immunogenetics, 4 (2002) 463-468.
Merchant, A. M. et al., "An efficient route to human bispecific IgG," Nat Biotechnol., 16(7) :677-681 (1998).
Metes. D., et al., "Expression of Functional CD32 Molecules on Human NK Cells Is Determined by and Allelic Polymorphism of the Fcγ RIIC Gene," Blood, 91(7):2369-2380 (Apr. 1, 1998).
Michaelson, T. E., et al., "Antibody Dependent Cell-Mediated Cytotoxicity Induced by Chimeric Mouse-Human IgG Subclass and IgG3 Antibodies with Altered Hinge Region," Molecular Immunology, 29(3):319-326 (1992).
Michaelson, T. E., et al., "One disulfide bond in front of the second heavy chain constant region is necessary and sufficient for effector functions of human IgG3 without a genetic hinge," PNAS, 91 :9243-9247 (Sep. 1994).
Michaelson, T. E., et al., "Primary Structure of the 'Hinge' Region of Human IgG3," J Bioi Chern., 252(3) :883-889 (Feb. 1977).
Miller, 1., et al., "ITRAs: a new family of immunoglobulinlike receptors differentially expressed in B cells," Blood, 99(8) :2662-2669 (Apr. 15, 2002).
Mimura et al., "Role of oligosaccharide residues of IgG1-Fc in FcγRIIb binding," J. Biol. Chem., 276:49 (2001) 45539-45547.
Mitchell, Paul et al., Targeting Primary Human Ph' B-Cell Precursor Leukemia-Engrafted SCID Mice Using Radiolabeled Anti-CD19 Monoclonal Antibodies, J. Nucl. Med., Jul. 2003, pp. 1105-1112, vol. 44.
Molhoj, Michael, et al., "CD19-/CD3-bispecific antibody of the BiTE class is far superior to tandem diabody with respect to redirected tumor cell lysis", Molecular Immunology, 2007, pp. 1935-1943, vol. 44.
Morea et al., "Antibody modeling: implications for engineering and design," Methods, 20 (2000) 267-279.
Morgan, A., et al., "The N-terminal end of the CH2 domain of chimeric human IgG1 anti-HLA-DR is necessary for C1q, Fc gamma R1 and Fc gamma RiII binding," Immunology, 86(2):319-324 (Oct. 1995).
Morrison, et al. "Variable Region Domain Exchange Influences the Functional Properties of IgGl1" The Journal of Immunology 1998, 160:2802-2808.

Nakamura, K., et al., "Dissection and optimization of immune effector functions of humanized anti-ganglioside GM2 monoclonal antibody," Molecular Immunology, 37:1035-1 046 (2000).
Neidhardt-Berard, E., et al., "Dendritic cells loaded with killed breast cells induce differentiation of tumor-specific cytoxic T lymphocytes" Breast Cancer Res., 6R322-R328 (Apr. 30, 2004).
Nimmerjahn, F., et al., "Divergent Immunoglobulin-G Subclass Activity Through Selective Fc Receptor Binding" Science, 310:1510 (2005).
Nimmerjahn, F., et al., "Fcγ RIV: A Novel FeR with Distinct IgG Subclass Specificity," Immunity, 23:41-51 (Jul. 2005).
Nimmerjahn, F., et al., "Supporting Online Material for: Divergent Immunoglobulin G Subclass Activity Through Selective Fc Receptor Binding" Science, 310:1510 (2005).
Niwa et al., "Enhancement of the antibody-dependent cellular cytotoxicity of low-fucose IgC1 is independent of FcγRIIIa functional polymorphism," Clinical Cander Rsch., 10 (2004) 6248-6255.
Niwa, R., et al., "Defucosylated Chimeric Anti-CC Chemokine Receptor 4 IgG1 with Enhanced Antibody-Depenndnet Cellular cytotoxicity Shows Potent Therapeutic Activity to T-Cell Leukemia and Lymphoma," Cancer Research, 64:2127-2133 (Mar. 15, 2004).
Norderhaug, L., et al., "Chimeric mouse human IgG3 antibodies with an IgG4-like hinge region induce complement-mediated lysis more efficiently than IgG3 with normal hinge," Eur J Immunol., 21(1 0):2379-2384 (Oct. 1991).
Ober, R. J., et al., "Differences in promiscuity for antibody-FeRn interactions across species: implications for therapeutic antibodies," International Immunology, 13(12):1551-1559 (2001).
Ober, R. J., et al., "Exocytosis of IgG as mediated by the receptor, FeRn: An analysis at the single-molecule level" PNAS, 101 (30) :11076-11081 (Jul. 27, 2004).
O'Connor, S., et al., "Humanization of an antibody against human protein C and calcium-dependence involving framework residues," Protein Engineering, 11(4):321-328 (1998).
Okazaki, A., et al., "Fucose Depletion from Human IgG1 Oligosaccharide Enhances Binding Enthalpy and Association Rate Between IgG1 and Fcγ RIIIa," J. Mol. Bioi., 336:1239-1249 (2004).
Parren, P. W., et al., "Characterization of IgG FeR-mediated proliferation of human T-cells induced by mouse and human anti-CD3 monoclonal antibodies. Identification of a functional polymorphism to human IgG2 anti-CD3," J. Immunol., 148(3):695-701 (Feb. 1992).
Parren, P. W., et al., "On the interaction of IgG subclasses with the low affinity Fc gamma RIIa (CD32) on human monocytes, neutrophils, and platelets. Analysis of a functional polymorphism to human IgG2," J Clin Invest., 90(4):1537-1546 (Oct. 1992).
Pearce, K. H., et al., "Mutational Analysis of Thrombopoietin for Identification of Receptor and Neutralizing Antibody Sites," J. Bioi. Chem., 272(33) :20595-20602 (1997).
Penichet, M., et al., "Antibody-cytokine fusion proteins for the therapy of cancer," Journal of Immunological Methods, 248:91-1010 (2001).
Pietersz, Geoffrey A., et al., in vitro and in vivo antitumour activity of a chimeric anti-CD19 antibody, Cancer Immunol. Immunother., 1995, pp. 53-60, vol. 41.
Preithner, S., et al., "High concentrations of therapeutic Igg1 antibodies are needed to compensate for inhibition of antibody-dependnent cellular cytotoxicity by excess endoQenous immunoQiobulin G," Molecular Immunology, (2005).
Presta, L.G., et al., "Engineering therapeutic antibodies for improved function," Biochemical Society Transactions, 30(part 4) :487-490 (2002).
Radaev et al., "Recognition of IgG by FcγReceptor," J. Biol. Chem., 276:19 (2001) 16478-16483.
Radaev et al., "The structure of a human type III Fcγ receptor in complex with Fc," J. Bio. Chem., 276:19 (2001) 16468-16477.
Radaev, S., et al., "Review: Recognition of immunoglobulins by Fcγ recptors," Molecular Immunology, 38:1073-1083 (2001).
Rafiq, K., et al., "Immune complex-mediated antigen presentation induces tumor immunity" J. Clin. Invest. 110:71-79 (2002).
Raghavan et al., "Fc receptors and their interactions with immunoglobulins" Annu. Rev. Cell Div. Biol., 12 (1996) 181-220.

(56) References Cited

OTHER PUBLICATIONS

Ravetch et al., "IgG Fc receptors" Annu. Rev. Immunol., 19 (2001) 275-290.
Ravetch et al., "Immune inhibitory receptors: frontiers in cellular immunology," Science, 290 (2000) 84-89.
Ravetch, J.V., et al., "Fc Receptors," Annu. Rev. Immunol., 9:457-492 (1991).
Reddy, P.R., et al., "Elimination of Fc Receptor-Dependent Effector Functions of a Modified IgG4 Monoclonal Antibody to Human CD4" J. Immunol., 164:1925-1933 (2000).
Redpath, S., et al., "The Influence of the Hinge Region Length in Binding of Human IgG to Human Fcγ Receptors," Human Immunology, 59:720-727 (1998).
Reichert, J., "Monoclonal antibodies in the clinic," Nature Biotechnology, 19:819-822 (2001).
Rozsnyay, Z., et al., "Distinctive role of IgG1 and IgG3 isotypes in FcR-mediated functions," Immunology, 66(4):491-498 (Apr. 1989).
Rudikoff, et al., "Single amino acid substitution altering antigen-binding specificity", Proceedings of the National Academy of Sciences, vol. 79, 1982, 1979-1983.
Sandlie, A.A., "The extended hinge region of IgG3 is not required for high phagocytic capacity mediated by Fc gamma receptors, but the heavy chains must be disulfide bonded," Eur J. Immunol. 23(7):1546-1551 (Jul. 1993).
Sapra, Puja, et al., "Improved Therapeutic Responses in a Xenograft Model of Human B Lymphoma (Namalwa) for Liposomal Vincristine versus Liposomal Doxorubicin Targeted via Anti-CD19 IgG2a or Fab' Fragments", Clinical Cancer Research, Feb. 1, 2004, pp. 1100-1111, vol. 10.
Sarmay, G., et al., "Mapping and Comparison of the Interaction Sites on the Fc Region of IgG Responsible for Triggering Antibody Dependent Cellular Cytotoxicity (ADCC) Through Different Types of Human FCγ Receptor," Molecular Immunology, 29(5):633-639 (1992).
Sautes-Fridman, C., et al., " Fc Gamma Receptors: A Magic Link with the Outside World," ASH! Quarterly, 148-151, (Fourth Quarter 2003).
Schlereth, Bernd, et al., "T-cell activation and B-cell depletion in chimpanzees treated with a bispecific anti-CD19/anti-CD3 single-chain antibody construct", Cancer Immunol. Immunother, 2006, pp. 503-514, vol. 55.
Schwemmlein, M. et al., "A CD19-specific single-chain immunotoxin mediates potent apoptosis of B-lineage leukemic cells", Leukemia, 2007, pp. 1405-1412, vol. 21.
Sensel, M.G., et al., "Amino Acid Differences in the N-Teminus of CH2 Influence the Relative abilities of IgG2 and IgG3 to Activate Complement" MoL Immunol., 34(14):1019-1029 (1997).
Shields et al., "High resolution mapping of the binding site on human IgG1 for Fcγ RI, Fcγ RII, Fcγ RIII, and FcRn and design of IgG1 varients with improved binding to the FcγR," J. Biol. Chem., 276:9 (2001) 6591-6604.
Shields et al., "Lack of fucose on human IgG1 n-linked oligosaccharide improves binding to human Fcγ RIII and antibody-dependent cellular toxicity," J. Biol. Chem., 277:30 (2002) 26733-26740.
Shinkawa et al., "The absence of fucose but not the presence of galactose or bisecting n-acetylglucosamine of human IgG1 complex-type oligosaccharides shows the critical role of enhancing antibody-dependent cellular cytotoxicity," J. Biol. Chem., 278:5 (2003) 3466-3473.
Shopes et al., "A genetically engineered human IgG mutant with enhanced cytolytic activity," J Immunol., 148:9 (1992) 2918-2922.
Shopes, B., et al., "Recombinant human IgG1-murine IgE chimeric Ig. Construction, expression, and binding to human Fc gamma receptors," J. Immunol., 145(11):3842-3848 (Dec. 1, 1990).
Sieber, Thomas, et al., "Selective internalization of monoclonal antibodies by B-cell chronic lymphocytic leukaemia cells", British Journal of Haematology, 2003, pp. 458-461, vol. 121.

Simmons et al., "Expression of full-length immunoglobulins in *Esherichia coli*; rapid and efficient production of a aglycosylated antibodies," J. Immunol. Methods, 263 (2002) 133-147.
Smith, I. F. R., et al., "Addition of a μ-Tailpiece to IgG Results in Polymeric Antibodies with Enhanced Effector Functions Including Complement-Mediated Cytolysis by IgG4," J. Immunology, pp. 2226-2236 (1995).
Smith, K.G., et al., "T cell activation by anti-T3 antibodies: comparison of IgG1 and IgG2b switch variants and direct evidence for accessory function of macrophage Fc receptors," EurJ Immunol., 16(5):478-486 (May 1986).
Sonderman et al., "Molecular basis for immune complex recognition: A comparison of Fc-Receptor structures," J. Mol. Biol., 309 (2001) 737-749.
Sonderman et al., "The 3.2-Å crystal structure of the human IgG1 Fc fragment-FcγRIII complex" Nature, 406 (2000) 267-273.
Sonderman, P. et al., "Crystal structure of the soluble form of the human FCγ-receptor lib: a new member of the immunoglobulin superfamily at 1.7A resolution" EMBO Journal, 18(5):1095-1103 (1999).
Sonderman, P., et al., "Human Fcγ Receptor lib Expressed in *Escherichia coli* Reveals IgG Binding Capability" Bioi. Chern. 380:717-721 (Jun. 1999).
Sorenson, V., et al., "Effect of the IgM and IgA secretory tailpieces on polymerization and secretion of IgM and IgG," J Immunol., 156(8):2858-2865 (Apr. 1996).
Steplewski, Z., et al., "Biological activity of human-mouse IgG1, IgG2, IgG3, and IgG4 chimeric monoclonal antibodies with anti-tumor specificity," PNAS USA, 85:4852-4856 (Jul. 1988).
Stevenson, G. T., et al., "Preparation of Fcγ for addition to sulthydryl-expressing ligands with minimal disturbance of the hinge," J. of Immunological Methods, 231:169-175 (1999).
Stone, Marvin J., et al., "A Phase I Study of Bolus Versus Continuous Infusion of the Anti-CD19 Immunotoxin, IgG-HG37-dgA, in Patients With B-Cell Lymphoma", Blood, Aug. 15, 1996, pp. 1188-1197, vol. 88, No. 4.
Sun, Jishan, et al., "Characterization of porcine CD19 and anti-CD19 monoclonal antibodies", Molecular Immunology, 2004, pp. 929-938, vol. 41.
Tao, M., et al., "Structural Features of Human immunoglobulin G that Determine Isotype-specific Differences in Complement Activation," J. Exp. Med. 178:661-667 (Aug. 1993).
Tao, M., et al., "The Differential Ability of Human IgG1 and IgG4 to Activate Complement Is Determined by the COOH-terminal Sequence of the CH2 domain" J. Exp. Med, 173:1025-1028 (Apr. 1991).
Tedder, Thomas F., et al., "Fcγ receptor-dependent effector mechanisms regulate CD19 and CD20 antibody immunotherapies for B lymphocyte malignancies and autoimmunity", Springer Semin. Immun., 2006, pp. 351-364, vol. 28, No. 4.
Tedder, Thomas F., et al., "The CD19-CD21 Signal Transduction Complex of B Lymphocytes Regulates the Balance between Health and Autoimmune Disease: Systemic Sclerosis as a Model System", Curr. Dir. Autoimmun. Basel, Karger, 2005, pp. 55-90, vol. 8.
Tedder, Thomas F., et al., Isolation of cDNAs Encoding the CD19 Antigen of Human and Mouse B Lymphocytes, The Journal of Immunology, Jul. 15, 1989, pp. 712-717, vol. 143, No. 2.
Thommesen, J. E., et al. "Lysine 322 in the human IgG3 CH2 domain is crucial for antibody dependent complement activation" Molecular Immunology, 37:995-1 014 (2000).
Thrush et al., "Immunotoxins: an update," Ann. Rev. Immunol., 14:49 (1996) 71.
Tiroch, Klaus, et al., "Intracellular Domains of Target Antigens Influence Their Capacity to Trigger Antibody-Dependent Cell-Mediated Cytotoxicity", The Journal of Immunology, 2002, pp. 3275-3282, vol. 168.
Torphy, T., et al., "Pharmaceutical biotechnology Monoclonal antibodies: boundless potential, daunting challenges—Editorial Overview," Curr. Opin. Biotechnol., 13:589-591 (2002).
Trail et al., "Monoclonal antibody drug conjugates in the treatment of cancer," Curr. Opin. Immunol., 11 (1999) 584-588.
Trikha, M., "Monoclonal antibodies as therapeutics in oncology," Curr. Opin. Biotech., 13:609-614 (2002).

(56) References Cited

OTHER PUBLICATIONS

Tuijnman W. B., et al., "A flow cytometric rosetting assay for the analysis of IgG-Fc receptor interactions," J Immunol Methods, 127(2):207-214 (Mar. 1990).
Uchida, J. et al., "The Innate Mononuclear Phagocyte Network Depletes B Lymphocytes through Fc Receptor-dependent mechanisms during Anti-CD20 Antibody Immunotherapy" J. Exp. Med. 199(12):1659-1669 (Jun. 21, 2004).
Uckun F. M., et al., "Immunotoxin-Mediated Elimination of Clonogenic Tumor Cells in the Presence of Human Bone Marrow", The Journal of Immunology, Mar. 1985, pp. 2010-2016, vol. 134, No. 3.
Uckun, Faith M., et al., "Detailed Studies on Expression and Function of CD19 Surface Determinant by Using B43 Monoclonal Antibody and the Clinical Potential of Anti-CD19 Immunotoxins", Blood, Jan. 1988, pp. 13-29, vol. 71, No. 1.
Umana et al., "Engineered glycoforms of an antineuro-blastoma IgG1 with optimized antibody-dependent cellular cytotoxic activity," Nature, 17 (1999) 176-180.
Vallera, Daniel A., et al., "A Bispecific Recombinant Immunotoxin, DT2219, Targeting Human CD19 and CD22 Receptors in a Mouse Xenograft Model of B-Cell Leukemia/Lymphoma", Clin. Cancer Res., May 15, 2005, pp. 3879-3888, vol. 11, No. 10.
Vajdos, Felix F. et al., "Comprehensive functional maps of the antigen-binding site of an anti-ErbB2 antibody obtained with shotgun scanning mutagenesis", Journal of Molecular Biology, vol. 320, 2002, 415-428.
Van Dijk, M., et al., "Human antibodies as next generation therapeutics," Curr Opin. Chern. Bioi., 5:368-374 (2001).
Van Royen-Kerkhof, A, et al., "Flow cytometric determination of Fcγ RIIa (CD32) polymorphism," J. Immunol. Methods, 294:135-144 (2004).
Van Schie, R.C.A.A., et al., "Evaluation of Human FCγ RIIa (CD32) and Fcγ RIIIB (CD16) Polymorphisms in Caucasians and African-Americans Using Salivary DNA," Clinical and Diagnostic Laboratory Immunology, 7(4):676-681 (Jul. 2000).
Van Sorge, N., et al., "Fcγ R polymorphisms: Implications for function, disease susceptibility and immunotherapy," Tissue Antigens, 61 :189-202 (2003).
Vasserot, A., et al., "Optimization of protein therapeutics by directed evolution," Drug Discovery Today, 8(3) :118-126 (2003).
Vidarte, L., et al., "Serine 132 Is the C3 Covalent Attachment Point of the CH1 domain of Human IgG1" J. Bioi. Chern., 276(41):38217-38223 (2001).
Vlasveld, L. Tom, et al., "Treatment of low-grade non-Hodgkin's lymphoma with continuous infusion of low-dose recombinant interleukin-2 in combination with the B-cell-specific monoclonal antibody CLBCD19", Cancer Immunol. Immunother., 1995, pp. 37-47, vol. 40.
Vuist, W.M.J., et al., "Potentiation by Interleukin 2 of Burkitt's Lymphoma Therapy with Anti-Pan B (AntiCD19) Monoclonal Antibodies in a Mouse Xenotransplantation Model", Cancer Research, Jul. 15, 1989, pp. 3783-3788, vol. 49.
Vuist, Wim M.J., et al., "Two Distinct Mechanisms of Antitumor Activity Mediated by the Combination of Interleukin 2 and Monoclonal Antibodies", Cancer Research, Sep. 15, 1990, pp. 5767-5772, vol. 50.
Waldmann, T., et al. "Emerging Therapies: Spectrum of Application of Monoclonal Antibody Therapy," Hematology, 394-408 (2000).
Ward, E. S., et al., "Evidence to support the cellular mechanism involved in serum IgG homeostatic in humans" International Immunology, 15(2) :187-195 (2003).
Wark, et al. "Latest technologies for enhancement of antibody affinity" Advanced Drug Delivery Reviews, 2006, 657-670, vol. 58, No. 5-6.
Warmerdam, P. A., et al., "Interaction of a human Fc gamma RIIb1 (CD32) isoform with murine and human IgG subclasses," tnt Immunol, 5(3):239-247 (Mar. 1993).
Wawrzynczak, E. J., et al., "Recombinant mouse monoclonal antibodies with single amino acid substitutions affecting Clq and high affinity Fc receptor binding have identical serum half-lives in the BALB/c mouse," Mol. Immunol, 29(2) :221-227 (Feb. 1992).
Weiner, L. M., et al., "Tunable antibodies," Nature Biotechnology, 23(5):556-557 (May 2005).
Weng et al., "Two immunoglobulin G fragment C receptor polymorphisms independently predict response to rituximab in patients with follicular lymphoma," J. Clin. Oncol., 21 (2003) 3940-3947.
Weng, W., et al., "Clinical Outcome of Lymphoma Patients After Idiotype Vaccination Is Correlated With Humoral Immune Response and Immunoglobulin G Fc Receptor Genotype," J. Clin Oneal., 22(23):1-8 (2004).
West, A. P., et al., "Crystal Structure and immunoglobulin G Binding Properties of the Human Major Histocompatibility Complex-Related Fc Receptor," Biochemistry, 39:9698-9708 (2000).
White, et al., "Antibody-targeted immunotherapy for treatment of malignancy," Annu Rev Med, 52:125-145 (2001).
Wines, B.D. et al. "The IgG Fc contains distinct Fc receptor (FeR) binding sites: the leukocyte receptors Fc[gamma] RIIa bind to a region in the Fc distinct from that recognized by neonatal FeR and protein A" Journal of Immunology, (2000), pp. 5313-5318.
Wing, M.G., et al., "Mechanism of First-Dose Cytokine-Release Syndrome of CAMPATH 1-H:involvement of CD16 (FcγR111) and CD11a/CD18 (LFA-1)on NK Cells," J. Clin.Invest., 98(12):2819-2826 (Dec. 1996).
Wolff, E.A., et al., "Monoclonal antibody homodimers: enhanced antitumor activity in nude mice," Cancer Res., 53(11):2560-2565 (Jun. 1, 1993).
Wright, A., et al., "Effect of C2-Associated carbohydrate Structure on Ig Effector Function: Studies with Chimeric Mouse-Human IgG1 Antibodies in Glycosylation Mutants of Chinese Hamster Ovary Cells" J. of Immunology, 160:3393-3402 (1998).
Wright, A., et al., "In vivo trafficking and catabolism of IgG1 antibodies with Fc associated carbohydrates of differing structure," Glycobiology, 10(12) :1347-1355 (2000).
Wu, et al., "Humanization of a murine monoclonal antibody by simultaneous optimization of framework and CDR residues", Journal of Molecular Biology, vol. 294, 1999, 151-162.
Xu, D., et al., "In Vitro Characterization of Five Humanized OKT3 Effector Function Varient Antibodies," Cellular Immunology, 200:16-26 (2000).
Xu, M., et al., "Molecular Cloning and Characterization of SPAP1, an Inhibitory Receptor," Biochemical and Biophysical Research Communications, 280:768-775 (2001).
Xu, Y., et al., "Residue at Position 331 in the IgG1 and IgG4 CH2 Domains Contributes to Their Differential Ability to Bind and Activate Complement" J. Bioi. Chern. 269(5):3469-3474 (1994).
Yamane-Ohnuki et al., "Establishment of FUT8 knockout Chinese hamster ovary cells: an ideal host cell line for producing completely defucosylated antibodies with enhanced antibody-dependent cellular cytotoxicity," Wiley InterScience, 87:5 (2004) 614-622.
Yan, Jun, et al., "Targeting antigen to CD19 on B cells efficiently activates T cells", International Immunology, 2005, pp. 869-877, vol. 17, No. 7.
Yazawa et al., "Immunotherapy using unconjugated CD19 monoclonal antibodies in animal models for B lymphocyte malignancies and autoimmune disease," PNAS, 102:42 (2005) 15178-15183.
Zelaschi, D., et al.," Human immunoglobulin allotypes: previously unrecognized determinants and alleles defined with monoclonal antibodies," PNAS, USA, 80:3762-3766 (Jun. 1983).
Zhou, H., et al., "DNA-based vaccines activate innate and adaptive antitumor immunity by engaging the NKG2D receptor" PNAS, 1 02(31):1 0846-10851 (Aug. 2, 2005).
Zhou, J., et al., "Generation of Mutated Variants of the Human Form of the MHC Class 1-related Receptor, FeRn, with Increased Affinity for Mouse Immunoglobulin G, "J. Mol. Bioi., 332(4):901-13 (Sep. 2003).
Zhu, D., et al., "A novel human immunoglobulin Fc gamma Fc epsilon bifunctional fusion protein inhibits Fc epsilon RI-mediated degranulation," Nat Med., 8(5):518-521 (May 2002).
U.S. Appl. No. 11/838,824.
Election/Restriction Requirement dated Oct. 29, 2009, U.S. Appl. No. 11/838,824, 9 pages.

(56) References Cited

OTHER PUBLICATIONS

Amendment and Response to Election/Restriction Requirement dated Nov. 30, 2009, U.S. Appl. No. 11/838,824, 11 pages.
Non-Final Office Action dated Mar. 8, 2010, U.S. Appl. No. 11/838,824, 24 pages.
Amendment and Response to Office Action dated Jun. 8, 2010, U.S. Appl. No. 11/838,824, 14 pages.
Non-Final Office Action dated Aug. 27, 2010, U.S. Appl. No. 11/838,824, 15 pages.
Amendment and Response to Office Action dated Nov. 22, 2010, U.S. Appl. No. 11/838,824, 13 pages.
Final Office Action dated Jan. 12, 2011, U.S. Appl. No. 11/838,824, 8 pages.
Notice of Abandonment dated Aug. 18, 2011, U.S. Appl. No. 11/838,824, 2 pages.
U.S. Appl. No. 12/377,251.
Requirement for Restrition and Election dated Apr. 13, 2012, U.S. Appl. No. 12/377,251, 12 pages.
Response to Restriction dated Jul. 13, 2012, U.S. Appl. No. 12/377,251, 12 pages.
Examiner initiated interview summary and Non Final Rejection dated Aug. 21, 2012, U.S. Appl. No. 12/377,251, 16 pages.
Response After Non Final Reject and Request for Interview Summary dated Nov. 21, 2012, U.S. Appl. No. 12/377,251, 12 pages.
Final Rejection and Examiner Initiated Interview Summary dated Jan. 25, 2013, U.S. Appl. No. 12/377,251, 10 pages.
Response After Final Action dated Mar. 25, 2013, U.S. Appl. No. 12/377,251, 8 pages.
Advisory Action dated Apr. 4, 2013, U.S. Appl. No. 12/377,251, 4 pages.
Response After Final dated Apr. 25, 2013, U.S. Appl. No. 12/377,251, 8 pages.
Notice of Allowance and Fees Due dated May 3, 2013, U.S. Appl. No. 12/377,251, 8 pages.
Issue Notification dated Aug. 14, 2013, U.S. Appl. No. 12/377,251, 1 page.
U.S. Appl. No. 13/221,811.
Restriction Requirement dated Apr. 4, 2012, U.S. Appl. No. 13/221,811, 9 pages.
Amendment and Response to Restriction Requirement dated Jul. 4, 2012, U.S. Appl. No. 13/221,811, 5 pages.
Non-Final Office Action dated Sep. 7, 2012, U.S. Appl. No. 13/221,811, 5 pages.
Response to Non-Final Office Action dated Dec. 7, 2012, U.S. Appl. No. 13/221,811, 4 pages.
Notice of Allowance dated Feb. 4, 2013, U.S. Appl. No. 13/221,811, 7 pages.
Notice of Abandonment dated Mar. 14, 2013, U.S. Appl. No. 13/221,811, 1 page.

Figure 1

> Human CD19 (SEQ ID NO:1).

MPPPRLLFFLLFLTPMEVRPEEPLVVKVEEGDNAVLQCLKGTSDGPTQQLTWSRESPLKPF
LKLSLGLPGLGIHMRPLAIWLFIFNVSQQMGGFYLCQPGPPSEKAWQPGWTVNVEGSGEL
FRWNVSDLGGLGCGLKNRSSEGPSSPSGKLMSPKLYVWAKDRPEIWEGEPPCLPPRDSL
NQSLSQDLTMAPGSTLWLSCGVPPDSVSRGPLSWTHVHPKGPKSLLSLELKDDRPARDM
WVMETGLLLPRATAQDAGKYYCHRGNLTMSFHLEITARPVLWHWLLRTGGWKVSAVTLAY
LIFCLCSLVGILHLQRALVLRRKRKRMTDPTRRFFKVTPPPGSGPQNQYGNVLSLPTPTSGL
GRAQRWAAGLGGTAPSYGNPSSDVQADGALGSRSPPGVGPEEEEGEGYEEPDSEEDSE
FYENDSNLGQDQLSQDGSGYENPEDEPLGPEDEDSFSNAESYENEDEELTQPVARTMDFL
SPHGSAWDPSREATSLGSQSYEDMRGILYAAPQLRSIRGQPGPNHEEDADSYENMDNPD
GPDPAWGGGGRMGTWSTR

Figure 2

> Kappa constant light chain (Cκ) (SEQ ID NO:2)

RTVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC

> IgG1 constant heavy chain (CH) (SEQ ID NO:3)

ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGN
VFSCSVMHEALHNHYTQKSLSLSPGK

> IgG2 constant heavy chain (CH) (SEQ ID NO:4)

ASTKGPSVFPLAPCSRSTSESTAALGCLVKDYFPEPVTVSWNSGALTSGVHTFPAVLQSSG
LYSLSSVVTVPSSNFGTQTYTCNVDHKPSNTKVDKTVERKCCVECPPCPAPPVAGPSVFLF
PPKPKDTLMISRTPEVTCVVVDVSHEDPEVQFNWYVDGVEVHNAKTKPREEQFNSTFRVV
SVLTVVHQDWLNGKEYKCKVSNKGLPAPIEKTISKTKGQPREPQVYTLPPSREEMTKNQVS
LTCLVKGFYPSDIAVEWESNGQPENNYKTTPPMLDSDGSFFLYSKLTVDKSRWQQGNVFS
CSVMHEALHNHYTQKSLSLSPGK

> IgG3 constant heavy chain (CH) (SEQ ID NO:5)

ASTKGPSVFPLAPCSRSTSGGTAALGCLVKDYFPEPVTVSWNSGALTSGVHTFPAVLQSS
GLYSLSSVVTVPSSSLGTQTYTCNVNHKPSNTKVDKRVELKTPLGDTTHTCPRCPEPKSCD
TPPPCPRCPEPKSCDTPPPCPRCPEPKSCDTPPPCPRCPAPELLGGPSVFLFPPKPKDTL
MISRTPEVTCVVVDVSHEDPEVQFKWYVDGVEVHNAKTKPREEQYNSTFRVVSVLTVLHQ
DWLNGKEYKCKVSNKALPAPIEKTISKTKGQPREPQVYTLPPSREEMTKNQVSLTCLVKGF
YPSDIAVEWESSGQPENNYNTTPPMLDSDGSFFLYSKLTVDKSRWQQGNIFSCSVMHEAL
HNRFTQKSLSLSPGK

> IgG4 constant heavy chain (CH) (SEQ ID NO:6)

ASTKGPSVFPLAPCSRSTSESTAALGCLVKDYFPEPVTVSWNSGALTSGVHTFPAVLQSSG
LYSLSSVVTVPSSSLGTKTYTCNVDHKPSNTKVDKRVESKYGPPCPSCPAPEFLGGPSVFL
FPPKPKDTLMISRTPEVTCVVVDVSQEDPEVQFNWYVDGVEVHNAKTKPREEQFNSTYRV
VSVLTVLHQDWLNGKEYKCKVSNKGLPSSIEKTISKAKGQPREPQVYTLPPSQEEMTKNQV
SLTCLVKGFYPSDIAVEWESNGQPENNYKTTPPVLDSDGSFFLYSRLTVDKSRWQEGNVF
SCSVMHEALHNHYTQKSLSLSLGK

> Hybrid constant heavy chain (CH) (SEQ ID NO:7)

ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVQFNWYVDGVEVHNAKTKPREEQFNSTF
RVVSVLTVVHQDWLNGKEYKCKVSNKALPAPIEKTISKTKGQPREPQVYTLPPSREEMTKN
QVSLTCLVKGFYPSDIAVEWESNGQPENNYKTTPPMLDSDGSFFLYSKLTVDKSRWQQGN
VFSCSVMHEALHNHYTQKSLSLSPGK

> Hybrid constant heavy chain (CH) with 239D and 332E substitutions (SEQ ID NO:8)

ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPD
VFLFPPKPKDTLMISRTPEVTCVVVDVSHEDPEVQFNWYVDGVEVHNAKTKPREEQFNSTF
RVVSVLTVVHQDWLNGKEYKCKVSNKALPAPEEKTISKTKGQPREPQVYTLPPSREEMTK
NQVSLTCLVKGFYPSDIAVEWESNGQPENNYKTTPPMLDSDGSFFLYSKLTVDKSRWQQG
NVFSCSVMHEALHNHYTQKSLSLSPGK

Figure 3A

| CH1 | | | | | | | | | | | | | | | | | | | | | |
|---|---|---|---|---|---|---|---|---|---|---|---|---|---|---|---|---|---|---|---|---|---|
| EU Index | 118 | 119 | 120 | 121 | 122 | 123 | 124 | 125 | 126 | 127 | 128 | 129 | 130 | 131 | 132 | 133 | 134 | 135 | 136 | 137 | 138 |
| IgG1 | A | S | T | K | G | P | S | V | F | P | L | A | P | S | S | K | S | T | S | G | G |
| IgG2 | A | S | T | K | G | P | S | V | F | P | L | A | P |   | S |   | S | T | S |   |   |
| IgG3 | A | S | T | K | G | P | S | V | F | P | L | A | P |   | S |   | S | T | S |   |   |
| IgG4 | A | S | T | K | G | P | S | V | F | P | L | A | P |   | S |   | S | T | S |   |   |

| EU Index | 139 | 140 | 141 | 142 | 143 | 144 | 145 | 146 | 147 | 148 | 149 | 150 | 151 | 152 | 153 | 154 | 155 | 156 | 157 | 158 | 159 |
|---|---|---|---|---|---|---|---|---|---|---|---|---|---|---|---|---|---|---|---|---|---|
| IgG1 | T | A | A | L | G | C | L | V | K | D | Y | F | P | E | P | V | T | V | S | W | N |
| IgG2 | T | A | A | L | G | C | L | V | K | D | Y | F | P | E | P | V | T | V | S | W | N |
| IgG3 | T | A | A | L | G | C | L | V | K | D | Y | F | P | E | P | V | T | V | S | W | N |
| IgG4 | T | A | A | L | G | C | L | V | K | D | Y | F | P | E | P | V | T | V | S | W | N |

| EU Index | 160 | 161 | 162 | 163 | 164 | 165 | 166 | 167 | 168 | 169 | 170 | 171 | 172 | 173 | 174 | 175 | 176 | 177 | 178 | 179 | 180 |
|---|---|---|---|---|---|---|---|---|---|---|---|---|---|---|---|---|---|---|---|---|---|
| IgG1 | S | G | A | L | T | S | G | V | H | T | F | P | A | V | L | Q | S | S | G | L | Y |
| IgG2 | S | G | A | L | T | S | G | V | H | T | F | P | A | V | L | Q | S | S | G | L | Y |
| IgG3 | S | G | A | L | T | S | G | V | H | T | F | P | A | V | L | Q | S | S | G | L | Y |
| IgG4 | S | G | A | L | T | S | G | V | H | T | F | P | A | V | L | Q | S | S | G | L | Y |

| EU Index | 181 | 182 | 183 | 184 | 185 | 186 | 187 | 188 | 189 | 190 | 191 | 192 | 193 | 194 | 195 | 196 | 197 | 198 | 199 | 200 | 201 |
|---|---|---|---|---|---|---|---|---|---|---|---|---|---|---|---|---|---|---|---|---|---|
| IgG1 | S | L | S | S | V | V | T | V | P | S | S | S | L | G | T | Q | T | Y | I | C | N |
| IgG2 | S | L | S | S | V | V | T | V | P | S | S |   |   | G | T | Q | T | Y |   | C | N |
| IgG3 | S | L | S | S | V | V | T | V | P | S | S | S | L | G | T | Q | T | Y |   | C | N |
| IgG4 | S | L | S | S | V | V | T | V | P | S | S | S | L | G | T |   | T | Y |   | C | N |

| EU Index | 202 | 203 | 204 | 205 | 206 | 207 | 208 | 209 | 210 | 211 | 212 | 213 | 214 | 215 | 216 | 217 | 218 | 219 | 220 |
|---|---|---|---|---|---|---|---|---|---|---|---|---|---|---|---|---|---|---|---|
| IgG1 | V | N | H | K | P | S | N | T | K | V | D | K | K | V | E | P | K | S | C |
| IgG2 | V |   | H | K | P | S | N | T | K | V | D | K |   | V | E |   | K |   | C |
| IgG3 | V | N | H | K | P | S | N | T | K | V | D | K |   | V | E |   | K |   |   |
| IgG4 | V |   | H | K | P | S | N | T | K | V | D | K |   | V | E |   | K |   |   |

Hinge / Fc >

| EU Index | 221 | 222 | 223 | 224 | 225 | 226 | 227 | 228 |
|---|---|---|---|---|---|---|---|---|
| IgG1 | D |   | K | T | H | T | C | P | P |
| IgG2 |   |   |   |   |   |   | C | P | P |
| IgG3 |   |   |   | T | H | T | C | P |   |
| IgG4 |   |   |   |   |   |   | C | P |   |

| EU Index | | | | | | |
|---|---|---|---|---|---|---|
| IgG1 | | | | | | |
| IgG2 | | | | | | |
| IgG3 | | | | | | |
| IgG4 | | | | | | |

Fc >

| EU Index | 229 | 230 | 231 | 232 | 233 | 234 | 235 | 236 |
|---|---|---|---|---|---|---|---|---|
| IgG1 | C | P | A | P | E | L | L | G |
| IgG2 | C | P | A | P |   |   |   |   |
| IgG3 | C | P | A | P | E | L | L | G |
| IgG4 | C | P | A | P | E |   | L | G |

| Allotype | Allotype | Position | | |
|---|---|---|---|---|
| | | 214 | 356 358 | 431 |
| G1m(1,17) | G1m(a,z) | K | D L | A |
| G1m(1,2,17) | G1m(a,x,z) | K | D L | G |
| G1m(3) | G1m(f) | R | E M | A |
| G1m(1,3) | G1m(a,f) | R | D L | A |

Figure 4B

| Allotype | Allotype | Position |
|---|---|---|
| | | 282 |
| G2m(23) | G2m(n+) | V |
| | G2m(n-) | M |

Figure 5

| Receptor binding improvement | Receptor binding reduction | Cell activity | Therapeutic activity |
|---|---|---|---|
| Solely I | - | Enhance dendritic cell activity and uptake, and subsequent presentation of antigens; enhance monocyte and macrophage response to antibody | Enhance cell-based immune response against target |
| IIIa | | Enhance ADCC and phagocytosis of broad range of cell types | Increased target cell lysis |
| IIIa | IIb | Enhance ADCC and phagocytosis of broad range of cell types | Increased target cell lysis |
| IIb, IIc | | Reduction of activity of all FcR bearing cell types except NK cells and possible activation of NK cells via IIc receptor signaling | Enhancement of target cell lysis selective for NK cell accessible target cells |
| IIb, IIIa | - | Possible NK cell specific activation and enhancement of NK cell mediated ADCC | Enhancement of target cell lysis selective for NK cell accessible target cells |
| IIIb | | Neutrophil mediated phagocytosis enhancement | Enhanced target cell destruction for neutrophil accessible cells |
| FcαR | | Neutrophil mediated phagocytosis enhancement | Enhanced target cell destruction for neutrophil accessible cells |
| I,IIa,IIIa | IIb | Enhance dendritic cell activity and uptake, and subsequent presentation of antigens to T cells; enhance monocyte and macrophage response to antibody | Enhance cell-based immune response against target |
| IIb | IIIa,IIa,I | Reduction in activity of monocytes, macrophages, neutrophils, NK, dendritic and other gamma receptor bearing cells | Eliminate or reduce cell-mediated cytotoxicity against target bearing cells |

Figure 6A

> H0 4G7 (SEQ ID NO:9)

EVQLQQSGPELIKPGASVKMSCKASGYTFTSYVMHWVKQKPGQGLEWIGYINPYNDGTKY
NEKFKGKATLTSDKSSSTAYMELSSLTSEDSAVYYCARGTYYYGSRVFDYWGQGTTLTVS
S

> L0 4G7 (SEQ ID NO:10)

DIVMTQAAPSIPVTPGESVSISCRSSKSLLNSNGNTYLYWFLQRPGQSPQLLIYRMSNLASG
VPDRFSGSGSGTAFTLRISRVEAEDVGVYYCMQHLEYPFTFGAGTKLELK

> H0 HD37 (SEQ ID NO:11)

QVQLQQSGAELVRPGSSVKISCKASGYAFSSYWMNWVKQRPGQGLEWIGQIWPGDGDT
NYNGKFKGKATLTADESSSTAYMQLSSLASEDSAVYFCARRETTTVGRYYYAMDYWGQG
TSVTVSS

> L0 HD37 (SEQ ID NO:12)

DILLTQTPASLAVSLGQRATISCKASQSVDYDGDSYLNWYQQIPGQPPKLLIYDASNLVSGIP
PRFSGSGSGTDFTLNIHPVEKVDAATYHCQQSTEDPWTFGGGTKLEIK

Figure 6B

| | |
|---|---|
| > 4G7 VH CDR1 (SEQ ID NO:132): | SYVMH |
| > 4G7 VH CDR2 (SEQ ID NO:133): | YINPYNDGTKYNEKFKG |
| > 4G7 VH CDR3 (SEQ ID NO:134): | GTYYYGSRVFDY |
| > 4G7 VL CDR1 (SEQ ID NO:135): | RSSKSLLNSNGNTYLY |
| > 4G7 VL CDR2 (SEQ ID NO:136): | RMSNLAS |
| > 4G7 VL CDR3 (SEQ ID NO:137): | MQHLEYPFT |
| > HD37 VH CDR1 (SEQ ID NO:138): | SYWMN |
| > HD37 VH CDR2 (SEQ ID NO:139): | QIWPGDGDTNYNGKFKG |
| > HD37 VH CDR3 (SEQ ID NO:140): | RETTTVGRYYYAMDY |
| > HD37 VL CDR1 (SEQ ID NO:141): | KASQSVDYDGDSYLN |
| > HD37 VL CDR2 (SEQ ID NO:142): | DASNLVS |
| > HD37 VL CDR3 (SEQ ID NO:143): | QQSTEDPWT |

Daudi (BL)

Figure 10A
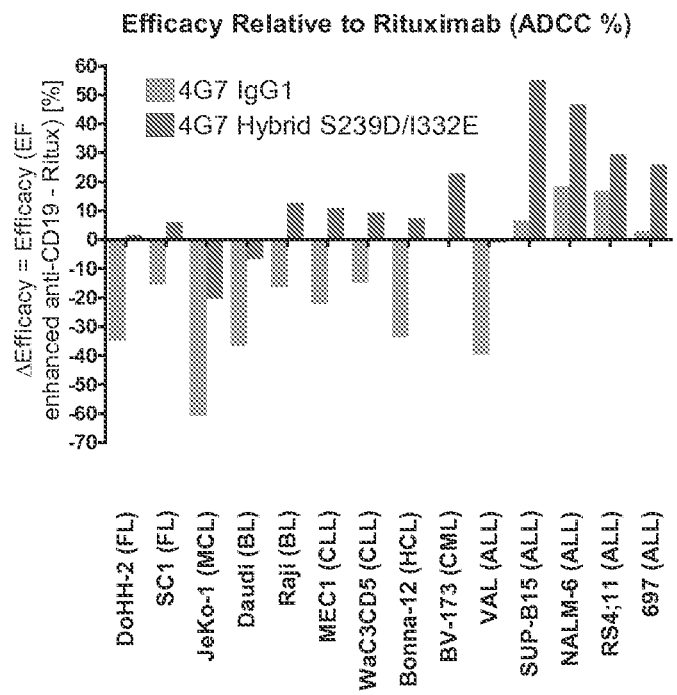
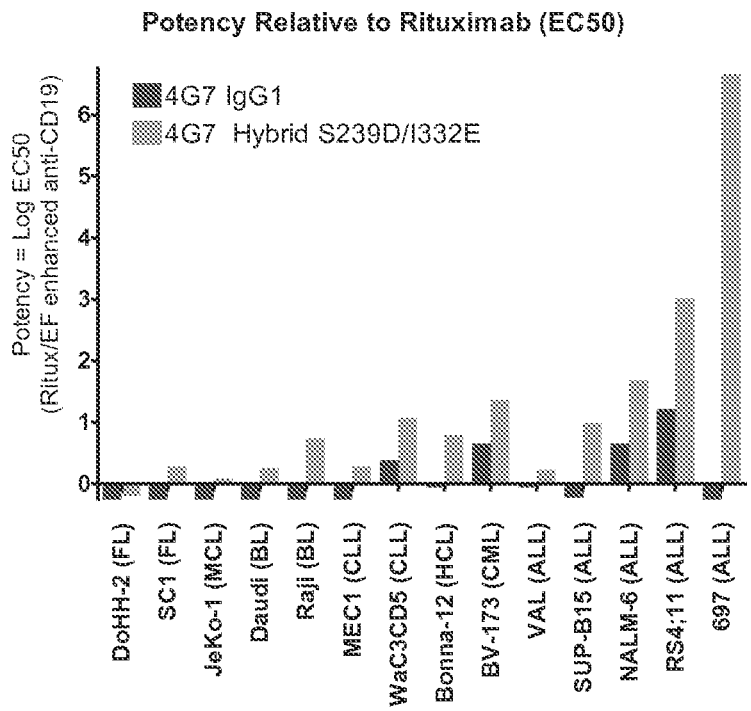

Figure 10B

| Cancer cell type | Cell line |
|---|---|
| Hairy Cell Leukemia (HCL) | Bonna 12 |
| Mantle Cell Lymphoma (MCL) | Jeko-1 |
| Chronic Lymphocytic Leukemia (CLL) | Wac3CD5, MEC-1 |
| Burkitt's Lymphoma (BL) | Daudi, Raji |
| Chronic Myelogenous Leukemia (CML) | BV-173 |
| Follicular Lymphoma (FL) | DoHH-2, SC1 |
| Acute Lymphoblastic Leukemia (ALL) | VAL, SUP-B15, NALM-6, RS4;11, 697 |

Figure 11

> H1 4G7 (SEQ ID NO:13)

EVQLVESGGGLVKPGGSLKLSCAASGYTFTSYVMHWVRQAPGKGLEWIGYINPYNDGTKY
NEKFQGRVTISSDKSISTAYMELSSLRSEDTAMYYCARGTYYYGSRVFDYWGQGTLVTVSS

> H2 4G7 (SEQ ID NO:14)

QVQLQESGSGLVKPGGSLRLSCAASGYTFTSYVMHWVRQAPGKGLEWMGYINPYNDGTK
YNESLKSRVTISSDKSISTAYMELSSLRAEDTAVYYCARGTYYYGSRVFDYWGQGTLVTVS
S

> H3 4G7 (SEQ ID NO:15)

EVQLVESGGGLVQPGRSLRLSCAASGYTFTSYVMHWVRQMPGKGLEWMGYINPYNDGTK
YNEKFQGRVTITSDKSTSTAYMELSRLRSDDTAVYYCARGTYYYGSRVFDYWGQGTLVTV
SS

> H4 4G7 (SEQ ID NO:16)

EVQLQQSGPEVKKPGTSVKVSCKASGYTFTSYVMHWVRQAPGKGLVWVSYINPYNDGTK
YNESLKSRVTISSDKSISTAYLQMNSLRAEDTAVYYCARGTYYYGSRVFDYWGQGTLVTVS
S

Figure 12

> L1 4G7 (SEQ ID NO:17)

DIVMTQSPATLSLSPGERATLSCRSSKSLLNSNGNTYLYWFQQKPGQSPQLLIYRMSNLAS
GVPDRFSGSGSGTEFTLTISSLEPEDFAVYYCMQHLEYPFTFGAGTKLEIK

> L2 4G7 (SEQ ID NO:18)

DIVMTQSPSSLSASVGDRVTISCRSSKSLLNSNGNTYLYWFQQKPGQSPQLLIYRMSNLAS
GVPDRFSGSGSGTEFTLTISSLQPEDVAVYYCMQHLEYPFTFGAGTKLEIK

> L3 4G7 (SEQ ID NO:19)

DIVMTQSPATLSVSPGERATISCRSSKSLLNSNGNTYLYWFLQKPGQSPQLLIYRMSNLASG
VPDRFSGSGSGTDFTLTISRVEAEDVGVYYCMQHLEYPFTFGAGTKLEIK

Figure 13

> H1 HD37 (SEQ ID NO:20)

TVQLVESGGGVVRPGGSLRLSCAASGYAFSSYWMNWVRQAPGKGLEWIGQIWPGDGDT
NYNGKFQDRVTITADESTSTAYMELRSLRSDDTAVYFCARRETTTVGRYYYAMDYWGQGT
LVTVSS

> H2 HD37 (SEQ ID NO:21)

QVQLVESGGGLVEPGGSLRLSCAASGYAFSSYWMNWVRQMPGKGLEWMGQIWPGDGD
TNYNPSLKSRVTITADESTSTAYMELSSLKAEDTAVYFCARRETTTVGRYYYAMDYWGQGT
LVTVSS

> H3 HD37 (SEQ ID NO:22)

QVQLQESGPGLVKPSQTLSLTCAASGYAFSSYWMNWVRQAPGKGLEWMGQIWPGDGDT
NYNGALKSRVTITADESTSTAYMELSSLRSEDTAVYFCARRETTTVGRYYYAMDYWGQGT
LVTVSS

> H4 HD37 (SEQ ID NO:23)

EVQLVQSGSELKKPGASVKVSCKASGYAFSSYWMNWVRQAPGKGLEWVAQIWPGDGDT
NYADSVKGRFTITADESTSTAYLQMNSLRAGDTAMYFCARRETTTVGRYYYAMDYWGQGT
LVTVSS

Figure 14

> L1 HD37 (SEQ ID NO:24)

DILLTQSPATLSLSPGERATLSCRASQSVDYDGDSYLNWYQQKPGQPPKLLIYDASNLVSGI
PPRFSGSGSGTDFTLTISRLEPEDFAVYHCQQSTEDPWTFGGGTKLEIK

> L2 HD37 (SEQ ID NO:25)

DILLTQSPSSLSVTPGEKVTITCRASQSVDYDGDSYLNWYQQKPGQPPKLLIYDASNLVSGI
PPRFSGSGSGTDFTLTINSLEAEDAATYHCQQSTEDPWTFGGGTKLEIK

> L3 HD37 (SEQ ID NO:26)

DILLTQTPLSLPVTPGEPASISCRASQSVDYDGDSYLNWYQQKPGQPPKLLIYDASNLVSGI
PPRFSGSGSGTDFTLKISRVEAEDVGVYHCQQSTEDPWTFGGGTKLEIK

Figure 15A
4G7
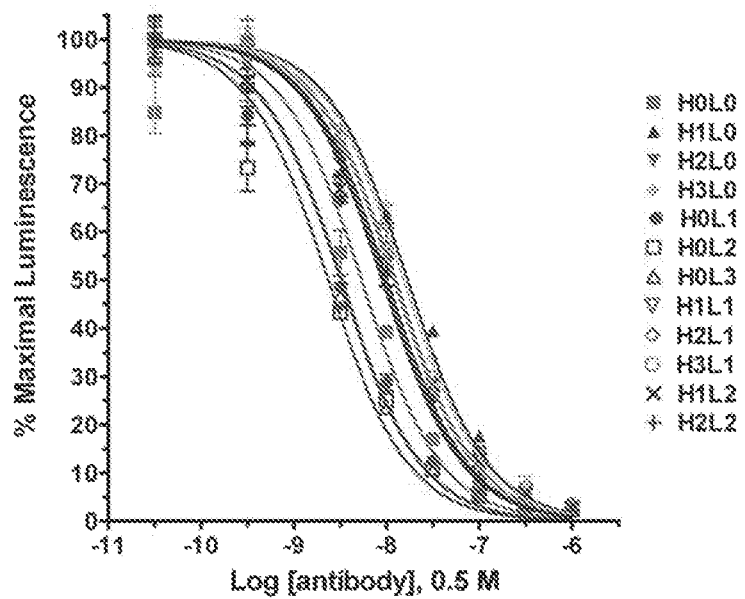
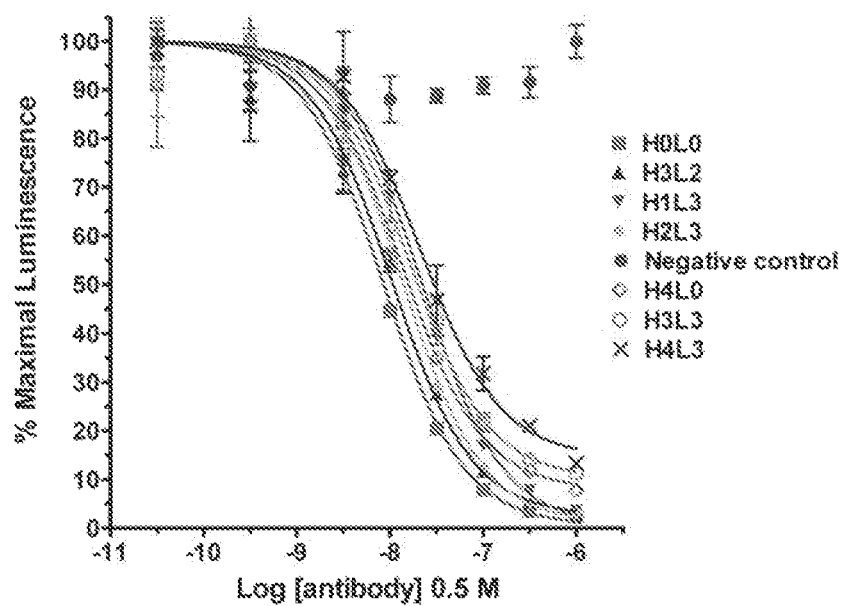

Figure 18

> 4G7 H1.109 (SEQ ID NO:27)
EVQLVESGGGLVKPGGSLKLSCAASGYTFTSYVMHWVRQAPGKGLEWIGYINPYNDGPKY
NEKFQGRVTISSDKSISTAYMELSSLRSEDTAMYYCARGTYYYGSRVFDYWGQGTLVTVSS

> 4G7 H1.113 (SEQ ID NO:28)
EVQLVESGGGLVKPGGSLKLSCAASGYTFTSYVMHWVRQAPGKGLEWIGYINPYNDGHKY
NEKFQGRVTISSDKSISTAYMELSSLRSEDTAMYYCARGTYYYGSRVFDYWGQGTLVTVSS

> 4G7 H1.144 (SEQ ID NO:29)
EVQLVESGGGLVKPGGSLKLSCAASGYTFTSYVMHWVRQAPGKGLEWIGYINPYNDGTKY
NEKFQGRVTISSDKSISTAYMELSSLRSEDTAMYYCARGTYYYGSRVFNYWGQGTLVTVSS

> 4G7 H1.146 (SEQ ID NO:30)
EVQLVESGGGLVKPGGSLKLSCAASGYTFTSYVMHWVRQAPGKGLEWIGYINPYNDGTKY
NEKFQGRVTISSDKSISTAYMELSSLRSEDTAMYYCARGTYYYGSRVFHYWGQGTLVTVSS

> 4G7 H1.147 (SEQ ID NO:31)
EVQLVESGGGLVKPGGSLKLSCAASGYTFTSYVMHWVRQAPGKGLEWIGYINPYNDGTKY
NEKFQGRVTISSDKSISTAYMELSSLRSEDTAMYYCARGTYYYGSRVFSYWGQGTLVTVSS

> 4G7 H1.191 (SEQ ID NO:32)
EVQLVESGGGLVKPGGSLKLSCAASGYTFTSYVMHWVRQAPGKGLEWIGYINPYNDGTEY
NEKFQGRVTISSDKSISTAYMELSSLRSEDTAMYYCARGTYYYGTRVFDYWGQGTLVTVSS

> 4G7 H1.192 (SEQ ID NO:33)
EVQLVESGGGLVKPGGSLKLSCAASGYTFTSYVMHWVRQAPGKGLEWIGYINPYNDGPKY
NEKFQGRVTISSDKSISTAYMELSSLRSEDTAMYYCARGTYYYGTRVFDYWGQGTLVTVSS

> 4G7 H1.196 (SEQ ID NO:34)
EVQLVESGGGLVKPGGSLKLSCAASGYTFTSYVMHWVRQAPGKGLEWIGYINPYNDGPKY
NEKFQGRVTISSDKSISTAYMELSSLRSEDTAMYYCARGTYYYGTSVFDYWGQGTLVTVSS

> 4G7 H1.199 (SEQ ID NO:35)
EVQLVESGGGLVKPGGSLKLSCAASGYTFTSYVMHWVRQAPGKGLEWIGYINPYNDGPEY
NEKFQGRVTISSDKSISTAYMELSSLRSEDTAMYYCARGTYYYGTRVFDYWGQGTLVTVSS

> 4G7 H1.201 (SEQ ID NO:36)
EVQLVESGGGLVKPGGSLKLSCAASGYTFTSYVMHWVRQAPGKGLEWIGYINPYNSGTKY
NEKFQGRVTISSDKSISTAYMELSSLRSEDTAMYYCARGTYYYGTRVFDYWGQGTLVTVSS

> 4G7 H1.202 (SEQ ID NO:37)
EVQLVESGGGLVKPGGSLKLSCAASGYTFTSYVMHWVRQAPGKGLEWIGYINPYNEGTKY
NEKFQGRVTISSDKSISTAYMELSSLRSEDTAMYYCARGTYYYGTRVFDYWGQGTLVTVSS

> 4G7 H1.203 (SEQ ID NO:38)
EVQLVESGGGLVKPGGSLKLSCAASGYTFTSYVMHWVRQAPGKGLEWIGYINPYNSGTEY
NEKFQGRVTISSDKSISTAYMELSSLRSEDTAMYYCARGTYYYGTRVFDYWGQGTLVTVSS

Figure 18 (continued)

> 4G7 H1.204 (SEQ ID NO:39)

EVQLVESGGGLVKPGGSLKLSCAASGYTFTSYVMHWVRQAPGKGLEWIGYINPYNEGTEY
NEKFQGRVTISSDKSISTAYMELSSLRSEDTAMYYCARGTYYYGTRVFDYWGQGTLVTVSS

> 4G7 H1.52 (SEQ ID NO:40)

EVQLVESGGGLVKPGGSLKLSCAASGYTFTSYVMHWVRQAPGKGLEWIGYINPYNDGTKY
NEKFQGRVTISSDKSISTAYMELSSLRSEDTAMYYCARGTYYYGTRVFDYWGQGTLVTVSS

> 4G7 H1.60 (SEQ ID NO:41)

EVQLVESGGGLVKPGGSLKLSCAASGYTFTSYVMHWVRQAPGKGLEWIGYINPYNDGTKY
NEKFQGRVTISSDKSISTAYMELSSLRSEDTAMYYCARGTYYYGLRVFDYWGQGTLVTVSS

> 4G7 H1.62 (SEQ ID NO:42)

EVQLVESGGGLVKPGGSLKLSCAASGYTFTSYVMHWVRQAPGKGLEWIGYINPYNDGTKY
NEKFQGRVTISSDKSISTAYMELSSLRSEDTAMYYCARGTYYYGSEVFDYWGQGTLVTVSS

> 4G7 H1.65 (SEQ ID NO:43)

EVQLVESGGGLVKPGGSLKLSCAASGYTFTSYVMHWVRQAPGKGLEWIGYINPYNDGTKY
NEKFQGRVTISSDKSISTAYMELSSLRSEDTAMYYCARGTYYYGSSVFDYWGQGTLVTVSS

> 4G7 H1.78 (SEQ ID NO:44)

EVQLVESGGGLVKPGGSLKLSCAASGYTFTSYVMHWVRQAPGKGLEWIGYINPYNAGTKY
NEKFQGRVTISSDKSISTAYMELSSLRSEDTAMYYCARGTYYYGSRVFDYWGQGTLVTVSS

Figure 19

> 4G7 L1.11 (SEQ ID NO:45)
DIVMTQSPATLSLSPGERATLSCRSSKSLLNSNGNTYLYWFQQKPGQSPQLLIYRMSNLAS
GVPDRFSGSGSGTEFTLTISSLEPEDFAVYYCMQHLNYPFTFGAGTKLEIK

> 4G7 L1.124 (SEQ ID NO:46)
DIVMTQSPATLSLSPGERATLSCRSSKSLLNSNGNTYLYWFQQKPGQSPQLLIYRMSNWAS
GVPDRFSGSGSGTEFTLTISSLEPEDFAVYYCMQHLEYPFTFGAGTKLEIK

> 4G7 L1.138 (SEQ ID NO:47)
DIVMTQSPATLSLSPGERATLSCRSSKSLLNVNGNTYLYWFQQKPGQSPQLLIYRMSNLNS
GVPDRFSGSGSGTEFTLTISSLEPEDFAVYYCMQHLEYPFTFGAGTKLEIK

> 4G7 L1.139 (SEQ ID NO:48)
DIVMTQSPATLSLSPGERATLSCRSSKSLLNVNGNTYLYWFQQKPGQSPQLLIYRMSNLAS
GVPDRFSGSGSGTEFTLTISSLEPEDFAVYYCMQHLEYPNTFGAGTKLEIK

> 4G7 L1.141 (SEQ ID NO:49)
DIVMTQSPATLSLSPGERATLSCRSSKSLLNSNGNTYLYWFQQKPGQSPQLLIYRMSNLNS
GVPDRFSGSGSGTEFTLTISSLEPEDFAVYYCMQHLEYPNTFGAGTKLEIK

> 4G7 L1.143 (SEQ ID NO:50)
DIVMTQSPATLSLSPGERATLSCRSSKSLQNSNGNTYLYWFQQKPGQSPQLLIYRMSNLNS
GVPDRFSGSGSGTEFTLTISSLEPEDFAVYYCMQHLEYPFTFGAGTKLEIK

> 4G7 L1.144 (SEQ ID NO:51)
DIVMTQSPATLSLSPGERATLSCRSSKSLQNSNGNTYLYWFQQKPGQSPQLLIYRMSNLAS
GVPDRFSGSGSGTEFTLTISSLEPEDFAVYYCMQHLEYPNTFGAGTKLEIK

> 4G7 L1.145 (SEQ ID NO:52)
DIVMTQSPATLSLSPGERATLSCRSSKSLQNSNGNTYLYWFQQKPGQSPQLLIYRMSNLAS
GVPDRFSGSGSGTEFTLTISSLEPEDFAVYYCMQHLEYPITFGAGTKLEIK

> 4G7 L1.146 (SEQ ID NO:53)
DIVMTQSPATLSLSPGERATLSCRSSKSLLNVNGNTYLYWFQQKPGQSPQLLIYRMSNLNS
GVPDRFSGSGSGTEFTLTISSLEPEDFAVYYCMQHLEYPNTFGAGTKLEIK

> 4G7 L1.148 (SEQ ID NO:54)
DIVMTQSPATLSLSPGERATLSCRSSKSLQNSNGNTYLYWFQQKPGQSPQLLIYRMSNLNS
GVPDRFSGSGSGTEFTLTISSLEPEDFAVYYCMQHLEYPNTFGAGTKLEIK

> 4G7 L1.149 (SEQ ID NO:55)
DIVMTQSPATLSLSPGERATLSCRSSKSLQNSNGNTYLYWFQQKPGQSPQLLIYRMSNLNS
GVPDRFSGSGSGTEFTLTISSLEPEDFAVYYCMQHLEYPITFGAGTKLEIK

> 4G7 L1.152 (SEQ ID NO:56)
DIVMTQSPATLSLSPGERATLSCRSSKSLQNVNGNTYLYWFQQKPGQSPQLLIYRMSNLAS
GVPDRFSGSGSGTEFTLTISSLEPEDFAVYYCMQHLEYPNTFGAGTKLEIK

Figure 19 (continued)

> 4G7 L1.154 (SEQ ID NO:57)

DIVMTQSPATLSLSPGERATLSCRSSKSLQNVNGNTYLYWFQQKPGQSPQLLIYRMSNLNS
GVPDRFSGSGSGTEFTLTISSLEPEDFAVYYCMQHLEYPNTFGAGTKLEIK

> 4G7 L1.155 (SEQ ID NO:58)

DIVMTQSPATLSLSPGERATLSCRSSKSLQNVNGNTYLYWFQQKPGQSPQLLIYRMSNLNS
GVPDRFSGSGSGTEFTLTISSLEPEDFAVYYCMQHLEYPITFGAGTKLEIK

> 4G7 L1.160 (SEQ ID NO:59)

DIVMTQSPATLSLSPGERATLSCRSSKSLQNVNANTYLYWFQQKPGQSPQLLIYRMSNLNS
GVPDRFSGSGSGTEFTLTISSLEPEDFAVYYCMQHLEYPITFGAGTKLEIK

> 4G7 L1.161 (SEQ ID NO:60)

DIVMTQSPATLSLSPGERATLSCRSSKSLQNVNSNTYLYWFQQKPGQSPQLLIYRMSNLNS
GVPDRFSGSGSGTEFTLTISSLEPEDFAVYYCMQHLEYPITFGAGTKLEIK

> 4G7 L1.162 (SEQ ID NO:61)

DIVMTQSPATLSLSPGERATLSCRSSKSLQNANANTYLYWFQQKPGQSPQLLIYRMSNLNS
GVPDRFSGSGSGTEFTLTISSLEPEDFAVYYCMQHLEYPITFGAGTKLEIK

> 4G7 L1.163 (SEQ ID NO:62)

DIVMTQSPATLSLSPGERATLSCRSSKSLQNANSNTYLYWFQQKPGQSPQLLIYRMSNLNS
GVPDRFSGSGSGTEFTLTISSLEPEDFAVYYCMQHLEYPITFGAGTKLEIK

> 4G7 L1.164 (SEQ ID NO:63)

DIVMTQSPATLSLSPGERATLSCRSSKSLQNANGNTYLYWFQQKPGQSPQLLIYRMSNLNS
GVPDRFSGSGSGTEFTLTISSLEPEDFAVYYCMQHLEYPITFGAGTKLEIK

> 4G7 L1.17 (SEQ ID NO:64)

DIVMTQSPATLSLSPGERATLSCRSSKSLLNSNGNTYLYWFQQKPGQSPQLLIYRMSNLAS
GVPDRFSGSGSGTEFTLTISSLEPEDFAVYYCMQHLTYPFTFGAGTKLEIK

> 4G7 L1.19 (SEQ ID NO:65)

DIVMTQSPATLSLSPGERATLSCRSSKSLLNSNGNTYLYWFQQKPGQSPQLLIYRMSNLAS
GVPDRFSGSGSGTEFTLTISSLEPEDFAVYYCMQHLYYPFTFGAGTKLEIK

> 4G7 L1.26 (SEQ ID NO:66)

DIVMTQSPATLSLSPGERATLSCRSSKSLQNSNGNTYLYWFQQKPGQSPQLLIYRMSNLAS
GVPDRFSGSGSGTEFTLTISSLEPEDFAVYYCMQHLEYPFTFGAGTKLEIK

> 4G7 L1.3 (SEQ ID NO:67)

DIVMTQSPATLSLSPGERATLSCRSSKSLLNSNGNTYLYWFQQKPGQSPQLLIYRMQNLAS
GVPDRFSGSGSGTEFTLTISSLEPEDFAVYYCMQHLEYPFTFGAGTKLEIK

> 4G7 L1.32 (SEQ ID NO:68)

DIVMTQSPATLSLSPGERATLSCRSSKSLLNVNGNTYLYWFQQKPGQSPQLLIYRMSNLAS
GVPDRFSGSGSGTEFTLTISSLEPEDFAVYYCMQHLEYPFTFGAGTKLEIK

Figure 19 (continued)

> 4G7 L1.46 (SEQ ID NO:69)

DIVMTQSPATLSLSPGERATLSCRSSKSLLNSNGNTYLYWFQQKPGQSPQLLIYRMSHLAS
GVPDRFSGSGSGTEFTLTISSLEPEDFAVYYCMQHLEYPFTFGAGTKLEIK

> 4G7 L1.54 (SEQ ID NO:70)

DIVMTQSPATLSLSPGERATLSCRSSKSLLNSNGNTYLYWFQQKPGQSPQLLIYRMSGLAS
GVPDRFSGSGSGTEFTLTISSLEPEDFAVYYCMQHLEYPFTFGAGTKLEIK

> 4G7 L1.55 (SEQ ID NO:71)

DIVMTQSPATLSLSPGERATLSCRSSKSLLNSNGNTYLYWFQQKPGQSPQLLIYRMSYLAS
GVPDRFSGSGSGTEFTLTISSLEPEDFAVYYCMQHLEYPFTFGAGTKLEIK

> 4G7 L1.64 (SEQ ID NO:72)

DIVMTQSPATLSLSPGERATLSCRSSKSLLNSNGNTYLYWFQQKPGQSPQLLIYRMSNLAS
GVPDRFSGSGSGTEFTLTISSLEPEDFAVYYCMQHLEYPITFGAGTKLEIK

> 4G7 L1.67 (SEQ ID NO:73)

DIVMTQSPATLSLSPGERATLSCRSSKSLLNSNGNTYLYWFQQKPGQSPQLLIYRMSNLAS
GVPDRFSGSGSGTEFTLTISSLEPEDFAVYYCMQHLEYPVTFGAGTKLEIK

> 4G7 L1.68 (SEQ ID NO:74)

DIVMTQSPATLSLSPGERATLSCRSSKSLLNSNGNTYLYWFQQKPGQSPQLLIYRMSNLAS
GVPDRFSGSGSGTEFTLTISSLEPEDFAVYYCMQHLEYPNTFGAGTKLEIK

> 4G7 L1.8 (SEQ ID NO:75)

DIVMTQSPATLSLSPGERATLSCRSSKSLLNSNGNTYLYWFQQKPGQSPQLLIYRMKNLAS
GVPDRFSGSGSGTEFTLTISSLEPEDFAVYYCMQHLEYPFTFGAGTKLEIK

> 4G7 L1.80 (SEQ ID NO:76)

DIVMTQSPATLSLSPGERATLSCRSSKSLLNSNGNTYLFWFQQKPGQSPQLLIYRMSNLAS
GVPDRFSGSGSGTEFTLTISSLEPEDFAVYYCMQHLEYPFTFGAGTKLEIK

> 4G7 L1.9 (SEQ ID NO:77)

DIVMTQSPATLSLSPGERATLSCRSSKSLLNSNGNTYLYWFQQKPGQSPQLLIYRMLNLAS
GVPDRFSGSGSGTEFTLTISSLEPEDFAVYYCMQHLEYPFTFGAGTKLEIK

> 4G7 L1.92 (SEQ ID NO:78)

DIVMTQSPATLSLSPGERATLSCRSSKSLLNSNGNTYLYWFQQKPGQSPQLLIYRMSNLLS
GVPDRFSGSGSGTEFTLTISSLEPEDFAVYYCMQHLEYPFTFGAGTKLEIK

> 4G7 L1.96 (SEQ ID NO:79)

DIVMTQSPATLSLSPGERATLSCRSSKSLLNSNGNTYLYWFQQKPGQSPQLLIYRMSNLNS
GVPDRFSGSGSGTEFTLTISSLEPEDFAVYYCMQHLEYPFTFGAGTKLEIK

Figure 21
Crosslinked with a secondary anti-Fc mAb
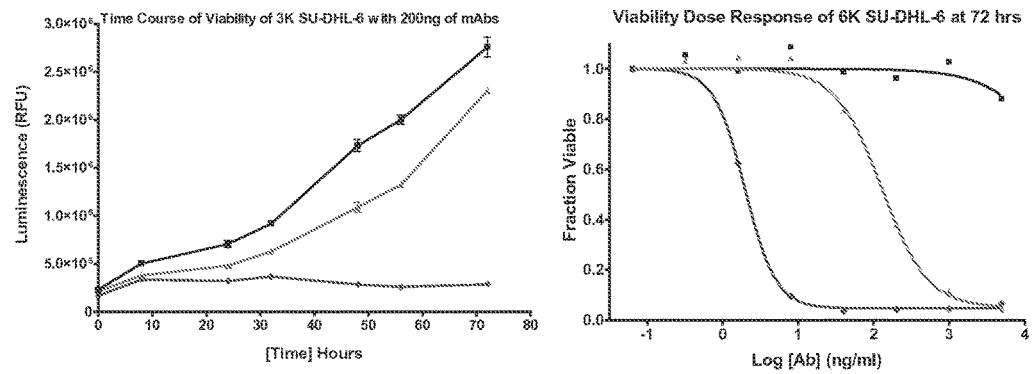
Not crosslinked with a secondary anti-Fc mAb
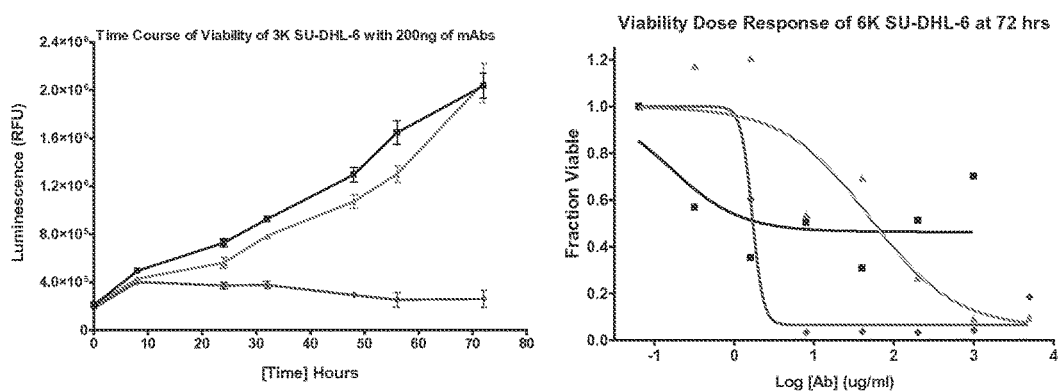
- 4G7 stability + affinity improved Hybrid S239D/I332E
- rituximab
- isotype control

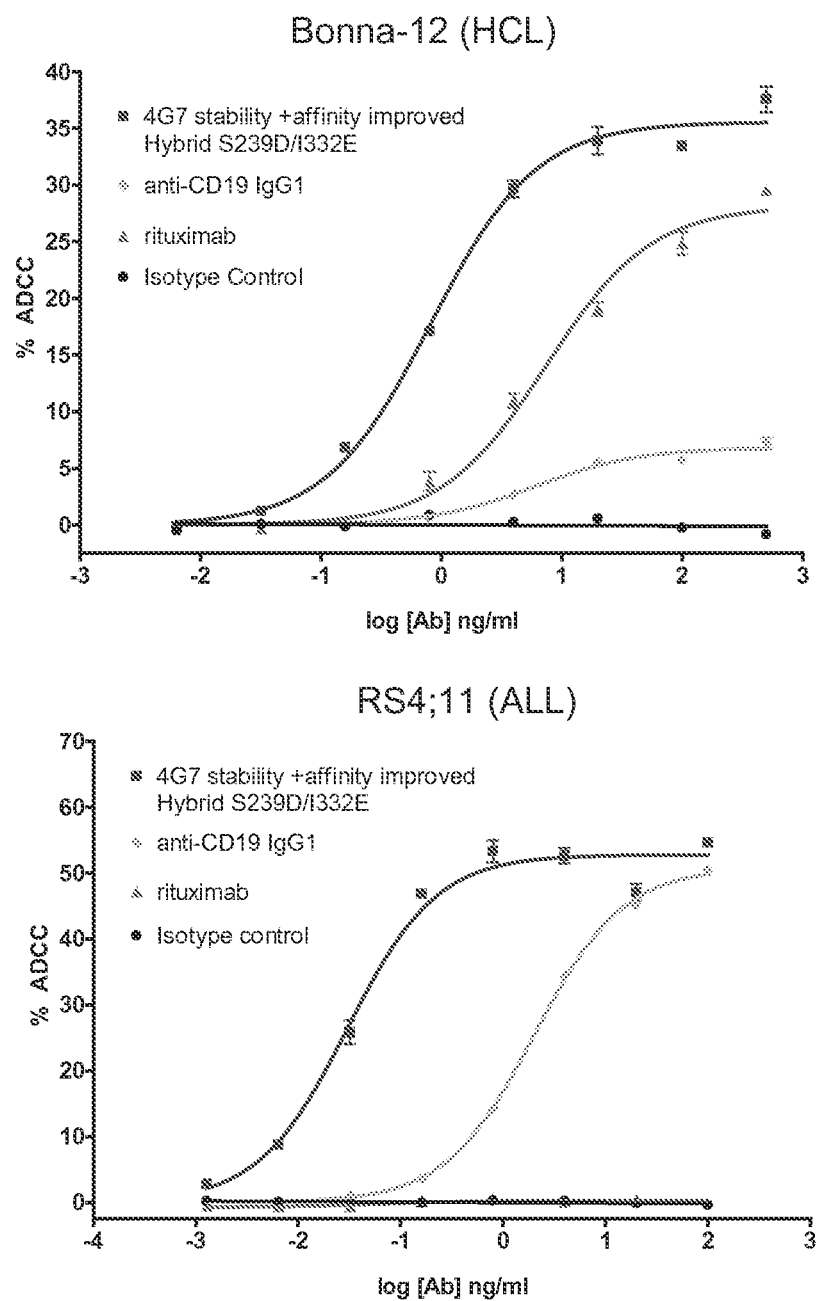
Figure 23 – Continued

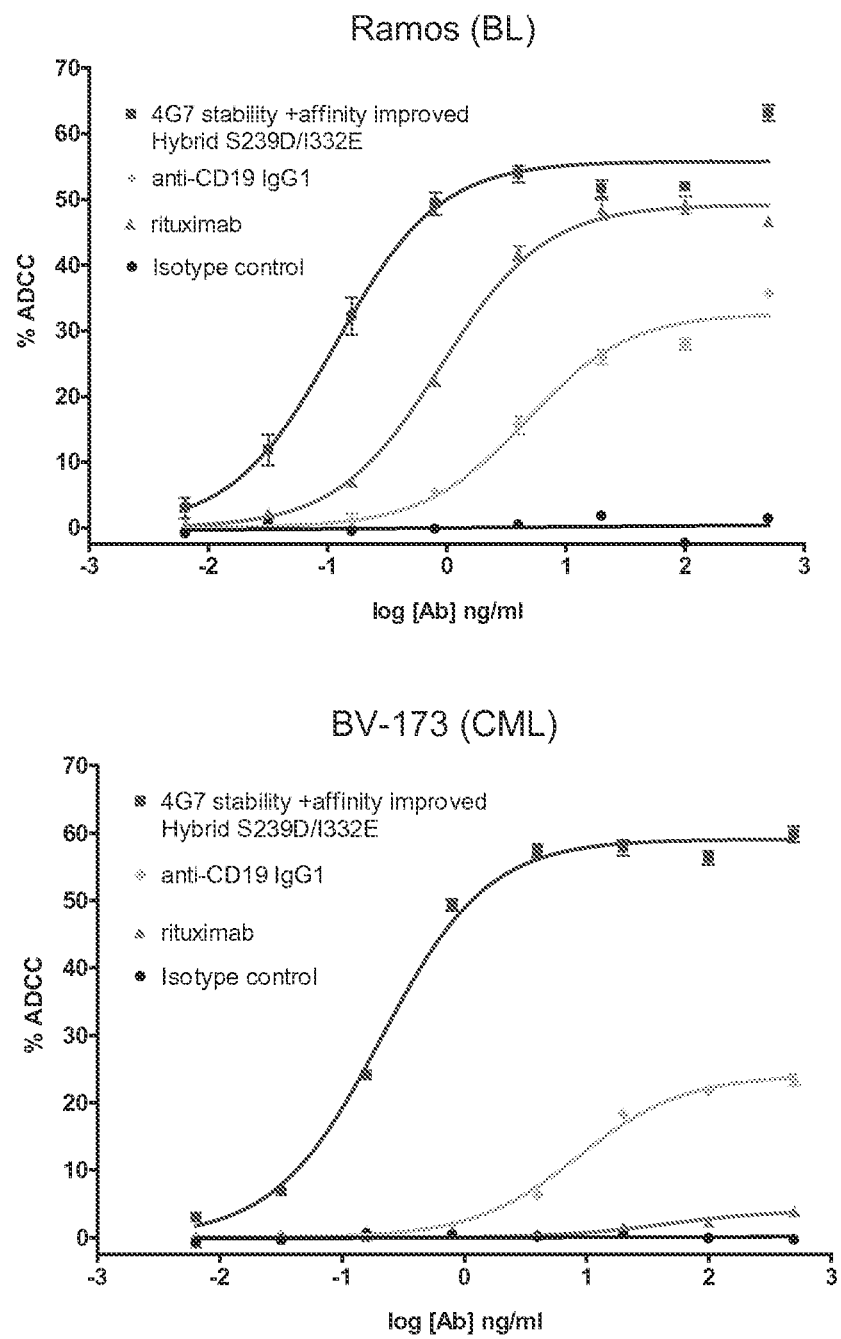
Figure 23 – Continued

Figure 26
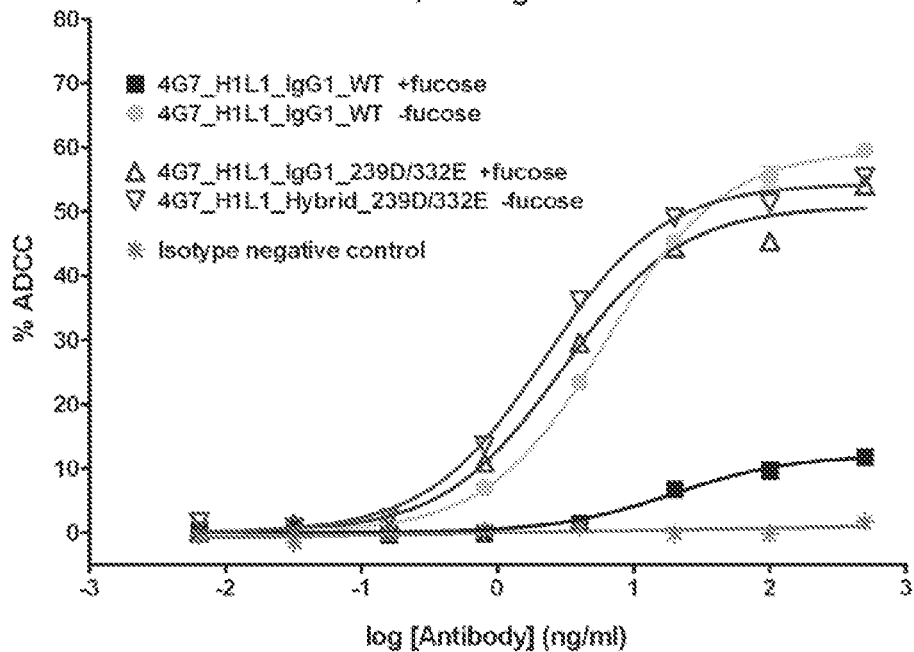
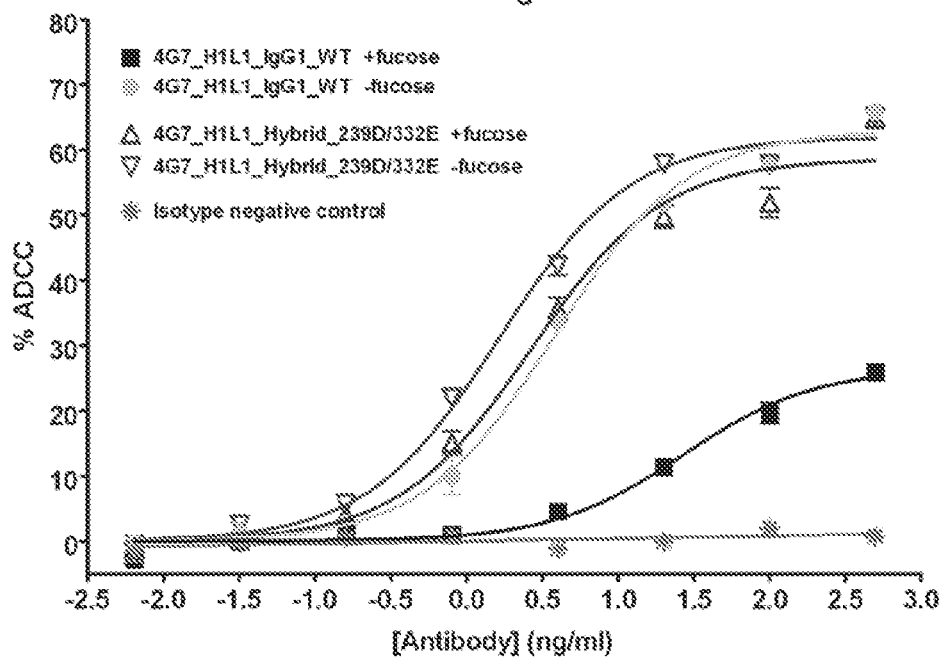

Variants (Kabat numbering)

| Template | | Heavy chain | | | | Light chain | | | | |
|---|---|---|---|---|---|---|---|---|---|---|
| Heavy chain | Light chain | 1 | 2 | 3 | 4 | 1 | 2 | 3 | 4 | 5 |
| H3.1 | L0 | Y27F | | | | | | | | |
| H3.10 | L0 | Y34H | | | | | | | | |
| H3.11 | L0 | V35I | | | | | | | | |
| H3.12 | L0 | V35T | | | | | | | | |
| H3.13 | L0 | H35bN | | | | | | | | |
| H3.14 | L0 | H35bY | | | | | | | | |
| H3.15 | L0 | W47F | | | | | | | | |
| H3.16 | L0 | Y50F | | | | | | | | |
| H3.17 | L0 | Y50H | | | | | | | | |
| H3.18 | L0 | N52D | | | | | | | | |
| H3.19 | L0 | N52S | | | | | | | | |
| H3.2 | L0 | Y27H | | | | | | | | |
| H3.20 | L0 | P52aS | | | | | | | | |
| H3.21 | L0 | P52aA | | | | | | | | |
| H3.22 | L0 | N54D | | | | | | | | |
| H3.23 | L0 | N54S | | | | | | | | |
| H3.24 | L0 | D55E | | | | | | | | |
| H3.25 | L0 | D55S | | | | | | | | |
| H3.26 | L0 | G56A | | | | | | | | |
| H3.27 | L0 | G56N | | | | | | | | |
| H3.28 | L0 | T57A | | | | | | | | |
| H3.29 | L0 | T57S | | | | | | | | |
| H3.3 | L0 | T28A | | | | | | | | |
| H3.30 | L0 | K58R | | | | | | | | |
| H3.31 | L0 | K58Q | | | | | | | | |
| H3.32 | L0 | Y59F | | | | | | | | |
| H3.33 | L0 | Y59H | | | | | | | | |
| H3.34 | L0 | G95A | | | | | | | | |
| H3.35 | L0 | G95S | | | | | | | | |
| H3.36 | L0 | T96A | | | | | | | | |
| H3.37 | L0 | T96S | | | | | | | | |
| H3.38 | L0 | Y97F | | | | | | | | |
| H3.39 | L0 | Y97H | | | | | | | | |
| H3.4 | L0 | T28S | | | | | | | | |
| H3.40 | L0 | Y98F | | | | | | | | |
| H3.41 | L0 | Y98H | | | | | | | | |
| H3.42 | L0 | Y99F | | | | | | | | |
| H3.43 | L0 | Y99H | | | | | | | | |
| H3.44 | L0 | G100bA | | | | | | | | |
| H3.45 | L0 | G100bS | | | | | | | | |
| H3.46 | L0 | S100cA | | | | | | | | |
| H3.47 | L0 | S100cN | | | | | | | | |
| H3.48 | L0 | R100dK | | | | | | | | |
| H3.49 | L0 | R100dQ | | | | | | | | |
| H3.5 | L0 | T30A | | | | | | | | |
| H3.50 | L0 | V100eI | | | | | | | | |
| H3.51 | L0 | F100fL | | | | | | | | |

Figure 28 - continued

Variants (Kabat numbering)

| Template | | Heavy chain | | | | Light chain | | | | |
|---|---|---|---|---|---|---|---|---|---|---|
| Heavy chain | Light chain | 1 | 2 | 3 | 4 | 1 | 2 | 3 | 4 | 5 |
| H3.6 | L0 | T30S | | | | | | | | |
| H3.7 | L0 | S31A | | | | | | | | |
| H3.8 | L0 | S31N | | | | | | | | |
| H3.9 | L0 | Y34F | | | | | | | | |
| H1.100 | L1 | N54Q | | | | | | | | |
| H1.101 | L1 | N54P | | | | | | | | |
| H1.102 | L1 | N54R | | | | | | | | |
| H1.103 | L1 | N54A | | | | | | | | |
| H1.104 | L1 | N54L | | | | | | | | |
| H1.105 | L1 | N54T | | | | | | | | |
| H1.106 | L1 | N54G | | | | | | | | |
| H1.107 | L1 | N54Y | | | | | | | | |
| H1.108 | L1 | T57V | | | | | | | | |
| H1.109 | L1 | T57P | | | | | | | | |
| H1.110 | L1 | T57I | | | | | | | | |
| H1.111 | L1 | T57Q | | | | | | | | |
| H1.112 | L1 | T57G | | | | | | | | |
| H1.113 | L1 | T57H | | | | | | | | |
| H1.114 | L1 | T57N | | | | | | | | |
| H1.115 | L1 | T57Y | | | | | | | | |
| H1.116 | L1 | T57K | | | | | | | | |
| H1.128 | L1 | K58E | | | | | | | | |
| H1.128 | L1 | K58E | | | | | | | | |
| H1.129 | L1 | K58H | | | | | | | | |
| H1.130 | L1 | K58S | | | | | | | | |
| H1.131 | L1 | K58D | | | | | | | | |
| H1.132 | L1 | K58P | | | | | | | | |
| H1.133 | L1 | K58T | | | | | | | | |
| H1.134 | L1 | K58Y | | | | | | | | |
| H1.135 | L1 | T30V | | | | | | | | |
| H1.136 | L1 | T30P | | | | | | | | |
| H1.137 | L1 | T30I | | | | | | | | |
| H1.138 | L1 | T30Q | | | | | | | | |
| H1.139 | L1 | T30G | | | | | | | | |
| H1.140 | L1 | T30H | | | | | | | | |
| H1.141 | L1 | T30N | | | | | | | | |
| H1.142 | L1 | T30Y | | | | | | | | |
| H1.143 | L1 | T30K | | | | | | | | |
| H1.144 | L1 | D101N | | | | | | | | |
| H1.145 | L1 | D101E | | | | | | | | |
| H1.146 | L1 | D101H | | | | | | | | |
| H1.147 | L1 | D101S | | | | | | | | |
| H1.148 | L1 | D101Q | | | | | | | | |
| H1.149 | L1 | D101R | | | | | | | | |
| H1.150 | L1 | D101P | | | | | | | | |
| H1.151 | L1 | D101K | | | | | | | | |
| H1.152 | L1 | D101A | | | | | | | | |

Figure 28 - continued

Variants (Kabat numbering)

| Template | | Heavy chain | | | | Light chain | | | | |
|---|---|---|---|---|---|---|---|---|---|---|
| Heavy chain | Light chain | 1 | 2 | 3 | 4 | 1 | 2 | 3 | 4 | 5 |
| H1.153 | L1 | D101L | | | | | | | | |
| H1.154 | L1 | D101T | | | | | | | | |
| H1.155 | L1 | D101G | | | | | | | | |
| H1.156 | L1 | D101Y | | | | | | | | |
| H1.157 | L1 | Y34P | | | | | | | | |
| H1.158 | L1 | Y34L | | | | | | | | |
| H1.159 | L1 | Y34W | | | | | | | | |
| H1.160 | L1 | Y34V | | | | | | | | |
| H1.161 | L1 | Y34A | | | | | | | | |
| H1.162 | L1 | Y34N | | | | | | | | |
| H1.163 | L1 | Y34Q | | | | | | | | |
| H1.164 | L1 | Y34K | | | | | | | | |
| H1.165 | L1 | Y99P | | | | | | | | |
| H1.166 | L1 | Y99L | | | | | | | | |
| H1.167 | L1 | Y99W | | | | | | | | |
| H1.168 | L1 | Y99V | | | | | | | | |
| H1.169 | L1 | Y99A | | | | | | | | |
| H1.170 | L1 | Y99S | | | | | | | | |
| H1.171 | L1 | Y99Q | | | | | | | | |
| H1.172 | L1 | Y99K | | | | | | | | |
| H1.173 | L1 | G56E | | | | | | | | |
| H1.174 | L1 | G56L | | | | | | | | |
| H1.175 | L1 | G56Q | | | | | | | | |
| H1.176 | L1 | G56H | | | | | | | | |
| H1.177 | L1 | G56P | | | | | | | | |
| H1.178 | L1 | G56V | | | | | | | | |
| H1.179 | L1 | G56Y | | | | | | | | |
| H1.180 | L1 | G56K | | | | | | | | |
| H1.181 | L1 | Y102F | | | | | | | | |
| H1.182 | L1 | Y102H | | | | | | | | |
| H1.183 | L1 | Y102P | | | | | | | | |
| H1.184 | L1 | Y102L | | | | | | | | |
| H1.185 | L1 | Y102W | | | | | | | | |
| H1.186 | L1 | Y102V | | | | | | | | |
| H1.187 | L1 | Y102A | | | | | | | | |
| H1.188 | L1 | Y102N | | | | | | | | |
| H1.189 | L1 | Y102Q | | | | | | | | |
| H1.190 | L1 | Y102K | | | | | | | | |
| H1.191 | L1 | K58E | S100cT | | | | | | | |
| H1.192 | L1 | T57P | S100cT | | | | | | | |
| H1.193 | L1 | K58E | R100dS | | | | | | | |
| H1.194 | L1 | T57P | R100dS | | | | | | | |
| H1.195 | L1 | S100cT | R100dS | | | | | | | |
| H1.196 | L1 | T57P | S100cT | R100dS | | | | | | |
| H1.198 | L1 | T57P | K58E | S100cT | R100dS | | | | | |
| H1.199 | L1 | T57P | K58E | S100cT | | | | | | |
| H1.200 | L1 | T57P | K58E | | | | | | | |

Figure 28 - continued

Variants (Kabat numbering)

| Template | | Heavy chain | | | | Light chain | | | | |
|---|---|---|---|---|---|---|---|---|---|---|
| Heavy chain | Light chain | 1 | 2 | 3 | 4 | 1 | 2 | 3 | 4 | 5 |
| H1.52 | L1 | S100cT | | | | | | | | |
| H1.53 | L1 | S100cP | | | | | | | | |
| H1.54 | L1 | S100cQ | | | | | | | | |
| H1.55 | L1 | S100cG | | | | | | | | |
| H1.56 | L1 | S100cV | | | | | | | | |
| H1.57 | L1 | S100cH | | | | | | | | |
| H1.58 | L1 | S100cE | | | | | | | | |
| H1.59 | L1 | S100cK | | | | | | | | |
| H1.60 | L1 | S100cL | | | | | | | | |
| H1.61 | L1 | S100cY | | | | | | | | |
| H1.62 | L1 | R100dE | | | | | | | | |
| H1.63 | L1 | R100dD | | | | | | | | |
| H1.64 | L1 | R100dH | | | | | | | | |
| H1.65 | L1 | R100dS | | | | | | | | |
| H1.66 | L1 | R100dP | | | | | | | | |
| H1.67 | L1 | R100dY | | | | | | | | |
| H1.68 | L1 | S31T | | | | | | | | |
| H1.69 | L1 | S31P | | | | | | | | |
| H1.70 | L1 | S31Q | | | | | | | | |
| H1.71 | L1 | S31G | | | | | | | | |
| H1.72 | L1 | S31V | | | | | | | | |
| H1.73 | L1 | S31H | | | | | | | | |
| H1.74 | L1 | S31E | | | | | | | | |
| H1.75 | L1 | S31K | | | | | | | | |
| H1.76 | L1 | S31L | | | | | | | | |
| H1.77 | L1 | S31Y | | | | | | | | |
| H1.78 | L1 | D55A | | | | | | | | |
| H1.79 | L1 | D55H | | | | | | | | |
| H1.80 | L1 | D55Q | | | | | | | | |
| H1.81 | L1 | D55R | | | | | | | | |
| H1.82 | L1 | D55P | | | | | | | | |
| H1.83 | L1 | D55K | | | | | | | | |
| H1.84 | L1 | D55L | | | | | | | | |
| H1.85 | L1 | D55T | | | | | | | | |
| H1.86 | L1 | D55G | | | | | | | | |
| H1.87 | L1 | D55Y | | | | | | | | |
| H1.88 | L1 | V35P | | | | | | | | |
| H1.89 | L1 | V35S | | | | | | | | |
| H1.90 | L1 | V35L | | | | | | | | |
| H1.91 | L1 | V35A | | | | | | | | |
| H1.92 | L1 | V35Y | | | | | | | | |
| H1.93 | L1 | V35F | | | | | | | | |
| H1.94 | L1 | V35Q | | | | | | | | |
| H1.95 | L1 | V35G | | | | | | | | |
| H1.96 | L1 | V35N | | | | | | | | |
| H1.97 | L1 | V35K | | | | | | | | |
| H1.98 | L1 | N54H | | | | | | | | |

Figure 28 - continued

Variants (Kabat numbering)

| Template | | Heavy chain | | | | Light chain | | | | |
|---|---|---|---|---|---|---|---|---|---|---|
| Heavy chain | Light chain | 1 | 2 | 3 | 4 | 1 | 2 | 3 | 4 | 5 |
| H1.99 | L1 | N54E | | | | | | | | |
| H3.117 | L1 | P52aL | | | | | | | | |
| H3.118 | L1 | P52aI | | | | | | | | |
| H3.119 | L1 | P52aT | | | | | | | | |
| H3.120 | L1 | P52aV | | | | | | | | |
| H3.121 | L1 | P52aY | | | | | | | | |
| H3.122 | L1 | P52aQ | | | | | | | | |
| H3.123 | L1 | P52aN | | | | | | | | |
| H3.124 | L1 | P52aH | | | | | | | | |
| H3.125 | L1 | P52aG | | | | | | | | |
| H3.126 | L1 | P52aF | | | | | | | | |
| H3.127 | L1 | P52aK | | | | | | | | |
| H1 | L1.1 | | | | | S52T | | | | |
| H1 | L1.10 | | | | | S52Y | | | | |
| H1 | L1.100 | | | | | S56P | | | | |
| H1 | L1.101 | | | | | S56Q | | | | |
| H1 | L1.102 | | | | | S56G | | | | |
| H1 | L1.103 | | | | | S56N | | | | |
| H1 | L1.104 | | | | | S56V | | | | |
| H1 | L1.105 | | | | | S56H | | | | |
| H1 | L1.106 | | | | | S56E | | | | |
| H1 | L1.107 | | | | | S56K | | | | |
| H1 | L1.108 | | | | | S56L | | | | |
| H1 | L1.109 | | | | | S56Y | | | | |
| H1 | L1.11 | | | | | E93N | | | | |
| H1 | L1.110 | | | | | S27aT | | | | |
| H1 | L1.111 | | | | | S27aP | | | | |
| H1 | L1.112 | | | | | S27aQ | | | | |
| H1 | L1.113 | | | | | S27aG | | | | |
| H1 | L1.114 | | | | | S27aV | | | | |
| H1 | L1.115 | | | | | S27aH | | | | |
| H1 | L1.116 | | | | | S27aE | | | | |
| H1 | L1.117 | | | | | S27aK | | | | |
| H1 | L1.118 | | | | | S27aL | | | | |
| H1 | L1.119 | | | | | S27aY | | | | |
| H1 | L1.12 | | | | | E93K | | | | |
| H1 | L1.120 | | | | | L54I | | | | |
| H1 | L1.121 | | | | | L54P | | | | |
| H1 | L1.122 | | | | | L54F | | | | |
| H1 | L1.123 | | | | | L54Y | | | | |
| H1 | L1.124 | | | | | L54W | | | | |
| H1 | L1.125 | | | | | L54D | | | | |
| H1 | L1.126 | | | | | L54S | | | | |
| H1 | L1.127 | | | | | L54H | | | | |
| H1 | L1.128 | | | | | L54Q | | | | |
| H1 | L1.129 | | | | | L54K | | | | |
| H1 | L1.13 | | | | | E93S | | | | |

Figure 28 - continued

Variants (Kabat numbering)

| Template | | Heavy chain | | | | Light chain | | | | |
|---|---|---|---|---|---|---|---|---|---|---|
| Heavy chain | Light chain | 1 | 2 | 3 | 4 | 1 | 2 | 3 | 4 | 5 |
| H1 | L1.130 | | | | | Y49P | | | | |
| H1 | L1.131 | | | | | Y49L | | | | |
| H1 | L1.132 | | | | | Y49W | | | | |
| H1 | L1.133 | | | | | Y49V | | | | |
| H1 | L1.134 | | | | | Y49A | | | | |
| H1 | L1.135 | | | | | Y49N | | | | |
| H1 | L1.136 | | | | | Y49Q | | | | |
| H1 | L1.137 | | | | | Y49R | | | | |
| H1 | L1.138 | | | | | S27eV | A55N | | | |
| H1.109 | L1.138 | T57P | | | | S27eV | A55N | | | |
| H1.191 | L1.138 | K58E | S100cT | | | S27eV | A55N | | | |
| H1.192 | L1.138 | T57P | S100cT | | | S27eV | A55N | | | |
| H1.195 | L1.138 | S100cT | R100dS | | | S27eV | A55N | | | |
| H1.196 | L1.138 | T57P | S100cT | R100dS | | S27eV | A55N | | | |
| H1.198 | L1.138 | T57P | K58E | S100cT | R100dS | S27eV | A55N | | | |
| H1.199 | L1.138 | T57P | K58E | S100cT | | S27eV | A55N | | | |
| H1.52 | L1.138 | S100cT | | | | S27eV | A55N | | | |
| H1 | L1.139 | | | | | S27eV | F96N | | | |
| H1.109 | L1.139 | T57P | | | | S27eV | F96N | | | |
| H1.191 | L1.139 | K58E | S100cT | | | S27eV | F96N | | | |
| H1.192 | L1.139 | T57P | S100cT | | | S27eV | F96N | | | |
| H1.193 | L1.139 | K58E | R100dS | | | S27eV | F96N | | | |
| H1.194 | L1.139 | T57P | R100dS | | | S27eV | F96N | | | |
| H1.195 | L1.139 | S100cT | R100dS | | | S27eV | F96N | | | |
| H1.196 | L1.139 | T57P | S100cT | R100dS | | S27eV | F96N | | | |
| H1.198 | L1.139 | T57P | K58E | S100cT | R100dS | S27eV | F96N | | | |
| H1.199 | L1.139 | T57P | K58E | S100cT | | S27eV | F96N | | | |
| H1.52 | L1.139 | S100cT | | | | S27eV | F96N | | | |
| H1 | L1.14 | | | | | E93H | | | | |
| H1 | L1.140 | | | | | S27eV | F96I | | | |
| H1.109 | L1.140 | T57P | | | | S27eV | F96I | | | |
| H1.191 | L1.140 | K58E | S100cT | | | S27eV | F96I | | | |
| H1.192 | L1.140 | T57P | S100cT | | | S27eV | F96I | | | |
| H1.52 | L1.140 | S100cT | | | | S27eV | F96I | | | |
| H1 | L1.141 | | | | | A55N | F96N | | | |
| H1.109 | L1.141 | T57P | | | | A55N | F96N | | | |
| H1.191 | L1.141 | K58E | S100cT | | | A55N | F96N | | | |
| H1.192 | L1.141 | T57P | S100cT | | | A55N | F96N | | | |
| H1.193 | L1.141 | K58E | R100dS | | | A55N | F96N | | | |
| H1.194 | L1.141 | T57P | R100dS | | | A55N | F96N | | | |
| H1.195 | L1.141 | S100cT | R100dS | | | A55N | F96N | | | |
| H1.196 | L1.141 | T57P | S100cT | R100dS | | A55N | F96N | | | |
| H1.198 | L1.141 | T57P | K58E | S100cT | R100dS | A55N | F96N | | | |
| H1.199 | L1.141 | T57P | K58E | S100cT | | A55N | F96N | | | |
| H1.52 | L1.141 | S100cT | | | | A55N | F96N | | | |
| H1 | L1.142 | | | | | A55N | F96I | | | |
| H1.109 | L1.142 | T57P | | | | A55N | F96I | | | |

Figure 28 - continued

| Template | | Variants (Kabat numbering) | | | | | | | | |
|---|---|---|---|---|---|---|---|---|---|---|
| | | Heavy chain | | | | Light chain | | | | |
| Heavy chain | Light chain | 1 | 2 | 3 | 4 | 1 | 2 | 3 | 4 | 5 |
| H1.191 | L1.142 | K58E | S100cT | | | A55N | F96I | | | |
| H1.192 | L1.142 | T57P | S100cT | | | A55N | F96I | | | |
| H1.193 | L1.142 | K58E | R100dS | | | A55N | F96I | | | |
| H1.194 | L1.142 | T57P | R100dS | | | A55N | F96I | | | |
| H1.52 | L1.142 | S100cT | | | | A55N | F96I | | | |
| H1 | L1.143 | | | | | L27cQ | A55N | | | |
| H1.109 | L1.143 | T57P | | | | L27cQ | A55N | | | |
| H1.191 | L1.143 | K58E | S100cT | | | L27cQ | A55N | | | |
| H1.192 | L1.143 | T57P | S100cT | | | L27cQ | A55N | | | |
| H1.195 | L1.143 | S100cT | R100dS | | | L27cQ | A55N | | | |
| H1.196 | L1.143 | T57P | S100cT | R100dS | | L27cQ | A55N | | | |
| H1.198 | L1.143 | T57P | K58E | S100cT | R100dS | L27cQ | A55N | | | |
| H1.199 | L1.143 | T57P | K58E | S100cT | | L27cQ | A55N | | | |
| H1.52 | L1.143 | S100cT | | | | L27cQ | A55N | | | |
| H1 | L1.144 | | | | | L27cQ | F96N | | | |
| H1.109 | L1.144 | T57P | | | | L27cQ | F96N | | | |
| H1.191 | L1.144 | K58E | S100cT | | | L27cQ | F96N | | | |
| H1.192 | L1.144 | T57P | S100cT | | | L27cQ | F96N | | | |
| H1.193 | L1.144 | K58E | R100dS | | | L27cQ | F96N | | | |
| H1.194 | L1.144 | T57P | R100dS | | | L27cQ | F96N | | | |
| H1.195 | L1.144 | S100cT | R100dS | | | L27cQ | F96N | | | |
| H1.196 | L1.144 | T57P | S100cT | R100dS | | L27cQ | F96N | | | |
| H1.198 | L1.144 | T57P | K58E | S100cT | R100dS | L27cQ | F96N | | | |
| H1.199 | L1.144 | T57P | K58E | S100cT | | L27cQ | F96N | | | |
| H1.52 | L1.144 | S100cT | | | | L27cQ | F96N | | | |
| H1 | L1.145 | | | | | L27cQ | F96I | | | |
| H1.109 | L1.145 | T57P | | | | L27cQ | F96I | | | |
| H1.191 | L1.145 | K58E | S100cT | | | L27cQ | F96I | | | |
| H1.192 | L1.145 | T57P | S100cT | | | L27cQ | F96I | | | |
| H1.52 | L1.145 | S100cT | | | | L27cQ | F96I | | | |
| H1 | L1.146 | | | | | S27eV | A55N | F96N | | |
| H1.109 | L1.146 | T57P | | | | S27eV | A55N | F96N | | |
| H1.191 | L1.146 | K58E | S100cT | | | S27eV | A55N | F96N | | |
| H1.192 | L1.146 | T57P | S100cT | | | S27eV | A55N | F96N | | |
| H1.193 | L1.146 | K58E | R100dS | | | S27eV | A55N | F96N | | |
| H1.194 | L1.146 | T57P | R100dS | | | S27eV | A55N | F96N | | |
| H1.195 | L1.146 | S100cT | R100dS | | | S27eV | A55N | F96N | | |
| H1.196 | L1.146 | T57P | S100cT | R100dS | | S27eV | A55N | F96N | | |
| H1.198 | L1.146 | T57P | K58E | S100cT | R100dS | S27eV | A55N | F96N | | |
| H1.199 | L1.146 | T57P | K58E | S100cT | | S27eV | A55N | F96N | | |
| H1.52 | L1.146 | S100cT | | | | S27eV | A55N | F96N | | |
| H1 | L1.147 | | | | | S27eV | A55N | F96I | | |
| H1.109 | L1.147 | T57P | | | | S27eV | A55N | F96I | | |
| H1.191 | L1.147 | K58E | S100cT | | | S27eV | A55N | F96I | | |
| H1.192 | L1.147 | T57P | S100cT | | | S27eV | A55N | F96I | | |
| H1.193 | L1.147 | K58E | R100dS | | | S27eV | A55N | F96I | | |
| H1.194 | L1.147 | T57P | R100dS | | | S27eV | A55N | F96I | | |

Figure 28 - continued

Variants (Kabat numbering)

| Template | | Heavy chain | | | | Light chain | | | | |
|---|---|---|---|---|---|---|---|---|---|---|
| Heavy chain | Light chain | 1 | 2 | 3 | 4 | 1 | 2 | 3 | 4 | 5 |
| H1.52 | L1.147 | S100cT | | | | S27eV | A55N | F96I | | |
| H1 | L1.148 | | | | | L27cQ | A55N | F96N | | |
| H1.109 | L1.148 | T57P | | | | L27cQ | A55N | F96N | | |
| H1.191 | L1.148 | K58E | S100cT | | | L27cQ | A55N | F96N | | |
| H1.192 | L1.148 | T57P | S100cT | | | L27cQ | A55N | F96N | | |
| H1.193 | L1.148 | K58E | R100dS | | | L27cQ | A55N | F96N | | |
| H1.194 | L1.148 | T57P | R100dS | | | L27cQ | A55N | F96N | | |
| H1.195 | L1.148 | S100cT | R100dS | | | L27cQ | A55N | F96N | | |
| H1.196 | L1.148 | T57P | S100cT | R100dS | | L27cQ | A55N | F96N | | |
| H1.198 | L1.148 | T57P | K58E | S100cT | R100dS | L27cQ | A55N | F96N | | |
| H1.199 | L1.148 | T57P | K58E | S100cT | | L27cQ | A55N | F96N | | |
| H1.52 | L1.148 | S100cT | | | | L27cQ | A55N | F96N | | |
| H1 | L1.149 | | | | | L27cQ | A55N | F96I | | |
| H1.109 | L1.149 | T57P | | | | L27cQ | A55N | F96I | | |
| H1.191 | L1.149 | K58E | S100cT | | | L27cQ | A55N | F96I | | |
| H1.192 | L1.149 | T57P | S100cT | | | L27cQ | A55N | F96I | | |
| H1.193 | L1.149 | K58E | R100dS | | | L27cQ | A55N | F96I | | |
| H1.194 | L1.149 | T57P | R100dS | | | L27cQ | A55N | F96I | | |
| H1.52 | L1.149 | S100cT | | | | L27cQ | A55N | F96I | | |
| H1 | L1.15 | | | | | E93R | | | | |
| H1 | L1.150 | | | | | L27cQ | S27eV | | | |
| H1 | L1.151 | | | | | L27cQ | S27eV | A55N | | |
| H1.192 | L1.151 | T57P | S100cT | | | L27cQ | S27eV | A55N | | |
| H1.195 | L1.151 | S100cT | R100dS | | | L27cQ | S27eV | A55N | | |
| H1.196 | L1.151 | T57P | S100cT | R100dS | | L27cQ | S27eV | A55N | | |
| H1.198 | L1.151 | T57P | K58E | S100cT | R100dS | L27cQ | S27eV | A55N | | |
| H1.199 | L1.151 | T57P | K58E | S100cT | | L27cQ | S27eV | A55N | | |
| H1.52 | L1.151 | S100cT | | | | L27cQ | S27eV | A55N | | |
| H1 | L1.152 | | | | | L27cQ | S27eV | F96N | | |
| H1.192 | L1.152 | T57P | S100cT | | | L27cQ | S27eV | F96N | | |
| H1.195 | L1.152 | S100cT | R100dS | | | L27cQ | S27eV | F96N | | |
| H1.196 | L1.152 | T57P | S100cT | R100dS | | L27cQ | S27eV | F96N | | |
| H1.198 | L1.152 | T57P | K58E | S100cT | R100dS | L27cQ | S27eV | F96N | | |
| H1.199 | L1.152 | T57P | K58E | S100cT | | L27cQ | S27eV | F96N | | |
| H1.52 | L1.152 | S100cT | | | | L27cQ | S27eV | F96N | | |
| H1 | L1.153 | | | | | L27cQ | S27eV | F96I | | |
| H1 | L1.154 | | | | | L27cQ | S27eV | A55N | F96N | |
| H1.192 | L1.154 | T57P | S100cT | | | L27cQ | S27eV | A55N | F96N | |
| H1.195 | L1.154 | S100cT | R100dS | | | L27cQ | S27eV | A55N | F96N | |
| H1.196 | L1.154 | T57P | S100cT | R100dS | | L27cQ | S27eV | A55N | F96N | |
| H1.198 | L1.154 | T57P | K58E | S100cT | R100dS | L27cQ | S27eV | A55N | F96N | |
| H1.199 | L1.154 | T57P | K58E | S100cT | | L27cQ | S27eV | A55N | F96N | |
| H1.52 | L1.154 | S100cT | | | | L27cQ | S27eV | A55N | F96N | |
| H1 | L1.155 | | | | | L27cQ | S27eV | A55N | F96I | |
| H1.191 | L1.155 | K58E | S100cT | | | L27cQ | S27eV | A55N | F96I | |
| H1.201 | L1.155 | D55S | S100cT | | | L27cQ | S27eV | A55N | F96I | |
| H1.203 | L1.155 | D55S | K58E | S100cT | | L27cQ | S27eV | A55N | F96I | |

Figure 28 - continued

Variants (Kabat numbering)

| Template | | Heavy chain | | | | Light chain | | | | |
|---|---|---|---|---|---|---|---|---|---|---|
| Heavy chain | Light chain | 1 | 2 | 3 | 4 | 1 | 2 | 3 | 4 | 5 |
| H1.52 | L1.155 | S100cT | | | | L27cQ | S27eV | A55N | F96I | |
| H1 | L1.16 | | | | | E93P | | | | |
| H1.191 | L1.160 | K58E | S100cT | | | L27cQ | S27eV | G29A | A55N | F96I |
| H1.201 | L1.160 | D55S | S100cT | | | L27cQ | S27eV | G29A | A55N | F96I |
| H1.202 | L1.160 | D55E | S100cT | | | L27cQ | S27eV | G29A | A55N | F96I |
| H1.203 | L1.160 | D55S | K58E | S100cT | | L27cQ | S27eV | G29A | A55N | F96I |
| H1.204 | L1.160 | D55E | K58E | S100cT | | L27cQ | S27eV | G29A | A55N | F96I |
| H1.52 | L1.160 | S100cT | | | | L27cQ | S27eV | G29A | A55N | F96I |
| H1.191 | L1.161 | K58E | S100cT | | | L27cQ | S27eV | G29S | A55N | F96I |
| H1.201 | L1.161 | D55S | S100cT | | | L27cQ | S27eV | G29S | A55N | F96I |
| H1.202 | L1.161 | D55E | S100cT | | | L27cQ | S27eV | G29S | A55N | F96I |
| H1.203 | L1.161 | D55S | K58E | S100cT | | L27cQ | S27eV | G29S | A55N | F96I |
| H1.204 | L1.161 | D55E | K58E | S100cT | | L27cQ | S27eV | G29S | A55N | F96I |
| H1.52 | L1.161 | S100cT | | | | L27cQ | S27eV | G29S | A55N | F96I |
| H1.191 | L1.162 | K58E | S100cT | | | L27cQ | S27eA | G29A | A55N | F96I |
| H1.201 | L1.162 | D55S | S100cT | | | L27cQ | S27eA | G29A | A55N | F96I |
| H1.202 | L1.162 | D55E | S100cT | | | L27cQ | S27eA | G29A | A55N | F96I |
| H1.203 | L1.162 | D55S | K58E | S100cT | | L27cQ | S27eA | G29A | A55N | F96I |
| H1.204 | L1.162 | D55E | K58E | S100cT | | L27cQ | S27eA | G29A | A55N | F96I |
| H1.52 | L1.162 | S100cT | | | | L27cQ | S27eA | G29A | A55N | F96I |
| H1.191 | L1.163 | K58E | S100cT | | | L27cQ | S27eA | G29S | A55N | F96I |
| H1.201 | L1.163 | D55S | S100cT | | | L27cQ | S27eA | G29S | A55N | F96I |
| H1.202 | L1.163 | D55E | S100cT | | | L27cQ | S27eA | G29S | A55N | F96I |
| H1.203 | L1.163 | D55S | K58E | S100cT | | L27cQ | S27eA | G29S | A55N | F96I |
| H1.204 | L1.163 | D55E | K58E | S100cT | | L27cQ | S27eA | G29S | A55N | F96I |
| H1.52 | L1.163 | S100cT | | | | L27cQ | S27eA | G29S | A55N | F96I |
| H1.201 | L1.164 | D55S | S100cT | | | L27cQ | S27eA | A55N | F96I | |
| H1.203 | L1.164 | D55S | K58E | S100cT | | L27cQ | S27eA | A55N | F96I | |
| H1 | L1.17 | | | | | E93T | | | | |
| H1 | L1.18 | | | | | E93G | | | | |
| H1 | L1.19 | | | | | E93Y | | | | |
| H1 | L1.2 | | | | | S52P | | | | |
| H1 | L1.20 | | | | | L27cP | | | | |
| H1 | L1.21 | | | | | L27cF | | | | |
| H1 | L1.22 | | | | | L27cY | | | | |
| H1 | L1.23 | | | | | L27cW | | | | |
| H1 | L1.24 | | | | | L27cH | | | | |
| H1 | L1.25 | | | | | L27cS | | | | |
| H1 | L1.26 | | | | | L27cQ | | | | |
| H1 | L1.27 | | | | | L27cK | | | | |
| H1 | L1.28 | | | | | S27eT | | | | |
| H1 | L1.29 | | | | | S27eP | | | | |
| H1 | L1.3 | | | | | S52Q | | | | |
| H1 | L1.30 | | | | | S27eQ | | | | |
| H1 | L1.31 | | | | | S27eG | | | | |
| H1 | L1.32 | | | | | S27eV | | | | |
| H1.109 | L1.32 | T57P | | | | | | | | |

Figure 28 - continued

| Template | | Variants (Kabat numbering) | | | | | | | | |
|---|---|---|---|---|---|---|---|---|---|---|
| | | Heavy chain | | | | Light chain | | | | |
| Heavy chain | Light chain | 1 | 2 | 3 | 4 | 1 | 2 | 3 | 4 | 5 |
| H1.52 | L1.32 | S100cT | | | | S27eV | | | | |
| H1 | L1.33 | | | | | S27eH | | | | |
| H1 | L1.34 | | | | | S27eE | | | | |
| H1 | L1.35 | | | | | S27eK | | | | |
| H1 | L1.36 | | | | | S27eY | | | | |
| H1 | L1.37 | | | | | L92P | | | | |
| H1 | L1.38 | | | | | L92F | | | | |
| H1 | L1.39 | | | | | L92Y | | | | |
| H1 | L1.4 | | | | | S52G | | | | |
| H1 | L1.40 | | | | | L92W | | | | |
| H1 | L1.41 | | | | | L92N | | | | |
| H1 | L1.42 | | | | | L92S | | | | |
| H1 | L1.43 | | | | | L92H | | | | |
| H1 | L1.44 | | | | | L92Q | | | | |
| H1 | L1.45 | | | | | L92K | | | | |
| H1 | L1.46 | | | | | N53H | | | | |
| H1 | L1.47 | | | | | N53E | | | | |
| H1 | L1.48 | | | | | N53Q | | | | |
| H1 | L1.49 | | | | | N53P | | | | |
| H1 | L1.5 | | | | | S52V | | | | |
| H1 | L1.50 | | | | | N53R | | | | |
| H1 | L1.51 | | | | | N53A | | | | |
| H1 | L1.52 | | | | | N53L | | | | |
| H1 | L1.53 | | | | | N53T | | | | |
| H1 | L1.54 | | | | | N53G | | | | |
| H1 | L1.55 | | | | | N53Y | | | | |
| H1 | L1.56 | | | | | K27E | | | | |
| H1 | L1.57 | | | | | K27H | | | | |
| H1 | L1.58 | | | | | K27S | | | | |
| H1 | L1.59 | | | | | K27D | | | | |
| H1 | L1.6 | | | | | S52H | | | | |
| H1 | L1.60 | | | | | K27P | | | | |
| H1 | L1.61 | | | | | K27T | | | | |
| H1 | L1.62 | | | | | K27Y | | | | |
| H1 | L1.63 | | | | | F96W | | | | |
| H1 | L1.64 | | | | | F96I | | | | |
| H1.191 | L1.64 | K58E | S100cT | | | F96I | | | | |
| H1.192 | L1.64 | T57P | S100cT | | | F96I | | | | |
| H1 | L1.65 | | | | | F96H | | | | |
| H1 | L1.66 | | | | | F96P | | | | |
| H1 | L1.67 | | | | | F96V | | | | |
| H1 | L1.68 | | | | | F96N | | | | |
| H1.109 | L1.68 | T57P | | | | | | | | |
| H1.191 | L1.68 | K58E | S100cT | | | F96N | | | | |
| H1.192 | L1.68 | T57P | S100cT | | | F96N | | | | |
| H1.195 | L1.68 | S100cT | R100dS | | | F96N | | | | |
| H1.196 | L1.68 | T57P | S100cT | R100dS | | F96N | | | | |

Figure 28 - continued

Variants (Kabat numbering)

| Template | | Heavy chain | | | | Light chain | | | | |
|---|---|---|---|---|---|---|---|---|---|---|
| Heavy chain | Light chain | 1 | 2 | 3 | 4 | 1 | 2 | 3 | 4 | 5 |
| H1.198 | L1.68 | T57P | K58E | S100cT | R100dS | F96N | | | | |
| H1.199 | L1.68 | T57P | K58E | S100cT | | F96N | | | | |
| H1.52 | L1.68 | S100cT | | | | F96N | | | | |
| H1 | L1.69 | | | | | F96A | | | | |
| H1 | L1.7 | | | | | S52E | | | | |
| H1 | L1.70 | | | | | F96Q | | | | |
| H1 | L1.71 | | | | | F96K | | | | |
| H1 | L1.72 | | | | | Y94P | | | | |
| H1 | L1.73 | | | | | Y94L | | | | |
| H1 | L1.74 | | | | | Y94W | | | | |
| H1 | L1.75 | | | | | Y94V | | | | |
| H1 | L1.76 | | | | | Y94A | | | | |
| H1 | L1.77 | | | | | Y94N | | | | |
| H1 | L1.78 | | | | | Y94Q | | | | |
| H1 | L1.79 | | | | | Y94R | | | | |
| H1 | L1.8 | | | | | S52K | | | | |
| H1 | L1.80 | | | | | Y34F | | | | |
| H1 | L1.81 | | | | | Y34H | | | | |
| H1 | L1.82 | | | | | Y34P | | | | |
| H1 | L1.83 | | | | | Y34L | | | | |
| H1 | L1.84 | | | | | Y34W | | | | |
| H1 | L1.85 | | | | | Y34V | | | | |
| H1 | L1.86 | | | | | Y34A | | | | |
| H1 | L1.87 | | | | | Y34N | | | | |
| H1 | L1.88 | | | | | Y34Q | | | | |
| H1 | L1.89 | | | | | Y34T | | | | |
| H1 | L1.9 | | | | | S52L | | | | |
| H1 | L1.90 | | | | | Y34K | | | | |
| H1 | L1.91 | | | | | A55D | | | | |
| H1 | L1.92 | | | | | A55L | | | | |
| H1 | L1.93 | | | | | A55P | | | | |
| H1 | L1.94 | | | | | A55H | | | | |
| H1 | L1.95 | | | | | A55Q | | | | |
| H1 | L1.96 | | | | | A55N | | | | |
| H1.191 | L1.96 | K58E | S100cT | | | A55N | | | | |
| H1.192 | L1.96 | T57P | S100cT | | | A55N | | | | |
| H1.198 | L1.96 | T57P | K58E | S100cT | R100dS | A55N | | | | |
| H1.199 | L1.96 | T57P | K58E | S100cT | | A55N | | | | |
| H1 | L1.97 | | | | | A55Y | | | | |
| H1 | L1.98 | | | | | A55K | | | | |
| H1 | L1.99 | | | | | S56T | | | | |
| H3 | L2.1 | | | | | K27R | | | | |
| H3 | L2.10 | | | | | S27eN | | | | |
| H3 | L2.11 | | | | | N28D | | | | |
| H3 | L2.12 | | | | | N28H | | | | |
| H3 | L2.13 | | | | | G39A | | | | |
| H3 | L2.14 | | | | | G39S | | | | |

Figure 28 - continued

| Template | | Variants (Kabat numbering) | | | | | | | | |
|---|---|---|---|---|---|---|---|---|---|---|
| | | Heavy chain | | | | Light chain | | | | |
| Heavy chain | Light chain | 1 | 2 | 3 | 4 | 1 | 2 | 3 | 4 | 5 |
| H3 | L2.15 | | | | | N30D | | | | |
| H3 | L2.16 | | | | | N30H | | | | |
| H3 | L2.17 | | | | | T31A | | | | |
| H3 | L2.18 | | | | | T31S | | | | |
| H3 | L2.19 | | | | | Y32F | | | | |
| H3 | L2.2 | | | | | K27Q | | | | |
| H3 | L2.20 | | | | | Y32H | | | | |
| H3 | L2.21 | | | | | Y34F | | | | |
| H3 | L2.22 | | | | | Y49F | | | | |
| H3 | L2.23 | | | | | Y49H | | | | |
| H3 | L2.24 | | | | | R50K | | | | |
| H3 | L2.25 | | | | | R50Q | | | | |
| H3 | L2.26 | | | | | S52A | | | | |
| H3 | L2.27 | | | | | S52N | | | | |
| H3 | L2.28 | | | | | N53D | | | | |
| H3 | L2.29 | | | | | N53S | | | | |
| H3 | L2.3 | | | | | S27aA | | | | |
| H3 | L2.30 | | | | | L54V | | | | |
| H3 | L2.31 | | | | | A55G | | | | |
| H3 | L2.32 | | | | | A55V | | | | |
| H3 | L2.33 | | | | | S56A | | | | |
| H3 | L2.34 | | | | | H91N | | | | |
| H3 | L2.35 | | | | | N91Y | | | | |
| H3 | L2.36 | | | | | L92I | | | | |
| H3 | L2.37 | | | | | L92V | | | | |
| H3 | L2.38 | | | | | E93D | | | | |
| H3 | L2.39 | | | | | E93Q | | | | |
| H3 | L2.4 | | | | | S27aN | | | | |
| H3 | L2.40 | | | | | Y94F | | | | |
| H3 | L2.41 | | | | | Y94H | | | | |
| H3 | L2.42 | | | | | F96L | | | | |
| H3 | L2.43 | | | | | F96Y | | | | |
| H3 | L2.5 | | | | | L27cI | | | | |
| H3 | L2.6 | | | | | L27cV | | | | |
| H3 | L2.7 | | | | | N27dD | | | | |
| H3 | L2.8 | | | | | N27dS | | | | |
| H3 | L2.9 | | | | | S27eA | | | | |

Figure 29

Variants (Kabat numbering)

| Template | | Heavy chain | | | | Light chain | | | | | Fold change |
|---|---|---|---|---|---|---|---|---|---|---|---|
| Heavy chain | Light chain | 1 | 2 | 3 | 4 | 1 | 2 | 3 | 4 | 5 | binding |
| H1.109 | L1 | T57P | | | | | | | | | 1.52 |
| H1.113 | L1 | T57H | | | | | | | | | 1.29 |
| H1.144 | L1 | D101N | | | | | | | | | 2.26 |
| H1.146 | L1 | D101H | | | | | | | | | 2.45 |
| H1.147 | L1 | D101S | | | | | | | | | 2.65 |
| H1.196 | L1 | T57P | S100cT | R100dS | | | | | | | 3.42 |
| H1.52 | L1 | S100cT | | | | | | | | | 3.22 |
| H1.60 | L1 | S100cL | | | | | | | | | 1.56 |
| H1.62 | L1 | R100dE | | | | | | | | | 1.65 |
| H1.65 | L1 | R100dS | | | | | | | | | 1.41 |
| H1.78 | L1 | D55A | | | | | | | | | 1.14 |
| H1 | L1.11 | | | | | E93N | | | | | 1.59 |
| H1 | L1.124 | | | | | L54W | | | | | 1.47 |
| H1.52 | L1.138 | S100cT | | | | S27eV | A55N | | | | 3.93 |
| H1.199 | L1.139 | T57P | K58E | S100cT | | S27eV | F96N | | | | 2.36 |
| H1.52 | L1.139 | S100cT | | | | S27eV | F96N | | | | 1.80 |
| H1.192 | L1.141 | T57P | S100cT | | | A55N | F96N | | | | 2.57 |
| H1.199 | L1.141 | T57P | K58E | S100cT | | A55N | F96N | | | | 4.02 |
| H1.52 | L1.143 | S100cT | | | | L27cQ | A55N | | | | 3.83 |
| H1.192 | L1.144 | T57P | S100cT | | | L27cQ | F96N | | | | 3.63 |
| H1.52 | L1.145 | S100cT | | | | L27cQ | F96I | | | | 6.41 |
| H1.192 | L1.146 | T57P | S100cT | | | S27eV | A55N | F96N | | | 3.19 |
| H1.196 | L1.146 | T57P | S100cT | R100dS | | S27eV | A55N | F96N | | | 3.57 |
| H1.199 | L1.146 | T57P | K58E | S100cT | | S27eV | A55N | F96N | | | 4.11 |
| H1.192 | L1.148 | T57P | S100cT | | | L27cQ | A55N | F96N | | | 4.63 |
| H1.199 | L1.148 | T57P | K58E | S100cT | | L27cQ | A55N | F96N | | | 4.34 |
| H1.191 | L1.149 | K58E | S100cT | | | L27cQ | A55N | F96I | | | 6.02 |
| H1.52 | L1.149 | S100cT | | | | L27cQ | A55N | F96I | | | 8.60 |
| H1.192 | L1.152 | T57P | S100cT | | | L27cQ | S27eV | F96N | | | 2.98 |
| H1.196 | L1.152 | T57P | S100cT | R100dS | | L27cQ | S27eV | F96N | | | 4.36 |
| H1.199 | L1.152 | T57P | K58E | S100cT | | L27cQ | S27eV | F96N | | | 3.55 |
| H1.192 | L1.154 | T57P | S100cT | | | L27cQ | S27eV | A55N | F96N | | 5.12 |
| H1.196 | L1.154 | T57P | S100cT | R100dS | | L27cQ | S27eV | A55N | F96N | | 4.44 |
| H1.191 | L1.155 | K58E | S100cT | | | L27cQ | S27eV | A55N | F96I | | 4.56 |
| H1.201 | L1.155 | D55S | S100cT | | | L27cQ | S27eV | A55N | F96I | | 4.48 |
| H1.203 | L1.155 | D55S | K58E | S100cT | | L27cQ | S27eV | A55N | F96I | | 4.73 |
| H1.52 | L1.155 | S100cT | | | | L27cQ | S27eV | A55N | F96I | | 6.16 |
| H1.191 | L1.160 | K58E | S100cT | | | L27cQ | S27eV | G29A | A55N | F96I | 2.91 |
| H1.201 | L1.160 | D55S | S100cT | | | L27cQ | S27eV | G29A | A55N | F96I | 4.51 |
| H1.202 | L1.160 | D55E | S100cT | | | L27cQ | S27eV | G29A | A55N | F96I | 3.96 |
| H1.203 | L1.160 | D55S | K58E | S100cT | | L27cQ | S27eV | G29A | A55N | F96I | 1.76 |
| H1.204 | L1.160 | D55E | K58E | S100cT | | L27cQ | S27eV | G29A | A55N | F96I | 3.46 |
| H1.52 | L1.160 | S100cT | | | | L27cQ | S27eV | G29A | A55N | F96I | 4.18 |
| H1.191 | L1.161 | K58E | S100cT | | | L27cQ | S27eV | G29S | A55N | F96I | 3.97 |
| H1.201 | L1.161 | D55S | S100cT | | | L27cQ | S27eV | G29S | A55N | F96I | 3.89 |
| H1.202 | L1.161 | D55E | S100cT | | | L27cQ | S27eV | G29S | A55N | F96I | 4.30 |
| H1.203 | L1.161 | D55S | K58E | S100cT | | L27cQ | S27eV | G29S | A55N | F96I | 2.92 |

Figure 29 - continued

| Template | | Variants (Kabat numbering) | | | | | | | | | Fold change binding |
|---|---|---|---|---|---|---|---|---|---|---|---|
| | | Heavy chain | | | | Light chain | | | | | |
| Heavy chain | Light chain | 1 | 2 | 3 | 4 | 1 | 2 | 3 | 4 | 5 | |
| H1.204 | L1.161 | D55E | K58E | S100cT | | L27cQ | S27eV | G29S | A55N | F96I | 3.27 |
| H1.52 | L1.161 | S100cT | | | | L27cQ | S27eV | G29S | A55N | F96I | 3.18 |
| H1.191 | L1.162 | K58E | S100cT | | | L27cQ | S27eA | G29A | A55N | F96I | 3.35 |
| H1.201 | L1.162 | D55S | S100cT | | | L27cQ | S27eA | G29A | A55N | F96I | 3.97 |
| H1.202 | L1.162 | D55E | S100cT | | | L27cQ | S27eA | G29A | A55N | F96I | 4.32 |
| H1.203 | L1.162 | D55S | K58E | S100cT | | L27cQ | S27eA | G29A | A55N | F96I | 3.25 |
| H1.204 | L1.162 | D55E | K58E | S100cT | | L27cQ | S27eA | G29A | A55N | F96I | 4.07 |
| H1.52 | L1.162 | S100cT | | | | L27cQ | S27eA | G29A | A55N | F96I | 5.57 |
| H1.191 | L1.163 | K58E | S100cT | | | L27cQ | S27eA | G29S | A55N | F96I | 5.32 |
| H1.201 | L1.163 | D55S | S100cT | | | L27cQ | S27eA | G29S | A55N | F96I | 3.87 |
| H1.202 | L1.163 | D55E | S100cT | | | L27cQ | S27eA | G29S | A55N | F96I | 3.57 |
| H1.203 | L1.163 | D55S | K58E | S100cT | | L27cQ | S27eA | G29S | A55N | F96I | 3.20 |
| H1.204 | L1.163 | D55E | K58E | S100cT | | L27cQ | S27eA | G29S | A55N | F96I | 4.73 |
| H1.52 | L1.163 | S100cT | | | | L27cQ | S27eA | G29S | A55N | F96I | 3.74 |
| H1.201 | L1.164 | D55S | S100cT | | | L27cQ | S27eA | A55N | F96I | | 4.41 |
| H1.203 | L1.164 | D55S | K58E | S100cT | | L27cQ | S27eA | A55N | F96I | | 5.58 |
| H1 | L1.17 | | | | | E93T | | | | | 1.57 |
| H1 | L1.19 | | | | | E93Y | | | | | 1.76 |
| H1 | L1.26 | | | | | L27cQ | | | | | 1.73 |
| H1 | L1.3 | | | | | S52Q | | | | | 1.85 |
| H1 | L1.32 | | | | | S27eV | | | | | 2.61 |
| H1 | L1.46 | | | | | N53H | | | | | 1.75 |
| H1 | L1.54 | | | | | N53G | | | | | 1.50 |
| H1 | L1.55 | | | | | N53Y | | | | | 1.58 |
| H1 | L1.64 | | | | | F96I | | | | | 1.80 |
| H1 | L1.67 | | | | | F96V | | | | | 1.73 |
| H1 | L1.68 | | | | | F96N | | | | | 2.12 |
| H1 | L1.8 | | | | | S52K | | | | | 2.18 |
| H1 | L1.80 | | | | | Y34F | | | | | 1.62 |
| H1 | L1.9 | | | | | S52L | | | | | 1.84 |
| H1 | L1.92 | | | | | A55L | | | | | 1.54 |
| H1 | L1.96 | | | | | A55N | | | | | 1.58 |

Proliferation of purified B cells at varying concentration of anti-mu after 3 days Viability of purified B cells after 3 days in the presence of anti-CD19 antibodies with fixed amount (2 mg/ml) anti-mu as co-stimulator

SEQUENCE LISTING

<160> NUMBER OF SEQ ID NOS: 147

<210> SEQ ID NO 1
<211> LENGTH: 556
<212> TYPE: PRT
<213> ORGANISM: Homo sapiens

<400> SEQUENCE: 1

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320
```

```
Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400

Pro Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
        435                 440                 445

Pro Glu Asp Glu Asp Ser Phe Ser Asn Ala Glu Ser Tyr Glu Asn Glu
    450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
        515                 520                 525

Asp Ser Tyr Glu Asn Met Asp Asn Pro Asp Gly Pro Asp Pro Ala Trp
    530                 535                 540

Gly Gly Gly Gly Arg Met Gly Thr Trp Ser Thr Arg
545                 550                 555

<210> SEQ ID NO 2
<211> LENGTH: 107
<212> TYPE: PRT
<213> ORGANISM: Homo sapiens

<400> SEQUENCE: 2

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 3
<211> LENGTH: 330
<212> TYPE: PRT
<213> ORGANISM: Homo sapiens
```

<400> SEQUENCE: 3

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 4
<211> LENGTH: 326
<212> TYPE: PRT
<213> ORGANISM: Homo sapiens

<400> SEQUENCE: 4

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

-continued

```
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 5
<211> LENGTH: 377
<212> TYPE: PRT
<213> ORGANISM: Homo sapiens

<400> SEQUENCE: 5

Ala Ser Thr Lys Gly Pro Ser Val Phe Pro Leu Ala Pro Cys Ser Arg
1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
```

```
            65                  70                  75                  80
Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 6
<211> LENGTH: 327
<212> TYPE: PRT
<213> ORGANISM: Homo sapiens

<400> SEQUENCE: 6

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60
```

```
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 7
<211> LENGTH: 330
<212> TYPE: PRT
<213> ORGANISM: Artificial Sequence
<220> FEATURE:
<223> OTHER INFORMATION: Hybrid constant heavy chain (CH)

<400> SEQUENCE: 7

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95
```

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Val
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Thr Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Met Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 8
<211> LENGTH: 330
<212> TYPE: PRT
<213> ORGANISM: Artificial Sequence
<220> FEATURE:
<223> OTHER INFORMATION: Hybrid constant heavy chain (CH) with 239D and
      332E substitutions

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
            115                 120                 125
```

Lys Pro Lys Asp Thr Leu Met Ile Ser Arg Thr Pro Glu Val Thr Cys
            130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Val
            180                 185                 190

His Gln Asp Trp Leu Asn Gly Lys Glu Tyr Lys Cys Lys Val Ser Asn
        195                 200                 205

Lys Ala Leu Pro Ala Pro Glu Glu Lys Thr Ile Ser Lys Thr Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Met Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 9
<211> LENGTH: 121
<212> TYPE: PRT
<213> ORGANISM: Mus musculus

<400> SEQUENCE: 9

Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Thr Tyr Tyr Tyr Gly Ser Arg Val Phe Ala Tyr Trp Gly
            100                 105                 110

Gln Gly Thr Thr Leu Thr Val Ser Ser
        115                 120

<210> SEQ ID NO 10
<211> LENGTH: 112
<212> TYPE: PRT
<213> ORGANISM: Mus musculus

<400> SEQUENCE: 10

Asp Ile Val Met Thr Gln Ala Ala Pro Ser Ile Pro Val Thr Pro Gly
1               5                   10                  15

Glu Ser Val Ser Ile Ser Cys Arg Ser Ser Lys Ser Leu Leu Asn Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Leu Lys
            100                 105                 110

<210> SEQ ID NO 11
<211> LENGTH: 124
<212> TYPE: PRT
<213> ORGANISM: Mus musculus

<400> SEQUENCE: 11

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
                20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Ser Val Thr Val Ser Ser
            115                 120

<210> SEQ ID NO 12
<211> LENGTH: 111
<212> TYPE: PRT
<213> ORGANISM: Mus musculus

<400> SEQUENCE: 12

Asp Ile Leu Leu Thr Gln Thr Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

-continued

Glu Asp Pro Trp Thr Phe Gly Gly Gly Thr Lys Leu Glu Ile Lys
            100                 105                 110

<210> SEQ ID NO 13
<211> LENGTH: 121
<212> TYPE: PRT
<213> ORGANISM: Artificial Sequence
<220> FEATURE:
<223> OTHER INFORMATION: H1 4G7

<400> SEQUENCE: 13

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Ser Arg Val Phe Asp Tyr Trp Gly
            100                 105                 110

Gln Gly Thr Leu Val Thr Val Ser Ser
        115                 120

<210> SEQ ID NO 14
<211> LENGTH: 121
<212> TYPE: PRT
<213> ORGANISM: Artificial Sequence
<220> FEATURE:
<223> OTHER INFORMATION: H2 4G7

<400> SEQUENCE: 14

Gln Val Gln Leu Gln Glu Ser Gly Ser Gly Leu Val Lys Pro Gly Gly
1               5                   10                  15

Ser Leu Arg Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Met
        35                  40                  45

Gly Tyr Ile Asn Pro Tyr Asn Asp Gly Thr Lys Tyr Asn Glu Ser Leu
    50                  55                  60

Lys Ser Arg Val Thr Ile Ser Ser Asp Lys Ser Ile Ser Thr Ala Tyr
65                  70                  75                  80

Met Glu Leu Ser Ser Leu Arg Ala Glu Asp Thr Ala Val Tyr Tyr Cys
                85                  90                  95

Ala Arg Gly Thr Tyr Tyr Tyr Gly Ser Arg Val Phe Asp Tyr Trp Gly
            100                 105                 110

Gln Gly Thr Leu Val Thr Val Ser Ser
        115                 120

<210> SEQ ID NO 15
<211> LENGTH: 121
<212> TYPE: PRT
<213> ORGANISM: Artificial Sequence
<220> FEATURE:
<223> OTHER INFORMATION: H3 4G7

```
<400> SEQUENCE: 15

Glu Val Gln Leu Val Glu Ser Gly Gly Leu Val Gln Pro Gly Arg
1               5                   10                  15

Ser Leu Arg Leu Ser Cys Ala Ala Ser Gly Tyr Thr Phe Thr Ser Tyr
            20                  25                  30

Val Met His Trp Val Arg Gln Met Pro Gly Lys Gly Leu Glu Trp Met
        35                  40                  45

Gly Tyr Ile Asn Pro Tyr Asn Asp Gly Thr Lys Tyr Asn Glu Lys Phe
    50                  55                  60

Gln Gly Arg Val Thr Ile Thr Ser Asp Lys Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Thr Tyr Tyr Tyr Gly Ser Arg Val Phe Asp Tyr Trp Gly
            100                 105                 110

Gln Gly Thr Leu Val Thr Val Ser Ser
        115                 120

<210> SEQ ID NO 16
<211> LENGTH: 121
<212> TYPE: PRT
<213> ORGANISM: Artificial Sequence
<220> FEATURE:
<223> OTHER INFORMATION: H4 4G7

<400> SEQUENCE: 16

Glu Val Gln Leu Gln Gln Ser Gly Pro Glu Val Lys Lys Pro Gly Thr
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Lys Gly Leu Val Trp Val
        35                  40                  45

Ser Tyr Ile Asn Pro Tyr Asn Asp Gly Thr Lys Tyr Asn Glu Ser Leu
    50                  55                  60

Lys Ser Arg Val Thr Ile Ser Ser Asp Lys Ser Ile Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Thr Tyr Tyr Tyr Gly Ser Arg Val Phe Asp Tyr Trp Gly
            100                 105                 110

Gln Gly Thr Leu Val Thr Val Ser Ser
        115                 120

<210> SEQ ID NO 17
<211> LENGTH: 112
<212> TYPE: PRT
<213> ORGANISM: Artificial Sequence
<220> FEATURE:
<223> OTHER INFORMATION: L1 4G7

<400> SEQUENCE: 17

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Ser
            20                  25                  30

Asn Gly Asn Thr Tyr Leu Tyr Trp Phe Gln Gln Lys Pro Gly Gln Ser
        35                  40                  45
```

```
Pro Gln Leu Leu Ile Tyr Arg Met Ser Asn Leu Ala Ser Gly Val Pro
        50                  55                  60

Asp Arg Phe Ser Gly Ser Gly Ser Gly Thr Glu Phe Thr Leu Thr Ile
 65                  70                  75                  80

Ser Ser Leu Glu Pro Glu Asp Phe Ala Val Tyr Tyr Cys Met Gln His
                 85                  90                  95

Leu Glu Tyr Pro Phe Thr Phe Gly Ala Gly Thr Lys Leu Glu Ile Lys
                100                 105                 110
```

<210> SEQ ID NO 18
<211> LENGTH: 112
<212> TYPE: PRT
<213> ORGANISM: Artificial Sequence
<220> FEATURE:
<223> OTHER INFORMATION: L2 4G7

<400> SEQUENCE: 18

```
Asp Ile Val Met Thr Gln Ser Pro Ser Ser Leu Ser Ala Ser Val Gly
 1               5                  10                  15

Asp Arg Val Thr Ile Ser Cys Arg Ser Ser Lys Ser Leu Leu Asn Ser
                20                  25                  30

Asn Gly Asn Thr Tyr Leu Tyr Trp Phe Gln Gln Lys Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Glu Phe Thr Leu Thr Ile
 65                  70                  75                  80

Ser Ser Leu Gln Pro Glu Asp Val Ala Val Tyr Tyr Cys Met Gln His
                 85                  90                  95

Leu Glu Tyr Pro Phe Thr Phe Gly Ala Gly Thr Lys Leu Glu Ile Lys
                100                 105                 110
```

<210> SEQ ID NO 19
<211> LENGTH: 112
<212> TYPE: PRT
<213> ORGANISM: Artificial Sequence
<220> FEATURE:
<223> OTHER INFORMATION: L3 4G7

<400> SEQUENCE: 19

```
Asp Ile Val Met Thr Gln Ser Pro Ala Thr Leu Ser Val Ser Pro Gly
 1               5                  10                  15

Glu Arg Ala Thr Ile Ser Cys Arg Ser Ser Lys Ser Leu Leu Asn Ser
                20                  25                  30

Asn Gly Asn Thr Tyr Leu Tyr Trp Phe Leu Gln Lys Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Asp Phe Thr Leu Thr Ile
 65                  70                  75                  80

Ser Arg Val Glu Ala Glu Asp Val Gly Val Tyr Tyr Cys Met Gln His
                 85                  90                  95

Leu Glu Tyr Pro Phe Thr Phe Gly Ala Gly Thr Lys Leu Glu Ile Lys
                100                 105                 110
```

<210> SEQ ID NO 20
<211> LENGTH: 124
<212> TYPE: PRT

<213> ORGANISM: Artificial Sequence
<220> FEATURE:
<223> OTHER INFORMATION: H1 HD37

<400> SEQUENCE: 20

Thr Val Gln Leu Val Glu Ser Gly Gly Gly Val Val Arg Pro Gly
1               5                   10                  15

Ser Leu Arg Leu Ser Cys Ala Ala Ser Gly Tyr Ala Phe Ser Ser Tyr
            20                  25                  30

Trp Met Asn Trp Val Arg Gln Ala Pro Gly Lys Gly Leu Glu Trp Ile
        35                  40                  45

Gly Gln Ile Trp Pro Gly Asp Gly Asp Thr Asn Tyr Asn Gly Lys Phe
    50                  55                  60

Gln Asp Arg Val Thr Ile Thr Ala Asp Glu Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Leu Val Thr Val Ser Ser
        115                 120

<210> SEQ ID NO 21
<211> LENGTH: 124
<212> TYPE: PRT
<213> ORGANISM: Artificial Sequence
<220> FEATURE:
<223> OTHER INFORMATION: H2 HD37

<400> SEQUENCE: 21

Gln Val Gln Leu Val Glu Ser Gly Gly Gly Leu Val Glu Pro Gly Gly
1               5                   10                  15

Ser Leu Arg Leu Ser Cys Ala Ala Ser Gly Tyr Ala Phe Ser Ser Tyr
            20                  25                  30

Trp Met Asn Trp Val Arg Gln Met Pro Gly Lys Gly Leu Glu Trp Met
        35                  40                  45

Gly Gln Ile Trp Pro Gly Asp Gly Asp Thr Asn Tyr Asn Pro Ser Leu
    50                  55                  60

Lys Ser Arg Val Thr Ile Thr Ala Asp Glu Ser Thr Ser Thr Ala Tyr
65                  70                  75                  80

Met Glu Leu Ser Ser Leu Lys Ala Glu Asp Thr Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Leu Val Thr Val Ser Ser
        115                 120

<210> SEQ ID NO 22
<211> LENGTH: 124
<212> TYPE: PRT
<213> ORGANISM: Artificial Sequence
<220> FEATURE:
<223> OTHER INFORMATION: H3 HD37

<400> SEQUENCE: 22

Gln Val Gln Leu Gln Glu Ser Gly Pro Gly Leu Val Lys Pro Ser Gln
1               5                   10                  15

Thr Leu Ser Leu Thr Cys Ala Ala Ser Gly Tyr Ala Phe Ser Ser Tyr
            20                  25                  30

Trp Met Asn Trp Val Arg Gln Ala Pro Gly Lys Gly Leu Glu Trp Met
            35                  40                  45

Gly Gln Ile Trp Pro Gly Asp Gly Asp Thr Asn Tyr Asn Gly Ala Leu
        50                  55                  60

Lys Ser Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Leu Val Thr Val Ser Ser
        115                 120

<210> SEQ ID NO 23
<211> LENGTH: 124
<212> TYPE: PRT
<213> ORGANISM: Artificial Sequence
<220> FEATURE:
<223> OTHER INFORMATION: H4 HD37

<400> SEQUENCE: 23

Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Ala Phe Ser Ser Tyr
            20                  25                  30

Trp Met Asn Trp Val Arg Gln Ala Pro Gly Lys Gly Leu Glu Trp Val
            35                  40                  45

Ala Gln Ile Trp Pro Gly Asp Gly Asp Thr Asn Tyr Ala Asp Ser Val
        50                  55                  60

Lys Gly Arg Phe Thr Ile Thr Ala Asp Glu Ser Thr Ser Thr Ala Tyr
65                  70                  75                  80

Leu Gln Met Asn Ser Leu Arg Ala Gly Asp Thr Ala Met Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Leu Val Thr Val Ser Ser
        115                 120

<210> SEQ ID NO 24
<211> LENGTH: 111
<212> TYPE: PRT
<213> ORGANISM: Artificial Sequence
<220> FEATURE:
<223> OTHER INFORMATION: L1 HD37

<400> SEQUENCE: 24

Asp Ile Leu Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Tyr Asp
            20                  25                  30

Gly Asp Ser Tyr Leu Asn Trp Tyr Gln Gln Lys Pro Gly Gln Pro Pro
        35                  40                  45

Lys Leu Leu Ile Tyr Asp Ala Ser Asn Leu Val Ser Gly Ile Pro Pro
        50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr His Cys Gln Gln Ser Thr

```
                    85                  90                  95
Glu Asp Pro Trp Thr Phe Gly Gly Gly Thr Lys Leu Glu Ile Lys
            100                 105                 110

<210> SEQ ID NO 25
<211> LENGTH: 111
<212> TYPE: PRT
<213> ORGANISM: Artificial Sequence
<220> FEATURE:
<223> OTHER INFORMATION: L2 HD37

<400> SEQUENCE: 25

Asp Ile Leu Leu Thr Gln Ser Pro Ser Ser Leu Ser Val Thr Pro Gly
1               5                   10                  15

Glu Lys Val Thr Ile Thr Cys Arg Ala Ser Gln Ser Val Asp Tyr Asp
            20                  25                  30

Gly Asp Ser Tyr Leu Asn Trp Tyr Gln Gln Lys Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 26
<211> LENGTH: 111
<212> TYPE: PRT
<213> ORGANISM: Artificial Sequence
<220> FEATURE:
<223> OTHER INFORMATION: L3 HD37

<400> SEQUENCE: 26

Asp Ile Leu Leu Thr Gln Thr Pro Leu Ser Leu Pro Val Thr Pro Gly
1               5                   10                  15

Glu Pro Ala Ser Ile Ser Cys Arg Ala Ser Gln Ser Val Asp Tyr Asp
            20                  25                  30

Gly Asp Ser Tyr Leu Asn Trp Tyr Gln Gln Lys Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 27
<211> LENGTH: 121
<212> TYPE: PRT
<213> ORGANISM: Artificial Sequence
<220> FEATURE:
<223> OTHER INFORMATION: 4G7 H1.109

<400> SEQUENCE: 27

Glu Val Gln Leu Val Glu Ser Gly Gly Gly Leu Val Lys Pro Gly Gly
1               5                   10                  15
```

-continued

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
            35                  40                  45

Gly Tyr Ile Asn Pro Tyr Asn Asp Gly Pro Lys Tyr Asn Glu Lys Phe
        50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Gly Ser Arg Val Phe Asp Tyr Trp Gly
            100                 105                 110

Gln Gly Thr Leu Val Thr Val Ser Ser
            115                 120

<210> SEQ ID NO 28
<211> LENGTH: 121
<212> TYPE: PRT
<213> ORGANISM: Artificial Sequence
<220> FEATURE:
<223> OTHER INFORMATION: 4G7 H1.113

<400> SEQUENCE: 28

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
            35                  40                  45

Gly Tyr Ile Asn Pro Tyr Asn Asp Gly His Lys Tyr Asn Glu Lys Phe
        50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Gly Ser Arg Val Phe Asp Tyr Trp Gly
            100                 105                 110

Gln Gly Thr Leu Val Thr Val Ser Ser
            115                 120

<210> SEQ ID NO 29
<211> LENGTH: 121
<212> TYPE: PRT
<213> ORGANISM: Artificial Sequence
<220> FEATURE:
<223> OTHER INFORMATION: 4G7 H1.144

<400> SEQUENCE: 29

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
            35                  40                  45

Gly Tyr Ile Asn Pro Tyr Asn Asp Gly Thr Lys Tyr Asn Glu Lys Phe
        50                  55                  60

Gln Gly Arg Val Thr Ile Ser Ser Asp Lys Ser Ile Ser Thr Ala Tyr

```
                65                  70                  75                  80
Met Glu Leu Ser Ser Leu Arg Ser Glu Asp Thr Ala Met Tyr Tyr Cys
                    85                  90                  95

Ala Arg Gly Thr Tyr Tyr Tyr Gly Ser Arg Val Phe Asn Tyr Trp Gly
                100                 105                 110

Gln Gly Thr Leu Val Thr Val Ser Ser
                115                 120
```

<210> SEQ ID NO 30
<211> LENGTH: 121
<212> TYPE: PRT
<213> ORGANISM: Artificial Sequence
<220> FEATURE:
<223> OTHER INFORMATION: 4G7 H1.146

<400> SEQUENCE: 30

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
                20                  25                  30

Val Met His Trp Val Arg Gln Ala Pro Gly Lys Gly Leu Glu Trp Ile
            35                  40                  45

Gly Tyr Ile Asn Pro Tyr Asn Asp Gly Thr Lys Tyr Asn Glu Lys Phe
        50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                    85                  90                  95

Ala Arg Gly Thr Tyr Tyr Tyr Gly Ser Arg Val Phe His Tyr Trp Gly
                100                 105                 110

Gln Gly Thr Leu Val Thr Val Ser Ser
                115                 120
```

<210> SEQ ID NO 31
<211> LENGTH: 121
<212> TYPE: PRT
<213> ORGANISM: Artificial Sequence
<220> FEATURE:
<223> OTHER INFORMATION: 4G7 H1.147

<400> SEQUENCE: 31

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
                20                  25                  30

Val Met His Trp Val Arg Gln Ala Pro Gly Lys Gly Leu Glu Trp Ile
            35                  40                  45

Gly Tyr Ile Asn Pro Tyr Asn Asp Gly Thr Lys Tyr Asn Glu Lys Phe
        50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                    85                  90                  95

Ala Arg Gly Thr Tyr Tyr Tyr Gly Ser Arg Val Phe Ser Tyr Trp Gly
                100                 105                 110

Gln Gly Thr Leu Val Thr Val Ser Ser
                115                 120
```

```
<210> SEQ ID NO 32
<211> LENGTH: 121
<212> TYPE: PRT
<213> ORGANISM: Artificial Sequence
<220> FEATURE:
<223> OTHER INFORMATION: 4G7 H1.191

<400> SEQUENCE: 32

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Glu Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
            100                 105                 110

Gln Gly Thr Leu Val Thr Val Ser Ser
        115                 120

<210> SEQ ID NO 33
<211> LENGTH: 121
<212> TYPE: PRT
<213> ORGANISM: Artificial Sequence
<220> FEATURE:
<223> OTHER INFORMATION: 4G7 H1.192

<400> SEQUENCE: 33

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Pro Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
            100                 105                 110

Gln Gly Thr Leu Val Thr Val Ser Ser
        115                 120

<210> SEQ ID NO 34
<211> LENGTH: 121
<212> TYPE: PRT
<213> ORGANISM: Artificial Sequence
<220> FEATURE:
<223> OTHER INFORMATION: 4G7 H1.196

<400> SEQUENCE: 34

Glu Val Gln Leu Val Glu Ser Gly Gly Gly Leu Val Lys Pro Gly Gly
```

```
1               5                   10                  15
Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
            35                  40                  45

Gly Tyr Ile Asn Pro Tyr Asn Asp Gly Pro Lys Tyr Asn Glu Lys Phe
            50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
            85                  90                  95

Ala Arg Gly Thr Tyr Tyr Tyr Gly Thr Ser Val Phe Asp Tyr Trp Gly
            100                 105                 110

Gln Gly Thr Leu Val Thr Val Ser Ser
            115                 120
```

<210> SEQ ID NO 35
<211> LENGTH: 121
<212> TYPE: PRT
<213> ORGANISM: Artificial Sequence
<220> FEATURE:
<223> OTHER INFORMATION: 4G7 H1.199

<400> SEQUENCE: 35

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
            35                  40                  45

Gly Tyr Ile Asn Pro Tyr Asn Asp Gly Pro Glu Tyr Asn Glu Lys Phe
            50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
            85                  90                  95

Ala Arg Gly Thr Tyr Tyr Tyr Gly Thr Arg Val Phe Asp Tyr Trp Gly
            100                 105                 110

Gln Gly Thr Leu Val Thr Val Ser Ser
            115                 120
```

<210> SEQ ID NO 36
<211> LENGTH: 121
<212> TYPE: PRT
<213> ORGANISM: Artificial Sequence
<220> FEATURE:
<223> OTHER INFORMATION: 4G7 H1.201

<400> SEQUENCE: 36

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
            35                  40                  45

Gly Tyr Ile Asn Pro Tyr Asn Ser Gly Thr Lys Tyr Asn Glu Lys Phe
            50                  55                  60
```

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
                100                 105                 110

Gln Gly Thr Leu Val Thr Val Ser Ser
            115                 120

<210> SEQ ID NO 37
<211> LENGTH: 121
<212> TYPE: PRT
<213> ORGANISM: Artificial Sequence
<220> FEATURE:
<223> OTHER INFORMATION: 4G7 H1.202

<400> SEQUENCE: 37

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
                20                  25                  30

Val Met His Trp Val Arg Gln Ala Pro Gly Lys Gly Leu Glu Trp Ile
            35                  40                  45

Gly Tyr Ile Asn Pro Tyr Asn Glu Gly Thr Lys Tyr Asn Glu Lys Phe
50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
                100                 105                 110

Gln Gly Thr Leu Val Thr Val Ser Ser
            115                 120

<210> SEQ ID NO 38
<211> LENGTH: 121
<212> TYPE: PRT
<213> ORGANISM: Artificial Sequence
<220> FEATURE:
<223> OTHER INFORMATION: 4G7 H1.203

<400> SEQUENCE: 38

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
                20                  25                  30

Val Met His Trp Val Arg Gln Ala Pro Gly Lys Gly Leu Glu Trp Ile
            35                  40                  45

Gly Tyr Ile Asn Pro Tyr Asn Ser Gly Thr Glu Tyr Asn Glu Lys Phe
50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
                100                 105                 110

Gln Gly Thr Leu Val Thr Val Ser Ser
            115                 120

<210> SEQ ID NO 39
<211> LENGTH: 121
<212> TYPE: PRT
<213> ORGANISM: Artificial Sequence
<220> FEATURE:
<223> OTHER INFORMATION: 4G7 H1.204

<400> SEQUENCE: 39

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Glu Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
            100                 105                 110

Gln Gly Thr Leu Val Thr Val Ser Ser
        115                 120
```

<210> SEQ ID NO 40
<211> LENGTH: 121
<212> TYPE: PRT
<213> ORGANISM: Artificial Sequence
<220> FEATURE:
<223> OTHER INFORMATION: 4G7 H1.52

<400> SEQUENCE: 40

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
            100                 105                 110

Gln Gly Thr Leu Val Thr Val Ser Ser
        115                 120
```

<210> SEQ ID NO 41
<211> LENGTH: 121
<212> TYPE: PRT
<213> ORGANISM: Artificial Sequence
<220> FEATURE:
<223> OTHER INFORMATION: 4G7 H1.60

<400> SEQUENCE: 41

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Leu Arg Val Phe Asp Tyr Trp Gly
            100                 105                 110

Gln Gly Thr Leu Val Thr Val Ser Ser
            115                 120

<210> SEQ ID NO 42
<211> LENGTH: 121
<212> TYPE: PRT
<213> ORGANISM: Artificial Sequence
<220> FEATURE:
<223> OTHER INFORMATION: 4G7 H1.62

<400> SEQUENCE: 42

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Ser Glu Val Phe Asp Tyr Trp Gly
            100                 105                 110

Gln Gly Thr Leu Val Thr Val Ser Ser
            115                 120

<210> SEQ ID NO 43
<211> LENGTH: 121
<212> TYPE: PRT
<213> ORGANISM: Artificial Sequence
<220> FEATURE:
<223> OTHER INFORMATION: 4G7 H1.65

<400> SEQUENCE: 43

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Ser Ser Val Phe Asp Tyr Trp Gly
            100                 105                 110

Gln Gly Thr Leu Val Thr Val Ser Ser
            115                 120

<210> SEQ ID NO 44
<211> LENGTH: 121
<212> TYPE: PRT
<213> ORGANISM: Artificial Sequence
<220> FEATURE:
<223> OTHER INFORMATION: 4G7 H1.78

<400> SEQUENCE: 44

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
                20                  25                  30

Val Met His Trp Val Arg Gln Ala Pro Gly Lys Gly Leu Glu Trp Ile
            35                  40                  45

Gly Tyr Ile Asn Pro Tyr Asn Ala Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Ser Arg Val Phe Asp Tyr Trp Gly
            100                 105                 110

Gln Gly Thr Leu Val Thr Val Ser Ser
            115                 120

<210> SEQ ID NO 45
<211> LENGTH: 112
<212> TYPE: PRT
<213> ORGANISM: Artificial Sequence
<220> FEATURE:
<223> OTHER INFORMATION: 4G7 L1.11

<400> SEQUENCE: 45

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Ser
                20                  25                  30

Asn Gly Asn Thr Tyr Leu Tyr Trp Phe Gln Gln Lys Pro Gly Gln Ser
            35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Asn Tyr Pro Phe Thr Phe Gly Ala Gly Thr Lys Leu Glu Ile Lys
            100                 105                 110

<210> SEQ ID NO 46
<211> LENGTH: 112
<212> TYPE: PRT
<213> ORGANISM: Artificial Sequence
<220> FEATURE:
<223> OTHER INFORMATION: 4G7 L1.124

<400> SEQUENCE: 46

```
Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Ser
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Trp Ala Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Phe Thr Phe Gly Ala Gly Thr Lys Leu Glu Ile Lys
            100                 105                 110
```

<210> SEQ ID NO 47
<211> LENGTH: 112
<212> TYPE: PRT
<213> ORGANISM: Artificial Sequence
<220> FEATURE:
<223> OTHER INFORMATION: 4G7 L1.138

<400> SEQUENCE: 47

```
Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Phe Thr Phe Gly Ala Gly Thr Lys Leu Glu Ile Lys
            100                 105                 110
```

<210> SEQ ID NO 48
<211> LENGTH: 112
<212> TYPE: PRT
<213> ORGANISM: Artificial Sequence
<220> FEATURE:
<223> OTHER INFORMATION: 4G7 L1.139

<400> SEQUENCE: 48

```
Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Val
            20                  25                  30

Asn Gly Asn Thr Tyr Leu Tyr Trp Phe Gln Gln Lys Pro Gly Gln Ser
        35                  40                  45
```

```
Pro Gln Leu Leu Ile Tyr Arg Met Ser Asn Leu Ala Ser Gly Val Pro
        50                  55                  60

Asp Arg Phe Ser Gly Ser Gly Ser Gly Thr Glu Phe Thr Leu Thr Ile
 65                  70                  75                  80

Ser Ser Leu Glu Pro Glu Asp Phe Ala Val Tyr Tyr Cys Met Gln His
                 85                  90                  95

Leu Glu Tyr Pro Asn Thr Phe Gly Ala Gly Thr Lys Leu Glu Ile Lys
            100                 105                 110
```

<210> SEQ ID NO 49
<211> LENGTH: 112
<212> TYPE: PRT
<213> ORGANISM: Artificial Sequence
<220> FEATURE:
<223> OTHER INFORMATION: 4G7 L1.141

<400> SEQUENCE: 49

```
Asp Ile Val Met Thr Gln Ser Pro Ala Thr Leu Ser Leu Ser Pro Gly
 1               5                  10                  15

Glu Arg Ala Thr Leu Ser Cys Arg Ser Ser Lys Ser Leu Leu Asn Ser
             20                  25                  30

Asn Gly Asn Thr Tyr Leu Tyr Trp Phe Gln Gln Lys Pro Gly Gln Ser
         35                  40                  45

Pro Gln Leu Leu Ile Tyr Arg Met Ser Asn Leu Asn Ser Gly Val Pro
        50                  55                  60

Asp Arg Phe Ser Gly Ser Gly Ser Gly Thr Glu Phe Thr Leu Thr Ile
 65                  70                  75                  80

Ser Ser Leu Glu Pro Glu Asp Phe Ala Val Tyr Tyr Cys Met Gln His
                 85                  90                  95

Leu Glu Tyr Pro Asn Thr Phe Gly Ala Gly Thr Lys Leu Glu Ile Lys
            100                 105                 110
```

<210> SEQ ID NO 50
<211> LENGTH: 112
<212> TYPE: PRT
<213> ORGANISM: Artificial Sequence
<220> FEATURE:
<223> OTHER INFORMATION: 4G7 L1.143

<400> SEQUENCE: 50

```
Asp Ile Val Met Thr Gln Ser Pro Ala Thr Leu Ser Leu Ser Pro Gly
 1               5                  10                  15

Glu Arg Ala Thr Leu Ser Cys Arg Ser Ser Lys Ser Leu Gln Asn Ser
             20                  25                  30

Asn Gly Asn Thr Tyr Leu Tyr Trp Phe Gln Gln Lys Pro Gly Gln Ser
         35                  40                  45

Pro Gln Leu Leu Ile Tyr Arg Met Ser Asn Leu Asn Ser Gly Val Pro
        50                  55                  60

Asp Arg Phe Ser Gly Ser Gly Ser Gly Thr Glu Phe Thr Leu Thr Ile
 65                  70                  75                  80

Ser Ser Leu Glu Pro Glu Asp Phe Ala Val Tyr Tyr Cys Met Gln His
                 85                  90                  95

Leu Glu Tyr Pro Phe Thr Phe Gly Ala Gly Thr Lys Leu Glu Ile Lys
            100                 105                 110
```

<210> SEQ ID NO 51
<211> LENGTH: 112
<212> TYPE: PRT

```
<213> ORGANISM: Artificial Sequence
<220> FEATURE:
<223> OTHER INFORMATION: 4G7 L1.144

<400> SEQUENCE: 51

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Ser
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Asn Thr Phe Gly Ala Gly Thr Lys Leu Glu Ile Lys
            100                 105                 110

<210> SEQ ID NO 52
<211> LENGTH: 112
<212> TYPE: PRT
<213> ORGANISM: Artificial Sequence
<220> FEATURE:
<223> OTHER INFORMATION: 4G7 L1.145

<400> SEQUENCE: 52

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Ser
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110

<210> SEQ ID NO 53
<211> LENGTH: 112
<212> TYPE: PRT
<213> ORGANISM: Artificial Sequence
<220> FEATURE:
<223> OTHER INFORMATION: 4G7 L1.146

<400> SEQUENCE: 53

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60
```

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Asn Thr Phe Gly Ala Gly Thr Lys Leu Glu Ile Lys
            100                 105                 110

<210> SEQ ID NO 54
<211> LENGTH: 112
<212> TYPE: PRT
<213> ORGANISM: Artificial Sequence
<220> FEATURE:
<223> OTHER INFORMATION: 4G7 L1.148

<400> SEQUENCE: 54

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Ser
                20                  25                  30

Asn Gly Asn Thr Tyr Leu Tyr Trp Phe Gln Gln Lys Pro Gly Gln Ser
            35                  40                  45

Pro Gln Leu Leu Ile Tyr Arg Met Ser Asn Leu Asn Ser Gly Val Pro
        50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Asn Thr Phe Gly Ala Gly Thr Lys Leu Glu Ile Lys
            100                 105                 110

<210> SEQ ID NO 55
<211> LENGTH: 112
<212> TYPE: PRT
<213> ORGANISM: Artificial Sequence
<220> FEATURE:
<223> OTHER INFORMATION: 4G7 L1.149

<400> SEQUENCE: 55

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Ser
                20                  25                  30

Asn Gly Asn Thr Tyr Leu Tyr Trp Phe Gln Gln Lys Pro Gly Gln Ser
            35                  40                  45

Pro Gln Leu Leu Ile Tyr Arg Met Ser Asn Leu Asn Ser Gly Val Pro
        50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110

<210> SEQ ID NO 56
<211> LENGTH: 112
<212> TYPE: PRT
<213> ORGANISM: Artificial Sequence
<220> FEATURE:
<223> OTHER INFORMATION: 4G7 L1.152

<400> SEQUENCE: 56

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Asn Thr Phe Gly Ala Gly Thr Lys Leu Glu Ile Lys
            100                 105                 110

<210> SEQ ID NO 57
<211> LENGTH: 112
<212> TYPE: PRT
<213> ORGANISM: Artificial Sequence
<220> FEATURE:
<223> OTHER INFORMATION: 4G7 L1.154

<400> SEQUENCE: 57

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Asn Thr Phe Gly Ala Gly Thr Lys Leu Glu Ile Lys
            100                 105                 110

<210> SEQ ID NO 58
<211> LENGTH: 112
<212> TYPE: PRT
<213> ORGANISM: Artificial Sequence
<220> FEATURE:
<223> OTHER INFORMATION: 4G7 L1.155

<400> SEQUENCE: 58

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

```
Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110
```

<210> SEQ ID NO 59
<211> LENGTH: 112
<212> TYPE: PRT
<213> ORGANISM: Artificial Sequence
<220> FEATURE:
<223> OTHER INFORMATION: 4G7 L1.160

<400> SEQUENCE: 59

```
Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Ala Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110
```

<210> SEQ ID NO 60
<211> LENGTH: 112
<212> TYPE: PRT
<213> ORGANISM: Artificial Sequence
<220> FEATURE:
<223> OTHER INFORMATION: 4G7 L1.161

<400> SEQUENCE: 60

```
Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Ser Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110
```

<210> SEQ ID NO 61
<211> LENGTH: 112
<212> TYPE: PRT
<213> ORGANISM: Artificial Sequence
<220> FEATURE:
<223> OTHER INFORMATION: 4G7 L1.162

<400> SEQUENCE: 61

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Ala
            20                  25                  30

Asn Ala Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110

<210> SEQ ID NO 62
<211> LENGTH: 112
<212> TYPE: PRT
<213> ORGANISM: Artificial Sequence
<220> FEATURE:
<223> OTHER INFORMATION: 4G7 L1.163

<400> SEQUENCE: 62

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Ala
            20                  25                  30

Asn Ser Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110

<210> SEQ ID NO 63
<211> LENGTH: 112
<212> TYPE: PRT
<213> ORGANISM: Artificial Sequence
<220> FEATURE:
<223> OTHER INFORMATION: 4G7 L1.164

<400> SEQUENCE: 63

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Ala
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

```
Leu Glu Tyr Pro Ile Thr Phe Gly Ala Gly Thr Lys Leu Glu Ile Lys
                100                 105                 110
```

<210> SEQ ID NO 64
<211> LENGTH: 112
<212> TYPE: PRT
<213> ORGANISM: Artificial Sequence
<220> FEATURE:
<223> OTHER INFORMATION: 4G7 L1.17

<400> SEQUENCE: 64

```
Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Ser
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Thr Tyr Pro Phe Thr Phe Gly Ala Gly Thr Lys Leu Glu Ile Lys
                100                 105                 110
```

<210> SEQ ID NO 65
<211> LENGTH: 112
<212> TYPE: PRT
<213> ORGANISM: Artificial Sequence
<220> FEATURE:
<223> OTHER INFORMATION: 4G7 L1.19

<400> SEQUENCE: 65

```
Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Ser
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Tyr Tyr Pro Phe Thr Phe Gly Ala Gly Thr Lys Leu Glu Ile Lys
                100                 105                 110
```

<210> SEQ ID NO 66
<211> LENGTH: 112
<212> TYPE: PRT
<213> ORGANISM: Artificial Sequence
<220> FEATURE:
<223> OTHER INFORMATION: 4G7 L1.26

<400> SEQUENCE: 66

```
Asp Ile Val Met Thr Gln Ser Pro Ala Thr Leu Ser Leu Ser Pro Gly
1               5                   10                  15
```

-continued

Glu Arg Ala Thr Leu Ser Cys Arg Ser Ser Lys Ser Leu Gln Asn Ser
                20                  25                  30

Asn Gly Asn Thr Tyr Leu Tyr Trp Phe Gln Gln Lys Pro Gly Gln Ser
            35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Phe Thr Phe Gly Ala Gly Thr Lys Leu Glu Ile Lys
            100                 105                 110

<210> SEQ ID NO 67
<211> LENGTH: 112
<212> TYPE: PRT
<213> ORGANISM: Artificial Sequence
<220> FEATURE:
<223> OTHER INFORMATION: 4G7 L1.3

<400> SEQUENCE: 67

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Ser
                20                  25                  30

Asn Gly Asn Thr Tyr Leu Tyr Trp Phe Gln Gln Lys Pro Gly Gln Ser
            35                  40                  45

Pro Gln Leu Leu Ile Tyr Arg Met Gln Asn Leu Ala Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Phe Thr Phe Gly Ala Gly Thr Lys Leu Glu Ile Lys
            100                 105                 110

<210> SEQ ID NO 68
<211> LENGTH: 112
<212> TYPE: PRT
<213> ORGANISM: Artificial Sequence
<220> FEATURE:
<223> OTHER INFORMATION: 4G7 L1.32

<400> SEQUENCE: 68

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Val
                20                  25                  30

Asn Gly Asn Thr Tyr Leu Tyr Trp Phe Gln Gln Lys Pro Gly Gln Ser
            35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Phe Thr Phe Gly Ala Gly Thr Lys Leu Glu Ile Lys
            100                 105                 110

<210> SEQ ID NO 69
<211> LENGTH: 112
<212> TYPE: PRT
<213> ORGANISM: Artificial Sequence
<220> FEATURE:
<223> OTHER INFORMATION: 4G7 L1.46

<400> SEQUENCE: 69

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Ser
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser His Leu Ala Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Phe Thr Phe Gly Ala Gly Thr Lys Leu Glu Ile Lys
            100                 105                 110

<210> SEQ ID NO 70
<211> LENGTH: 112
<212> TYPE: PRT
<213> ORGANISM: Artificial Sequence
<220> FEATURE:
<223> OTHER INFORMATION: 4G7 L1.54

<400> SEQUENCE: 70

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Ser
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Gly Leu Ala Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Phe Thr Phe Gly Ala Gly Thr Lys Leu Glu Ile Lys
            100                 105                 110

<210> SEQ ID NO 71
<211> LENGTH: 112
<212> TYPE: PRT
<213> ORGANISM: Artificial Sequence
<220> FEATURE:
<223> OTHER INFORMATION: 4G7 L1.55

<400> SEQUENCE: 71

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Ser
            20                  25                  30

```
Asn Gly Asn Thr Tyr Leu Tyr Trp Phe Gln Gln Lys Pro Gly Gln Ser
            35                  40                  45

Pro Gln Leu Leu Ile Tyr Arg Met Ser Tyr Leu Ala Ser Gly Val Pro
        50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Phe Thr Phe Gly Ala Gly Thr Lys Leu Glu Ile Lys
            100                 105                 110
```

<210> SEQ ID NO 72
<211> LENGTH: 112
<212> TYPE: PRT
<213> ORGANISM: Artificial Sequence
<220> FEATURE:
<223> OTHER INFORMATION: 4G7 L1.64

<400> SEQUENCE: 72

```
Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Ser
            20                  25                  30

Asn Gly Asn Thr Tyr Leu Tyr Trp Phe Gln Gln Lys Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110
```

<210> SEQ ID NO 73
<211> LENGTH: 112
<212> TYPE: PRT
<213> ORGANISM: Artificial Sequence
<220> FEATURE:
<223> OTHER INFORMATION: 4G7 L1.67

<400> SEQUENCE: 73

```
Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Ser
            20                  25                  30

Asn Gly Asn Thr Tyr Leu Tyr Trp Phe Gln Gln Lys Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Val Thr Phe Gly Ala Gly Thr Lys Leu Glu Ile Lys
            100                 105                 110
```

<210> SEQ ID NO 74

```
<211> LENGTH: 112
<212> TYPE: PRT
<213> ORGANISM: Artificial Sequence
<220> FEATURE:
<223> OTHER INFORMATION: 4G7 L1.68

<400> SEQUENCE: 74

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Ser
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Asn Thr Phe Gly Ala Gly Thr Lys Leu Glu Ile Lys
            100                 105                 110

<210> SEQ ID NO 75
<211> LENGTH: 112
<212> TYPE: PRT
<213> ORGANISM: Artificial Sequence
<220> FEATURE:
<223> OTHER INFORMATION: 4G7 L1.8

<400> SEQUENCE: 75

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Ser
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Lys Asn Leu Ala Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Phe Thr Phe Gly Ala Gly Thr Lys Leu Glu Ile Lys
            100                 105                 110

<210> SEQ ID NO 76
<211> LENGTH: 112
<212> TYPE: PRT
<213> ORGANISM: Artificial Sequence
<220> FEATURE:
<223> OTHER INFORMATION: 4G7 L1.80

<400> SEQUENCE: 76

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Ser
            20                  25                  30

Asn Gly Asn Thr Tyr Leu Phe Trp Phe Gln Gln Lys Pro Gly Gln Ser
        35                  40                  45
```

```
Pro Gln Leu Leu Ile Tyr Arg Met Ser Asn Leu Ala Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Phe Thr Phe Gly Ala Gly Thr Lys Leu Glu Ile Lys
            100                 105                 110
```

<210> SEQ ID NO 77
<211> LENGTH: 112
<212> TYPE: PRT
<213> ORGANISM: Artificial Sequence
<220> FEATURE:
<223> OTHER INFORMATION: 4G7 L1.9

<400> SEQUENCE: 77

```
Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Ser
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Leu Asn Leu Ala Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Phe Thr Phe Gly Ala Gly Thr Lys Leu Glu Ile Lys
            100                 105                 110
```

<210> SEQ ID NO 78
<211> LENGTH: 112
<212> TYPE: PRT
<213> ORGANISM: Artificial Sequence
<220> FEATURE:
<223> OTHER INFORMATION: 4G7 L1.92

<400> SEQUENCE: 78

```
Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Ser
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Phe Thr Phe Gly Ala Gly Thr Lys Leu Glu Ile Lys
            100                 105                 110
```

<210> SEQ ID NO 79
<211> LENGTH: 112
<212> TYPE: PRT
<213> ORGANISM: Artificial Sequence

<220> FEATURE:
<223> OTHER INFORMATION: 4G7 L1.96

<400> SEQUENCE: 79

| | | | | | | | | | | | | | | |
|---|---|---|---|---|---|---|---|---|---|---|---|---|---|---|
| Asp | Ile | Val | Met | Thr | Gln | Ser | Pro | Ala | Thr | Leu | Ser | Leu | Ser | Pro | Gly |
| 1 | | | | 5 | | | | | 10 | | | | | 15 | |

Glu Arg Ala Thr Leu Ser Cys Arg Ser Ser Lys Ser Leu Leu Asn Ser
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Phe Thr Phe Gly Ala Gly Thr Lys Leu Glu Ile Lys
            100                 105                 110

<210> SEQ ID NO 80
<211> LENGTH: 330
<212> TYPE: PRT
<213> ORGANISM: Homo sapiens

<400> SEQUENCE: 80

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 81
<211> LENGTH: 330
<212> TYPE: PRT
<213> ORGANISM: Homo sapiens

<400> SEQUENCE: 81

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
    290                 295                 300

Val Phe Ser Cys Ser Val Met His Glu Gly Leu His Asn His Tyr Thr
305                 310                 315                 320

Gln Lys Ser Leu Ser Leu Ser Pro Gly Lys
                325                 330

<210> SEQ ID NO 82
<211> LENGTH: 330
<212> TYPE: PRT
<213> ORGANISM: Homo sapiens

<400> SEQUENCE: 82

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325
```

-continued

<210> SEQ ID NO 83
<211> LENGTH: 330
<212> TYPE: PRT
<213> ORGANISM: Homo sapiens

<400> SEQUENCE: 83

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 84
<211> LENGTH: 326
<212> TYPE: PRT
<213> ORGANISM: Homo sapiens

<400> SEQUENCE: 84

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 85
<211> LENGTH: 326
<212> TYPE: PRT
<213> ORGANISM: Homo sapiens

<400> SEQUENCE: 85

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Met Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
            210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 86
<211> LENGTH: 451
<212> TYPE: PRT
<213> ORGANISM: Artificial Sequence
<220> FEATURE:
<223> OTHER INFORMATION: 4G7 H1 Hybrid S239D/I332E

<400> SEQUENCE: 86

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
            85                  90                  95

Ala Arg Gly Thr Tyr Tyr Gly Ser Arg Val Phe Asp Tyr Trp Gly
        100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Asp Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
        290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Ala Leu Pro Ala Pro Glu
            325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 87
<211> LENGTH: 451
<212> TYPE: PRT

<213> ORGANISM: Artificial Sequence
<220> FEATURE:
<223> OTHER INFORMATION: 4G7 H1.52 Hybrid S239D/I332E

<400> SEQUENCE: 87

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Lys | Pro | Gly | Gly |
| 1 | | | | 5 | | | | | 10 | | | | | 15 | |
| Ser | Leu | Lys | Leu | Ser | Cys | Ala | Ala | Ser | Gly | Tyr | Thr | Phe | Thr | Ser | Tyr |
| | | | 20 | | | | | 25 | | | | | 30 | | |
| Val | Met | His | Trp | Val | Arg | Gln | Ala | Pro | Gly | Lys | Gly | Leu | Glu | Trp | Ile |
| | | 35 | | | | | 40 | | | | | 45 | | | |
| Gly | Tyr | Ile | Asn | Pro | Tyr | Asn | Asp | Gly | Thr | Lys | Tyr | Asn | Glu | Lys | Phe |
| | 50 | | | | | 55 | | | | | 60 | | | | |
| Gln | Gly | Arg | Val | Thr | Ile | Ser | Ser | Asp | Lys | Ser | Ile | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Met | Tyr | Tyr | Cys |
| | | | | 85 | | | | | 90 | | | | | 95 | |
| Ala | Arg | Gly | Thr | Tyr | Tyr | Gly | Thr | Arg | Val | Phe | Asp | Tyr | Trp | Gly | |
| | | | 100 | | | | | 105 | | | | | 110 | | |
| Gln | Gly | Thr | Leu | Val | Thr | Val | Ser | Ser | Ala | Ser | Thr | Lys | Gly | Pro | Ser |
| | | 115 | | | | | 120 | | | | | 125 | | | |
| Val | Phe | Pro | Leu | Ala | Pro | Ser | Ser | Lys | Ser | Thr | Ser | Gly | Gly | Thr | Ala |
| 130 | | | | | 135 | | | | | 140 | | | | | |
| Ala | Leu | Gly | Cys | Leu | Val | Lys | Asp | Tyr | Phe | Pro | Glu | Pro | Val | Thr | Val |
| 145 | | | | | 150 | | | | | 155 | | | | | 160 |
| Ser | Trp | Asn | Ser | Gly | Ala | Leu | Thr | Ser | Gly | Val | His | Thr | Phe | Pro | Ala |
| | | | | 165 | | | | | 170 | | | | | 175 | |
| Val | Leu | Gln | Ser | Ser | Gly | Leu | Tyr | Ser | Leu | Ser | Ser | Val | Val | Thr | Val |
| | | | 180 | | | | | 185 | | | | | 190 | | |
| Pro | Ser | Ser | Ser | Leu | Gly | Thr | Gln | Thr | Tyr | Ile | Cys | Asn | Val | Asn | His |
| | | 195 | | | | | 200 | | | | | 205 | | | |
| Lys | Pro | Ser | Asn | Thr | Lys | Val | Asp | Lys | Lys | Val | Glu | Pro | Lys | Ser | Cys |
| 210 | | | | | 215 | | | | | 220 | | | | | |
|

| | | | | | | 385 | | | 390 | | | | | 395 | | | 400 |
|---|---|---|---|---|---|---|---|---|---|---|---|---|---|---|---|---|---|

Met Leu Asp Ser Asp Gly Ser Phe Phe Leu Tyr Ser Lys Leu Thr Val
                    405                 410                 415

Asp Lys Ser Arg Trp Gln Gln Gly Asn Val Phe Ser Cys Ser Val Met
                    420                 425                 430

His Glu Ala Leu His Asn His Tyr Thr Gln Lys Ser Leu Ser Leu Ser
                    435                 440                 445

Pro Gly Lys
     450

<210> SEQ ID NO 88
<211> LENGTH: 451
<212> TYPE: PRT
<213> ORGANISM: Artificial Sequence
<220> FEATURE:
<223> OTHER INFORMATION: 4G7 H1.78 Hybrid S239D/I332E

<400> SEQUENCE: 88

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
                20                  25                  30

Val Met His Trp Val Arg Gln Ala Pro Gly Lys Gly Leu Glu Trp Ile
            35                  40                  45

Gly Tyr Ile Asn Pro Tyr Asn Ala Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Gly Ser Arg Val Phe Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
                230                 235                 240
225

Gly Pro Asp Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
    275                 280                 285

His Asn Ala Lys Thr Lys Pro Arg Glu Glu Gln Phe Asn Ser Thr Phe

```
                    290                 295                 300
Arg Val Ser Val Leu Thr Val Val His Gln Asp Trp Leu Asn Gly
305                 310                 315                 320

Lys Glu Tyr Lys Cys Lys Val Ser Asn Lys Ala Leu Pro Ala Pro Glu
                325                 330                 335

Glu Lys Thr Ile Ser Lys Thr Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 89
<211> LENGTH: 451
<212> TYPE: PRT
<213> ORGANISM: Artificial Sequence
<220> FEATURE:
<223> OTHER INFORMATION: 4G7 H1.191 Hybrid S239D/I332E

<400> SEQUENCE: 89

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
                20                  25                  30

Val Met His Trp Val Arg Gln Ala Pro Gly Lys Gly Leu Glu Trp Ile
            35                  40                  45

Gly Tyr Ile Asn Pro Tyr Asn Asp Gly Thr Glu Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
```

```
            195                 200                 205
Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Asp Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
            275                 280                 285

His Asn Ala Lys Thr Lys Pro Arg Glu Glu Gln Phe Asn Ser Thr Phe
290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Ala Leu Pro Ala Pro Glu
            325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 90
<211> LENGTH: 451
<212> TYPE: PRT
<213> ORGANISM: Artificial Sequence
<220> FEATURE:
<223> OTHER INFORMATION: 4G7 H1.192 Hybrid S239D/I332E

<400> SEQUENCE: 90

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Pro Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
```

100                 105                 110
Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Asp Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val His Gln Asp Trp Leu Asn Gly
305                 310                 315                 320

Lys Glu Tyr Lys Cys Lys Val Ser Asn Lys Ala Leu Pro Ala Pro Glu
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 91
<211> LENGTH: 451
<212> TYPE: PRT
<213> ORGANISM: Artificial Sequence
<220> FEATURE:
<223> OTHER INFORMATION: 4G7 H1.196 Hybrid S239D/I332E

<400> SEQUENCE: 91

Glu Val Gln Leu Val Glu Ser Gly Gly Gly Leu Val Lys Pro Gly Gly

```
            1               5                  10                 15
Ser Leu Lys Leu Ser Cys Ala Ala Ser Gly Tyr Thr Phe Thr Ser Tyr
                20                  25                 30

Val Met His Trp Val Arg Gln Ala Pro Gly Lys Gly Leu Glu Trp Ile
                35                  40                 45

Gly Tyr Ile Asn Pro Tyr Asn Asp Gly Pro Lys Tyr Asn Glu Lys Phe
                50                  55                 60

Gln Gly Arg Val Thr Ile Ser Ser Asp Lys Ser Ile Ser Thr Ala Tyr
65                  70                  75                 80

Met Glu Leu Ser Ser Leu Arg Ser Glu Asp Thr Ala Met Tyr Tyr Cys
                85                  90                 95

Ala Arg Gly Thr Tyr Tyr Gly Thr Ser Val Phe Asp Tyr Trp Gly
                100                 105                110

Gln Gly Thr Leu Val Thr Val Ser Ser Ala Ser Thr Lys Gly Pro Ser
                115                 120                125

Val Phe Pro Leu Ala Pro Ser Ser Lys Ser Thr Ser Gly Gly Thr Ala
                130                 135                140

Ala Leu Gly Cys Leu Val Lys Asp Tyr Phe Pro Glu Pro Val Thr Val
145                 150                 155                160

Ser Trp Asn Ser Gly Ala Leu Thr Ser Gly Val His Thr Phe Pro Ala
                165                 170                175

Val Leu Gln Ser Ser Gly Leu Tyr Ser Leu Ser Ser Val Val Thr Val
                180                 185                190

Pro Ser Ser Ser Leu Gly Thr Gln Thr Tyr Ile Cys Asn Val Asn His
                195                 200                205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                240

Gly Pro Asp Val Phe Leu Phe Pro Pro Lys Pro Lys Asp Thr Leu Met
                245                 250                255

Ile Ser Arg Thr Pro Glu Val Thr Cys Val Val Val Asp Val Ser His
                260                 265                270

Glu Asp Pro Glu Val Gln Phe Asn Trp Tyr Val Asp Gly Val Glu Val
                275                 280                285

His Asn Ala Lys Thr Lys Pro Arg Glu Glu Gln Phe Asn Ser Thr Phe
                290                 295                300

Arg Val Val Ser Val Leu Thr Val Val His Gln Asp Trp Leu Asn Gly
305                 310                 315                320

Lys Glu Tyr Lys Cys Lys Val Ser Asn Lys Ala Leu Pro Ala Pro Glu
                325                 330                335

Glu Lys Thr Ile Ser Lys Thr Lys Gly Gln Pro Arg Glu Pro Gln Val
                340                 345                350

Tyr Thr Leu Pro Pro Ser Arg Glu Glu Met Thr Lys Asn Gln Val Ser
                355                 360                365

Leu Thr Cys Leu Val Lys Gly Phe Tyr Pro Ser Asp Ile Ala Val Glu
                370                 375                380

Trp Glu Ser Asn Gly Gln Pro Glu Asn Asn Tyr Lys Thr Thr Pro Pro
385                 390                 395                400

Met Leu Asp Ser Asp Gly Ser Phe Phe Leu Tyr Ser Lys Leu Thr Val
                405                 410                415

Asp Lys Ser Arg Trp Gln Gln Gly Asn Val Phe Ser Cys Ser Val Met
                420                 425                430
```

His Glu Ala Leu His Asn His Tyr Thr Gln Lys Ser Leu Ser Leu Ser
            435                 440                 445
Pro Gly Lys
    450

<210> SEQ ID NO 92
<211> LENGTH: 451
<212> TYPE: PRT
<213> ORGANISM: Artificial Sequence
<220> FEATURE:
<223> OTHER INFORMATION: 4G7 H1.201 Hybrid S239D/I332E

<400> SEQUENCE: 92

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Ser Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Asp Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Ala Leu Pro Ala Pro Glu
                325                 330                 335

```
Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 93
<211> LENGTH: 451
<212> TYPE: PRT
<213> ORGANISM: Artificial Sequence
<220> FEATURE:
<223> OTHER INFORMATION: 4G7 H1.202 Hybrid S239D/I332E

<400> SEQUENCE: 93

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Glu Gly Thr Lys Tyr Asn Glu Lys Phe
    50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Gly Thr Arg Val Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240
```

```
Gly Pro Asp Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
            275                 280                 285

His Asn Ala Lys Thr Lys Pro Arg Glu Glu Gln Phe Asn Ser Thr Phe
            290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Ala Leu Pro Ala Pro Glu
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 94
<211> LENGTH: 451
<212> TYPE: PRT
<213> ORGANISM: Artificial Sequence
<220> FEATURE:
<223> OTHER INFORMATION: 4G7 H1.203 Hybrid S239D/I332E

<400> SEQUENCE: 94

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
            35                  40                  45

Gly Tyr Ile Asn Pro Tyr Asn Ser Gly Thr Glu Tyr Asn Glu Lys Phe
        50                  55                  60

Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Gly Thr Arg Val Phe Ala Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140
```

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Thr Val
        180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Asp Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
            275                 280                 285

His Asn Ala Lys Thr Lys Pro Arg Glu Glu Gln Phe Asn Ser Thr Phe
            290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Ala Leu Pro Ala Pro Glu
            325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 95
<211> LENGTH: 451
<212> TYPE: PRT
<213> ORGANISM: Artificial Sequence
<220> FEATURE:
<223> OTHER INFORMATION: 4G7 H1.204 Hybrid S239D/I332E

<400> SEQUENCE: 95

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

```
Gly Tyr Ile Asn Pro Tyr Asn Glu Gly Thr Glu Tyr Asn Glu Lys Phe
 50                  55                  60

Gln Gly Arg Val Thr Ile Ser Ser Asp Lys Ser Ile Ser Thr Ala Tyr
 65                  70                  75                  80

Met Glu Leu Ser Ser Leu Arg Ser Glu Asp Thr Ala Met Tyr Tyr Cys
                 85                  90                  95

Ala Arg Gly Thr Tyr Tyr Tyr Gly Thr Arg Val Phe Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Asp Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Gln Phe Asn Trp Tyr Val Asp Gly Val Glu Val
            275                 280                 285

His Asn Ala Lys Thr Lys Pro Arg Glu Glu Gln Phe Asn Ser Thr Phe
290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Ala Leu Pro Ala Pro Glu
                325                 330                 335

Glu Lys Thr Ile Ser Lys Thr Lys Gly Gln Pro Arg Glu Pro Gln Val
                340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450
```

<210> SEQ ID NO 96
<211> LENGTH: 219
<212> TYPE: PRT
<213> ORGANISM: Artificial Sequence
<220> FEATURE:
<223> OTHER INFORMATION: 4G7 L1

<400> SEQUENCE: 96

```
Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Ser
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Phe Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 97
<211> LENGTH: 219
<212> TYPE: PRT
<213> ORGANISM: Artificial Sequence
<220> FEATURE:
<223> OTHER INFORMATION: 4G7 L1.26

<400> SEQUENCE: 97

```
Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Ser
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95
```

Leu Glu Tyr Pro Phe Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 98
<211> LENGTH: 219
<212> TYPE: PRT
<213> ORGANISM: Artificial Sequence
<220> FEATURE:
<223> OTHER INFORMATION: 4G7 L1.32

<400> SEQUENCE: 98

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Phe Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 99

```
<211> LENGTH: 219
<212> TYPE: PRT
<213> ORGANISM: Artificial Sequence
<220> FEATURE:
<223> OTHER INFORMATION: 4G7 L1.64

<400> SEQUENCE: 99

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Ser
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 100
<211> LENGTH: 219
<212> TYPE: PRT
<213> ORGANISM: Artificial Sequence
<220> FEATURE:
<223> OTHER INFORMATION: 4G7 L1.68

<400> SEQUENCE: 100

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Ser
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Asn Thr Phe Gly Ala Gly Thr Lys Leu Glu Ile Lys
```

```
                100              105             110
Arg Thr Val Ala Ala Pro Ser Val Phe Ile Phe Pro Pro Ser Asp Glu
            115                 120             125

Gln Leu Lys Ser Gly Thr Ala Ser Val Val Cys Leu Leu Asn Asn Phe
        130                 135             140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170             175

Thr Tyr Ser Leu Ser Ser Thr Leu Thr Leu Ser Lys Ala Asp Tyr Glu
                180                 185             190

Lys His Lys Val Tyr Ala Cys Glu Val Thr His Gln Gly Leu Ser Ser
            195                 200             205

Pro Val Thr Lys Ser Phe Asn Arg Gly Glu Cys
        210                 215

<210> SEQ ID NO 101
<211> LENGTH: 219
<212> TYPE: PRT
<213> ORGANISM: Artificial Sequence
<220> FEATURE:
<223> OTHER INFORMATION: 4G7 L1.96

<400> SEQUENCE: 101

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Leu Asn Ser
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Phe Thr Phe Gly Ala Gly Thr Lys Leu Glu Ile Lys
            100                 105             110

Arg Thr Val Ala Ala Pro Ser Val Phe Ile Phe Pro Pro Ser Asp Glu
            115                 120             125

Gln Leu Lys Ser Gly Thr Ala Ser Val Val Cys Leu Leu Asn Asn Phe
        130                 135             140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170             175

Thr Tyr Ser Leu Ser Ser Thr Leu Thr Leu Ser Lys Ala Asp Tyr Glu
                180                 185             190

Lys His Lys Val Tyr Ala Cys Glu Val Thr His Gln Gly Leu Ser Ser
            195                 200             205

Pro Val Thr Lys Ser Phe Asn Arg Gly Glu Cys
        210                 215

<210> SEQ ID NO 102
<211> LENGTH: 219
<212> TYPE: PRT
```

<213> ORGANISM: Artificial Sequence
<220> FEATURE:
<223> OTHER INFORMATION: 4G7 L1.145

<400> SEQUENCE: 102

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Ser
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 103
<211> LENGTH: 219
<212> TYPE: PRT
<213> ORGANISM: Artificial Sequence
<220> FEATURE:
<223> OTHER INFORMATION: 4G7 L1.148

<400> SEQUENCE: 103

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Ser
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Asn Thr Phe Gly Ala Gly Thr Lys Leu Glu Ile Lys
            100                 105                 110

Arg Thr Val Ala Ala Pro Ser Val Phe Ile Phe Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 104
<211> LENGTH: 219
<212> TYPE: PRT
<213> ORGANISM: Artificial Sequence
<220> FEATURE:
<223> OTHER INFORMATION: 4G7 L1.149

<400> SEQUENCE: 104

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Ser
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110

Arg Thr Val Ala Ala Pro Ser Val Phe Ile Phe Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 105
<211> LENGTH: 219
<212> TYPE: PRT
<213> ORGANISM: Artificial Sequence
<220> FEATURE:

-continued

<223> OTHER INFORMATION: 4G7 L1.154

<400> SEQUENCE: 105

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Asn Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 106
<211> LENGTH: 219
<212> TYPE: PRT
<213> ORGANISM: Artificial Sequence
<220> FEATURE:
<223> OTHER INFORMATION: 4G7 L1.155

<400> SEQUENCE: 106

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

```
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 107
<211> LENGTH: 219
<212> TYPE: PRT
<213> ORGANISM: Artificial Sequence
<220> FEATURE:
<223> OTHER INFORMATION: 4G7 L1.160

<400> SEQUENCE: 107

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Ala Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 108
<211> LENGTH: 219
<212> TYPE: PRT
<213> ORGANISM: Artificial Sequence
<220> FEATURE:
<223> OTHER INFORMATION: 4G7 L1.162
```

<400> SEQUENCE: 108

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Ala
            20                  25                  30

Asn Ala Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 109
<211> LENGTH: 219
<212> TYPE: PRT
<213> ORGANISM: Artificial Sequence
<220> FEATURE:
<223> OTHER INFORMATION: 4G7 L1.163

<400> SEQUENCE: 109

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Ala
            20                  25                  30

Asn Ser Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe

```
                130                135                140
Tyr Pro Arg Glu Ala Lys Val Gln Trp Lys Val Asp Asn Ala Leu Gln
145                150                155                160

Ser Gly Asn Ser Gln Glu Ser Val Thr Glu Gln Asp Ser Lys Asp Ser
                165                170                175

Thr Tyr Ser Leu Ser Ser Thr Leu Thr Leu Ser Lys Ala Asp Tyr Glu
                180                185                190

Lys His Lys Val Tyr Ala Cys Glu Val Thr His Gln Gly Leu Ser Ser
                195                200                205

Pro Val Thr Lys Ser Phe Asn Arg Gly Glu Cys
                210                215

<210> SEQ ID NO 110
<211> LENGTH: 219
<212> TYPE: PRT
<213> ORGANISM: Artificial Sequence
<220> FEATURE:
<223> OTHER INFORMATION: 4G7 L1.164

<400> SEQUENCE: 110

Asp Ile Val Met Thr Gln Ser Pro Ala Thr Leu Ser Leu Ser Pro Gly
1               5                  10                 15

Glu Arg Ala Thr Leu Ser Cys Arg Ser Ser Lys Ser Leu Gln Asn Ala
                20                 25                 30

Asn Gly Asn Thr Tyr Leu Tyr Trp Phe Gln Gln Lys Pro Gly Gln Ser
                35                 40                 45

Pro Gln Leu Leu Ile Tyr Arg Met Ser Asn Leu Asn Ser Gly Val Pro
50                  55                 60

Asp Arg Phe Ser Gly Ser Gly Ser Gly Thr Glu Phe Thr Leu Thr Ile
65                  70                 75                 80

Ser Ser Leu Glu Pro Glu Asp Phe Ala Val Tyr Tyr Cys Met Gln His
                85                 90                 95

Leu Glu Tyr Pro Ile Thr Phe Gly Ala Gly Thr Lys Leu Glu Ile Lys
                100                105                110

Arg Thr Val Ala Ala Pro Ser Val Phe Ile Phe Pro Pro Ser Asp Glu
                115                120                125

Gln Leu Lys Ser Gly Thr Ala Ser Val Val Cys Leu Leu Asn Asn Phe
130                 135                140

Tyr Pro Arg Glu Ala Lys Val Gln Trp Lys Val Asp Asn Ala Leu Gln
145                 150                155                160

Ser Gly Asn Ser Gln Glu Ser Val Thr Glu Gln Asp Ser Lys Asp Ser
                165                170                175

Thr Tyr Ser Leu Ser Ser Thr Leu Thr Leu Ser Lys Ala Asp Tyr Glu
                180                185                190

Lys His Lys Val Tyr Ala Cys Glu Val Thr His Gln Gly Leu Ser Ser
                195                200                205

Pro Val Thr Lys Ser Phe Asn Arg Gly Glu Cys
                210                215

<210> SEQ ID NO 111
<211> LENGTH: 17
<212> TYPE: PRT
<213> ORGANISM: Artificial Sequence
<220> FEATURE:
<223> OTHER INFORMATION: 4G7 VH CDR2 D55A

<400> SEQUENCE: 111
```

-continued

Tyr Ile Asn Pro Tyr Asn Ala Gly Thr Lys Tyr Asn Glu Lys Phe Lys
1               5                   10                  15

Gly

<210> SEQ ID NO 112
<211> LENGTH: 17
<212> TYPE: PRT
<213> ORGANISM: Artificial Sequence
<220> FEATURE:
<223> OTHER INFORMATION: 4G7 VH CDR2 T57P

<400> SEQUENCE: 112

Tyr Ile Asn Pro Tyr Asn Asp Gly Pro Lys Tyr Asn Glu Lys Phe Lys
1               5                   10                  15

Gly

<210> SEQ ID NO 113
<211> LENGTH: 17
<212> TYPE: PRT
<213> ORGANISM: Artificial Sequence
<220> FEATURE:
<223> OTHER INFORMATION: 4G7 VH CDR2 K58E

<400> SEQUENCE: 113

Tyr Ile Asn Pro Tyr Asn Asp Gly Thr Glu Tyr Asn Glu Lys Phe Lys
1               5                   10                  15

Gly

<210> SEQ ID NO 114
<211> LENGTH: 17
<212> TYPE: PRT
<213> ORGANISM: Artificial Sequence
<220> FEATURE:
<223> OTHER INFORMATION: 4G7 VH CDR2 D55S

<400> SEQUENCE: 114

Tyr Ile Asn Pro Tyr Asn Ser Gly Thr Lys Tyr Asn Glu Lys Phe Lys
1               5                   10                  15

Gly

<210> SEQ ID NO 115
<211> LENGTH: 17
<212> TYPE: PRT
<213> ORGANISM: Artificial Sequence
<220> FEATURE:
<223> OTHER INFORMATION: 4G7 VH CDR2 D55E

<400> SEQUENCE: 115

Tyr Ile Asn Pro Tyr Asn Glu Gly Thr Lys Tyr Asn Glu Lys Phe Lys
1               5                   10                  15

Gly

<210> SEQ ID NO 116
<211> LENGTH: 12
<212> TYPE: PRT
<213> ORGANISM: Artificial Sequence
<220> FEATURE:
<223> OTHER INFORMATION: 4G7 VH CDR3 S100T

<400> SEQUENCE: 116

Gly Thr Tyr Tyr Tyr Gly Thr Arg Val Phe Asp Tyr
1               5                   10

```
<210> SEQ ID NO 117
<211> LENGTH: 12
<212> TYPE: PRT
<213> ORGANISM: Artificial Sequence
<220> FEATURE:
<223> OTHER INFORMATION: 4G7 VH CDR3 R100dS

<400> SEQUENCE: 117

Gly Thr Tyr Tyr Tyr Gly Ser Ser Val Phe Asp Tyr
1               5                   10

<210> SEQ ID NO 118
<211> LENGTH: 12
<212> TYPE: PRT
<213> ORGANISM: Artificial Sequence
<220> FEATURE:
<223> OTHER INFORMATION: 4G7 VH CDR3 S100cT/R100dS

<400> SEQUENCE: 118

Gly Thr Tyr Tyr Tyr Gly Thr Ser Val Phe Asp Tyr
1               5                   10

<210> SEQ ID NO 119
<211> LENGTH: 16
<212> TYPE: PRT
<213> ORGANISM: Artificial Sequence
<220> FEATURE:
<223> OTHER INFORMATION: 4G7 VL CDR1 L27cQ

<400> SEQUENCE: 119

Arg Ser Ser Lys Ser Leu Gln Asn Ser Asn Gly Asn Thr Tyr Leu Tyr
1               5                   10                  15

<210> SEQ ID NO 120
<211> LENGTH: 16
<212> TYPE: PRT
<213> ORGANISM: Artificial Sequence
<220> FEATURE:
<223> OTHER INFORMATION: 4G7 VL CDR1 L27cQ/S27eV

<400> SEQUENCE: 120

Arg Ser Ser Lys Ser Leu Gln Asn Val Asn Gly Asn Thr Tyr Leu Tyr
1               5                   10                  15

<210> SEQ ID NO 121
<211> LENGTH: 16
<212> TYPE: PRT
<213> ORGANISM: Artificial Sequence
<220> FEATURE:
<223> OTHER INFORMATION: 4G7 VL CDR1 S27eV

<400> SEQUENCE: 121

Arg Ser Ser Lys Ser Leu Leu Asn Val Asn Gly Asn Thr Tyr Leu Tyr
1               5                   10                  15

<210> SEQ ID NO 122
<211> LENGTH: 16
<212> TYPE: PRT
<213> ORGANISM: Artificial Sequence
<220> FEATURE:
<223> OTHER INFORMATION: 4G7 VL CDR1 G29A

<400> SEQUENCE: 122

Arg Ser Ser Lys Ser Leu Leu Asn Ser Asn Ala Asn Thr Tyr Leu Tyr
1               5                   10                  15

<210> SEQ ID NO 123
```

<211> LENGTH: 16
<212> TYPE: PRT
<213> ORGANISM: Artificial Sequence
<220> FEATURE:
<223> OTHER INFORMATION: 4G7 VL CDR1 L27cQ/S27eV/G29A

<400> SEQUENCE: 123

Arg Ser Ser Lys Ser Leu Gln Asn Val Asn Ala Asn Thr Tyr Leu Tyr
1               5                   10                  15

<210> SEQ ID NO 124
<211> LENGTH: 16
<212> TYPE: PRT
<213> ORGANISM: Artificial Sequence
<220> FEATURE:
<223> OTHER INFORMATION: 4G7 VL CDR1 S27eA

<400> SEQUENCE: 124

Arg Ser Ser Lys Ser Leu Leu Asn Ala Asn Gly Asn Thr Tyr Leu Tyr
1               5                   10                  15

<210> SEQ ID NO 125
<211> LENGTH: 16
<212> TYPE: PRT
<213> ORGANISM: Artificial Sequence
<220> FEATURE:
<223> OTHER INFORMATION: 4G7 VL CDR1 L27cQ/S27eA/G29A

<400> SEQUENCE: 125

Arg Ser Ser Lys Ser Leu Gln Asn Ala Asn Ala Asn Thr Tyr Leu Tyr
1               5                   10                  15

<210> SEQ ID NO 126
<211> LENGTH: 16
<212> TYPE: PRT
<213> ORGANISM: Artificial Sequence
<220> FEATURE:
<223> OTHER INFORMATION: 4G7 VL CDR1 G29S

<400> SEQUENCE: 126

Arg Ser Ser Lys Ser Leu Leu Asn Ser Asn Ser Asn Thr Tyr Leu Tyr
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: 4G7 VL CDR1 L27cQ/S27eA/G29S

<400> SEQUENCE: 127

Arg Ser Ser Lys Ser Leu Gln Asn Ala Asn Ser Asn Thr Tyr Leu Tyr
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: 4G7 VL CDR1 L27cQ/S27eA

<400> SEQUENCE: 128

Arg Ser Ser Lys Ser Leu Gln Asn Ala Asn Gly Asn Thr Tyr Leu Tyr
1               5                   10                  15

<210> SEQ ID NO 129
<211> LENGTH: 7

```
<212> TYPE: PRT
<213> ORGANISM: Artificial Sequence
<220> FEATURE:
<223> OTHER INFORMATION: 4G7 VL CDR2 A55N

<400> SEQUENCE: 129

Arg Met Ser Asn Leu Asn Ser
1               5

<210> SEQ ID NO 130
<211> LENGTH: 9
<212> TYPE: PRT
<213> ORGANISM: Artificial Sequence
<220> FEATURE:
<223> OTHER INFORMATION: 4G7 VL CDR3 F96I

<400> SEQUENCE: 130

Met Gln His Leu Glu Tyr Pro Ile Thr
1               5

<210> SEQ ID NO 131
<211> LENGTH: 9
<212> TYPE: PRT
<213> ORGANISM: Artificial Sequence
<220> FEATURE:
<223> OTHER INFORMATION: 4G7 VL CDR3 F96N

<400> SEQUENCE: 131

Met Gln His Leu Glu Tyr Pro Asn Thr
1               5

<210> SEQ ID NO 132
<211> LENGTH: 5
<212> TYPE: PRT
<213> ORGANISM: Mus musculus

<400> SEQUENCE: 132

Ser Tyr Val Met His
1               5

<210> SEQ ID NO 133
<211> LENGTH: 17
<212> TYPE: PRT
<213> ORGANISM: Mus musculus

<400> SEQUENCE: 133

Tyr Ile Asn Pro Tyr Asn Asp Gly Thr Lys Tyr Asn Glu Lys Phe Lys
1               5                   10                  15

Gly

<210> SEQ ID NO 134
<211> LENGTH: 12
<212> TYPE: PRT
<213> ORGANISM: Mus musculus

<400> SEQUENCE: 134

Gly Thr Tyr Tyr Tyr Gly Ser Arg Val Phe Asp Tyr
1               5                   10

<210> SEQ ID NO 135
<211> LENGTH: 16
<212> TYPE: PRT
<213> ORGANISM: Mus musculus

<400> SEQUENCE: 135
```

-continued

Arg Ser Ser Lys Ser Leu Leu Asn Ser Asn Gly Asn Thr Tyr Leu Tyr
1               5                   10                  15

<210> SEQ ID NO 136
<211> LENGTH: 7
<212> TYPE: PRT
<213> ORGANISM: Mus musculus

<400> SEQUENCE: 136

Arg Met Ser Asn Leu Ala Ser
1               5

<210> SEQ ID NO 137
<211> LENGTH: 9
<212> TYPE: PRT
<213> ORGANISM: Mus musculus

<400> SEQUENCE: 137

Met Gln His Leu Glu Tyr Pro Phe Thr
1               5

<210> SEQ ID NO 138
<211> LENGTH: 5
<212> TYPE: PRT
<213> ORGANISM: Mus musculus

<400> SEQUENCE: 138

Ser Tyr Trp Met Asn
1               5

<210> SEQ ID NO 139
<211> LENGTH: 17
<212> TYPE: PRT
<213> ORGANISM: Mus musculus

<400> SEQUENCE: 139

Gln Ile Trp Pro Gly Asp Gly Asp Thr Asn Tyr Asn Gly Lys Phe Lys
1               5                   10                  15

Gly

<210> SEQ ID NO 140
<211> LENGTH: 15
<212> TYPE: PRT
<213> ORGANISM: Mus musculus

<400> SEQUENCE: 140

Arg Glu Thr Thr Thr Val Gly Arg Tyr Tyr Tyr Ala Met Asp Tyr
1               5                   10                  15

<210> SEQ ID NO 141
<211> LENGTH: 15
<212> TYPE: PRT
<213> ORGANISM: Mus musculus

<400> SEQUENCE: 141

Lys Ala Ser Gln Ser Val Asp Tyr Asp Gly Asp Ser Tyr Leu Asn
1               5                   10                  15

<210> SEQ ID NO 142
<211> LENGTH: 7
<212> TYPE: PRT
<213> ORGANISM: Mus musculus

<400> SEQUENCE: 142

```
Asp Ala Ser Asn Leu Val Ser
1               5

<210> SEQ ID NO 143
<211> LENGTH: 9
<212> TYPE: PRT
<213> ORGANISM: Mus musculus

<400> SEQUENCE: 143

Gln Gln Ser Thr Glu Asp Pro Trp Thr
1               5

<210> SEQ ID NO 144
<211> LENGTH: 5
<212> TYPE: PRT
<213> ORGANISM: Artificial Sequence
<220> FEATURE:
<223> OTHER INFORMATION: Peptide Linker

<400> SEQUENCE: 144

Gly Ser Gly Gly Ser
1               5

<210> SEQ ID NO 145
<211> LENGTH: 5
<212> TYPE: PRT
<213> ORGANISM: Artificial Sequence
<220> FEATURE:
<223> OTHER INFORMATION: Peptide Linker

<400> SEQUENCE: 145

Gly Gly Gly Gly Ser
1               5

<210> SEQ ID NO 146
<211> LENGTH: 4
<212> TYPE: PRT
<213> ORGANISM: Artificial Sequence
<220> FEATURE:
<223> OTHER INFORMATION: Peptide Linker

<400> SEQUENCE: 146

Gly Gly Gly Ser
1

<210> SEQ ID NO 147
<211> LENGTH: 14
<212> TYPE: PRT
<213> ORGANISM: Mus musculus

<400> SEQUENCE: 147

Trp Ile Gly Tyr Ile Asn Pro Tyr Asn Asp Gly Thr Lys Tyr
1               5                   10
```

OPTIMIZED ANTIBODIES THAT TARGET CD19

CROSS REFERENCE TO RELATED APPLICATIONS

This application is a division of U.S. patent application Ser. No. 13/959,587, filed Aug. 5, 2013, which is a division of U.S. patent application Ser. No. 12/377,251, filed Feb. 11, 2009, which is the national stage application of PCT Patent Application No. PCT/US7/75932, filed Aug. 14, 2007, and which claims benefit under 35 U.S.C. § 119(e) U.S. Provisional Patent Application No. 60/822,362, filed Aug. 14, 2006, all of which are incorporated herein by reference in their entireties.

SEQUENCE LISTING

A Sequence Listing submitted in computer readable form (CRF) is hereby incorporated by reference. The CRF file is named 189519.ST25.txt was created on Aug. 30, 2011 and contains 190 kilobytes.

BACKGROUND

B Cells

B cells are lymphocytes that play a large role in the humoral immune response. They are produced in the bone marrow of most mammals, and represent 5-15% of the circulating lymphoid pool. The principal function of B cells is to make antibodies against various antigens, and are an essential component of the adaptive immune system.

The human body makes millions of different types of B cells each day that circulate in the blood and lymph performing the role of immune surveillance. B cells, also referred to as B lymphocytes, do not produce antibodies until they become fully activated. Each B cell has a unique receptor protein (referred to as the B cell receptor (BCR)) on its surface that will bind to one particular antigen. The BCR is a membrane-bound immunoglobulin, and it is this molecule that allows the distinction of B cells from other types of lymphocytes, as well as being the main receptor involved in B-cell activation. Once a B cell encounters its cognate antigen and receives an additional signal from a T helper cell, it can further differentiate into various types of B cells listed below. The B cell may either become one of these cell types directly or it may undergo an intermediate differentiation step, the germinal center reaction, where the B cell will hypermutate the variable region of its immunoglobulin gene and possibly undergo class switching.

B-cell development occurs through several stages, each stage representing a change in the genome content at the antibody loci. The stages of B-cell development include Progenitor B cells, Early Pro-B cells, Late Pro-B cells, Large Pre-B cells, Small Pre-B cells, Immature B cells, and Mature B cells.

Mature B cells can be divided into four major types:

B-1 cells express CD5, a marker usually found on T cells. B-1 cells also express IgM in greater quantities than IgG. They secrete natural low affinity polyreactive antibodies found in the serum and often have specificities directed toward self-antigens, and common bacterial polysaccharides. B-1 cells are present in low numbers in the lymph nodes and spleen and are instead found predominantly in the peritoneal and pleural cavities.

B-2 cells are the conventional B cells to which most texts refer. They reside in bone marrow, spleen, and lymph nodes. They are short-lived, and when triggered by antigens may differentiate into IgG-producing memory B cells. In the course of these antibody responses IgG may undergo substantial affinity maturation.

Plasma B cells (also known as plasma cells) are large B cells that have been exposed to antigen and produce and secrete large amounts of antibodies, which assist in the destruction of microbes by binding and facilitating targeting by phagocytes, as well as activation of the complement system. Plasma cells are sometimes referred to as antibody factories.

Memory B cells are formed from activated B cells that are specific to the antigen encountered during the primary immune response. These cells live for a long time, and can respond quickly following a second exposure to the same antigen.

When a B cell fails in any step of the maturation process, it will die by a mechanism called apoptosis. If it recognizes self-antigen during the maturation process, the B cell will become suppressed (known as anergy) or undergo apoptosis. B cells are continuously produced in the bone marrow, but only a small portion of newly made B cells survive to participate in the long-lived peripheral B-cell pool.

In recent years, data have emerged suggesting that B lymphocytes play a broader role in immune responses and are not merely the passive recipients of signals that result in differentiation into antibody-producing plasma cells. Along with their traditional roles as antigen presenting cells and precursors of antibody-producing plasma cells, B cells have also been found to regulate antigen presenting cells (APCs) and T-cell functions, produce cytokines, and express receptor/ligand pairs that previously had been thought to be restricted to other cell types.

B-Cell Disorders

Because of their critical role in regulating the immune system, disregulation of B cells is associated with a variety of disorders. B-cell disorders, also referred to herein as B-cell related diseases, are divided into excessive or uncontrolled proliferation (lymphomas, leukemias), and defects of B-cell development/immunoglobulin production (immunodeficiencies). The majority (80%) of lymphoma cases are of B-cell origin. These include non-Hodgkin's lymphoma (NHL), acute lymphoblastic leukemia (ALL), and autoimmune related diseases.

NHL is a heterogeneous malignancy originating from lymphocytes. In the United States (U.S.), the incidence is estimated at 65,000/year with mortality of approximately 20,000 (American Cancer Society, 2006; and SEER Cancer Statistics Review). The disease can occur in all ages, the usual onset begins in adults over 40 years, with the incidence increasing with age. NHL is characterized by a clonal proliferation of lymphocytes that accumulate in the lymph nodes, blood, bone marrow and spleen, although any major organ may be involved.

The diagnosis and histologic characterization of NHL is made using a combination of morphologic and immunophenotype criteria. The current classification system used by pathologists and clinicians is the World Health Organization (WHO) Classification of Tumours, which organizes NHL into precursor and mature B-cell or T-cell neoplasms. The PDQ is currently dividing NHL as indolent or aggressive for entry into clinical trials. For consistency the present document will also use a similar division. The indolent NHL group is comprised primarily of follicular subtypes, small lymphocytic lymphoma, MALT, and marginal zone; indolent encompasses approximately 50% of newly diagnosed B-cell NHL patients. Aggressive NHL includes patients with histologic diagnoses of primarily diffuse large B cell (40% of all newly diagnosed patients have diffuse large cell), Burkitt's, and mantle cell.

The clinical course of NHL is highly variable. A major determinant of clinical course is the histologic subtype. Most indolent types of NHL are considered to be incurable disease. Patients respond initially to either chemotherapy or antibody therapy and most will relapse. Studies to date have not demonstrated an improvement in survival with early intervention. In asymptomatic patients, it is acceptable to "watch and wait" until the patient becomes symptomatic or the disease pace appears to be accelerating. Over time, the disease may transform to a more aggressive histology. The median survival is 8 to 10 years, and indolent patients often receive 3 or more treatments during the treatment phase of their disease. Initial treatment of the symptomatic indolent NHL patient historically has been combination chemotherapy. The most commonly used agents include: cyclophosphamide, vincristine and prednisone (CVP); cyclophosphamide, adriamycin, vincristine, prednisone (CHOP); or the purine analog, fludarabine. Approximately 70% to 80% of patients will respond to their initial chemotherapy, duration of remissions last on the order of 2-3 years. Ultimately the majority of patients relapse. The discovery and clinical use of the anti-CD20 antibody, rituximab, has provided significant improvements in response and survival rate. The current standard of care for most patients is rituximab+ CHOP (R-CHOP) or rituximab+CVP (R-CVP). Interferon is approved for initial treatment of NHL in combination with alkylating agents, but has limited use in the U.S.

Rituximab therapy has been shown to be efficacious in several types of NHL, and is currently approved as a first line treatment for both indolent (follicular lymphoma) and aggressive NHL (diffuse large B cell lymphoma). However, there are significant limitations of anti-CD20 monoclonal antibody (mAb), including primary resistance (50% response in relapsed indolent patients), acquired resistance (50% response rate upon re-treatment), rare complete response (2% complete resonse rate in relapsed population), and a continued pattern of relapse. Finally, many B cells do not express CD20, and thus many B-cell disorders are not treatable using anti-CD20 antibody therapy. Antibodies against antigens other than CD20 may have anti-lymphoma effects that could overcome anti-CD20 resistance or augment the activity of anti-CD20 therapy.

In addition to NHL there are several types of leukemias that result from disregulation of B cells. Chronic lymphocytic leukemia (also known as "chronic lymphoid leukemia" or "CLL"), is a type of adult leukemia caused by an abnormal accumulation of B lymphocytes. In CLL, the malignant lymphocytes may look normal and mature, but they are not able to cope effectively with infection. CLL is the most common form of leukemia in adults. Men are twice as likely to develop CLL as women. However, the key risk factor is age. Over 75% of new cases are diagnosed in patients over age 50. More than 10,000 cases are diagnosed every year and the mortality is almost 5,000 a year (American Cancer Society, 2006; and SEER Cancer Statistics Review).

CLL is an incurable disease but progresses slowly in most cases. Many people with CLL lead normal and active lives for many years. Because of its slow onset, early-stage CLL is generally not treated since it is believed that early CLL intervention does not improve survival time or quality of life. Instead, the condition is monitored over time. Initial CLL treatments vary depending on the exact diagnosis and the progression of the disease. There are dozens of agents used for CLL therapy. Although the purine analogue fludarabine was shown to give superior response rates than chlorambucil as primary therapy, there is no evidence that early use of fludarabine improves overall survival. Combination chemotherapy regimens such as fludarabine with cyclophosphamide, FCR (fludarabine, cyclophosphamide and rituximab) and CHOP are effective in both newly-diagnosed and relapsed CLL. Allogeneic bone marrow (stem cell) transplantation is rarely used as a first-line treatment for CLL due to its risk.

"Refractory" CLL is a disease that no longer responds favorably to treatment. In this case more aggressive therapies, including bone marrow (stem cell) transplantation, are considered. The monoclonal antibody alemtuzumab, directed against CD52, may be used in patients with refractory, bone marrow-based disease.

Another type of leukemia is acute lymphoblastic leukemia (ALL), also known as acute lymphocytic leukemia. ALL is characterised by the overproduction and continuous multiplication of malignant and immature white blood cells (also known as lymphoblasts) in the bone marrow. 'Acute' refers to the undifferentiated, immature state of the circulating lymphocytes ("blasts"), and that the disease progresses rapidly with life expectancy of weeks to months if left untreated. ALL is most common in childhood with a peak incidence of 4-5 years of age. Children of age 12-16 die more easily from it than others. Currently, at least 80% of childhood ALL are considered curable. Under 4,000 cases are diagnosed every year and the mortality is almost 1,500 a year (American Cancer Society, 2006; and SEER Cancer Statistics Review).

Autoimmunity results from a breakdown of self-tolerance involving humoral and/or cell-mediated immune mechanisms in. Among of the consequences of failure in central and/or peripheral tolerance, are survival and activation of self-reactive B cells and T cells. Examples of autoimmune diseases include, for example, rheumatoid arthritis (RA), systemic lupus erythematosus (SLE or lupus), multiple sclerosis, Sjogren's syndrome, and idiopathic thrombocytopenia purpura (ITP). The pathogenesis of most autoimmune diseases is coupled to the production of autoantibodies against self antigens, leading to a variety of associated pathologies. Autoantibodies are produced by terminally differentiated plasma cells that are derived from naive or memory B cells. Furthermore, B cells can have other effects on autoimmune pathology, as antigen-presenting cells (APCs) that can interact with and stimulate helper T cells, further stimulating the cycle of anti-self immune response. Depletion of B cells can have direct impact on the production of autoantibodies. Indeed, treatment of RA and SLE with B-cell depletion therapies such as Rituxan has been demonstrated to have clinical benefit for both disease classes (Edwards & Cambridge, Nat. Rev. Immunol. 2006; Dass et al., Future Rheumatol. 2006; Martin & Chan, Annu. Rev. Immunol. 2006).

Unfortunately, it is not known a priori which mechanisms of action may be optimal for a given target antigen. Furthermore, it is not known which antibodies may be capable of mediating a given mechanism of action against a target cell. In some cases a lack of antibody activity, either Fv-mediated or Fc-mediated, may be due to the targeting of an epitope on the target antigen that is poor for mediating such activity. In other cases, the targeted epitope may be amenable to a desired Fv-mediated or Fc-mediated activity, yet the affinity (affinity of the Fv region for antigen or affinity of the Fc region for Fc receptors) may be insufficient. Towards addressing this problem, the present invention describes modifications to anti-CD19 antibodies that provide optimized Fv- and Fc-mediated activities. A broad array of applications of these optimized antibodies are contemplated.

SUMMARY OF THE INVENTION

In one aspect, the present invention is directed to an antibody binds CD19, wherein said antibody comprises at least one modification in the constant region relative to a parent antibody. In a preferred embodiment, the antibody of the invention binds with altered affinity to an Fc receptor or alters effector function as compared to the parent antibody.

In one aspect, the invention is directed to antibody that binds CD19, including at least one modification in the constant region relative to a parent anti-CD19 antibody, wherein the antibody binds with increased affinity to the FcγRIIIa receptor as compared to the parent antibody.

In certain aspects, the modification is an amino acid. The modification can be at a position selected from the group consisting of 221, 222, 223, 224, 225, 227, 228, 230, 231, 232, 233, 234, 235, 236, 237, 238, 239, 240, 241, 243, 244, 245, 246, 247, 249, 255, 258, 260, 262, 263, 264, 265, 266, 267, 268, 269, 270, 271, 272, 273, 274, 275, 276, 278, 280, 281, 282, 283, 284, 285, 286, 288, 290, 291, 292, 293, 294, 295, 296, 297, 298, 299, 300, 301, 302, 303, 304, 305, 313, 317, 318, 320, 322, 323, 324, 325, 326, 327, 328, 329, 330, 331, 332, 333, 334, 335, 336, and 337, wherein numbering is according to the EU index. The amino acid modification can be a substitution selected from the group consisting of 221K, 221Y, 222E, 222Y, 223E, 223K, 224E, 224Y, 225E, 225K, 225W, 227E, 227G, 227K, 227Y, 228E, 228G, 228K, 228Y, 230A, 230E, 230G, 230Y, 231E, 231G, 231K, 231P, 231Y, 232E, 232G, 232K, 232Y, 233A, 233D, 233F, 233G, 233H, 233I, 233K, 233L, 233M, 233N, 233Q, 233R, 233S, 233T, 233V, 233W, 233Y, 234A, 234D, 234E, 234F, 234G, 234H, 234I, 234K, 234M, 234N, 234P, 234Q, 234R, 234S, 234T, 234V, 234W, 234Y, 235A, 235D, 235E, 235F, 235G, 235H, 235I, 235K, 235M, 235N, 235P, 235Q, 235R, 235S, 235T, 235V, 235W, 235Y, 236A, 236D, 236E, 236F, 236H, 236I, 236K, 236L, 236M, 236N, 236P, 236Q, 236R, 236S, 236T, 236V, 236W, 236Y, 237D, 237E, 237F, 237H, 237I, 237K, 237L, 237M, 237N, 237P, 237Q, 237R, 237S, 237T, 237V, 237W, 237Y, 238D, 238E, 238F, 238G, 238H, 238I, 238K, 238L, 238M, 238N, 238Q, 238R, 238S, 238T, 238V, 238W, 238Y, 239D, 239E, 239F, 239G, 239H, 239I, 239K, 239L, 239M, 239N, 239P, 239Q, 239R, 239T, 239V, 239W, 239Y, 240A, 240I, 240M, 240T, 241D, 241E, 241L, 241R, 241S, 241W, 241Y, 243E, 243H, 243L, 243Q, 243R, 243W, 243Y, 244H, 245A, 246D, 246E, 246H, 246Y, 247G, 247V, 249H, 249Q, 249Y, 255E, 255Y, 258H, 258S, 258Y, 260D, 260E, 260H, 260Y, 262A, 262E, 262F, 262I, 262T, 263A, 263I, 263M, 263T, 264A, 264D, 264E, 264F, 264G, 264H, 264I, 264K, 264L, 264M, 264N, 264P, 264Q, 264R, 264S, 264T, 264W, 264Y, 265F, 265G, 265H, 265I, 265K, 265L, 265M, 265N, 265P, 265Q, 265R, 265S, 265T, 265V, 265W, 265Y, 266A, 266I, 266M, 266T, 267D, 267E, 267F, 267H, 267I, 267K, 267L, 267M, 267N, 267P, 267Q, 267R, 267T, 267V, 267W, 267Y, 268D, 268E, 268F, 268G, 268I, 268K, 268L, 268M, 268P, 268Q, 268R, 268T, 268V, 268W, 269F, 269G, 269H, 269I, 269K, 269L, 269M, 269N, 269P, 269R, 269S, 269T, 269V, 269W, 269Y, 270F, 270G, 270H, 270I, 270L, 270M, 270P, 270Q, 270R, 270S, 270T, 270W, 270Y, 271A, 271D, 271E, 271F, 271G, 271H, 271I, 271K, 271L, 271M, 271N, 271Q, 271R, 271S, 271T, 271V, 271W, 271Y, 272D, 272F, 272G, 272H, 272I, 272K, 272L, 272M, 272P, 272R, 272S, 272T, 272V, 272W, 272Y, 273I, 274D, 274E, 274F, 274G, 274H, 274I, 274L, 274M, 274N, 274P, 274R, 274T, 274V, 274W, 274Y, 275L, 275W, 276D, 276E, 276F, 276G, 276H, 276I, 276L, 276M, 276P, 276R, 276S, 276T, 276V, 276W, 276Y, 278D, 278E, 278G, 278H, 278I, 278K, 278L, 278M, 278N, 278P, 278Q, 278R, 278S, 278T, 278V, 278W, 280G, 280K, 280L, 280P, 280W, 281D, 281E, 281K, 281N, 281P, 281Q, 281Y, 282E, 282G, 282K, 282P, 282Y, 283G, 283H, 283K, 283L, 283P, 283R, 283Y, 284D, 284E, 284L, 284N, 284Q, 284T, 284Y, 285D, 285E, 285K, 285Q, 285W, 285Y, 286E, 286G, 286P, 286Y, 288D, 288E, 288Y, 290D, 290H, 290L, 290N, 290W, 291D, 291E, 291G, 291H, 291I, 291Q, 291T, 292D, 292E, 292T, 292Y, 293F, 293G, 293H, 293I, 293L, 293M, 293N, 293P, 293R, 293S, 293T, 293V, 293W, 293Y, 294F, 294G, 294H, 294I, 294K, 294L, 294M, 294P, 294R, 294S, 294T, 294V, 294W, 294Y, 295D, 295E, 295F, 295G, 295H, 295I, 295M, 295N, 295P, 295R, 295S, 295T, 295V, 295W, 295Y, 296A, 296D, 296E, 296G, 296H, 296I, 296K, 296L, 296M, 296N, 296Q, 296R, 296S, 296T, 296V, 297D, 297E, 297F, 297G, 297H, 297I, 297K, 297L, 297M, 297P, 297Q, 297R, 297S, 297T, 297V, 297W, 297Y, 298A, 298D, 298E, 298F, 298H, 298I, 298K, 298M, 298N, 298Q, 298R, 298T, 298W, 298Y, 299A, 299D, 299E, 299F, 299G, 299H, 299I, 299K, 299L, 299M, 299N, 299P, 299Q, 299R, 299S, 299V, 299W, 299Y, 300A, 300D, 300E, 300G, 300H, 300K, 300M, 300N, 300P, 300Q, 300R, 300S, 300T, 300V, 300W, 301D, 301E, 301H, 301Y, 302I, 303D, 303E, 303Y, 304D, 304H, 304L, 304N, 304T, 305E, 305T, 305Y, 313F, 317E, 317Q, 318H, 318L, 318Q, 318R, 318Y, 320D, 320F, 320G, 320H, 320I, 320L, 320N, 320P, 320S, 320T, 320V, 320W, 320Y, 322D, 322F, 322G, 322H, 322I, 322P, 322S, 322T, 322V, 322W, 322Y, 323I, 324D, 324F, 324G, 324H, 324I, 324L, 324M, 324P, 324R, 324T, 324V, 324W, 324Y, 325A, 325D, 325E, 325F, 325G, 325H, 325I, 325K, 325L, 325M, 325P, 325Q, 325R, 325S, 325T, 325V, 325W, 325Y, 326E, 326I, 326L, 326P, 326T, 327D, 327E, 327F, 327H, 327I, 327K, 327L, 327M, 327N, 327P, 327R, 327S, 327T, 327V, 327W, 327Y, 328A, 328D, 328E, 328F, 328G, 328H, 328I, 328K, 328M, 328N, 328P, 328Q, 328R, 328S, 328T, 328V, 328W, 328Y, 329D, 329E, 329F, 329G, 329H, 329I, 329K, 329L, 329M, 329N, 329Q, 329R, 329S, 329T, 329V, 329W, 329Y, 330E, 330F, 330G, 330H, 330I, 330L, 330M, 330N, 330P, 330R, 330S, 330T, 330V, 330W, 330Y, 331D, 331F, 331H, 331I, 331L, 331M, 331Q, 331R, 331T, 331V, 331W, 331Y, 332A, 332D, 332E, 332F, 332H, 332K, 332L, 332M, 332N, 332P, 332Q, 332R, 332S, 332T, 332V, 332W, 332Y, 333A, 333F, 333H, 333I, 333L, 333M, 333P, 333T, 333Y, 334A, 334F, 334I, 334L, 334P, 334T, 335D, 335F, 335G, 335H, 335I, 335L, 335M, 335N, 335P, 335R, 335S, 335V, 335W, 335Y, 336E, 336K, 336Y, 337E, 337H, and 337N, wherein numbering is according to the EU index.

In further aspects, the amino acid modification can be at a position selected from the group consisting of 221, 222, 223, 224, 225, 227, 228, 230, 231, 232, 233, 234, 235, 236, 237, 238, 239, 240, 241, 243, 245, 246, 247, 249, 255, 258, 260, 262, 263, 264, 265, 266, 267, 268, 269, 270, 271, 272, 274, 275, 276, 278, 280, 281, 282, 283, 284, 285, 286, 288, 290, 291, 292, 293, 294, 295, 296, 297, 298, 299, 300, 301, 302, 303, 304, 305, 313, 317, 318, 320, 322, 324, 325, 326, 327, 328, 329, 330, 331, 332, 333, 334, 335, 336, and 337.In additional aspects, the substitution can be selected from the group consisting of 221K, 222Y, 223E, 223K, 224E, 224Y, 225E, 225W, 227E, 227G, 227K, 227Y, 228E, 228G, 228K, 228Y, 230A, 230E, 230G, 230Y, 231E, 231G, 231K, 231P, 231Y, 232E, 232G, 232K, 232Y, 233A, 233F, 233H, 233I, 233K, 233L, 233M, 233N, 233Q, 233R, 233S, 233T, 233V, 233W, 233Y, 234D, 234E, 234F, 234G, 234H, 234I, 234K, 234M, 234N, 234P, 234Q, 234R, 234S, 234T, 234W, 234Y, 235D, 235F, 235G, 235H, 235I, 235K, 235M, 235N, 235Q, 235R, 235S, 235T, 235V, 235W, 235Y, 236D, 236E, 236F, 236H, 236I, 236K, 236L, 236M, 236N, 236P, 236Q, 236R, 236S, 236T, 236V, 236W, 236Y, 237D, 237E, 237F, 237H, 237I, 237K, 237L, 237M, 237N, 237P, 237Q, 237R, 237S, 237T, 237V, 237W, 237Y, 238D, 238E, 238F, 238G, 238H, 238I, 238K, 238L, 238M, 238N, 238Q, 238R, 238S, 238T, 238V, 238W, 238Y, 239D, 239E, 239F, 239G, 239H, 239I, 239K, 239L, 239M, 239N, 239P, 239Q, 239R, 239T, 239V, 239W, 239Y, 240M, 240T, 241D, 241E, 241R, 241S, 241W, 241Y, 243E, 243H, 243Q, 243R, 243W, 243Y, 245A, 246D, 246H, 246Y, 247G, 247V, 249H, 249Q, 249Y, 255E, 255Y, 258H, 258S, 258Y, 260D, 260E, 260H, 260Y, 262A, 262E, 262F, 262I, 262T, 263A, 263I, 263M, 263T, 264D, 264E, 264F, 264G, 264H, 264I, 264K, 264L, 264M, 264N, 264P, 264Q, 264R, 264S, 264T, 264W, 264Y, 265F, 265G, 265H, 265I, 265K, 265L, 265M, 265P, 265Q, 265R, 265S, 265T, 265V, 265W, 265Y, 266A, 266I, 266M, 266T, 267D, 267E, 267F, 267H, 267I, 267K, 267L, 267M, 267N, 267P, 267Q, 267R, 267V, 267W, 267Y, 268F, 268G, 268I, 268M, 268P, 268T, 268V, 268W, 269F, 269G, 269H, 269I, 269L, 269M, 269N, 269P, 269R, 269S, 269T, 269V, 269W, 269Y, 270F, 270G, 270H, 270I, 270L, 270M, 270P, 270Q, 270R, 270S, 270T, 270W, 270Y, 271A, 271D, 271E, 271F, 271G, 271H, 271I, 271K, 271L, 271M, 271N, 271Q, 271R, 271S, 271T, 271V, 271W, 271Y, 272F, 272G, 272H, 272I, 272K, 272L, 272M, 272P, 272R, 272S, 272T, 272V, 272W, 272Y, 274D, 274E, 274F, 274G, 274H, 274I, 274L, 274M, 274P, 274R, 274T, 274V, 274W, 274Y, 275W, 276D, 276E, 276F, 276G, 276H, 276I, 276L, 276M, 276P, 276R, 276S, 276T, 276V, 276W, 278D, 278E, 278G, 278H, 278I, 278K, 278L, 278M, 278N, 278P, 278Q, 278R, 278S, 278T, 278V, 278W, 280G, 280P, 280W, 281E, 281K, 281N, 281P, 281Y, 282G, 282P, 282Y, 283G, 283H, 283K, 283L, 283P, 283R, 283Y, 284L, 284N, 284Q, 284T, 284Y, 285K, 285Q, 285W, 285Y, 286G, 286P, 286Y, 288Y, 290H, 290L, 290W, 291D, 291E, 291G, 291H, 291I, 291Q, 291T, 292D, 292E, 292T, 292Y, 293F, 293G, 293H, 293I, 293L, 293M, 293N, 293P, 293R, 293S, 293T, 293W, 293Y, 294F, 294G, 294H, 294I, 294K, 294L, 294M, 294P, 294R, 294S, 294T, 294V, 294W, 294Y, 295D, 295F, 295G, 295H, 295I, 295M, 295N, 295P, 295R, 295S, 295T, 295V, 295W, 295Y, 296A, 296D, 296E, 296G, 296I, 296K, 296L, 296M, 296N, 296Q, 296R, 296S, 296T, 296V, 297D, 297E, 297F, 297G, 297H, 297I, 297K, 297L, 297M, 297P, 297R, 297S, 297T, 297V, 297W, 297Y, 298E, 298F, 298H, 298I, 298K, 298M, 298Q, 298R, 298W, 298Y, 299A, 299D, 299E, 299F, 299G, 299H, 299I, 299K, 299L, 299M, 299N, 299P, 299Q, 299R, 299S, 299V, 299W, 299Y, 300A, 300D, 300E, 300G, 300H, 300K, 300M, 300N, 300P, 300Q, 300R, 300S, 300T, 300V, 300W, 301D, 301E, 301Y, 302I, 303D, 303E, 303Y, 304H, 304L, 304N, 304T, 305E, 305T, 305Y, 313F, 317E, 317Q, 318H, 318L, 318Q, 318R, 318Y, 320D, 320F, 320G, 320H, 320I, 320L, 320N, 320P, 320S, 320T, 320V, 320W, 320Y, 322D, 322F, 322G, 322H, 322I, 322P, 322S, 322T, 322V, 322W, 322Y, 324D, 324F, 324G, 324H, 324I, 324L, 324M, 324P, 324R, 324T, 324V, 324W, 324Y, 325A, 325D, 325E, 325F, 325G, 325H, 325I, 325K, 325L, 325M, 325P, 325Q, 325R, 325S, 325T, 325V, 325W, 325Y, 326L, 326P, 326T, 327D, 327E, 327F, 327H, 327I, 327K, 327L, 327M, 327P, 327R, 327V, 327W, 327Y, 328A, 328D, 328E, 328F, 328G, 328H, 328K, 328M, 328N, 328P, 328Q, 328R, 328S, 328T, 328V, 328W, 328Y, 329D, 329E, 329F, 329G, 329H, 329I, 329K, 329L, 329M, 329N, 329Q, 329R, 329S, 329T, 329V, 329W, 329Y, 330E, 330F, 330H, 330I, 330L, 330M, 330N, 330P, 330W, 330Y, 331D, 331F, 331H, 331I, 331L, 331M, 331Q, 331R, 331T, 331V, 331W, 331Y, 332A, 332F, 332H, 332L, 332M, 332N, 332P, 332Q, 332S, 332T, 332V, 332W, 332Y, 333F, 333H, 333I, 333L, 333M, 333P, 333T, 333Y, 334F, 334P, 334T, 335D, 335F, 335G, 335H, 335I, 335L, 335M, 335P, 335R, 335S, 335V, 335W, 335Y, 336E, 336K, 336Y, 337H, and 337N.

In further aspect, the modification is at a position selected from the group consisting of 221, 222, 223, 224, 225, 228, 230, 231, 232, 240, 244, 245, 247, 262, 263, 266, 271, 273, 275, 281, 284, 291, 299, 302, 304, 313, 323, 325, 328, 332, 336, wherein the positional numbering is according to the EU index. In additional aspects, the modification is selected from the group consisting of 221K, 221Y, 222E, 222Y, 223E, 223K, 224E, 224Y, 225E, 225K, 225W, 228E, 228G, 228K, 228Y, 230A, 230E, 230G, 230Y, 231E, 231G, 231K, 231P, 231Y, 232E, 232G, 232K, 232Y, 240A, 240I, 240M, 240T, 244H, 245A, 247G, 247V, 262A, 262E, 262F, 262I, 262T, 263A, 263I, 263M, 263T, 266A, 266I, 266M, 266T, 271A, 271D, 271E, 271F, 271G, 271H, 271I, 271K, 271L, 271M, 271N, 271Q, 271R, 271S, 271T, 271V, 271W, 271Y, 273I, 275L, 275W, 281D, 281E, 281K, 281N, 281P, 281Q, 281Y, 284D, 284E, 284L, 284N, 284Q, 284T, 284Y, 291D, 291E, 291G, 291H, 291I, 291Q, 291T, 299A, 299D, 299E, 299F, 299G, 299H, 299I, 299K, 299L, 299M, 299N, 299P, 299Q, 299S, 299V, 299W, 299Y, 304D, 304H, 304L, 304N, 304T, 313F, 323I, 325A, 325D, 325E, 325F, 325G, 325H, 325I, 325K, 325L, 325M, 325P, 325Q, 325R, 325S, 325T, 325V, 325W, 325Y, 328A, 328D, 328E, 328F, 328G, 328H, 328I, 328K, 328M, 328N, 328P, 328Q, 328R, 328S, 328T, 328V, 328W, 328Y, 332A, 332D, 332E, 332F, 332H, 332K, 332L, 332M, 332N, 332P, 332Q, 332R, 332S, 332T, 332V, 332W, 332Y, 336E, 336K, and 336Y.

The antibody can further include a second amino acid modification at a position selected from the group consisting of 221, 222, 223, 224, 225, 227, 228, 230, 231, 232, 233, 234, 235, 236, 237, 238, 239, 240, 241, 243, 244, 245, 246, 247, 249, 255, 258, 260, 262, 263, 264, 265, 266, 267, 268, 269, 270, 271, 272, 273, 274, 275, 276, 278, 280, 281, 282, 283, 284, 285, 286, 288, 290, 291, 292, 293, 294, 295, 296, 297, 298, 299, 300, 301, 302, 303, 304, 305, 313, 317, 318, 320, 322, 323, 324, 325, 326, 327, 328, 329, 330, 331, 332, 333, 334, 335, 336, and 337, wherein numbering is according to the EU index. The second amino acid modification can be a substitution selected from the group consisting of 221K, 221Y, 222E, 222Y, 223E, 223K, 224E, 224Y, 225E, 225K, 225W, 227E, 227G, 227K, 227Y, 228E, 228G, 228K, 228Y, 230A, 230E, 230G, 230Y, 231E, 231G, 231K, 231P, 231Y, 232E, 232G, 232K, 232Y, 233A, 233D, 233F, 233G, 233H, 233I, 233K, 233L, 233M, 233N, 233Q, 233R, 233S, 233T, 233V, 233W, 233Y, 234A, 234D, 234E, 234F, 234G, 234H, 234I, 234K, 234M, 234N, 234P, 234Q, 234R, 234S, 234T, 234V, 234W, 234Y, 235A, 235D, 235E, 235F, 235G, 235H, 235I, 235K, 235M, 235N, 235P, 235Q, 235R, 235S, 235T, 235V, 235W, 235Y, 236A, 236D, 236E, 236F, 236H, 236I, 236K, 236L, 236M, 236N, 236P, 236Q, 236R, 236S, 236T, 236V, 236W, 236Y, 237D, 237E, 237F, 237H, 237I, 237K, 237L, 237M, 237N, 237P, 237Q, 237R, 237S, 237T, 237V, 237W, 237Y, 238D, 238E, 238F, 238G, 238H, 238I, 238K, 238L, 238M, 238N, 238Q, 238R, 238S, 238T, 238V, 238W, 238Y, 239D, 239E, 239F, 239G, 239H, 239I, 239K, 239L, 239M, 239N, 239P, 239Q, 239R, 239T, 239V, 239W, 239Y, 240A, 240I, 240M, 240T, 241D, 241E, 241L, 241R, 241S, 241W, 241Y, 243E, 243H, 243L, 243Q, 243R, 243W, 243Y, 244H, 245A, 246D, 246E, 246H, 246Y, 247G, 247V, 249H, 249Q, 249Y, 255E, 255Y, 258H, 258S, 258Y, 260D, 260E, 260H, 260Y, 262A, 262E, 262F, 262I, 262T, 263A, 263I, 263M, 263T, 264A, 264D, 264E, 264F, 264G, 264H, 264I, 264K, 264L, 264M, 264N, 264P, 264Q, 264R, 264S, 264T, 264W, 264Y, 265F, 265G, 265H, 265I, 265K, 265L, 265M, 265N, 265P, 265Q, 265R, 265S, 265T, 265V, 265W, 265Y, 266A, 266I, 266M, 266T, 267D, 267E, 267F, 267H, 267I, 267K, 267L, 267M, 267N, 267P, 267Q, 267R, 267T, 267V, 267W, 267Y, 268D, 268E, 268F, 268G, 268I, 268K, 268L, 268M, 268P, 268Q, 268R, 268T, 268V, 268W, 269F, 269G, 269H, 269I, 269K, 269L, 269M, 269N, 269P, 269R, 269S, 269T, 269V, 269W, 269Y, 270F, 270G, 270H, 270I, 270L, 270M, 270P, 270Q, 270R, 270S, 270T, 270W, 270Y, 271A, 271D, 271E, 271F, 271G, 271H, 271I, 271K, 271L, 271M, 271N, 271Q, 271R, 271S, 271T, 271V, 271W, 271Y, 272D, 272F, 272G, 272H, 272I, 272K, 272L, 272M, 272P, 272R, 272S, 272T, 272V, 272W, 272Y, 273I, 274D, 274E, 274F, 274G, 274H, 274I, 274L, 274M, 274N, 274P, 274R, 274T, 274V, 274W, 274Y, 275L, 275W, 276D, 276E, 276F, 276G, 276H, 276I, 276L, 276M, 276P, 276R, 276S, 276T, 276V, 276W, 276Y, 278D, 278E, 278G, 278H, 278I, 278K, 278L, 278M, 278N, 278P, 278Q, 278R, 278S, 278T, 278V, 278W, 280G, 280K, 280L, 280P, 280W, 281D, 281E, 281K, 281N, 281P, 281Q, 281Y, 282E, 282G, 282K, 282P, 282Y, 283G, 283H, 283K, 283L, 283P, 283R, 283Y, 284D, 284E, 284L, 284N, 284Q, 284T, 284Y, 285D, 285E, 285K, 285Q, 285W, 285Y, 286E, 286G, 286P, 286Y, 288D, 288E, 288Y, 290D, 290H, 290L, 290N, 290W, 291D, 291E, 291G, 291H, 291I, 291Q, 291T, 292D, 292E, 292T, 292Y, 293F, 293G, 293H, 293I, 293L, 293M, 293N, 293P, 293R, 293S, 293T, 293V, 293W, 293Y, 294F, 294G, 294H, 294I, 294K, 294L, 294M, 294P, 294R, 294S, 294T, 294V, 294W, 294Y, 295D, 295E, 295F, 295G, 295H, 295I, 295M, 295N, 295P, 295R, 295S, 295T, 295V, 295W, 295Y, 296A, 296D, 296E, 296G, 296H, 296I, 296K, 296L, 296M, 296N, 296Q, 296R, 296S, 296T, 296V, 297D, 297E, 297F, 297G, 297H, 297I, 297K, 297L, 297M, 297P, 297Q, 297R, 297S, 297T, 297V, 297W, 297Y, 298A, 298D, 298E, 298F, 298H, 298I, 298K, 298M, 298N, 298Q, 298R, 298T, 298W, 298Y, 299A, 299D, 299E, 299F, 299G, 299H, 299I, 299K, 299L, 299M, 299N, 299P, 299Q, 299R, 299S, 299V, 299W, 299Y, 300A, 300D, 300E, 300G, 300H, 300K, 300M, 300N, 300P, 300Q, 300R, 300S, 300T, 300V, 300W, 301D, 301E, 301H, 301Y, 302I, 303D, 303E, 303Y, 304D, 304H, 304L, 304N, 304T, 305E, 305T, 305Y, 313F, 317E, 317Q, 318H, 318L, 318Q, 318R, 318Y, 320D, 320F, 320G, 320H, 320I, 320L, 320N, 320P, 320S, 320T, 320V, 320W, 320Y, 322D, 322F, 322G, 322H, 322I, 322P, 322S, 322T, 322V, 322W, 322Y, 323I, 324D, 324F, 324G, 324H, 324I, 324L, 324M, 324P, 324R, 324T, 324V, 324W, 324Y, 325A, 325D, 325E, 325F, 325G, 325H, 325I, 325K, 325L, 325M, 325P, 325Q, 325R, 325S, 325T, 325V, 325W, 325Y, 326E, 326I, 326L, 326P, 326T, 327D, 327E, 327F, 327H, 327I, 327K, 327L, 327M, 327N, 327P, 327R, 327S, 327T, 327V, 327W, 327Y, 328A, 328D, 328E, 328F, 328G, 328H, 328I, 328K, 328M, 328N, 328P, 328Q, 328R, 328S, 328T, 328V, 328W, 328Y, 329D, 329E, 329F, 329G, 329H, 329I, 329K, 329L, 329M, 329N, 329Q, 329R, 329S, 329T, 329V, 329W, 329Y, 330E, 330F, 330G, 330H, 330I, 330L, 330M, 330N, 330P, 330R, 330S, 330T, 330V, 330W, 330Y, 331D, 331F, 331H, 331I, 331L, 331M, 331Q, 331R, 331T, 331V, 331W, 331Y, 332A, 332D, 332E, 332F, 332H, 332K, 332L, 332M, 332N, 332P, 332Q, 332R, 332S, 332T, 332V, 332W, 332Y, 333A, 333F, 333H, 333I, 333L, 333M, 333P, 333T, 333Y, 334A, 334F, 334I, 334L, 334P, 334T, 335D, 335F, 335G, 335H, 335I, 335L, 335M, 335N, 335P, 335R, 335S, 335V, 335W, 335Y, 336E, 336K, 336Y, 337E, 337H, and 337N, wherein numbering is according to the EU index.

In further aspects, the amino acid modification is 332E. The second amino acid modification can be selected from the group consisting of: 236A, 239D, 332E, 268D, 268E, 330Y, and 330L. In certain preferred embodiments, the second amino acid modification is 239D.

In other aspects, the modification is a glycoform modification that reduces the level of fucose relative to the parent antibody. In still other aspects, the invention is directed to a composition including plurality of glycosylated antibodies, wherein about 80-100% of the glycosylated antibodies in the composition comprise a mature core carbohydrate structure which lacks fucose.

In a further embodiment, the antibody reduces binding to FcγRIIb as compared to the parent anti-CD19 antibody.

In another aspect, the invention is directed to an antibody that binds CD19 and includes a heavy chain and/or a light chain. The heavy chain has a CDR1 comprising the amino acid sequence selected from the group consisting of SEQ ID NO: 132 and 138, a CDR2 comprising an amino acid sequence selected from the group consisting of SEQ ID NOs:111-115 and a CDR3 comprising an amino acid sequence selected from the group consisting of SEQ ID NOs:116-118. The light chain has a CDR1 comprising an amino acid sequence selected from the group consisting of SEQ ID NOs: 119-128, a CDR2 comprising the amino acid sequence of SEQ ID NOs:129, and a CDR3 comprising an amino acid sequence selected from the group consisting of SEQ ID NOs:130-131.

In further variations, the antibody has a variable heavy chain sequence selected from the group consisting of SEQ ID NOS: 13-16, 20-23, and 27-44, and/or a variable light chain sequence selected from the group consisting of SEQ ID NOS: 17-19, 24-26, and 45-79.

In still further variations, the antibody includes a heavy chain sequence selected from the group consisting of SEQ ID NOS: 86-95, and/or a light chain sequence selected from the group consisting of SEQ ID NOS: 96-110.

In various additional aspects, the invention is directed to a nucleic acid sequence encoding any of the antibodies disclosed herein.

In further aspects, the invention is directed to a method of treating a B-cell related disease by administering an antibody according to claim 1. In certain variations, the disease is selected from non-Hodgkin's lymphomas (NHL), chronic lymphocytic leukemia (CLL), B-cell acute lymphoblastic leukemia/lymphoma (B-ALL), and mantle cell lymphoma (MCL). In certain aspects, the disease is an autoimmune disease, such as rheumatoid arthritis (RA), systemic lupus erythematosus (SLE or lupus), multiple sclerosis, Sjogren's syndrome, and idiopathic thrombocytopenia purpura (ITP).

In further aspects, the invention is directed to a composition comprising an antibody described herein and an acceptable carrier.

BRIEF DESCRIPTION OF THE DRAWINGS

The following drawings further illustrate aspects of the invention, and are not meant to constrain the invention to any particular application or theory of operation.

FIG. 1: Amino acid sequence of *Homo sapiens* CD19, as obtained from cDNA clone MGC:12802, IMAGE:4054919, GenBank Accession:BC006338.

FIG. 2. Sequences of the natural antibody constant regions, including the kappa constant light chain, and the gamma constant heavy chains for IgG1, IgG2, IgG3, and IgG4. Also provided is the sequence of a Hybrid IgG constant chain, and a Hybrid IgG constant chain comprising the substitutions 239D and 1332E.

FIGS. 3A and 3B. Alignment of the amino acid sequences of the human IgG immunoglobulins IgG1, IgG2, IgG3, and IgG4. FIG. 3A provides the sequences of the CH1 (Cγ1) and hinge domains, and FIG. 3B provides the sequences of the CH2 (Cγ2) and CH3 (Cγ3) domains. Positions are numbered according to the EU index of the IgG1 sequence, and differences between IgG1 and the other immunoglobulins IgG2, IgG3, and IgG4 are shown in gray. Allotypic polymorphisms exist at a number of positions, and thus slight differences between the presented sequences and sequences in the prior art may exist. The possible beginnings of the Fc region are labeled, defined herein as either EU position 226 or 230.

FIGS. 4A and 4B. The common haplotypes of the gamma chain of human IgG1 (FIG. 4A) and IgG2 (FIG. 4B) showing the positions and the relevant amino acid substitutions.

FIG. 5. Preferred embodiments of receptor binding profiles that include increases to, reductions to, or no effect to the binding to various receptors, where such changes may be beneficial in certain contexts.

FIGS. 6A and 6B. Amino acid sequences of the heavy chain and light chain variable regions of the original 4G7 and HD37 antibodies (H0 and L0). FIG. 6A provides the sequences of the VH and VL domains, and FIG. 6B provides the sequences of the CDRs. CDR boundaries are determined according to the convention of Kabat (VH CDR1: 31-35b, VH CDR2: 50-65, VH CDR3: 95-102, VL CDR1: 24-34, VL CDR2: 50-56, and VL CDR3: 89-97).

FIGS. 10A and 10B. FIG. 10A shows ADCC assays of 4G7 Hybrid S239D/I332E, 4G7 IgG1, and rituximab on a panel of 14 cell lines representing various lymphomas and leukemias. Both parameters potency (EC50) and efficacy (% ADCC) are normalized to that of rituximab (anti-CD20). FIG. 10B lists tested lymphoma and leukemia cell lines.

FIG. 11. Heavy chain variable region sequences with reduced immunogenicity for anti-CD19 antibody 4G7.

FIG. 12. Light chain variable region sequences with reduced immunogenicity for anti-CD19 antibody 4G7.

FIG. 13. Heavy chain variable region sequences with reduced immunogenicity for anti-CD19 antibody HD37.

FIG. 14. Light chain variable region sequences with reduced immunogenicity for anti-CD19 antibody HD37.

FIGS. 15A and 15B. Results of a cell-surface binding assay of reduced immunogenicity 4G7 variants to Raji cells (FIG. 15A) and ADCC of HD37_H2L1 Hybrid S239D/I332E and 4G7_H1L3 Hybrid S239D/I332E on MEC-1 cells (FIG. 15B).

FIG. 18. Sequences for heavy chain variants of anti-CD19 that increase affinity and/or stability.

FIG. 19. Sequences for light chain variants of anti-CD19 that increase affinity and/or stability.

FIG. 21. Anti-proliferative properties of 4G7 stability and affinity improved Hybrid S239D/I332E on SU-DHL-6 cells with and without cross-linking.

FIG. 26. ADCC on RS4; 11 and MEC-1 cells using an enhanced effector function anti-CD19 antibody (4G7 H1L1 Hybrid S239D/I332E) with lower fucose content afforded by expression in the Lec13 system.

FIG. 27. Single substitutions made for enhanced stability and/or affinity. Variable region numbering is according to Kabat. An expanded set of positions is included in the CDRs. The canonical CDR boundaries defined by Kabat, as listed in FIG. 6, are highlighted in gray.

FIG. 28. Anti-CD19 variable region variants constructed to optimize affinity and stability.

FIG. 29. Preferred variants and relative increase in binding affinity versus the parent H1L1 mAb.

FIG. 30a shows the dose-dependence of anti-mu antibody on B cell proliferation. FIG. 30b shows B cell proliferation in the presence of fixed anti-mu (2 mg/ml) plus varying concentrations of anti-CD19 WT and Fc variant, and anti-CD30 Fc variant control antibodies. Anti-Anti-CD19_IgG1_WT=4G7_H3_L1 IgG1_WT, Anti-CD19_Hybrid_S239D/I332E=4G7_H3_L1_Hybrid_239D/332E, and Anti-CD30_S239D/I332E, used here as a negative control, =AC10_H3.69V2_L3.71_Hybrid_239D/332E (as disclosed in U.S. Ser. No. 11/686,853, Lazar G. A. et al., filed Mar. 15, 2007).

DETAILED DESCRIPTION OF THE INVENTION

Figure 7:
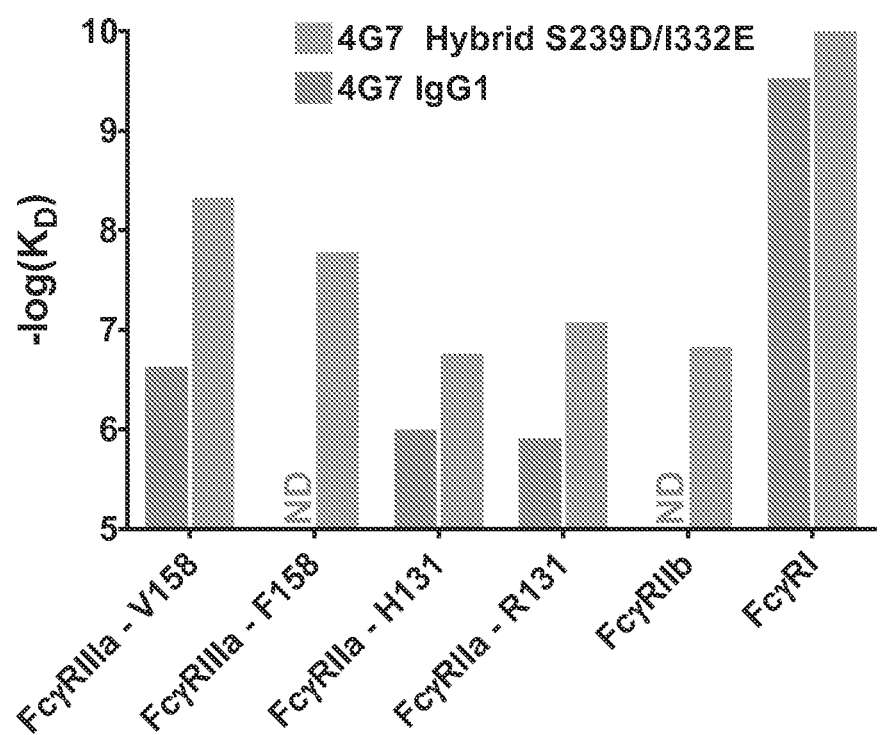
FIG. 7. The relative binding affinities of 4G7 Hybrid S239D/I332E and 4G7 IgG1 antibody to a panel of Fc receptors.

The disclosure is directed to modified anti-CD19 antibodies and methods of using the same. In various aspects, the antibodies can have a having a modified Fc region, specific CDR sequences, variable region sequences, and/or constant region modifications. In various embodiments, the antibodies are humanized. The disclosure is further directed to methods of using the antibodies in various disease indications, including those of B-cell origin such as B-cell origin non-Hodgkin's lymphoma (NHL), acute lymphoblastic leukemia (ALL), and autoimmune related diseases.

In order that the invention may be more completely understood, several definitions are set forth below. Such definitions are meant to encompass grammatical equivalents.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell. In various aspects, the enhanced ADCC effector function can mean enhanced potency or enhanced efficacy. By "potency" as used in the experimental context is meant the concentration of antibody when a particular therapeutic effect is observed EC50 (half maximal effective concentration). By "efficacy" as used in the experimental context is meant the maximal possible effector function at saturating levels of antibody.

By "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

By "amino acid" and "amino acid identity" as used herein is meant one of the 20 naturally occurring amino acids or any non-natural analogues that may be present at a specific, defined position. Thus "amino acid" as used herein means both naturally occurring and synthetic amino acids. For example, homophenylalanine, citrulline and norleucine are considered amino acids for the purposes of the invention. "Amino acid" also includes imino acid residues such as proline and hydroxyproline. The side chain may be in either the (R) or the (S) configuration. In the preferred embodiment, the amino acids are in the (S) or L-configuration. If non-naturally occurring side chains are used, non-amino acid substituents may be used, for example to prevent or retard in vivo degradation.

By "B cell" or "B lymphocyte" as used herein is meant a type of lymphocyte developed in bone marrow that circulates in the blood and lymph, and provides humoral immunity. B cells recognize free antigen molecules and differentiate or mature into plasma cells that secrete immunoglobulin (antibodies) that inactivate the antigens. Memory cells are also generated that make the specific Immunoglobulin (antibody) on subsequent encounters with such antigen. B cells are also known as "Beta cells" in the islet of Langerhans.

By "B-cell antigen" or "B-cell marker" as used herein is meant any protein that is expressed on B cells.

By "CD19" as used herein is meant the protein of SEQ ID NO:1 (depicted in FIG. 1). CD19 is also known as B-cell surface antigen B4, B-cell antigen CD19, CD19 antigen, and Leu-12. Human CD19 is designated GeneID:930 by Entrez Gene, and HGNC:1633 by HGNC. CD19 can be encoded by the gene designated CD19. The use of "CD19" herein is meant to encompass all known or as yet undiscovered alleles and polymorphic forms of CD19.

By "CDC" or "complement dependent cytotoxicity" as used herein is meant the reaction wherein one or more complement protein components recognize bound antibody on a target cell and subsequently cause lysis of the target cell.

By "constant region" as used herein is meant the polypeptide including at least a portion of the first three constant regions of an antibody, having at least one effector function. Thus constant region thus refers to the last three constant region immunoglobulin domains of IgA, IgD, and IgG, and the last four constant region immunoglobulin domains of IgE and IgM, and the flexible hinge N-terminal to these domains. For IgA and IgM, Fc may include the J chain. For IgG, the constant region include immunoglobulin domains Cgamma 1, Cgamma2 and Cgamma3 (Cγ1, Cγ2 and Cγ3) and the hinge between Cgamma1 (Cγ1) and Cgamma2 (Cγ2). Although the boundaries of the constant region may vary, the human IgG heavy chain Fc region is usually defined to comprise residues to its carboxyl-terminus, wherein the numbering is according to the EU index as in Kabat. The constant light chain typically comprises a single domain, and as defined herein refers to positions 108-214 of Cκ or Cλ, wherein numbering is according to the EU index.

For full length IgG antibodies, the constant heavy chain, as defined herein, refers to the N-terminus of the CH1 domain to the C-terminus of the CH3 domain, or positions 118-447, wherein numbering is according to the EU index. "Constant region" may refer to this region in isolation, or a truncation or fusion include antibodies, Fc fusions, isolated Fcs, and Fc fragments. In various embodiments, the constant region may be the region of the antibody that is encoded by one of the light or heavy chain immunoglobulin constant region genes, i.e. the region of an antibody encoded by the kappa (Cκ) or lambda (Cλ) light chains. In various embodiments, the constant heavy chain or heavy chain constant region can be the the region of an antibody encoded by the mu, delta, gamma, alpha, or epsilon genes to define the antibody's isotype as IgM, IgD, IgG, IgA, or IgE, respectively.

By "effector function" as used herein is meant a biochemical event that results from the interaction of an antibody Fc region with an Fc receptor or ligand. Effector functions include FcγR-mediated effector functions such as ADCC and ADCP, and complement-mediated effector functions such as CDC. By "effector cell" as used herein is meant a cell of the immune system that expresses one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and γδ T cells, and may be from any organism including but not limited to humans, mice, rats, rabbits, and monkeys.

By "Fab" or "Fab region" as used herein is meant the polypeptides that comprise the $V_H$, CH1, $V_H$, and $C_L$ immunoglobulin domains. Fab may refer to this region in isolation, or this region in the context of a full length antibody or antibody fragment.

By "Fc" or "Fc region", as used herein is meant the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index as in Kabat. Fc may refer to this region in isolation, or this region in the context of an Fc polypeptide, for example an antibody. By "Fc polypeptide" as used herein is meant a polypeptide that comprises all or part of an Fc region. Fc polypeptides include antibodies, Fc fusions, isolated Fcs, and Fc fragments.

By "Fc gamma receptor" or "FcγR" as used herein is meant any member of the family of proteins that bind the IgG antibody Fc region. In various embodiments, FcγR are substantially encoded by the FcγR genes. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, *Immunol Lett* 82:57-65, incorporated entirely by reference), as well as any undiscovered human FcγRs or FcγR isoforms or allotypes. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes. An FcγR may be from any organism, including but not limited to humans, mice, rats, rabbits, and monkeys.

By "Fc ligand" or "Fc receptor" as used herein is meant a molecule, preferably a polypeptide, from any organism that binds to the Fc region of an antibody to form an Fc-ligand complex. Fc ligands include but are not limited to FcγRs, FcRn, C1q, C3, mannan binding lectin, mannose receptor, *staphylococcal* protein A, *streptococcal* protein G, and viral FcγR. Fc ligands also include Fc receptor homologs (FcRH), which are a family of Fc receptors that are homologous to the FcγRs (Davis et al., 2002, *Immunological Reviews* 190:123-136, incorporated entirely by reference). Fc ligands may include undiscovered molecules that bind Fc.

By "IgG" as used herein is meant a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3. By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full length antibodies, antibody fragments, and individual immunoglobulin domains. By "immunoglobulin (Ig) domain" herein is meant a region of an immunoglobulin that exists as a distinct structural entity as ascertained by one skilled in the art of protein structure. Ig domains typically have a characteristic β-sandwich folding topology. The known Ig domains in the IgG class of antibodies are $V_H$, Cγ1, Cγ2, Cγ3, $V_L$, and $C_L$.

By "modification" herein is meant an alteration in the physical, chemical, or sequence properties of a protein, polypeptide, antibody, or immunoglobulin. Preferred modifications of the invention are amino acid modifications and glycoform modifications.

By "amino acid modification" herein is meant an amino acid substitution, insertion, and/or deletion in a polypeptide sequence. By "amino acid substitution" or "substitution" herein is meant the replacement of an amino acid at a particular position in a parent polypeptide sequence with another amino acid. For example, the substitution I332E refers to a variant polypeptide, in this case a constant heavy chain variant, in which the isoleucine at position 332 is replaced with glutamic acid. The WT residue may or may not be designated. For the preceding example, 332E indicates the substitution of position 332 with a glutamic acid. For the purposes herein, multiple substitutions are typically separated by a slash. For example, 239D/332E refers to a double variant comprising the substitutions 239D and 332E. By "amino acid insertion" or "insertion" as used herein is meant the addition of an amino acid at a particular position in a parent polypeptide sequence. For example, insert –236 designates an insertion of glycine at position 236. By "amino acid deletion" or "deletion" as used herein is meant the removal of an amino acid at a particular position in a parent polypeptide sequence. For example, G236-designates the deletion of glycine at position 236.

By "glycoform modification" or "modified glycoform" or "engineered glycoform" as used herein is meant a carbohydrate composition that is covalently attached to a protein, for example an antibody, wherein said carbohydrate composition differs chemically from that of a parent protein. Modified glycoform typically refers to the different carbohydrate or oligosaccharide; thus for example an antibody may comprise a modified glycoform. Alternatively, modified glycoform may refer to the antibody that comprises the different carbohydrate or oligosaccharide.

By "parent polypeptide", "parent protein", "precursor polypeptide", or "precursor protein" as used herein is meant an unmodified polypeptide that is subsequently modified to generate a variant. Said parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent antibody" or "parent immunoglobulin" as used herein is meant an antibody or immunoglobulin that is modified to generate a variant. By "parent anti-CD19 antibody" or "parent anti-CD19 immunoglobulin" as used herein is meant an antibody or immunoglobulin that binds CD19 and is modified to generate a variant.

By "protein" or "polypeptide" as used herein is meant at least two covalently attached amino acids, which includes proteins, polypeptides, oligopeptides and peptides. The protein may be made up of naturally occurring amino acids and peptide bonds, or synthetic peptidomimetic structures, i.e. "analogs", such as peptoids.

By "position" as used herein is meant a location in the sequence of a protein. Positions may be numbered sequentially, or according to an established format, for example the EU index as in Kabat. Corresponding positions are determined as outlined herein, generally through alignment with other parent sequences.

By "residue" as used herein is meant a position in a protein and its associated amino acid identity. For example, Asparagine 297 (also referred to as Asn297 and N297) is a residue at position 297 in the human antibody IgG1.

By "target antigen" or "target" or "antigen" as used herein is meant the molecule that is bound specifically by the variable region of a given antibody. A target antigen may be a protein, carbohydrate, lipid, or other chemical compound. By "target cell" as used herein is meant a cell that expresses a target antigen.

By "variable region" is meant the variable region of an antibody heavy chain or light chain. The heavy chain variable region (VH), as defined herein, refers to the N-terminus to the C-terminus of the VH domain, defined by residues 1-113 according to the numbering convention of Kabat. The light chain variable region (VL), as defined herein, refers to the N-terminus to the C-terminus of the VL domain, defined by residues 1-107 according to the numbering convention of Kabat. Those skilled in the art will recognize that the Kabat variable region numbering convention employs letters to account for the variable length of CDRs. Thus that a VH is defined by Kabat residues 1-113, and that a VL is defined by Kabat 1-107, does not necessarily mean that the VH domain contains exactly 113 residues, nor that VL contains exactly 107 residues. Rather, residues 1-113 of VH and 1-107 of VL according to Kabat are meant to encompass the structural domains that were determined by sequence alignments of a large set of variable length antibody variable regions of varying length ((Kabat et al., 1991, Sequences of Proteins of Immunological Interest, 5th Ed., United States Public Health Service, National Institutes of Health, Bethesda, incorporated entirely by reference). In certain embodiments, the variable region can comprises one or more Ig domains substantially encoded by any of the Vκ, Vλ, and/or $V_H$ genes that make up the kappa, lambda, and heavy chain immunoglobulin genetic loci respectively.

By "variant protein", "protein variant", "variant polypeptide", or "polypeptide variant" as used herein is meant a polypeptide sequence that differs from that of a parent polypeptide sequence by virtue of at least one amino acid modification. Variant polypeptide may refer to the polypeptide itself, a composition comprising the polypeptide, or the amino sequence that encodes it. Preferably, the variant polypeptide has at least one amino acid modification compared to the parent polypeptide, e.g. from about one to about ten amino acid modifications, and preferably from about one to about five amino acid modifications compared to the parent. The variant polypeptide sequence herein will preferably possess at least about 80% homology with a parent polypeptide sequence, and most preferably at least about 90% homology, more preferably at least about 95% homology. Accordingly, by "variant antibody" or "antibody variant" as used herein is meant an antibody sequence that differs from that of a parent antibody sequence by virtue of at least one amino acid modification. Antibody variant may refer to the antibody polypeptide itself, compositions comprising the antibody variant polypeptide, or the amino acid sequence that encodes it. Accordingly, by "variant antibody" or "antibody variant" as used herein is meant an antibody, as defined above, that differs in sequence from that of a parent antibody sequence by virtue of at least one amino acid modification. Variant antibody may refer to the protein itself, compositions comprising the protein, or the amino acid sequence that encodes it. Accordingly, by "constant heavy chain variant" or "constant light chain variant" or "Fc variant" as used herein is meant a constant heavy chain, constant light chain, or Fc region polypeptide or sequence, respectively, that differs in sequence from that of a parent sequence by virtue of at least one amino acid modification.

By "wild type or WT" herein is meant an amino acid sequence or a nucleotide sequence that is found in nature, including allelic variations. A WT protein, polypeptide, antibody, immunoglobulin, IgG, etc., has an amino acid sequence or a nucleotide sequence that has not been intentionally modified.

For all immunoglobulin heavy chain constant region positions discussed in the present invention, numbering is according to the EU index as in Kabat (Kabat et al., 1991, Sequences of Proteins of Immunological Interest, 5th Ed., United States Public Health Service, National Institutes of Health, Bethesda, incorporated entirely by reference). The "EU index as in Kabat" refers to the residue numbering of the human IgG1 EU antibody, as described in Edelman et al., 1969, Biochemistry 63:78-85, incorporated entirely by reference.

Antibodies

As used herein, the term "antibody" refers to a monomeric or multimeric protein comprising one or more polypeptide chains. An antibody binds specifically to an antigen (e.g. CD19) and may be able to modulate the biological activity of the antigen. As used herein, the term "antibody" can include "full length antibody" and "Fc polypeptide."

By "full length antibody" herein is meant the structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin domains $V_L$ and $C_L$, and each heavy chain comprising immunoglobulin domains $V_H$, CH1 (Cγ1), CH2 (Cγ2), and CH3 (Cγ3). In some mammals, for example in camels and llamas, IgG antibodies may consist of only two heavy chains, each heavy chain comprising a variable domain attached to the Fc region.

The term "antibody" also includes antibody fragments. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883), (viii) bispecific single chain Fv dimers (PCT/US92/09965) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448). In certain embodiments, antibodies are produced by recombinant DNA techniques. Other examples of antibody formats and architectures are described in Holliger & Hudson, 2006, Nature Biotechnology 23(9):1126-1136, and Carter 2006, Nature Reviews Immunology 6:343-357 and references cited therein, all expressly incorporated by reference. In additional embodiments, antibodies are produced by enzymatic or chemical cleavage of naturally occurring antibodies.

Natural antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Each of the light and heavy chains are made up of two distinct regions, referred to as the variable and constant regions. For the IgG class of immunoglobulins, the heavy chain is composed of four immunoglobulin domains linked from N- to C-terminus in the order $V_H$-CH1-CH2-CH3, referring to the heavy chain variable domain, heavy chain constant domain 1, heavy chain constant domain 2, and heavy chain constant domain 3 respectively (also referred to as $V_H$-Cγ1-Cγ2-Cγ3, referring to the heavy chain variable domain, constant gamma 1 domain, constant gamma 2 domain, and constant gamma 3 domain respectively). The IgG light chain is composed of two immunoglobulin domains linked from N- to C-terminus in the order $V_L$-$C_L$, referring to the light chain variable domain and the light chain constant domain respectively. The constant regions show less sequence diversity, and are responsible for binding a number of natural proteins to elicit important biochemical events.

The variable region of an antibody contains the antigen binding determinants of the molecule, and thus determines the specificity of an antibody for its target antigen. The variable region is so named because it is the most distinct in sequence from other antibodies within the same class. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. There are 6 CDRs total, three each per heavy and light chain, designated $V_H$ CDR1, $V_H$ CDR2, $V_H$ CDR3, $V_L$ CDR1, $V_L$ CDR2, and $V_L$ CDR3. The variable region outside of the CDRs is referred to as the framework (FR) region. Although not as diverse as the CDRs, sequence variability does occur in the FR region between different antibodies. Overall, this characteristic architecture of antibodies provides a stable scaffold (the FR region) upon which substantial antigen binding diversity (the CDRs) can be explored by the immune system to obtain specificity for a broad array of antigens. A number of high-resolution structures are available for a variety of variable region fragments from different organisms, some unbound and some in complex with antigen. Sequence and structural features of antibody variable regions are disclosed, for example, in Morea et al., 1997, *Biophys Chem* 68:9-16; Morea et al., 2000, *Methods* 20:267-279, and the conserved features of antibodies are disclosed, for example, in Maynard et al., 2000, *Annu Rev Biomed Eng* 2:339-376, both incorporated entirely by reference.

Figure 3B:
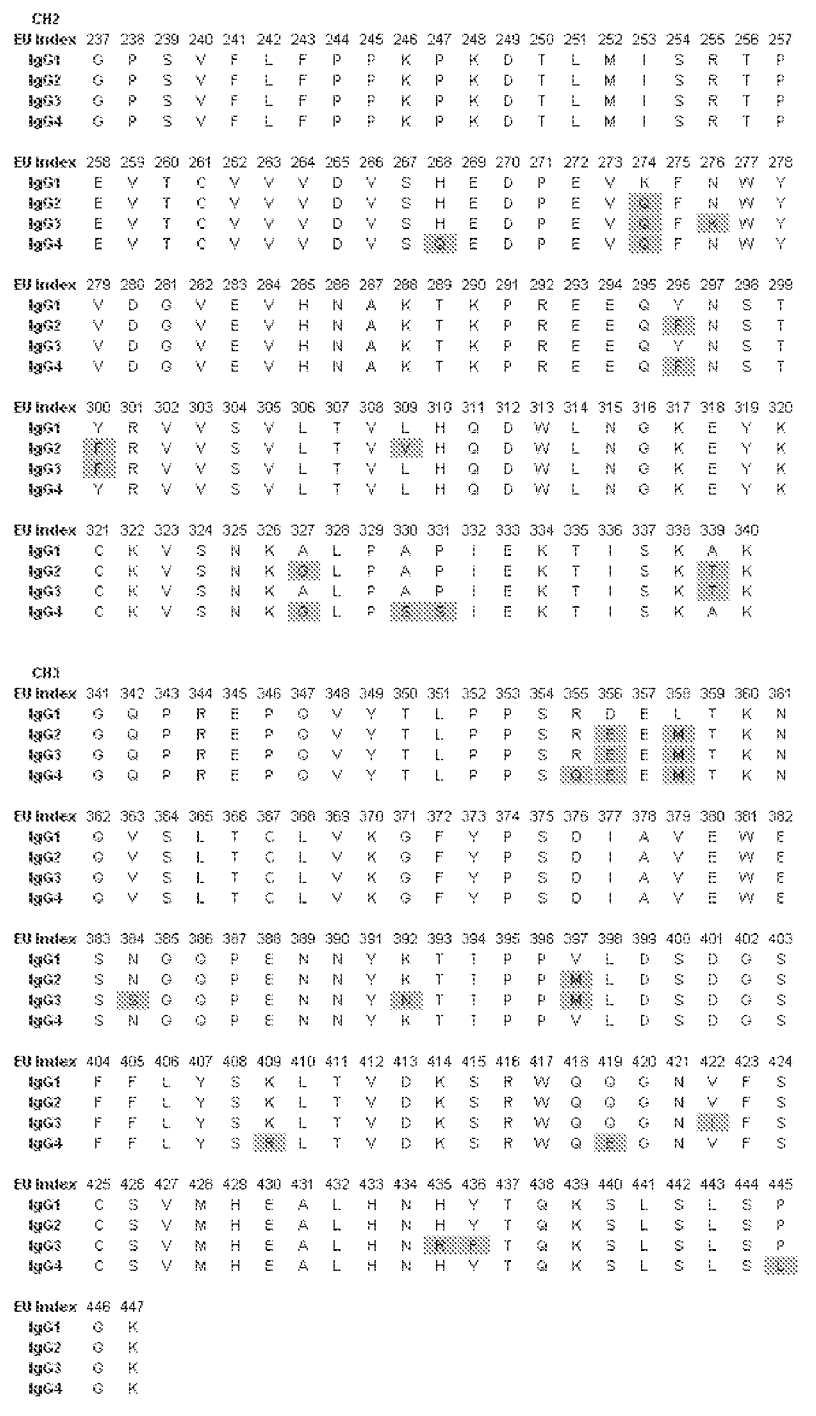

Antibodies are grouped into classes, also referred to as isotypes, as determined genetically by the constant region. Human constant light chains are classified as kappa (Cκ) and lambda (Cλ) light chains. Heavy chains are classified as mu, delta, gamma, alpha, or epsilon, and define the antibody's isotype as IgM, IgD, IgG, IgA, and IgE, respectively. The IgG class is the most commonly used for therapeutic purposes. In humans this class comprises subclasses IgG1, IgG2, IgG3, and IgG4. In mice this class comprises subclasses IgG1, IgG2a, IgG2b, IgG3. IgM has subclasses, including, but not limited to, IgM1 and IgM2. IgA has several subclasses, including but not limited to IgA1 and IgA2. Thus, "isotype" as used herein is meant any of the classes or subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE. FIG. 2 provides the sequences of the human light chain kappa and heavy chain gamma constant chains. FIG. 3 shows an alignment of the human IgG constant heavy chains.

Also useful for the invention may be IgGs that are hybrid compositions of the natural human IgG isotypes. Effector functions such as ADCC, ADCP, CDC, and serum half-life differ significantly between the different classes of antibodies, including for example human IgG1, IgG2, IgG3, IgG4, IgA1, IgA2, IgD, IgE, IgG, and IgM (Michaelsen et al., 1992, Molecular Immunology, 29(3): 319-326, entirely incorporated by reference). A number of studies have explored IgG1, IgG2, IgG3, and IgG4 variants in order to investigate the determinants of the effector function differences between them. See for example Canfield & Morrison, 1991, J. Exp. Med. 173: 1483-1491; Chappel et al., 1991, Proc. Natl. Acad. Sci. USA 88(20): 9036-9040; Chappel et al., 1993, Journal of Biological Chemistry 268:25124-25131; Tao et al., 1991, J. Exp. Med. 173: 1025-1028; Tao et al., 1993, J. Exp. Med. 178: 661-667; Redpath et al., 1998, Human Immunology, 59, 720-727, all entirely incorporated by reference.

As described in U.S. Ser. No. 11/256,060, filed Oct. 21, 2005, entitled "IgG Immunoglobulin Variants with Optimized Effector Function", herein expressly incorporated by reference, it is possible to engineer amino acid modifications in an antibody that comprise constant regions from other immunoglobulin classes, for example as those illustrated in the alignments in FIG. 3. Such engineered hybrid IgG compositions may provide improved effector function properties, including improved ADCC, phagocytosis, CDC, and serum half-life. For example, as illustrated by FIG. 3, an IgG1/IgG3 hybrid variant may be constructed by substituting IgG1 positions in the CH2 and CH3 region with the amino acids from IgG3 at positions where the two isotypes differ. Thus a hybrid variant IgG antibody may be constructed that comprises one or more substitutions selected from the group consisting of: 274Q, 276K, 300F, 339T, 356E, 358M, 384S, 392N, 397M, 422I, 435R, and 436F, wherein numbering is according to the EU index. Such variant may provide alternate and/or improved effector function properties.

As another example, relatively poor effector function of IgG2 may be improved by replacing key FcγR binding residues with the corresponding amino acids in an IgG with better effector function. For example, key residue differences between IgG2 and IgG1 with respect to FcγR binding may include P233, V234, A235, -236 (referring to a deletion in IgG2 relative to IgG1), and G327. Thus one or more amino acid modifications in the parent IgG2 wherein one or more of these residues is replaced with the corresponding IgG1 amino acids, P233E, V234L, A235L, -236G (referring to an insertion of a glycine at position 236), and G327A, may provide enhanced effector function. The sequence of such an IgG, comprising a hybrid of residues from IgG1 and IgG2, refered to herein as "Hybrid" in the Examples and Figures, is provided in FIG. 2.

As is well known in the art, immunoglobulin polymorphisms exist in the human population. Gm polymorphism is determined by the IGHG1, IGHG2 and IGHG3 genes which have alleles encoding allotypic antigenic determinants referred to as G1m, G2m, and G3m allotypes for markers of the human IgG1, IgG2 and IgG3 molecules (no Gm allotypes have been found on the gamma 4 chain). Markers may be classified into 'allotypes' and 'isoallotypes'. These are distinguished on different serological bases dependent upon the strong sequence homologies between isotypes. Allotypes are antigenic determinants specified by allelic forms of the Ig genes. Allotypes represent slight differences in the amino acid sequences of heavy or light chains of different individuals. Even a single amino acid difference can give rise to an allotypic determinant, although in many cases there are several amino acid substitutions that have occurred. Allotypes are sequence differences between alleles of a subclass whereby the antisera recognize only the allelic differences. An isoallotype is an allele in one isotype which produces an epitope which is shared with a non-polymorphic homologous region of one or more other isotypes and because of this the antisera will react with both the relevant allotypes and the relevant homologous isotypes (Clark, 1997, IgG effector mechanisms, Chem Immunol. 65:88-110; Gorman & Clark, 1990, Semin Immunol 2(6):457-66, both incorporated entirely by reference).

Allelic forms of human immunoglobulins have been well-characterized (WHO Review of the notation for the allotypic and related markers of human immunoglobulins. J Immunogen 1976, 3: 357-362; WHO Review of the notation for the allotypic and related markers of human immunoglobulins. 1976, Eur. J. Immunol. 6, 599-601; E. van Loghem, 1986, Allotypic markers, Monogr Allergy 19: 40-51, all incorporated entirely by reference). Additionally, other polymorphisms have been characterized (Kim et al., 2001, J. Mol. Evol. 54:1-9, incorporated entirely by reference). At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b5, b0, b3, b4, s, t, g1, c5, u, v, g5) (Lefranc, et al., The human IgG subclasses: molecular analysis of structure, function and regulation. Pergamon, Oxford, pp. 43-78 (1990); Lefranc, G.

et al., 1979, Hum. Genet.: 50, 199-211, both incorporated entirely by reference). Allotypes that are inherited in fixed combinations are called Gm haplotypes. FIG. 4 shows common haplotypes of the gamma chain of human IgG1 (FIG. 4a) and IgG2 (FIG. 4b) showing the positions and the relevant amino acid substitutions. Amino acid sequences of these allotypic versions of IgG1 and IgG2 are provided as SEQ IDs: 80-85. The antibodies of the present invention may be substantially encoded by any allotype, isoallotype, or haplotype of any immunoglobulin gene.

Allelic forms of human immunoglobulins have been well-characterized (WHO Review of the notation for the allotypic and related markers of human immunoglobulins. J Immunogen 1976, 3: 357-362; WHO Review of the notation for the allotypic and related markers of human immunoglobulins. 1976, Eur. J. Immunol. 6, 599-601; E. van Loghem, 1986, Allotypic markers, Monogr Allergy 19: 40-51, all incorporated entirely by reference). Additionally, other polymorphisms have been characterized (Kim et al., 2001, J. Mol. Evol. 54:1-9, incorporated entirely by reference). At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b5, b0, b3, b4, s, t, g1, c5, u, v, g5) (Lefranc, et al., The human IgG subclasses: molecular analysis of structure, function and regulation. Pergamon, Oxford, pp. 43-78 (1990); Lefranc, G. et al., 1979, Hum. Genet.: 50, 199-211, both incorporated entirely by reference). Allotypes that are inherited in fixed combinations are called Gm haplotypes. FIG. 4 shows common haplotypes of the gamma chain of human IgG1 (FIG. 4a) and IgG2 (FIG. 4b) showing the positions and the relevant amino acid substitutions. The antibodies of the present invention may be substantially encoded by any allotype, isoallotype, or haplotype of any immunoglobulin gene.

Antibodies of the present invention may be substantially encoded by genes from any organism, preferably mammals, including but not limited to humans, rodents including but not limited to mice and rats, lagomorpha including but not limited to rabbits and hares, camelidae including but not limited to camels, llamas, and dromedaries, and non-human primates, including but not limited to Prosimians, Platyrrhini (New World monkeys), Cercopithecoidea (Old World monkeys), and Hominoidea including the Gibbons and Lesser and Great Apes. In a most preferred embodiment, the antibodies of the present invention are substantially human. The antibodies of the present invention may be substantially encoded by immunoglobulin genes belonging to any of the antibody classes. In a most preferred embodiment, the antibodies of the present invention comprise sequences belonging to the IgG class of antibodies, including human subclasses IgG1, IgG2, IgG3, and IgG4. In an alternate embodiment, the antibodies of the present invention comprise sequences belonging to the IgA (including human subclasses IgA1 and IgA2), IgD, IgE, IgG, or IgM classes of antibodies. The antibodies of the present invention may comprise more than one protein chain. That is, the present invention may find use in an antibody that is a monomer or an oligomer, including a homo- or hetero-oligomer.

In the most preferred embodiment, the antibodies of the invention are based on human IgG sequences, and thus human IgG sequences are used as the "base" sequences against which other sequences are compared, including but not limited to sequences from other organisms, for example rodent and primate sequences, as well as sequences from other immunoglobulin classes such as IgA, IgE, IgGD, IgGM, and the like. It is contemplated that, although the antibodies of the present invention are engineered in the context of one parent antibody, the variants may be engineered in or "transferred" to the context of another, second parent antibody. This is done by determining the "equivalent" or "corresponding" residues and substitutions between the first and second antibodies, typically based on sequence or structural homology between the sequences of the two antibodies. In order to establish homology, the amino acid sequence of a first antibody outlined herein is directly compared to the sequence of a second antibody. After aligning the sequences, using one or more of the homology alignment programs known in the art (for example using conserved residues as between species), allowing for necessary insertions and deletions in order to maintain alignment (i.e., avoiding the elimination of conserved residues through arbitrary deletion and insertion), the residues equivalent to particular amino acids in the primary sequence of the first antibody are defined. Alignment of conserved residues preferably should conserve 100% of such residues. However, alignment of greater than 75% or as little as 50% of conserved residues is also adequate to define equivalent residues. Equivalent residues may also be defined by determining structural homology between a first and second antibody that is at the level of tertiary structure for antibodies whose structures have been determined. In this case, equivalent residues are defined as those for which the atomic coordinates of two or more of the main chain atoms of a particular amino acid residue of the parent or precursor (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the proteins. Regardless of how equivalent or corresponding residues are determined, and regardless of the identity of the parent antibody in which the antibodies are made, what is meant to be conveyed is that the antibodies discovered by the present invention may be engineered into any second parent antibody that has significant sequence or structural homology with said antibody. Thus for example, if a variant antibody is generated wherein the parent antibody is human IgG1, by using the methods described above or other methods for determining equivalent residues, said variant antibody may be engineered in a human IgG2 parent antibody, a human IgA parent antibody, a mouse IgG2a or IgG2b parent antibody, and the like. Again, as described above, the context of the parent antibody does not affect the ability to transfer the antibodies of the present invention to other parent antibodies. For example, the variant antibodies that are engineered in a human IgG1 antibody that targets one antigen epitope may be transferred into a human IgG2 antibody that targets a different antigen epitope, and so forth.

In the IgG class of immunoglobulins, there are several immunoglobulin domains in the heavy chain. By "immunoglobulin (Ig) domain" herein is meant a region of an immunoglobulin having a distinct tertiary structure. Of interest in the present invention are the domains of the constant heavy chain, including, the constant heavy (CH) domains and the hinge. In the context of IgG antibodies, the IgG isotypes each have three CH regions: "CH1" refers to positions 118-220, "CH2" refers to positions 237-340, and "CH3" refers to positions 341-447 according to the EU index as in Kabat. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230. The constant heavy chain, as defined herein, refers to the N-terminus of the CH1 domain to the C-terminus of the CH3 domain, thus comprising positions 118-447, wherein numbering is according to the EU index. The constant light chain comprises a single domain, and as defined herein refers to positions 108-214 of Cκ or Cλ, wherein numbering is according to the EU index.

Antibodies of the invention may include multispecific antibodies, notably bispecific antibodies, also sometimes referred to as "diabodies". These are antibodies that bind to two (or more) different antigens. Diabodies can be manufactured in a variety of ways known in the art, e.g., prepared chemically or from hybrid hybridomas. In one embodiment, the antibody is a minibody. Minibodies are minimized antibody-like proteins comprising a scFv joined to a CH3 domain. In some cases, the scFv can be joined to the Fc region, and may include some or all of the hinge region. For a description of multispecific antibodies see Holliger & Hudson, 2006, Nature Biotechnology 23(9):1126-1136 and references cited therein, all expressly incorporated by reference.

In one embodiment, the antibody of the invention is an antibody fragment. Of particular interest are antibodies that comprise Fc regions, Fc fusions, and the constant region of the heavy chain (CH1-hinge-CH2-CH3). Antibodies of the present invention may comprise Fc fragments. An Fc fragment of the present invention may comprise from 1-90% of the Fc region, with 10-90% being preferred, and 30-90% being most preferred. Thus for example, an Fc fragment of the present invention may comprise an IgG1 Cγ2 domain, an IgG1 Cγ2 domain and hinge region, an IgG1 Cγ3 domain, and so forth. In one embodiment, an Fc fragment of the present invention additionally comprises a fusion partner, effectively making it an Fc fragment fusion. Fc fragments may or may not contian extra polypeptide sequence.

Chimeric, Humanized, and Fully Human Antibodies

Immunogenicity is the result of a complex series of responses to a substance that is perceived as foreign, and may include production of neutralizing and non-neutralizing antibodies, formation of immune complexes, complement activation, mast cell activation, inflammation, hypersensitivity responses, and anaphylaxis. Several factors can contribute to protein immunogenicity, including but not limited to protein sequence, route and frequency of administration, and patient population. Immunogenicity may limit the efficacy and safety of a protein therapeutic in multiple ways. Efficacy can be reduced directly by the formation of neutralizing antibodies. Efficacy may also be reduced indirectly, as binding to either neutralizing or non-neutralizing antibodies typically leads to rapid clearance from serum. Severe side effects and even death may occur when an immune reaction is raised. Thus in a preferred embodiment, protein engineering is used to reduce the immunogenicity of the antibodies of the present invention.

In some embodiments, the scaffold components can be a mixture from different species. Such antibody may be a chimeric antibody and/or a humanized antibody. In general, both "chimeric antibodies" and "humanized antibodies" refer to antibodies that combine regions from more than one species. "Chimeric antibodies" traditionally comprise variable region(s) from a mouse (or rat, in some cases) and the constant region(s) from a human (Morrison et al., 1984, Proc Natl Acad Sci USA 81: 6851-6855, incorporated entirely by reference).

By "humanized" antibody as used herein is meant an antibody comprising a human framework region (FR) and one or more complementarity determining regions (CDR's) from a non-human (usually mouse or rat) antibody. The non-human antibody providing the CDR's is called the "donor" and the human immunoglobulin providing the framework is called the "acceptor". In certain embodiments, humanization relies principally on the grafting of donor CDRs onto acceptor (human) VL and VH frameworks (Winter U.S. Pat. No. 5,225,539, incorporated entirely by reference). This strategy is referred to as "CDR grafting". "Backmutation" of selected acceptor framework residues to the corresponding donor residues is often required to regain affinity that is lost in the initial grafted construct (U.S. Pat. No. 5,693,762, incorporated entirely by reference). The humanized antibody optimally also will comprise at least a portion of an immunoglobulin constant region, typically that of a human immunoglobulin, and thus will typically comprise a human Fc region. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein, all incorporated entirely by reference). Humanization or other methods of reducing the immunogenicity of nonhuman antibody variable regions may include resurfacing methods, as described for example in Roguska et al., 1994, Proc. Natl. Acad. Sci. USA 91:969-973, incorporated entirely by reference. In one embodiment, selection based methods may be employed to humanize and/or affinity mature antibody variable regions, that is, to increase the affinity of the variable region for its target antigen. Other humanization methods may involve the grafting of only parts of the CDRs, including but not limited to methods described in U.S. Ser. No. 09/810,502; Tan et al., 2002, J. Immunol. 169:1119-1125; De Pascalis et al., 2002, J. Immunol. 169:3076-3084, incorporated entirely by reference. Structure-based methods may be employed for humanization and affinity maturation, for example as described in U.S. Ser. No. 10/153,159 and related applications, all incorporated entirely by reference.

In certain variations, the immunogenicity of the antibody is reduced using a method described in U.S. Ser. No. 11/004,590, entitled "Methods of Generating Variant Proteins with Increased Host String Content and Compositions Thereof", filed on Dec. 3, 2004, incorporated entirely by reference.

Modifications to reduce immunogenicity may include modifications that reduce binding of processed peptides derived from the parent sequence to MHC proteins. For example, amino acid modifications would be engineered such that there are no or a minimal number of immune epitopes that are predicted to bind, with high affinity, to any prevalent MHC alleles. Several methods of identifying MHC-binding epitopes in protein sequences are known in the art and may be used to score epitopes in an antibody of the present invention. See for example U.S. Ser. No. 09/903,378, U.S. Ser. No. 10/754,296, U.S. Ser. No. 11/249,692, and references cited therein, all expressly incorporated by reference.

In an alternate embodiment, the antibodies of the present invention may be fully human, that is the sequences of the antibodies are completely or substantially human. "Fully human antibody" or "complete human antibody" refers to a human antibody having the gene sequence of an antibody derived from a human chromosome with the modifications outlined herein. A number of methods are known in the art for generating fully human antibodies, including the use of transgenic mice (Bruggemann et al., 1997, *Curr Opin Biotechnol* 8:455-458,) or human antibody libraries coupled with selection methods (Griffiths et al., 1998, *Curr Opin Biotechnol* 9:102-108,) both incorporated entirely by reference.

Antibodies that Target CD19

The antibodies of the present invention may be virtually any antibody that binds to CD19. The variable regions of any known or undiscovered anti-CD19 antibodies may find use in the present invention. Antibodies of the invention may display selectivity for CD19 versus alternative targets, or selectivity for a specific form of the target versus alternative forms. Examples include full-length versus splice variants, cell-surface vs. soluble forms, selectivity for various polymorphic variants, or selectivity for specific conformational forms of a target. An antibody of the present invention may bind any epitope or region on CD19, and may be specific for fragments, mutant forms, splice forms, or aberrant forms of said antigens. A number of useful antibodies have been discovered that target CD19 that may find use in the present invention. Suitable antibodies or immunoadhesins include the CD19 antibodies or immunoadhesins in MT-103 (a single-chain bispecific CD19/CD3 antibody; Hoffman, P. et al. 2005. Int. J. Cancer. 115: 98-104; Schlereth, B. et al. 2006. Cancer Immunol. Immunother. 55: 503-514), a CD19/CD16 diabody (Schlenzka, J. et al. 2004. Anti-cancer Drugs. 15: 915-919; Kipriyanov, S. M. et al. 2002. J. Immunol. 169: 137-144), BU12-saporin (Flavell, D. J. et al. 1995. Br. J. Cancer. 72: 1373-1379), and anti-CD19-idarubicin (Rowland, A. J. et al. 1993. Cancer Immunol. Immunother. 55: 503-514); Olson, US Pub. No. 2004/0136908A1, filed Mar. 4, 2004; U.S. Pat. No. 5,686,072; Olson, WO 02/080987A1, filed Mar. 29, 2002; Tedder, WO 06/133450A1, filed Jun. 8, 2006; Tedder, WO 06/121852A2, filed Apr. 5, 2006; Tedder, WO 06/089133A2, filed Feb. 15, 2006; Tedderm US Pub. No. 2006/280738A1, filed Jun. 8, 2006; U.S. Pat. No. 7,109,304; Hansen, US Pub. No. 2005/070693A1, filed Aug. 2, 2004; Hansen, US Pub. No. 2006/257398A1, filed Jun. 1, 2006; Hansen, WO 05/012493A2, filed Aug. 2, 2004; Rao-Naik, WO 07/002223A2, filed Jun. 20, 2006; Page, US Pub. 2002/182208A1, filed May 16, 2002; U.S. Pat. No. 5,686,072; Page, EP00481790B1, filed Oct. 17, 1991; Hariharan, US Pub. No. 2003/103971A1, filed Sep. 12, 2002; Goldenberg, US Pub. No. 2003/133930A1, filed Jan. 24, 2003; Goldenberg, US Pub. No. 2004/219156A1, filed Dec. 30, 2002; Hariharan, US Pub. No. 2007/0009519A1, filed Jul. 21, 2006; Curd, WO 00/067796A1, filed May 4, 2000; Kipriyanov, WO 03/088998A1, filed Apr. 15, 2003; U.S. Pat. Nos. 7,112,324, 7,129,330, Olson, US Pub. No. 2004/0136908A1, filed Mar. 4, 2004; Dorken, US Pub. No. 2006/0193852A1, filed May 5, 2006; Amphlett, US Pub. No. 2007/0009541A1, filed Sep. 14, 2006; Kersey, WO 96/36360A1, filed May 15, 1996; Kufer, WO 04/106381A1, filed May 26, 2004; Little, US Pub. No. 2007/031436A1, filed Oct. 10, 2006; Kufer, US Pub. No. 2007/123479A1, filed May 26, 2004; Baeuerle, WO 07/068354A1, filed Nov. 29, 2006; Le Gall, EP 01314741B1, filed Nov. 14, 2001; Pesando, WO 91/13974A1, filed Mar. 12, 1991; Allen et al, Clin. Cancer. Res 2005; 11(9) May 1, 2005; Barbin et al, J. Immunother, Vol. 29, No. 2, March/April 2006; Bruenke et al, Brit. J. Haem, 130, 218-2228 (2005); Callard, J. Immunol. Vol. 148, 2983-2987, No. 10, May 15, 1992; Carter et al, Immunol. Res. 2002; 26/1-3:45-54; Carter & Barrington, Curr. Dir. Autoimmun. Basel, Karger, 2004, vol 7, pp 4-32; WWWK Cheng et al, Biochim. Biophys. Acta 1768 (2007) 21-29; Cochlovius, Cancer Res. 60, 4336-4341, Aug. 15, 2000; LJN Cooper et al, Blood Cells, Molecules & Diseases, 33 (2004) 83-89; L J N Cooper et al, Blood, 15 Feb. 2005, Vol. 105, No. 4, pp 1622-1631; Culton et al, J. Clin. Immunol., Vol. 27, No. 1, January 2007; Daniel et al, Blood, Vol. 92, No. 12 (December 15), 1998: pp 4750-4757; Doody et al, Curr. Opin. Immun., 1996, pp 378-382; Dreier et al, Int. J. Cancer, 100, 690-697 (2002); Dreier et al, J. Immunol., 2003, pp. 4397-4402; Fearon & Carter, Annu. Rev. Immunol. 1995. 13:127-149; Fearon & Carroll, Annu. Rev. Immunol. 2000. 18:393-422; Fujimoto & Sato, J. Dermatol. Sci. (2007) in press; Le Gall et al, Prot. Engr, Des. & Select., vol. 17, no. 4, pp. 357-366, 2004; Ghetie et al, Blood, 1 Jul. 2004, Vol. 104, No. 1, pp. 178-183; Ghetie et al, Blood, Vol. 83, No. 5 (March 1), 1994: pp 1329-1336; Ghetie et al, Clin. Cancer Res., Vol. 5, 3920-2927, December 1999; Ginaldi et al, J. Clin. Pathol, 1998; 51:364-369; Grossbard et al, Clin. Cancer Res., Vol. 5, 2392-2398, September 1999; Grossbard et al, Brit. J. Haematol., 1998, 102, 509-515; Grossbard et al, Blood, Vol. 80, No. 4 (August 15), 1992: pp 863-878; Grossbard & Fidias, Clin. Immunol. & Immunolpath., Vol. 76, No. 2, August, pp. 107-114, 1995; M. Green, Cancer Immunol. Immunother. (2004) 53: 625-632; Harata et al, Blood, 1 Sep. 2004, Vol. 104, No. 5, pp 1442-1449; Hekman et al, Cancer Immunol. Immunother. (1991) 32: 364-372; Hoffmann et al, Int. J. Cancer: 115, 98-104 (2005); Kipriyanov et al, J. Immunol. (2002), pp. 138-144; Kipriyanov et al, Int. J. Cancer: 77, 763-772 (1998); Kipriyanov et al, J. Immunol. Meth 196 (1996) 51-62; Lang et al, Blood, 15 May 2004, Vol. 103, No. 10, pp 3982-3985; Lankester et al, J. Biol. Chem., Vol, 271, No. 37, September 13, pp. 22326-22330, 1996; Loeffler et al, Blood, 15 Mar. 2000, Vol. 95, No. 6, pp 2098-2103; Masir, et al Histopathol., 2006, 48, pps. 239-246; Bargou et al, MT103 (MEDI-538) Poster; Mitchell et al, J. Nucl. Med. 2003; 44:1106-1112; Molhoj et al, Molec. Immunol., 44 (2007) 1935-1943; Pietersz et al, Cancer Immunol. Immunother (1995) 41: 53-60; Sapra et al, Clin. Cancer Res. Vol. 10, 1100-1111, Feb. 1, 2004; Schlereth et al, Cancer Immunol. Immunother. (2006) 55: 503-514; Schwemmlein et al, Leukemia (2007) 21, 1405-1412; Sieber et al, Brit. J. Haematology, 2003, 121, 458-461; Stone et al, Blood, Vol, 88, No. 4 (August 15), 1996: 1188-1197; Sun et al, Molec. Immunolog. 41 (2004) 929-938; Tedder & Isaacs, J. Immunolog. Vol. 143, 712-717, No. 2 Jul. 15, 1989; Tedder et al, Curr. Dir. Autoimmun. Basel, Karger, 2005, vol 8, pp 55-90; Tedder et al, Springer Semin. Immun. (2006) 28: 351-364; Tiroch et al, J. Immunol., 2002, 168: 3275-3282; Uckun et al, Blood, Vol 71, No 1 (January), 1988: pp 13-29; Uckun et al, J. Immunol., Vol 134, No 3, March 1985, pp 2010-2016; Vallera et al, Clin. Cancer Res. 2005; 11(10) May 15, 2005; Vlasveld et al, Cancer Immunol. Immunother (1995) 40: 37-47; Vuist et al, Cancer Res, 49, 3783-3788, Jul. 15, 1989; Vuis et al, Cancer Res, 50, 5767-5772, Sep. 15, 1990; Yan et al, Int. Immunol. Vol 17, No. 7, pp 869-877 (2005); Yazawa, et la, PNAS 2005; 102; 15178-15183, all hereby incorporated entirely by reference. The molecules described in U.S. Pat. No. 5,686,072, WO 02/080987A1 and US Pub. No. 2004/0136908A1 and identified as 4G7, the molecules described in WO 1007/002223A2 and Tedder, are preferred.

The antibodies of the present invention may find use in a wide range of products. In one embodiment the antibody of the invention is a therapeutic, a diagnostic, or a research reagent, preferably a therapeutic. Alternatively, the antibody of the present invention may be used for agricultural or industrial uses. An antibody of the present invention may find use in an antibody composition that is monoclonal or polyclonal. The antibodies of the present invention may be agonists, antagonists, neutralizing, inhibitory, or stimulatory. In a preferred embodiment, the antibodies of the present invention are used to kill target cells that bear the target antigen, for example cancer cells. In an alternate embodiment, the antibodies of the present invention are used to block, antagonize, or agonize the target antigen. In an alternately preferred embodiment, the antibodies of the present invention are used to block, antagonize, or agonize the target antigen and kill the target cells that bear the target antigen.

Anti-CD19 Antibodies as Therapeutics to Treat B-Cell Disorders

Antibodies are a class of therapeutic proteins that may be used to treat B-cell disorders. A number of favorable properties of antibodies, including but not limited to specificity for target, ability to mediate immune effector mechanisms, and long half-life in serum, make antibodies powerful therapeutics. The present invention describes antibodies against the B-cell antigen CD19.

B-cell antigen CD19 (CD19, also known as B-cell surface antigen B4, Leu-12) is a human pan-B-cell surface marker that is expressed from early stages of pre-B cell development through terminal differentiation into plasma cells. CD19 promotes the proliferation and survival of mature B cells. It associates in a complex with CD21 on the cell surface. It also associates with CD81 and Leu-13 and potentiates B cell receptor (BCR) signaling. Together with the BCR, CD19 modulates intrinsic and antigen receptor-induced signaling thresholds critical for clonal expansion of B cells and humoral immunity. In collaboration with CD21 it links the adaptive and the innate immune system. Upon activation, the cytoplasmic tail of CD19 becomes phosphorylated which leads to binding by Src-family kinases and recruitment of PI-3 kinase. It is an attractive immunotherapy target for cancers of lymphoid origin since it is also expressed on the vast majority of NHL cells as well as some leukemias.

A number of antibodies or antibody conjugates that target CD19 have been evaluated in pre-clinical studies or in clinical trials for the treatment of cancers. These anti-CD19 antibodies or antibody conjugates include but are not limited to MT-103 (a single-chain bispecific CD19/CD3 antibody; Hoffman et al, 2005 Int J Cancer 115:98-104; Schlereth et al, 2006 Cancer Immunol Immunother 55:503-514), a CD19/CD16 diabody (Schlenzka et al, 2004 Anti-cancer Drugs 15:915-919; Kipriyanov et al, 2002 J Immunol 169:137-144), BU12-saporin (Flavell et al, 1995 Br J Cancer 72:1373-1379), and anti-CD19-idarubicin (Rowland et al, 1993 Cancer Immunol Immunother 55:503-514); all expressly incorporated by reference.

Fc Optimization of Anti-CD19 Antibodies

There are a number of characterized mechanisms by which antibodies mediate cellular effects, including antiproliferation via blockage of needed growth pathways, intracellular signaling leading to apoptosis, enhanced down regulation and/or turnover of receptors, complement-dependent cytotoxicity (CDC), antibody-dependent cell-mediated cytotoxicity (ADCC), antibody-dependent cell-mediated phagocytosis (ADCP) and promotion of an adaptive immune response (Cragg et al., 1999, Curr Opin Immunol 11:541-547; Glennie et al., 2000, Immunol Today 21:403-410, both incorporated entirely by reference). Antibody efficacy may be due to a combination of these mechanisms, and their relative importance in clinical therapy for oncology appears to be cancer dependent.

The importance of FcγR-mediated effector functions for the activity of some antibodies has been demonstrated in mice (Clynes et al., 1998, Proc Natl Acad Sci USA 95:652-656; Clynes et al., 2000, Nat Med 6:443-446, both incorporated entirely by reference), and from observed correlations between clinical efficacy in humans and their allotype of high (V158) or low (F158) affinity polymorphic forms of FcγRIIIa (Cartron et al., 2002, Blood 99:754-758; Weng & Levy, 2003, Journal of Clinical Oncology, 21:3940-3947, both incorporated entirely by reference). Together these data suggest that an antibody that is optimized for binding to certain FcγRs may better mediate effector functions, and thereby destroy target cells more effectively in patients. Thus a promising means for enhancing the anti-tumor potency of antibodies is via enhancement of their ability to mediate cytotoxic effector functions such as ADCC, ADCP, and CDC. Additionally, antibodies can mediate anti-tumor mechanism via growth inhibitory or apoptotic signaling that may occur when an antibody binds to its target on tumor cells. Such signaling may be potentiated when antibodies are presented to tumor cells bound to immune cells via FcγR. Therefore increased affinity of antibodies to FcγRs may result in enhanced anti-proliferative effects.

Antibody engineering for optimized effector function has been achieved using amino acid modifications (see for example U.S. Ser. No. 10/672,280 and U.S. Ser. No. 11/124,620 and references cited therein, all incorporated entirely by reference), and engineered glycoforms (see for example Umaña et al., 1999, Nat Biotechnol 17:176-180; Shinkawa et al., 2003, J Biol Chem 278:3466-3473, Yamane-Ohnuki et al., 2004, Biotechnology and Bioengineering 87(5):614-621, all incorporated entirely by reference).

Modifications for Optimizing Effector Function

The present invention is directed to antibodies comprising modifications, wherein said modifications alter affinity to one or more Fc receptors, and/or alter the ability of the antibody to mediate one or more effector functions. Modifications of the invention include amino acid modifications and glycoform modifications.

Amino Acid Modifications

As described in U.S. Ser. No. 11/124,620, filed May 5, 2005, entitled "Optimized Fc Variants", and incorporated entirely by reference, amino acid modifications at heavy chain constant region positions positions 221, 222, 223, 224, 225, 227, 228, 230, 231, 232, 233, 234, 235, 236, 237, 238, 239, 240, 241, 243, 244, 245, 246, 247, 249, 255, 258, 260, 262, 263, 264, 265, 266, 267, 268, 269, 270, 271, 272, 273, 274, 275, 276, 278, 280, 281, 282, 283, 284, 285, 286, 288, 290, 291, 292, 293, 294, 295, 296, 297, 298, 299, 300, 301, 302, 303, 304, 305, 313, 317, 318, 320, 322, 323, 324, 325, 326, 327, 328, 329, 330, 331, 332, 333, 334, 335, 336, and 337, allow modification of FcγR binding properties, effector function, and potentially clinical properties of antibodies.

In particular, variants that alter binding to one or more human Fc receptors may comprise an amino acid modification in the heavy chain constant region, as described herein, selected from the group consisting of 221K, 221Y, 222E, 222Y, 223E, 223K, 224E, 224Y, 225E, 225K, 225W, 227E, 227G, 227K, 227Y, 228E, 228G, 228K, 228Y, 230A, 230E, 230G, 230Y, 231E, 231G, 231K, 231P, 231Y, 232E, 232G, 232K, 232Y, 233A, 233D, 233F, 233G, 233H, 233I, 233K, 233L, 233M, 233N, 233Q, 233R, 233S, 233T, 233V, 233W, 233Y, 234A, 234D, 234E, 234F, 234G, 234H, 234I, 234K, 234M, 234N, 234P, 234Q, 234R, 234S, 234T, 234V, 234W, 234Y, 235A, 235D, 235E, 235F, 235G, 235H, 235I, 235K, 235M, 235N, 235P, 235Q, 235R, 235S, 235T, 235V, 235W, 235Y, 236A, 236D, 236E, 236F, 236H, 236I, 236K, 236L, 236M, 236N, 236P, 236Q, 236R, 236S, 236T, 236V, 236W, 236Y, 237D, 237E, 237F, 237H, 237I, 237K, 237L, 237M, 237N, 237P, 237Q, 237R, 237S, 237T, 237V, 237W, 237Y, 238D, 238E, 238F, 238G, 238H, 238I, 238K, 238L, 238M, 238N, 238Q, 238R, 238S, 238T, 238V, 238W, 238Y, 239D, 239E, 239F, 239G, 239H, 239I, 239K, 239L, 239M, 239N, 239P, 239Q, 239R, 239T, 239V, 239W, 239Y, 240A, 240I, 240M, 240T, 241D, 241E, 241L, 241R, 241S, 241W, 241Y, 243E, 243H, 243L, 243Q, 243R, 243W, 243Y, 244H, 245A, 246D, 246E, 246H, 246Y, 247G, 247V, 249H, 249Q, 249Y, 255E, 255Y, 258H, 258S, 258Y, 260D, 260E, 260H, 260Y, 262A, 262E, 262F, 262I, 262T, 263A, 263I, 263M, 263T, 264A, 264D, 264E, 264F, 264G, 264H, 264I, 264K, 264L, 264M, 264N, 264P, 264Q, 264R, 264S, 264T, 264W, 264Y, 265F, 265G, 265H, 265I, 265K, 265L, 265M, 265N, 265P, 265Q, 265R, 265S, 265T, 265V, 265W, 265Y, 266A, 266I, 266M, 266T, 267D, 267E, 267F, 267H, 267I, 267K, 267L, 267M, 267N, 267P, 267Q, 267R, 267T, 267V, 267W, 267Y, 268D, 268E, 268F, 268G, 268I, 268K, 268L, 268M, 268P, 268Q, 268R, 268T, 268V, 268W, 269F, 269G, 269H, 269I, 269K, 269L, 269M, 269N, 269P, 269R, 269S, 269T, 269V, 269W, 269Y, 270F, 270G, 270H, 270I, 270L, 270M, 270P, 270Q, 270R, 270S, 270T, 270W, 270Y, 271A, 271D, 271E, 271F, 271G, 271H, 271I, 271K, 271L, 271M, 271N, 271Q, 271R, 271S, 271T, 271V, 271W, 271Y, 272D, 272F, 272G, 272H, 272I, 272K, 272L, 272M, 272P, 272R, 272S, 272T, 272V, 272W, 272Y, 273I, 274D, 274E, 274F, 274G, 274H, 274I, 274L, 274M, 274N, 274P, 274R, 274T, 274V, 274W, 274Y, 275L, 275W, 276D, 276E, 276F, 276G, 276H, 276I, 276L, 276M, 276P, 276R, 276S, 276T, 276V, 276W, 276Y, 278D, 278E, 278G, 278H, 278I, 278K, 278L, 278M, 278N, 278P, 278Q, 278R, 278S, 278T, 278V, 278W, 280G, 280K, 280L, 280P, 280W, 281D, 281E, 281K, 281N, 281P, 281Q, 281Y, 282E, 282G, 282K, 282P, 282Y, 283G, 283H, 283K, 283L, 283P, 283R, 283Y, 284D, 284E, 284L, 284N, 284Q, 284T, 284Y, 285D, 285E, 285K, 285Q, 285W, 285Y, 286E, 286G, 286P, 286Y, 288D, 288E, 288Y, 290D, 290H, 290L, 290N, 290W, 291D, 291E, 291G, 291H, 291I, 291Q, 291T, 292D, 292E, 292T, 292Y, 293F, 293G, 293H, 293I, 293L, 293M, 293N, 293P, 293R, 293S, 293T, 293V, 293W, 293Y, 294F, 294G, 294H, 294I, 294K, 294L, 294M, 294P, 294R, 294S, 294T, 294V, 294W, 294Y, 295D, 295E, 295F, 295G, 295H, 295I, 295M, 295N, 295P, 295R, 295S, 295T, 295V, 295W, 295Y, 296A, 296D, 296E, 296G, 296H, 296I, 296K, 296L, 296M, 296N, 296Q, 296R, 296S, 296T, 296V, 297D, 297E, 297F, 297G, 297H, 297I, 297K, 297L, 297M, 297P, 297Q, 297R, 297S, 297T, 297V, 297W, 297Y, 298A, 298D, 298E, 298F, 298H, 298I, 298K, 298M, 298N, 298Q, 298R, 298T, 298W, 298Y, 299A, 299D, 299E, 299F, 299G, 299H, 299I, 299K, 299L, 299M, 299N, 299P, 299Q, 299R, 299S, 299V, 299W, 299Y, 300A, 300D, 300E, 300G, 300H, 300K, 300M, 300N, 300P, 300Q, 300R, 300S, 300T, 300V, 300W, 301D, 301E, 301H, 301Y, 302I, 303D, 303E, 303Y, 304D, 304H, 304L, 304N, 304T, 305E, 305T, 305Y, 313F, 317E, 317Q, 318H, 318L, 318Q, 318R, 318Y, 320D, 320F, 320G, 320H, 320I, 320L, 320N, 320P, 320S, 320T, 320V, 320W, 320Y, 322D, 322F, 322G, 322H, 322I, 322P, 322S, 322T, 322V, 322W, 322Y, 323I, 324D, 324F, 324G, 324H, 324I, 324L, 324M, 324P, 324R, 324T, 324V, 324W, 324Y, 325A, 325D, 325E, 325F, 325G, 325H, 325I, 325K, 325L, 325M, 325P, 325Q, 325R, 325S, 325T, 325V, 325W, 325Y, 326E, 326I, 326L, 326P, 326S, 326T, 327D, 327E, 327F, 327H, 327I, 327K, 327L, 327M, 327N, 327P, 327R, 327S, 327T, 327V, 327W, 327Y, 328A, 328D, 328E, 328F, 328G, 328H, 328I, 328K, 328M, 328N, 328P, 328Q, 328R, 328S, 328T, 328V, 328W, 328Y, 329D, 329E, 329F, 329G, 329H, 329I, 329K, 329L, 329M, 329N, 329Q, 329R, 329S, 329T, 329V, 329W, 329Y, 330E, 330F, 330G, 330H, 330I, 330L, 330M, 330N, 330P, 330R, 330S, 330T, 330V, 330W, 330Y, 331D, 331F, 331H, 331I, 331L, 331M, 331Q, 331R, 331T, 331V, 331W, 331Y, 332A, 332D, 332E, 332F, 332H, 332K, 332L, 332M, 332N, 332P, 332Q, 332R, 332S, 332T, 332V, 332W, 332Y, 333A, 333F, 333H, 333I, 333L, 333M, 333P, 333T, 333Y, 334A, 334F, 334I, 334L, 334P, 334T, 335D, 335F, 335G, 335H, 335I, 335L, 335M, 335N, 335P, 335R, 335S, 335V, 335W, 335Y, 336E, 336K, 336Y, 337E, 337H, and 337N, wherein numbering is according to the EU index.

As described in U.S. Ser. No. 11/090,981, filed Mar. 24, 2005, entitled "Immunoglobulin variants outside the Fc region", and incorporated entirely by reference, amino acid modifications at heavy chain constant region positions 118, 119, 120, 121, 122, 124, 126, 129, 131, 132, 133, 135, 136, 137, 138, 139, 147, 148, 150, 151, 152, 153, 155, 157, 159, 160, 161, 162, 163, 164, 165, 166, 167, 168, 169, 171, 172, 173, 174, 175, 176, 177, 178, 179, 180, 183, 187, 188, 189, 190, 191, 192, 193, 194, 195, 196, 197, 198, 199, 201, 203, 205, 206, 207, 208, 209, 210, 211, 212, 213, 214, 216, 217, 218, 219, 221, 222, 223, 224, 225, 226, 227, 228, 229, 230, 231, 232, 233, 234, 235, and 236, allow modification of FcγR binding properties, effector function, and potentially clinical properties of antibodies.

As described in U.S. Ser. No. 11/090,981, filed Mar. 24, 2005, entitled "Immunoglobulin variants outside the Fc region", and incorporated entirely by reference, amino acid modifications at light chain constant region positions 108, 109, 110, 111, 112, 114, 116, 121, 122, 123, 124, 125, 126, 127, 128, 129, 131, 137, 138, 140, 141, 142, 143, 145, 147, 149, 150, 151, 152, 153, 154, 155, 156, 157, 159, 160, 161, 162, 163, 164, 165, 166, 167, 168, 169, 170, 171, 172, 173, 174, 176, 180, 181, 182, 183, 184, 185, 187, 188, 189, 190, 191, 193, 195, 197, 199, 200, 202, 203, 204, 205, 206, 207, 208, 210, 211, 212, 213, allow modification of FcγR binding properties, effector function, and potentially clinical properties of antibodies.

In particular, variants that alter binding to one or more human Fc receptors may comprise an amino acid modification in the heavy chain constant region, as described herein, selected from the group consisting of 118K, 118E, 118Y, 119R, 119E, 119Y, 120R, 120E, 120I, 121E, 121Y, 121H, 122E, 122R, 124K, 124E, 124Y, 126K, 126D, 129L, 129D, 131G, 131T, 132D, 132R, 132L, 133R, 133E, 133L, 135I, 135E, 135K, 136E, 136K, 136I, 137E, 138S, 138R, 138D, 139I, 139E, 139K, 147A, 147E, 148Y, 148K, 150L, 150K, 150E, 151A, 151D, 152L, 152K, 153L, 153D, 155E, 155K, 155I, 157E, 157K, 157Y, 159K, 159D, 159L, 160K, 160E, 160Y, 161D, 162D, 162K, 162Y, 163R, 164R, 164E, 164Y, 165D, 165R, 165Y, 166D, 167A, 168L, 169E, 171G, 171H, 172K, 172L, 172E, 173T, 173D, 174E, 174K, 174Y, 175D, 175L, 176D, 176R, 176L, 177R, 177E, 177Y, 178D, 179K, 179Y, 179E, 180K, 180L, 180E, 183T, 187I, 187K, 187E, 188I, 189D, 189G, 190I, 190K, 190E, 191D, 191R, 191Y, 192N, 192R, 192L, 193F, 193E, 194R, 194D, 195R, 195D, 195Y, 196K, 196D, 196L, 197R, 197E, 197Y, 198L, 199T, 199D, 199K, 201E, 201K, 201L, 203D, 203L, 203K, 205D, 205L, 206A, 206E, 207K, 207D, 208R, 208E, 208Y, 209E, 209K, 209Y, 210L, 210E, 210Y, 211R, 211E, 211Y, 212Q, 212K, 212H, 212L, 212Y, 213N, 213E, 213H, 213L, 213Y, 214N, 214E, 214H, 214L, 214Y, 216N, 216K, 216H, 216L, 216Y, 217D, 217H, 217A, 217V, 217G, 218D, 218E, 218Q, 218T, 218H, 218L, 218Y, 219D, 219E, 219Q, 219K, 219T, 219H, 219L, 219I, 219Y, 205A, 210A, 213A, 214A, 218A, 221K, 221Y, 221E, 221N, 221Q, 221R, 221S, 221T, 221H, 221A, 221V, 221L, 221I, 221F, 221M, 221W, 221P, 221G, 222E, 222Y, 222D, 222N, 222Q, 222R, 222S, 222T, 222H, 222V, 222L, 222I, 222F, 222M, 222W, 222P, 222G, 222A, 223D, 223N, 223Q, 223R, 223S, 223H, 223A, 223V, 223L, 223I, 223F, 223M, 223Y, 223W, 223P, 223G, 223E, 223K, 224D, 224N, 224Q, 224K, 224R, 224S, 224T, 224V, 224L, 224I, 224F, 224M, 224W, 224P, 224G, 224E, 224Y, 224A, 225D, 225N, 225Q, 225R, 225S, 225H, 225A, 225V, 225L, 225I, 225F, 225M, 225Y, 225P, 225G, 225E, 225K, 225W, 226S, 227E, 227K, 227Y, 227G, 227D, 227N, 227Q, 227R, 227S, 227T, 227H, 227A, 227V, 227L, 227I, 227F, 227M, 227W, 228K, 228Y, 228G, 228D, 228N, 228Q, 228R, 228T, 228H, 228A, 228V, 228L, 228I, 228F, 228M, 228W, 229S, 230A, 230E, 230Y, 230G, 230D, 230N, 230Q, 230K, 230R, 230S, 230T, 230H, 230V, 230L, 230I, 230F, 230M, 230W, 231K, 231P, 231D, 231N, 231Q, 231R, 231S, 231T, 231H, 231V, 231L, 231I, 231F, 231M, 231W, 232E, 232K, 232Y, 232G, 232D, 232N, 232Q, 232R, 232S, 232T, 232H, 232A, 232V, 232L, 232I, 232F, 232M, 232W, 233D, 233N, 233Q, 233R, 233S, 233T, 233H, 233A, 233V, 233L, 233I, 233F, 233M, 233Y, 233W, 233G, 234D, 234E, 234N, 234Q, 234T, 234H, 234Y, 234I, 234V, 234F, 234K, 234R, 234S, 234A, 234M, 234G, 235D, 235S, 235N, 235Q, 235T, 235H, 235Y, 235I, 235V, 235F, 235E, 235K, 235R, 235A, 235M, 235W, 235P, 235G, 236D, 236E, 236N, 236Q, 236K, 236R, 236S, 236T, 236H, 236A, 236V, 236L, 236I, 236F, 236M, 236Y, 236W, and 236P, wherein numbering is according to the EU index.

In particular, variants that alter binding to one or more human Fc receptors may comprise an amino acid modification in the light chain constant region, as described herein, selected from the group consisting of 108D, 108I, 108Q, 109D, 109P, 109R, 110E, 110I, 110K, 111E, 111K, 111L, 112E, 112R, 112Y, 114D, 114I, 114K, 116T, 121D, 122R, 122S, 122Y, 123L, 123R, 124E, 125E, 125K, 126D, 126L, 126Q, 127A, 127D, 127K, 128N, 129E, 129I, 129K, 131T, 137K, 137S, 138D, 138K, 138L, 140E, 140H, 140K, 141E, 141K, 142D, 142G, 142L, 143A, 143L, 143R, 145D, 145T, 145Y, 147A, 147E, 147K, 149D, 149Y, 150A, 151I, 151K, 152L, 152R, 152S, 153D, 153H, 153S, 154E, 154R, 154V, 155E, 155I, 155K, 156A, 156D, 156R, 157N, 158D, 158L, 158R, 159E, 159K, 159L, 160E, 160V, 161K, 161L, 162T, 163E, 163K, 163T, 164Q, 165K, 165P, 165Y, 166E, 166M, 166S, 167K, 167L, 168K, 168Q, 168Y, 169D, 169H, 169S, 170I, 170N, 170R, 171A, 171N, 171V, 172E, 172I, 172K, 173K, 173L, 173Q, 174A, 176T, 180E, 180K, 180S, 181K, 182E, 182R, 182T, 183D, 183L, 183P, 184E, 184K, 184Y, 185I, 185Q, 185R, 187K, 187Y, 188E, 188S, 188Y, 189D, 189K, 189Y, 190E, 190L, 190R, 191E, 191R, 191S, 193E, 193K, 193S, 195I, 195K, 195Q, 197E, 197K, 197L, 199E, 199K, 199Y, 200S, 202D, 202R, 202Y, 203D, 203L, 203R, 204T, 205E, 205K, 206E, 206I, 206K, 207A, 207E, 207L, 208E, 208K, 208T, 210A, 210E, 210K, 211A, 211E, 211P, 212E, 212K, 212T, 213L, 213R, wherein numbering is according to the EU index.

Additional substitutions that may also be used in the present invention include other substitutions that modulate Fc receptor affinity, FcγR-mediated effector function, and/or complement mediated effector function include but are not limited to 298A, 298T, 326A, 326D, 326E, 326W, 326Y, 333A, 333S, 334L, and 334A (U.S. Pat. No. 6,737,056; Shields et al, Journal of Biological Chemistry, 2001, 276 (9):6591-6604; U.S. Pat. No. 6,528,624; Idusogie et al., 2001, J. Immunology 166:2571-2572), 247L, 255L, 270E, 392T, 396L, and 421K (U.S. Ser. No. 10/754,922; U.S. Ser. No. 10/902,588), and 280H, 280Q, and 280Y (U.S. Ser. No. 10/370,749), all incorporated entirely by reference.

In other embodiments, antibodies of the present invention may be combined with constant heavy chain variants that alter FcRn binding. These include modifications that modify FcRn affinity in a pH-specific manner. In particular, variants that increase Fc binding to FcRn include but are not limited to: 250E, 250Q, 428L, 428F, 250Q/428L (Hinton et al., 2004, J. Biol. Chem. 279(8): 6213-6216, Hinton et al. 2006 Journal of Immunology 176:346-356, U.S. Ser. No. 11/102, 621, PCT/US2003/033037, PCT/US2004/011,213, U.S. Ser. No. 10/822,300, U.S. Ser. No. 10/687,118, PCT/US2004/ 034440, U.S. Ser. No. 10/966,673, all incorporated entirely by reference), 256A, 272A, 286A, 305A, 307A, 311A, 312A, 376A, 378Q, 380A, 382A, 434A (Shields et al, Journal of Biological Chemistry, 2001, 276(9):6591-6604, U.S. Ser. No. 10/982,470, U.S. Pat. No. 6,737,056, U.S. Ser. No. 11/429,793, U.S. Ser. No. 11/429,786, PCT/US2005/ 029511, U.S. Ser. No. 11/208,422, all incorporated entirely by reference), 252F, 252T, 252Y, 252W, 254T, 256S, 256R, 256Q, 256E, 256D, 256T, 309P, 311S, 433R, 433S, 433I, 433P, 433Q, 434H, 434F, 434Y, 252Y/254T/256E, 433K/ 434F/436H, 308T/309P/311S (Dail Acqua et al. Journal of Immunology, 2002, 169:5171-5180, U.S. Pat. No. 7,083, 784, PCT/US97/03321, U.S. Pat. No. 6,821,505, PCT/ US01/48432, U.S. Ser. No. 11/397,328, all incorporated entirely by reference), 257C, 257M, 257L, 257N, 257Y, 279E, 279Q, 279Y, insertion of Ser after 281, 283F, 284E, 306Y, 307V, 308F, 308Y 311V, 385H, 385N, (PCT/US2005/ 041220, U.S. Ser. No. 11/274,065, U.S. Ser. No. 11/436,266, all incorporated entirely by reference) 204D, 284E, 285E, 286D, and 290E (PCT/US2004/037929 incorporated entirely by reference).

In some embodiments of the invention, antibodies may comprise isotypic modifications, that is modifications in a parent IgG to the amino acid type in an alternate IgG. For example as illustrated in FIG. 3, an IgG1/IgG3 hybrid variant may be constructed by substituting IgG1 positions in the CH2 and/or CH3 region with the amino acids from IgG3 at positions where the two isotypes differ. Thus a hybrid variant IgG antibody may be constructed that comprises one or more substitutions selected from the group consisting of: 274Q, 276K, 300F, 339T, 356E, 358M, 384S, 392N, 397M, 422I, 435R, and 436F. In other embodiments of the invention, an IgG1/IgG2 hybrid variant may be constructed by substituting IgG2 positions in the CH2 and/or CH3 region with amino acids from IgG1 at positions where the two isotypes differ. Thus a hybrid variant IgG antibody may be constructed that comprises one or more modifications selected from the group consisting of 233E, 234L, 235L, -236G (referring to an insertion of a glycine at position 236), and 327A.

Glycoform Modifications

Many polypeptides, including antibodies, are subjected to a variety of post-translational modifications involving carbohydrate moieties, such as glycosylation with oligosaccharides. There are several factors that can influence glycosylation. The species, tissue and cell type have all been shown to be important in the way that glycosylation occurs. In addition, the extracellular environment, through altered culture conditions such as serum concentration, may have a direct effect on glycosylation. (Lifely et al., 1995, Glycobiology 5(8): 813-822), incorporated entirely by reference.

All antibodies contain carbohydrate at conserved positions in the constant regions of the heavy chain. Each antibody isotype has a distinct variety of N-linked carbohydrate structures. Aside from the carbohydrate attached to the heavy chain, up to 30% of human IgGs have a glycosylated Fab region. IgG has a single N-linked biantennary carbohydrate at Asn297 of the CH2 domain. For IgG from either serum or produced ex vivo in hybridomas or engineered cells, the IgG are heterogeneous with respect to the Asn297 linked carbohydrate (Jefferis et al., 1998, Immunol. Rev. 163:59-76; Wright et al., 1997, Trends Biotech 15:26-32, both incorporated entirely by reference). For human IgG, the core oligosaccharide normally consists of GlcNAc$_2$Man$_3$GlcNAc, with differing numbers of outer residues.

The carbohydrate moieties of the present invention will be described with reference to commonly used nomenclature for the description of oligosaccharides. A review of carbohydrate chemistry which uses this nomenclature is found in Hubbard et al. 1981, Ann. Rev. Biochem. 50:555-583, incorporated entirely by reference. This nomenclature includes, for instance, Man, which represents mannose; GlcNAc, which represents 2-N-acetylglucosamine; Gal which represents galactose; Fuc for fucose; and Glc, which represents glucose. Sialic acids are described by the shorthand notation NeuNAc, for 5-N-acetylneuraminic acid, and NeuNGc for 5-glycolylneuraminic.

The term "glycosylation" means the attachment of oligosaccharides (carbohydrates containing two or more simple sugars linked together e.g. from two to about twelve simple sugars linked together) to a glycoprotein. The oligosaccharide side chains are typically linked to the backbone of the glycoprotein through either N- or O-linkages. The oligosaccharides of the present invention occur generally are attached to a CH2 domain of an Fc region as N-linked oligosaccharides. "N-linked glycosylation" refers to the attachment of the carbohydrate moiety to an asparagine residue in a glycoprotein chain. The skilled artisan will recognize that, for example, each of murine IgG1, IgG2a, IgG2b and IgG3 as well as human IgG1, IgG2, IgG3, IgG4, IgA and IgD CH2 domains have a single site for N-linked glycosylation at amino acid residue 297 (Kabat et al. Sequences of Proteins of Immunological Interest, 1991, incorporated entirely by reference).

For the purposes herein, a "mature core carbohydrate structure" refers to a processed core carbohydrate structure attached to an Fc region which generally consists of the following carbohydrate structure GlcNAc(Fucose)-GlcNAc-Man-(Man-GlcNAc)$_2$ typical of biantennary oligosaccharides. The mature core carbohydrate structure is attached to the Fc region of the glycoprotein, generally via N-linkage to Asn297 of a CH2 domain of the Fc region. A "bisecting GlcNAc" is a GlcNAc residue attached to the β1,4 mannose of the mature core carbohydrate structure. The bisecting GlcNAc can be enzymatically attached to the mature core carbohydrate structure by a β(1,4)-N-acetylglucosaminyltransferase III enzyme (GnTIII). CHO cells do not normally express GnTIII (Stanley et al., 1984, J. Biol. Chem. 261: 13370-13378), but may be engineered to do so (Umana et al., 1999, Nature Biotech. 17:176-180).

The present invention contemplates antibodies that comprise modified glycoforms or engineered glycoforms. By "modified glycoform" or "engineered glycoform" as used herein is meant a carbohydrate composition that is covalently attached to a protein, for example an antibody, wherein said carbohydrate composition differs chemically from that of a parent protein. Engineered glycoforms may be useful for a variety of purposes, including but not limited to enhancing or reducing FcγR-mediated effector function. In a preferred embodiment, the antibodies of the present invention are modified to control the level of fucosylated and/or bisecting oligosaccharides that are covalently attached to the Fc region.

Historically, antibodies produced in Chinese Hamster Ovary Cells (CHO), one of the most commonly used industrial hosts, contain about 2 to 6% in the population that are nonfucosylated. YB2/0 (rat myeloma) and Lec13 cell line (a lectin mutant of CHO line which has a deficient GDP-mannose 4,6 dehydratase leading to the deficiency of GDP-fucose or GDP-sugar intermediates that are the substrate of α1,6-fucosyltransferase (Ripka et al., 1986), however, can produce antibodies with 78% to 98% nonfucosylated species. Unfortunately, the yield of antibody from these cells is extremely poor and therefore these cell lines are not useful to make therapeutic antibody products commercially. The FUT8 gene encodes the α1,6-fucosyltransferase enzyme that catalyzes the transfer of a fucosyl residue from GDP-fucose to position 6 of Asn-linked (N-linked) GlcNac of an N-glycan (Yanagidani et al., 1997, J Biochem 121:626-632). It is known that the α1,6 fucosyltransferase is the only enzyme responsible for adding fucose to the N-linked biantennary carbohydrate at Asn297 in the CH2 domain of the IgG antibody.

A variety of methods are well known in the art for generating modified glycoforms (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473); (U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1); Yamane-Ohnuki et al., 2004, Biotechnology and Bioengineering 87(5):614-621; (Potelligent™ technology [Biowa, Inc., Princeton, N.J.]; GlycoMAb™ glycosylation engineering technology [GLYCART biotechnology AG, Zürich, Switzerland]; all of which are expressly incorporated by reference). These techniques control the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells), by regulating enzymes involved in the glycosylation pathway (for example FUT8 [α1,6-fucosyltranserase] and/or β1-4-N-acetylglucosaminyltransferase III [GnTIII]), or by modifying carbohydrate(s) after the IgG has been expressed.

Other methods for modifying glycoforms of the antibodies of the invention include using glycoengineered strains of yeast (Li et al., 2006, Nature Biotechnology 24(2):210-215), moss (Nechansky et al., 2007, Mol Immunjol 44(7):1826-8), and plants (Cox et al., 2006, Nat Biotechnol 24(12):1591-7). Methods for modifying glycoforms include but are not limited to using a glycoengineered strain of yeast Pichia pastoris (Li et al., 2006, Nature Biotechnology 24(2):210-215), a glycoengineered strain of the moss Physcomilrella patens wherein the enzymes β1,2-xylosyltransferase and/or α1,3-fucosyltransferase are knocked out in (Nechansky et al., 2007, Mol Immunjol 44(7):1826-8), and the use of RNA interference to inhibit endogenous alpha-1,3-fucosyltransferase and/or beta-1,2-xylosyltransferase in the aquatic plant Lemna minor (Cox et al., 2006, Nat Biotechnol 24(12): 1591-7).

Modified or engineered glycoform typically refers to the different carbohydrate or oligosaccharide; thus for example an antibody may comprise an engineered glycoform. Alternatively, engineered glycoform may refer to the antibody that comprises the different carbohydrate or oligosaccharide.

For the purposes of modified glycoforms described herein, a "parent antibody" is a glycosylated antibody having the same amino acid sequence and mature core carbohydrate structure as an engineered glycoform of the present invention, except that fucose is attached to the mature core carbohydrate structure of the parent antibody. For instance, in a composition comprising the parent glycoprotein about 50-100% or about 70-100% of the parent glycoprotein comprises a mature core carbohydrate structure having fucose attached thereto.

The present invention provides a composition comprising a glycosylated antibody having an Fc region, wherein about 51-100% of the glycosylated antibody in the composition comprises a mature core carbohydrate structure which lacks fucose, attached to the Fc region of the antibody. More preferably, about 80-100% of the antibody in the composition comprises a mature core carbohydrate structure which lacks fucose and most preferably about 90-99% of the antibody in the composition lacks fucose attached to the mature core carbohydrate structure. In a most preferred embodiment, the antibody in the composition both comprises a mature core carbohydrate structure that lacks fucose and additionally comprises at least one amino acid modification in the Fc region. In the most preferred embodiment, the combination of engineered glycoform and amino acid modification provides optimal Fc receptor binding properties to the antibody.

Optimized Properties of Antibodies

The present invention provides variant antibodies that are optimized for a number of therapeutically relevant properties. A variant antibody comprises one or more amino acid modifications relative to a parent antibody, wherein said amino acid modification(s) provide one or more optimized properties. Thus the antibodies of the present invention are variants antibodies. An antibody of the present invention differs in amino acid sequence from its parent antibody by virtue of at least one amino acid modification. Thus variant antibodies of the present invention have at least one amino acid modification compared to the parent. Alternatively, the variant antibodies of the present invention may have more than one amino acid modification as compared to the parent, for example from about one to fifty amino acid modifications, preferably from about one to ten amino acid modifications, and most preferably from about one to about five amino acid modifications compared to the parent. Thus the sequences of the variant antibodies and those of the parent antibodies are substantially homologous. For example, the variant antibody sequences herein will possess about 80% homology with the parent antibody sequence, preferably at least about 90% homology, and most preferably at least about 95% homology.

In a most preferred embodiment, the antibodies of the present invention comprise amino acid modifications that provide optimized effector function properties relative to the parent. Most preferred substitutions and optimized effector function properties are described in U.S. Ser. No. 10/672,280, PCT US03/30249, and U.S. Ser. No. 10/822,231, and U.S. Ser. No. 60/627,774, filed Nov. 12, 2004 and entitled "Optimized Fc Variants". Properties that may be optimized include but are not limited to enhanced or reduced affinity for an FcγR. In a preferred embodiment, the antibodies of the present invention are optimized to possess enhanced affinity for a human activating FcγR, preferably FcγRI, FcγRIIa, FcγRIIc, FcγRIIIa, and FcγRIIIb, most preferably FcγRIIIa. In an alternately preferred embodiment, the antibodies are optimized to possess reduced affinity for the human inhibitory receptor FcγRIIb. These preferred embodiments are anticipated to provide antibodies with enhanced therapeutic properties in humans, for example enhanced effector function and greater anti-cancer potency. In an alternate embodiment, the antibodies of the present invention are optimized to have reduced or ablated affinity for a human FcγR, including but not limited to FcγRI, FcγRIIa, FcγRIIb, FcγRIIc, FcγRIIIa, and FcγRIIIb. These embodiments are anticipated to provide antibodies with enhanced therapeutic properties in humans, for example reduced effector function and reduced toxicity. In other embodiments, antibodies of the present invention provide enhanced affinity for one or more FcγRs, yet reduced affinity for one or more other FcγRs. For example, an antibody of the present invention may have enhanced binding to FcγRIIIa, yet reduced binding to FcγRIIb. Alternately, an antibody of the present invention may have enhanced binding to FcγRIIa and FcγRI, yet reduced binding to FcγRIIb. In yet another embodiment, an antibody of the present invention may have enhanced affinity for FcγRIIb, yet reduced affinity to one or more activating FcγRs.

The modification of the invention preferably enhance binding affinity for one or more FcγRs. By "greater affinity" or "improved affinity" or "enhanced affinity" or "better affinity" than a parent immunoglobulin, as used herein is meant that an Fc variant binds to an Fc receptor with a significantly higher equilibrium constant of association (KA) or lower equilibrium constant of dissociation (KD) than the parent polypeptide when the amounts of variant and parent polypeptide in the binding assay are essentially the same. For example, the Fc variant with improved FcγR binding affinity may display from about 5 fold to about 1000 fold, e.g. from about 10 fold to about 500 fold improvement in Fc receptor binding affinity compared to the parent polypeptide, where Fc receptor binding affinity is determined, for example, as disclosed in the Examples herein. Accordingly, by "reduced affinity" as compared to a parent Fc polypeptide as used herein is meant that an Fc variant binds an Fc receptor with significantly lower KA or higher KD than the parent polypeptide.

Data in the present study indicate that human WT IgG1 binds to human V158 FcγRIIIa with an affinity of approximately 240 nM (Example 1). This is consistent with the literature which indicate that binding is approximately 200-500 nM, as determined by Biacore (210 nM as shown in Okazaki et al, 2004, J Mol Bio 336:1239-49; 250 nM as shown in Lazar et al, Proc Natl Acad Sci USA 103(11): 4005-4010) and calorimetry (530 nM, Okazaki et al, 2004, J Mol Bio 336:1239-49). However affinity as low as 750 nM was measured in one study (Ferrara et al., 2006, J Biol Chem 281(8):5032-5036). Although binding to F158 FcγRIIIa was lower than the 5 uM cutoff applied in the present study, the literature indicates that human WT IgG1 binds to human F158 FcγRIIIa with an affinity of approximately 3-5 uM, as indicated by calorimetry (2.7 uM, in Okazaki et al, 2004, J Mol Bio 336:1239-49) and Biacore (5.0 uM, Ferrara et al., 2006, J Biol Chem 281(8):5032-5036).

Preferred embodiments comprise optimization of Fc binding to a human FcγR, however in alternate embodiments the antibodies of the present invention possess enhanced or reduced affinity for FcγRs from nonhuman organisms, including but not limited to rodents and non-human primates. antibodies that are optimized for binding to a non-human FcγR may find use in experimentation. For example, mouse models are available for a variety of diseases that enable testing of properties such as efficacy, toxicity, and pharmacokinetics for a given drug candidate. As is known in the art, cancer cells can be grafted or injected into mice to mimic a human cancer, a process referred to as xenografting. Testing of antibodies that comprise antibodies that are optimized for one or more mouse FcγRs, may provide valuable information with regard to the efficacy of the protein, its mechanism of action, and the like. The antibodies of the present invention may also be optimized for enhanced functionality and/or solution properties in aglycosylated form. In a preferred embodiment, the aglycosylated antibodies of the present invention bind an Fc ligand with greater affinity than the aglycosylated form of the parent antibody. Said Fc ligands include but are not limited to FcγRs, C1q, FcRn, and proteins A and G, and may be from any source including but not limited to human, mouse, rat, rabbit, or monkey, preferably human. In an alternately preferred embodiment, the antibodies are optimized to be more stable and/or more soluble than the aglycosylated form of the parent antibody.

Antibodies of the invention may comprise modifications that modulate interaction with Fc ligands other than FcγRs, including but not limited to complement proteins, FcRn, and Fc receptor homologs (FcRHs). FcRHs include but are not limited to FcRH1, FcRH2, FcRH3, FcRH4, FcRH5, and FcRH6 (Davis et al., 2002, Immunol. Reviews 190:123-136, incorporated entirely by reference).

Preferably, the Fc ligand specificity of the antibody of the present invention will determine its therapeutic utility. The utility of a given antibody for therapeutic purposes will depend on the epitope or form of the target antigen and the disease or indication being treated. For some targets and indications, enhanced FcγR-mediated effector functions may be preferable. This may be particularly favorable for anti-cancer antibodies. Thus antibodies may be used that comprise antibodies that provide enhanced affinity for activating FcγRs and/or reduced affinity for inhibitory FcγRs. For some targets and indications, it may be further beneficial to utilize antibodies that provide differential selectivity for different activating FcγRs; for example, in some cases enhanced binding to FcγRIIa and FcγRIIIa may be desired, but not FcγRI, whereas in other cases, enhanced binding only to FcγRIIa may be preferred. For certain targets and indications, it may be preferable to utilize antibodies that enhance both FcγR-mediated and complement-mediated effector functions, whereas for other cases it may be advantageous to utilize antibodies that enhance either FcγR-mediated or complement-mediated effector functions. For some targets or cancer indications, it may be advantageous to reduce or ablate one or more effector functions, for example by knocking out binding to C1q, one or more FcγR's, FcRn, or one or more other Fc ligands. For other targets and indications, it may be preferable to utilize antibodies that provide enhanced binding to the inhibitory FcγRIIb, yet WT level, reduced, or ablated binding to activating FcγRs. This may be particularly useful, for example, when the goal of an antibody is to inhibit inflammation or auto-immune disease, or modulate the immune system in some way.

Clearly an important parameter that determines the most beneficial selectivity of a given antibody to treat a given disease is the context of the antibody, that is what type of antibody is being used. Thus the Fc ligand selectivity or specificity of a given antibody will provide different properties depending on whether it composes an antibody or an antibodies with a coupled fusion or conjugate partner. For example, toxin, radionucleotide, or other conjugates may be less toxic to normal cells if the antibody that comprises them has reduced or ablated binding to one or more Fc ligands. As another example, in order to inhibit inflammation or auto-immune disease, it may be preferable to utilize an antibody with enhanced affinity for activating FcγRs, such as to bind these FcγRs and prevent their activation. Conversely, an antibody that comprises two or more Fc regions with enhanced FcγRIIb affinity may co-engage this receptor on the surface of immune cells, thereby inhibiting proliferation of these cells. Whereas in some cases an antibodies may engage its target antigen on one cell type yet engage FcγRs on separate cells from the target antigen, in other cases it may be advantageous to engage FcγRs on the surface of the same cells as the target antigen. For example, if an antibody targets an antigen on a cell that also expresses one or more FcγRs, it may be beneficial to utilize an antibody that enhances or reduces binding to the FcγRs on the surface of that cell. This may be the case, for example when the antibody is being used as an anti-cancer agent, and co-engagement of target antigen and FcγR on the surface of the same cell promote signaling events within the cell that result in growth inhibition, apoptosis, or other anti-proliferative effect. Alternatively, antigen and FcγR co-engagement on the same cell may be advantageous when the antibody is being used to modulate the immune system in some way, wherein co-engagement of target antigen and FcγR provides some proliferative or anti-proliferative effect. Likewise, antibodies that comprise two or more Fc regions may benefit from antibodies that modulate FcγR selectivity or specificity to co-engage FcγRs on the surface of the same cell.

The Fc ligand specificity of the antibodies of the present invention can be modulated to create different effector function profiles that may be suited for particular antigen epitopes, indications or patient populations. FIG. 5 describes several preferred embodiments of receptor binding profiles that include improvements to, reductions to or no effect to the binding to various receptors, where such changes may be beneficial in certain contexts. The receptor binding profiles in FIG. 5 could be varied by degree of increase or decrease to the specified receptors. Additionally, the binding changes specified could be in the context of additional binding changes to other receptors such as C1q or FcRn, for example by combining with ablation of binding to C1q to shut off complement activation, or by combining with enhanced binding to C1q to increase complement activation. Other embodiments with other receptor binding profiles are possible, the listed receptor binding profiles are exemplary.

The presence of different polymorphic forms of FcγRs provides yet another parameter that impacts the therapeutic utility of the antibodies of the present invention. Whereas the specificity and selectivity of a given antibody for the different classes of FcγRs significantly affects the capacity of an antibody to target a given antigen for treatment of a given disease, the specificity or selectivity of an antibody for different polymorphic forms of these receptors may in part determine which research or pre-clinical experiments may be appropriate for testing, and ultimately which patient populations may or may not respond to treatment. Thus the specificity or selectivity of antibodies of the present invention to Fc ligand polymorphisms, including but not limited to FcγR, C1q, FcRn, and FcRH polymorphisms, may be used to guide the selection of valid research and pre-clinical experiments, clinical trial design, patient selection, dosing dependence, and/or other aspects concerning clinical trials.

Other Modifications

Antibodies of the present invention may comprise one or more modifications that provide optimized properties that are not specifically related to effector function per se. Said modifications may be amino acid modifications, or may be modifications that are made enzymatically or chemically. Such modification(s) likely provide some improvement in the antibody, for example an enhancement in its stability, solubility, function, or clinical use. The present invention contemplates a variety of improvements that made be made by coupling the antibodies of the present invention with additional modifications.

In one embodiment, the variable region of an antibody of the present invention may be affinity matured, that is to say that amino acid modifications have been made in the VH and/or VL domains of the antibody to enhance binding of the antibody to its target antigen. Such types of modifications may improve the association and/or the dissociation kinetics for binding to the target antigen. Other modifications include those that improve selectivity for target antigen vs. alternative targets. These include modifications that improve selectivity for antigen expressed on target vs. non-target cells. Other improvements to the target recognition properties may be provided by additional modifications. Such properties may include, but are not limited to, specific kinetic properties (i.e. association and dissociation kinetics), selectivity for the particular target versus alternative targets, and selectivity for a specific form of target versus alternative forms. Examples include full-length versus splice variants, cell-surface vs. soluble forms, selectivity for various polymorphic variants, or selectivity for specific conformational forms of the target antigen.

Antibodies of the invention may comprise one or more modifications that provide reduced or enhanced internalization of an antibody. In one embodiment, antibodies of the present invention can be utilized or combined with additional modifications in order to reduce the cellular internalization of an antibody that occurs via interaction with one or more Fc ligands. This property might be expected to enhance effector function, and potentially reduce immunogenicity of the antibodies of the invention. Alternatively, antibodies of the present antibodies of the present invention can be utilized directly or combined with additional modifications in order to enhance the cellular internalization of an antibody that occurs via interaction with one or more Fc ligands. For example, in a preferred embodiment, an antibody is used that provides enhanced binding to FcγRI, which is expressed on dendritic cells and active early in immune response. This strategy could be further enhanced by combination with additional modifications, either within the antibody or in an attached fusion or conjugate partner, that promote recognition and presentation of Fc peptide fragments by MHC molecules. These strategies are expected to enhance target antigen processing and thereby improve antigenicity of the target antigen (Bonnerot and Amigorena, 1999, *Immunol Rev.* 172:279-84, incorporated entirely by reference), promoting an adaptive immune response and greater target cell killing by the human immune system. These strategies may be particularly advantageous when the targeted antigen is shed from the cellular surface. An additional application of these concepts arises with idiotype vaccine immunotherapies, in which clone-specific antibodies produced by a patient's lymphoma cells are used to vaccinate the patient.

In a preferred embodiment, modifications are made to improve biophysical properties of the antibodies of the present invention, including but not limited to stability, solubility, and oligomeric state. Modifications can include, for example, substitutions that provide more favorable intramolecular interactions in the antibody such as to provide greater stability, or substitution of exposed nonpolar amino acids with polar amino acids for higher solubility. A number of optimization goals and methods are described in U.S. Ser. No. 10/379,392, incorporated entirely by reference, that may find use for engineering additional modifications to further optimize the antibodies of the present invention. The antibodies of the present invention can also be combined with additional modifications that reduce oligomeric state or size, such that tumor penetration is enhanced, or in vivo clearance rates are increased as desired.

Other modifications to the antibodies of the present invention include those that enable the specific formation or homodimeric or homomultimeric molecules. Such modifications include but are not limited to engineered disulfides, as well as chemical modifications or aggregation methods which may provide a mechanism for generating covalent homodimeric or homomultimers. For example, methods of engineering and compositions of such molecules are described in Kan et al., 2001, *J. Immunol.*, 2001, 166: 1320-1326; Stevenson et al., 2002, *Recent Results Cancer Res.* 159: 104-12; U.S. Pat. No. 5,681,566; Caron et al., 1992, J. Exp. Med. 176:1191-1195, and Shopes, 1992, J. Immunol. 148(9):2918-22, all incorporated entirely by reference. Additional modifications to the variants of the present invention include those that enable the specific formation or heterodimeric, heteromultimeric, bifunctional, and/or multifunctional molecules. Such modifications include, but are not limited to, one or more amino acid substitutions in the CH3 domain, in which the substitutions reduce homodimer formation and increase heterodimer formation. For example, methods of engineering and compositions of such molecules are described in Atwell et al., 1997, J. Mol. Biol. 270(1):26-35, and Carter et al., 2001, J. Immunol. Methods 248:7-15, both incorporated entirely by reference. Additional modifications include modifications in the hinge and CH3 domains, in which the modifications reduce the propensity to form dimers.

In further embodiments, the antibodies of the present invention comprise modifications that remove proteolytic degradation sites. These may include, for example, protease sites that reduce production yields, as well as protease sites that degrade the administered protein in vivo. In a preferred embodiment, additional modifications are made to remove covalent degradation sites such as deamidation (i.e. deamidation of glutaminyl and asparaginyl residues to the corresponding glutamyl and aspartyl residues), oxidation, and proteolytic degradation sites. Deamidation sites that are particular useful to remove are those that have enhance propensity for deamidation, including, but not limited to asparaginyl and gltuamyl residues followed by glycines (NG and QG motifs, respectively). In such cases, substitution of either residue can significantly reduce the tendency for deamidation. Common oxidation sites include methionine and cysteine residues. Other covalent modifications, that can either be introduced or removed, include hydroxylation of proline and lysine, phosphorylation of hydroxyl groups of seryl or threonyl residues, methylation of the "-amino groups of lysine, arginine, and histidine side chains (T. E. Creighton, Proteins: Structure and Molecular Properties, W.H. Freeman & Co., San Francisco, pp. 79-86 (1983), incorporated entirely by reference), acetylation of the N-terminal amine, and amidation of any C-terminal carboxyl group. Additional modifications also may include but are not limited to posttranslational modifications such as N-linked or O-linked glycosylation and phosphorylation.

Modifications may include those that improve expression and/or purification yields from hosts or host cells commonly used for production of biologics. These include, but are not limited to various mammalian cell lines (e.g. CHO), yeast cell lines, bacterial cell lines, and plants. Additional modifications include modifications that remove or reduce the ability of heavy chains to form inter-chain disulfide linkages. Additional modifications include modifications that remove or reduce the ability of heavy chains to form intra-chain disulfide linkages.

The antibodies of the present invention may comprise modifications that include the use of unnatural amino acids incorporated using, for example, the technologies developed by Schultz and colleagues, including but not limited to methods described by Cropp & Shultz, 2004, Trends Genet. 20(12):625-30, Anderson et al., 2004, Proc. Natl. Acad. Sci. U.S.A. 101(2):7566-71, Zhang et al., 2003, 303(5656):371-3, and Chin et al., 2003, Science 301(5635):964-7, all incorporated entirely by reference. In some embodiments, these modifications enable manipulation of various functional, biophysical, immunological, or manufacturing properties discussed above. In additional embodiments, these modifications enable additional chemical modification for other purposes. Other modifications are contemplated herein. For example, the antibody may be linked to one of a variety of nonproteinaceous polymers, e.g., polyethylene glycol (PEG), polypropylene glycol, polyoxyalkylenes, or copolymers of polyethylene glycol and polypropylene glycol. Additional amino acid modifications may be made to enable specific or non-specific chemical or posttranslational modification of the antibodies. Such modifications, include, but are not limited to PEGylation and glycosylation. Specific substitutions that can be utilized to enable PEGylation include, but are not limited to, introduction of novel cysteine residues or unnatural amino acids such that efficient and specific coupling chemistries can be used to attach a PEG or otherwise polymeric moiety. Introduction of specific glycosylation sites can be achieved by introducing novel N-X-T/S sequences into the antibodies of the present invention.

Covalent modifications of antibodies are included within the scope of this invention, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

In some embodiments, the covalent modification of the antibodies of the invention comprises the addition of one or more labels. The term "labeling group" means any detectable label. In some embodiments, the labeling group is coupled to the antibody via spacer arms of various lengths to reduce potential steric hindrance. Various methods for labeling proteins are known in the art and may be used in performing the present invention. In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labeling group is coupled to the antibody via spacer arms of various lengths to reduce potential steric hindrance. Various methods for labeling proteins are known in the art and may be used in performing the present invention. Specific labels include optical dyes, including, but not limited to, chromophores, phosphors and fluorophores, with the latter being specific in many instances. Fluorophores can be either "small molecule" fluores, or proteinaceous fluores. By "fluorescent label" is meant any molecule that may be detected via its inherent fluorescent properties.

Antibody Conjugates and Fusions

In one embodiment, the antibodies of the invention are antibody "fusion proteins", sometimes referred to herein as "antibody conjugates". The fusion partner or conjugate partner can be proteinaceous or non-proteinaceous; the latter generally being generated using functional groups on the antibody and on the conjugate partner. Conjugate and fusion partners may be any molecule, including small molecule chemical compounds and polypeptides. For example, a variety of antibody conjugates and methods are described in Trail et al., 1999, Curr. Opin. Immunol. 11:584-588, incorporated entirely by reference. Possible conjugate partners include but are not limited to cytokines, cytotoxic agents, toxins, radioisotopes, chemotherapeutic agent, anti-angiogenic agents, a tyrosine kinase inhibitors, and other therapeutically active agents. In some embodiments, conjugate partners may be thought of more as payloads, that is to say that the goal of a conjugate is targeted delivery of the conjugate partner to a targeted cell, for example a cancer cell or immune cell, by the antibody. Thus, for example, the conjugation of a toxin to an antibody targets the delivery of said toxin to cells expressing the target antigen. As will be appreciated by one skilled in the art, in reality the concepts and definitions of fusion and conjugate are overlapping. The designation of an antibody as a fusion or conjugate is not meant to constrain it to any particular embodiment of the present invention. Rather, these terms are used loosely to convey the broad concept that any antibody of the present invention may be linked genetically, chemically, or otherwise, to one or more polypeptides or molecules to provide some desirable property.

Suitable conjugates include, but are not limited to, labels as described below, drugs and cytotoxic agents including, but not limited to, cytotoxic drugs (e.g., chemotherapeutic agents) or toxins or active fragments of such toxins. Suitable toxins and their corresponding fragments include diphtheria A chain, exotoxin A chain, ricin A chain, abrin A chain, curcin, crotin, phenomycin, enomycin and the like. Cytotoxic agents also include radiochemicals made by conjugating radioisotopes to antibodies, or binding of a radionuclide to a chelating agent that has been covalently attached to the antibody. Additional embodiments utilize calicheamicin, auristatins, geldanamycin, maytansine, and duocarmycins and analogs; for the latter, see U.S. 2003/0050331, incorporated entirely by reference.

In one embodiment, the antibodies of the present invention are fused or conjugated to a cytokine. By "cytokine" as used herein is meant a generic term for proteins released by one cell population that act on another cell as intercellular mediators. For example, as described in Penichet et al., 2001, J. Immunol. Methods 248:91-101, incorporated entirely by reference, cytokines may be fused to antibody to provide an array of desirable properties. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; C5a; and other polypeptide factors including LIF and kit ligand (KL). As used herein, the term cytokine includes proteins from natural sources or from recombinant cell culture, and biologically active equivalents of the native sequence cytokines.

In an alternate embodiment, the antibodies of the present invention are fused, conjugated, or operably linked to a toxin, including but not limited to small molecule toxins and enzymatically active toxins of bacterial, fungal, plant or animal origin, including fragments and/or variants thereof. For example, a variety of immunotoxins and immunotoxin methods are described in Thrush et al., 1996, Ann. Rev. Immunol. 14:49-71, incorporated entirely by reference. Small molecule toxins include but are not limited to calicheamicin, maytansine (U.S. Pat. No. 5,208,020, incorporated entirely by reference), trichothene, and CC1065. In one embodiment of the invention, the antibody is conjugated to one or more maytansine molecules (e.g. about 1 to about 10 maytansine molecules per antibody molecule). Maytansine may, for example, be converted to May-SS-Me which may be reduced to May-SH3 and reacted with modified antibody (Chari et al., 1992, *Cancer Research* 52: 127-131, incorporated entirely by reference) to generate a maytansinoid-antibody conjugate. Another conjugate of interest comprises an antibody conjugated to one or more calicheamicin molecules. The calicheamicin family of antibiotics are capable of producing double-stranded DNA breaks at sub-picomolar concentrations. Structural analogues of calicheamicin that may be used include but are not limited to $\gamma_1^1$, $\alpha_2^1$, $\alpha_3$, N-acetyl-$\gamma_1^1$, PSAG, and $\Theta^1_1$, (Hinman et al., 1993, Cancer Research 53:3336-3342; Lode et al., 1998, Cancer Research 58:2925-2928) (U.S. Pat. Nos. 5,714,586; 5,712,374; 5,264,586; 5,773,001, all incorporated entirely by reference). Dolastatin 10 analogs such as auristatin E (AE) and monomethylauristatin E (MMAE) may find use as conjugates for the antibodies of the present invention (Doronina et al., 2003, Nat Biotechnol 21(7):778-84; Francisco et al., 2003 Blood 102(4):1458-65, both incorporated entirely by reference). Useful enyzmatically active toxins include but are not limited to diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, PCT WO 93/21232, incorporated entirely by reference. The present invention further contemplates a conjugate between an antibody of the present invention and a compound with nucleolytic activity, for example a ribonuclease or DNA endonuclease such as a deoxyribonuclease (Dnase).

In an alternate embodiment, an antibody of the present invention may be fused, conjugated, or operably linked to a radioisotope to form a radioconjugate. A variety of radioactive isotopes are available for the production of radioconjugate antibodies. Examples include, but are not limited to, At211, I131, I125, Y90, Re186, Re188, Sm153, Bi212, P32, and radioactive isotopes of Lu.

In yet another embodiment, an antibody of the present invention may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In an alternate embodiment, the antibody is conjugated or operably linked to an enzyme in order to employ Antibody Dependent Enzyme Mediated Prodrug Therapy (ADEPT). ADEPT may be used by conjugating or operably linking the antibody to a prodrug-activating enzyme that converts a prodrug (e.g. a peptidyl chemotherapeutic agent, see PCT WO 81/01145, incorporated entirely by reference) to an active anti-cancer drug. See, for example, PCT WO 88/07378 and U.S. Pat. No. 4,975,278, both incorporated entirely by reference. The enzyme component of the immunoconjugate useful for ADEPT includes any enzyme capable of acting on a prodrug in such a way so as to covert it into its more active, cytotoxic form. Enzymes that are useful in the method of this invention include but are not limited to alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as .beta.-galactosidase and neuramimidase useful for converting glycosylated prodrugs into free drugs; beta-lactamase useful for converting drugs derivatized with .alpha.-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, for example, Massey, 1987, *Nature* 328: 457-458, incorporated entirely by reference). Antibody-abzyme conjugates can be prepared for delivery of the abzyme to a tumor cell population. A variety of additional conjugates are contemplated for the antibodies of the present invention. A variety of chemotherapeutic agents, anti-angiogenic agents, tyrosine kinase inhibitors, and other therapeutic agents are described below, which may find use as antibody conjugates.

Also contemplated as fusion and conjugate partners are Fc polypeptides. Thus an antibody may be a multimeric Fc polypeptide, comprising two or more Fc regions. The advantage of such a molecule is that it provides multiple binding sites for Fc receptors with a single protein molecule. In one embodiment, Fc regions may be linked using a chemical engineering approach. For example, Fab's and Fc's may be linked by thioether bonds originating at cysteine residues in the hinges, generating molecules such as FabFc$_2$. Fc regions may be linked using disulfide engineering and/or chemical cross-linking. In a preferred embodiment, Fc regions may be linked genetically. In a preferred embodiment, Fc regions in an antibody are linked genetically to generated tandemly linked Fc regions as described in U.S. Ser. No. 11/022,289, filed Dec. 21, 2004, entitled "Fc polypeptides with novel Fc ligand binding sites," incorporated entirely by reference. Tandemly linked Fc polypeptides may comprise two or more Fc regions, preferably one to three, most preferably two Fc regions. It may be advantageous to explore a number of engineering constructs in order to obtain homo- or hetero-tandemly linked antibodies with the most favorable structural and functional properties. Tandemly linked antibodies may be homo-tandemly linked antibodies, that is an antibody of one isotype is fused genetically to another antibody of the same isotype. It is anticipated that because there are multiple Fc☐R, C1q, and/or FcRn binding sites on tandemly linked Fc polypeptides, effector functions and/or pharmacokinetics may be enhanced. In an alternate embodiment, antibodies from different isotypes may be tandemly linked, referred to as hetero-tandemly linked antibodies. For example, because of the capacity to target FcγR and FcαRI receptors, an antibody that binds both FcγRs and FcαRI may provide a significant clinical improvement.

In addition to antibodies, an antibody-like protein that is finding an expanding role in research and therapy is the Fc fusion (Chamow et al., 1996, *Trends Biotechnol* 14:52-60; Ashkenazi et al., 1997, *Curr Opin Immunol* 9:195-200, both incorporated entirely by reference). "Fc fusion" is herein meant to be synonymous with the terms "immunoadhesin", "Ig fusion", "Ig chimera", and "receptor globulin" (sometimes with dashes) as used in the prior art (Chamow et al., 1996, Trends Biotechnol 14:52-60; Ashkenazi et al., 1997, Curr Opin Immunol 9:195-200). An Fc fusion is a protein wherein one or more polypeptides is operably linked to Fc. An Fc fusion combines the Fc region of an antibody, and thus its favorable effector functions and pharmacokinetics, with the target-binding region of a receptor, ligand, or some other protein or protein domain. The role of the latter is to mediate target recognition, and thus it is functionally analogous to the antibody variable region. Because of the structural and functional overlap of Fc fusions with antibodies, the discussion on antibodies in the present invention extends also to Fc.

Virtually any protein or small molecule may be linked to Fc to generate an Fc fusion. Protein fusion partners may include, but are not limited to, the variable region of any antibody, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, preferably an extracellular receptor, that is implicated in disease.

Fusion and conjugate partners may be linked to any region of an antibody of the present invention, including at the N- or C-termini, or at some residue in-between the termini. In a preferred embodiment, a fusion or conjugate partner is linked at the N- or C-terminus of the antibody, most preferably the N-terminus. A variety of linkers may find use in the present invention to covalently link antibodies to a fusion or conjugate partner. By "linker", "linker sequence", "spacer", "tethering sequence" or grammatical equivalents thereof, herein is meant a molecule or group of molecules (such as a monomer or polymer) that connects two molecules and often serves to place the two molecules in a preferred configuration. Linkers are known in the art; for example, homo- or hetero-bifunctional linkers as are well known (see, 1994 Pierce Chemical Company catalog, technical section on cross-linkers, pages 155-200, incorporated entirely by reference). A number of strategies may be used to covalently link molecules together. These include, but are not limited to, polypeptide linkages between N- and C-termini of proteins or protein domains, linkage via disulfide bonds, and linkage via chemical cross-linking reagents. In one aspect of this embodiment, the linker is a peptide bond, generated by recombinant techniques or peptide synthesis. The linker may contain amino acid residues that provide flexibility. Thus, the linker peptide may predominantly include the following amino acid residues: Gly, Ser, Ala, or Thr. The linker peptide should have a length that is adequate to link two molecules in such a way that they assume the correct conformation relative to one another so that they retain the desired activity. Suitable lengths for this purpose include at least one and not more than 50 amino acid residues. Preferably, the linker is from about 1 to 30 amino acids in length, with linkers of 1 to 20 amino acids in length being most preferred. Useful linkers include glycine-serine polymers (including, for example, (GS)n, (GSGGS)n (GGGGS)n and (GGGS)n, where n is an integer of at least one), glycine-alanine polymers, alanine-serine polymers, and other flexible linkers, as will be appreciated by those in the art.—Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use to link the antibodies of the present invention to a fusion or conjugate partner, or to link the antibodies of the present invention to a conjugate.

Production of Antibodies

The present invention provides methods for producing and experimentally testing antibodies. The described methods are not meant to constrain the present invention to any particular application or theory of operation. Rather, the provided methods are meant to illustrate generally that one or more antibodies may be produced and experimentally tested to obtain variant antibodies. General methods for antibody molecular biology, expression, purification, and screening are described in Antibody Engineering, edited by Duebel & Kontermann, Springer-Verlag, Heidelberg, 2001; and Hayhurst & Georgiou, 2001, *Curr Opin Chem Biol* 5:683-689; Maynard & Georgiou, 2000, *Annu Rev Biomed Eng* 2:339-76; Antibodies: A Laboratory Manual by Harlow & Lane, New York: Cold Spring Harbor Laboratory Press, 1988, all incorporated entirely by reference.

In one embodiment of the present invention, nucleic acids are created that encode the antibodies, and that may then be cloned into host cells, expressed and assayed, if desired. Thus, nucleic acids, and particularly DNA, may be made that encode each protein sequence. These practices are carried out using well-known procedures. For example, a variety of methods that may find use in the present invention are described in Molecular Cloning—A Laboratory Manual, 3$^{rd}$ Ed. (Maniatis, Cold Spring Harbor Laboratory Press, New York, 2001), and Current Protocols in Molecular Biology (John Wiley & Sons), both incorporated entirely by reference. As will be appreciated by those skilled in the art, the generation of exact sequences for a library comprising a large number of sequences is potentially expensive and time consuming. By "library" herein is meant a set of variants in any form, including but not limited to a list of nucleic acid or amino acid sequences, a list of nucleic acid or amino acid substitutions at variable positions, a physical library comprising nucleic acids that encode the library sequences, or a physical library comprising the variant proteins, either in purified or unpurified form. Accordingly, there are a variety of techniques that may be used to efficiently generate libraries of the present invention. Such methods that may find use in the present invention are described or referenced in U.S. Pat. No. 6,403,312; U.S. Ser. No. 09/782,004; U.S. Ser. No. 09/927,790; U.S. Ser. No. 10/218,102; PCT WO 01/40091; and PCT WO 02/25588, all incorporated entirely by reference. Such methods include but are not limited to gene assembly methods, PCR-based method and methods which use variations of PCR, ligase chain reaction-based methods, pooled oligo methods such as those used in synthetic shuffling, error-prone amplification methods and methods which use oligos with random mutations, classical site-directed mutagenesis methods, cassette mutagenesis, and other amplification and gene synthesis methods. As is known in the art, there are a variety of commercially available kits and methods for gene assembly, mutagenesis, vector subcloning, and the like, and such commercial products find use in the present invention for generating nucleic acids that encode antibodies.

The antibodies of the present invention may be produced by culturing a host cell transformed with nucleic acid, preferably an expression vector, containing nucleic acid encoding the antibodies, under the appropriate conditions to induce or cause expression of the protein. The conditions appropriate for expression will vary with the choice of the expression vector and the host cell, and will be easily ascertained by one skilled in the art through routine experimentation. A wide variety of appropriate host cells may be used, including but not limited to mammalian cells, bacteria, insect cells, and yeast. For example, a variety of cell lines that may find use in the present invention are described in the ATCC® cell line catalog, available from the American Type Culture Collection.

In a preferred embodiment, the antibodies are expressed in mammalian expression systems, including systems in which the expression constructs are introduced into the mammalian cells using virus such as retrovirus or adenovirus. Any mammalian cells may be used, with human, mouse, rat, hamster, and primate cells being particularly preferred. Suitable cells also include known research cells, including but not limited to Jurkat T cells, NIH3T3, CHO, BHK, COS, HEK293, PER C.6, HeLa, Sp2/0, NS0 cells and variants thereof. In an alternately preferred embodiment, library proteins are expressed in bacterial cells. Bacterial expression systems are well known in the art, and include *Escherichia coli* (*E. coli*), *Bacillus subtilis, Streptococcus cremoris,* and *Streptococcus lividans*. In alternate embodiments, antibodies are produced in insect cells (e.g. Sf21/Sf9, Trichoplusia ni Bti-Tn5b1-4) or yeast cells (e.g. *S. cerevisiae, Pichia,* etc). In an alternate embodiment, antibodies are expressed in vitro using cell free translation systems. In vitro translation systems derived from both prokaryotic (e.g. *E. coli*) and eukaryotic (e.g. wheat germ, rabbit reticulocytes) cells are available and may be chosen based on the expression levels and functional properties of the protein of interest. For example, as appreciated by those skilled in the art, in vitro translation is required for some display technologies, for example ribosome display. In addition, the antibodies may be produced by chemical synthesis methods. Also transgenic expression systems both animal (e.g. cow, sheep or goat milk, embryonated hen's eggs, whole insect larvae, etc.) and plant (e.g. corn, tobacco, duckweed, etc.)

The nucleic acids that encode the antibodies of the present invention may be incorporated into an expression vector in order to express the protein. A variety of expression vectors may be utilized for protein expression. Expression vectors may comprise self-replicating extra-chromosomal vectors or vectors which integrate into a host genome. Expression vectors are constructed to be compatible with the host cell type. Thus expression vectors which find use in the present invention include but are not limited to those which enable protein expression in mammalian cells, bacteria, insect cells, yeast, and in in vitro systems. As is known in the art, a variety of expression vectors are available, commercially or otherwise, that may find use in the present invention for expressing antibodies.

Expression vectors typically comprise a protein operably linked with control or regulatory sequences, selectable markers, any fusion partners, and/or additional elements. By "operably linked" herein is meant that the nucleic acid is placed into a functional relationship with another nucleic acid sequence. Generally, these expression vectors include transcriptional and translational regulatory nucleic acid operably linked to the nucleic acid encoding the antibody, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used.

Antibodies may be operably linked to a fusion partner to enable targeting of the expressed protein, purification, screening, display, and the like. Fusion partners may be linked to the antibody sequence via a linker sequences. The linker sequence will generally comprise a small number of amino acids, typically less than ten, although longer linkers may also be used. Typically, linker sequences are selected to be flexible and resistant to degradation. As will be appreciated by those skilled in the art, any of a wide variety of sequences may be used as linkers. For example, a common linker sequence comprises the amino acid sequence GGGGS. A fusion partner may be a targeting or signal sequence that directs antibody and any associated fusion partners to a desired cellular location or to the extracellular media. As is known in the art, certain signaling sequences may target a protein to be either secreted into the growth media, or into the periplasmic space, located between the inner and outer membrane of the cell. A fusion partner may also be a sequence that encodes a peptide or protein that enables purification and/or screening. Such fusion partners include but are not limited to polyhistidine tags (His-tags) (for example $H_6$ and $H_{10}$ or other tags for use with Immobilized Metal Affinity Chromatography (IMAC) systems (e.g. $Ni^{+2}$ affinity columns)), GST fusions, MBP fusions, Strep-tag, the BSP biotinylation target sequence of the bacterial enzyme BirA, and epitope tags which are targeted by antibodies (for example c-myc tags, flag-tags, and the like). As will be appreciated by those skilled in the art, such tags may be useful for purification, for screening, or both. For example, an antibody may be purified using a His-tag by immobilizing it to a $Ni^{+2}$ affinity column, and then after purification the same His-tag may be used to immobilize the antibody to a $Ni^{+2}$ coated plate to perform an ELISA or other binding assay (as described below). A fusion partner may enable the use of a selection method to screen antibodies (see below). Fusion partners that enable a variety of selection methods are well-known in the art, and all of these find use in the present invention. For example, by fusing the members of an antibody library to the gene III protein, phage display can be employed (Kay et al., Phage display of peptides and proteins: a laboratory manual, Academic Press, San Diego, Calif., 1996; Lowman et al., 1991, *Biochemistry* 30:10832-10838; Smith, 1985, *Science* 228:1315-1317, incorporated entirely by reference). Fusion partners may enable antibodies to be labeled. Alternatively, a fusion partner may bind to a specific sequence on the expression vector, enabling the fusion partner and associated antibody to be linked covalently or noncovalently with the nucleic acid that encodes them.

The methods of introducing exogenous nucleic acid into host cells are well known in the art, and will vary with the host cell used. Techniques include but are not limited to dextran-mediated transfection, calcium phosphate precipitation, calcium chloride treatment, polybrene mediated transfection, protoplast fusion, electroporation, viral or phage infection, encapsulation of the polynucleotide(s) in liposomes, and direct microinjection of the DNA into nuclei. In the case of mammalian cells, transfection may be either transient or stable.

In a preferred embodiment, antibodies are purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use in the present invention for purification of antibodies. For example, the bacterial proteins A and G bind to the Fc region. Likewise, the bacterial protein L binds to the Fab region of some antibodies, as of course does the antibody's target antigen. Purification can often be enabled by a particular fusion partner. For example, antibodies may be purified using glutathione resin if a GST fusion is employed, $Ni^{+2}$ affinity chromatography if a His-tag is employed, or immobilized anti-flag antibody if a flag-tag is used. For general guidance in suitable purification techniques, see, e.g. incorporated entirely by reference Protein Purification: Principles and Practice, $3^{rd}$ Ed., Scopes, Springer-Verlag, N.Y., 1994, incorporated entirely by reference. The degree of purification necessary will vary depending on the screen or use of the antibodies. In some instances no purification is necessary. For example in one embodiment, if the antibodies are secreted, screening may take place directly from the media. As is well known in the art, some methods of selection do not involve purification of proteins. Thus, for example, if a library of antibodies is made into a phage display library, protein purification may not be performed.

In Vitro Experimentation

Antibodies may be screened using a variety of methods, including but not limited to those that use in vitro assays, in vivo and cell-based assays, and selection technologies. Automation and high-throughput screening technologies may be utilized in the screening procedures. Screening may employ the use of a fusion partner or label. The use of fusion partners has been discussed above. By "labeled" herein is meant that the antibodies of the invention have one or more elements, isotopes, or chemical compounds attached to enable the detection in a screen. In general, labels fall into three classes: a) immune labels, which may be an epitope incorporated as a fusion partner that is recognized by an antibody, b) isotopic labels, which may be radioactive or heavy isotopes, and c) small molecule labels, which may include fluorescent and colorimetric dyes, or molecules such as biotin that enable other labeling methods. Labels may be incorporated into the compound at any position and may be incorporated in vitro or in vivo during protein expression.

In a preferred embodiment, the functional and/or biophysical properties of antibodies are screened in an in vitro assay. In vitro assays may allow a broad dynamic range for screening properties of interest. Properties of antibodies that may be screened include but are not limited to stability, solubility, and affinity for Fc ligands, for example FcγRs. Multiple properties may be screened simultaneously or individually. Proteins may be purified or unpurified, depending on the requirements of the assay. In one embodiment, the screen is a qualitative or quantitative binding assay for binding of antibodies to a protein or nonprotein molecule that is known or thought to bind the antibody. In a preferred embodiment, the screen is a binding assay for measuring binding to the target antigen. In an alternately preferred embodiment, the screen is an assay for binding of antibodies to an Fc ligand, including but are not limited to the family of FcγRs, the neonatal receptor FcRn, the complement protein C1q, and the bacterial proteins A and G. Said Fc ligands may be from any organism, with humans, mice, rats, rabbits, and monkeys preferred. Binding assays can be carried out using a variety of methods known in the art, including but not limited to FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as Biacore™) isothermal titration calorimetry, differential scanning calorimetry, gel electrophoresis, and chromatography including gel filtration. These and other methods may take advantage of some fusion partner or label of the antibody. Assays may employ a variety of detection methods including but not limited to chromogenic, fluorescent, luminescent, or isotopic labels.

The biophysical properties of antibodies, for example stability and solubility, may be screened using a variety of methods known in the art. Protein stability may be determined by measuring the thermodynamic equilibrium between folded and unfolded states. For example, antibodies of the present invention may be unfolded using chemical denaturant, heat, or pH, and this transition may be monitored using methods including but not limited to circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions may also be monitored using these and other techniques. The solubility and overall structural integrity of an antibody may be quantitatively or qualitatively determined using a wide range of methods that are known in the art. Methods which may find use in the present invention for characterizing the biophysical properties of antibodies include gel electrophoresis, isoelectric focusing, capillary electrophoresis, chromatography such as size exclusion chromatography, ion-exchange chromatography, and reversed-phase high performance liquid chromatography, peptide mapping, oligosaccharide mapping, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay. Structural analysis employing X-ray crystallographic techniques and NMR spectroscopy may also find use. In one embodiment, stability and/or solubility may be measured by determining the amount of protein solution after some defined period of time. In this assay, the protein may or may not be exposed to some extreme condition, for example elevated temperature, low pH, or the presence of denaturant. Because function typically requires a stable, soluble, and/or well-folded/structured protein, the aforementioned functional and binding assays also provide ways to perform such a measurement. For example, a solution comprising an antibody could be assayed for its ability to bind target antigen, then exposed to elevated temperature for one or more defined periods of time, then assayed for antigen binding again. Because unfolded and aggregated protein is not expected to be capable of binding antigen, the amount of activity remaining provides a measure of the antibody's stability and solubility.

In a preferred embodiment, the library is screened using one or more cell-based or in vitro assays. For such assays, antibodies, purified or unpurified, are typically added exogenously such that cells are exposed to individual variants or groups of variants belonging to a library. These assays are typically, but not always, based on the biology of the ability of the antibody to bind to antigen and mediate some biochemical event, for example effector functions like cellular lysis, phagocytosis, ligand/receptor binding inhibition, inhibition of growth and/or proliferation, apoptosisand the like. Such assays often involve monitoring the response of cells to antibody, for example cell survival, cell death, cellular phagocytosis, cell lysis, change in cellular morphology, or transcriptional activation such as cellular expression of a natural gene or reporter gene. For example, such assays may measure the ability of antibodies to elicit ADCC, ADCP, or CDC. For some assays additional cells or components, that is in addition to the target cells, may need to be added, for example serum complement, or effector cells such as peripheral blood monocytes (PBMCs), NK cells, macrophages, and the like. Such additional cells may be from any organism, preferably humans, mice, rat, rabbit, and monkey. Crosslinked or monomeric antibodies may cause apoptosis of certain cell lines expressing the antibody's target antigen, or they may mediate attack on target cells by immune cells which have been added to the assay. Methods for monitoring cell death or viability are known in the art, and include the use of dyes, fluorophores, immunochemical, cytochemical, and radioactive reagents. For example, caspase assays or annexin-flourconjugates may enable apoptosis to be measured, and uptake or release of radioactive substrates (e.g. Chromium-51 release assays) or the metabolic reduction of fluorescent dyes such as alamar blue may enable cell growth, proliferationor activation to be monitored. In a preferred embodiment, the DELFIA® EuTDA-based cytotoxicity assay (Perkin Elmer, Mass.) is used. Alternatively, dead or damaged target cells may be monitored by measuring the release of one or more natural intracellular proteins, for example lactate dehydrogenase. Transcriptional activation may also serve as a method for assaying function in cell-based assays. In this case, response may be monitored by assaying for natural genes or proteins which may be upregulated or down-regulated, for example the release of certain interleukins may be measured, or alternatively readout may be via a luciferase or GFP-reporter construct. Cell-based assays may also involve the measure of morphological changes of cells as a response to the presence of an antibody. Cell types for such assays may be prokaryotic or eukaryotic, and a variety of cell lines that are known in the art may be employed. Alternatively, cell-based screens are performed using cells that have been transformed or transfected with nucleic acids encoding the antibodies.

In vitro assays include but are not limited to binding assays, ADCC, CDC, phagocytosis, cytotoxicity, proliferation, apoptosis, necrosis, cell cycle arrest, peroxide/ozone release, chemotaxis of effector cells, inhibition of such assays by reduced effector function antibodies; ranges of activities such as >100× improvement or >100× reduction, blends of receptor activation and the assay outcomes that are expected from such receptor profiles.

In Vivo Experimentation

The biological properties of the antibodies of the present invention may be characterized in cell, tissue, and whole organism experiments. As is know in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. Said animals may be referred to as disease models. With respect to the antibodies of the present invention, a particular challenge arises when using animal models to evaluate the potential for in-human efficacy of candidate polypeptides—this is due, at least in part, to the fact that antibodies that have a specific effect on the affinity for a human Fc receptor may not have a similar affinity effect with the orthologous animal receptor. These problems can be further exacerbated by the inevitable ambiguities associated with correct assignment of true orthologues (Mechetina et al., *Immunogenetics*, 2002 54:463-468, incorporated entirely by reference), and the fact that some orthologues simply do not exist in the animal (e.g. humans possess an FcγRIIa whereas mice do not). Therapeutics are often tested in mice, including but not limited to nude mice, SCID mice, xenograft mice, and transgenic mice (including knockins and knockouts). For example, an antibody of the present invention that is intended as an anti-cancer therapeutic may be tested in a mouse cancer model, for example a xenograft mouse. In this method, a tumor or tumor cell line is grafted onto or injected into a mouse, and subsequently the mouse is treated with the therapeutic to determine the ability of the antibody to reduce or inhibit cancer growth and metastasis. An alternative approach is the use of a SCID murine model in which immune-deficient mice are injected with human Periferal Blood Lymphocytes (PBLs), conferring a semi-functional and human immune system—with an appropriate array of human FcRs—to the mice that have subsequently been injected with antibodies or Fc-polypeptides that target injected human tumor cells. In such a model, the Fc-polypeptides that target the desired antigen (such as her2/neu on SkOV3 ovarian cancer cells) interact with human PBLs within the mice to engage tumoricidal effector functions. Such experimentation may provide meaningful data for determination of the potential of said antibody to be used as a therapeutic. Any organism, preferably mammals, may be used for testing. For example because of their genetic similarity to humans, monkeys can be suitable therapeutic models, and thus may be used to test the efficacy, toxicity, pharmacokinetics, or other property of the antibodies of the present invention. Tests of the antibodies of the present invention in humans are ultimately required for approval as drugs, and thus of course these experiments are contemplated. Thus the antibodies of the present invention may be tested in humans to determine their therapeutic efficacy, toxicity, pharmacokinetics, and/or other clinical properties.

The antibodies of the present invention may confer superior performance on Fc-containing therapeutics in animal models or in humans. The receptor binding profiles of such antibodies, as described in this specification, may, for example, be selected to increase the potency of cytotoxic drugs or to target specific effector functions or effector cells to improve the selectivity of the drug's action. Further, receptor binding profiles can be selected that may reduce some or all effector functions thereby reducing the side-effects or toxicity of such Fc-containing drug. For example, an antibody with reduced binding to FcγRIIIa, FcγRI and FcγRIIa can be selected to eliminate most cell-mediated effector function, or an antibody with reduced binding to C1q may be selected to limit complement-mediated effector functions. In some contexts, such effector functions are known to have potential toxic effects, therefore eliminating them may increase the safety of the Fc-bearing drug and such improved safety may be characterized in animal models. In some contexts, such effector functions are known to mediate the desirable therapeutic activity, therefore enhancing them may increase the activity or potency of the Fc-bearing drug and such improved activity or potency may be characterized in animal models.

Optimized antibodies can be tested in a variety of orthotopic tumor models. These clinically relevant animal models are important in the study of pathophysiology and therapy of aggressive cancers like pancreatic, prostate and breast cancer. Immune deprived mice including, but not limited to athymic nude or SCID mice are frequently used in scoring of local and systemic tumor spread from the site of intra-organ (e.g. pancreas, prostate or mammary gland) injection of human tumor cells or fragments of donor patients.

In preferred embodiments, antibodies of the present invention may be assessed for efficacy in clinically relevant animal models of various human diseases. In many cases, relevant models include various transgenic animals for specific tumor antigens.

Relevant transgenic models such as those that express human Fc receptors (e.g., CD16 including the gamma chain, FcγR1, RIIa/b, and others) could be used to evaluate and test antibodies and Fc-fusions in their efficacy. The evaluation of antibodies by the introduction of human genes that directly or indirectly mediate effector function in mice or other rodents that may enable physiological studies of efficacy in tumor toxicity or other diseases such as autoimmune disorders and RA. Human Fc receptors such as FcγRIIIa may possess polymorphisms such as that in position 158 V or F which would further enable the introduction of specific and combinations of human polymorphisms into rodents. The various studies involving polymorphism-specific FcRs are not limited to this section, however, and encompasses all discussions and applications of FcRs in general as specified in throughout this application. antibodies of the present invention may confer superior activity on Fc-containing drugs in such transgenic models, in particular variants with binding profiles optimized for human FcγRIIIa mediated activity may show superior activity in transgenic CD16 mice. Similar improvements in efficacy in mice transgenic for the other human Fc receptors, e.g. FcγRIIa, FcγRI, etc., may be observed for antibodies with binding profiles optimized for the respective receptors. Mice transgenic for multiple human receptors would show improved activity for antibodies with binding profiles optimized for the corresponding multiple receptors, for example as outlined in FIG. 5.

Because of the difficulties and ambiguities associated with using animal models to characterize the potential efficacy of candidate therapeutic antibodies in a human patient, some variant polypeptides of the present invention may find utility as proxies for assessing potential in-human efficacy. Such proxy molecules would preferably mimic—in the animal system—the FcR and/or complement biology of a corresponding candidate human antibody. This mimicry is most likely to be manifested by relative association affinities between specific antibodies and animal vs. human receptors. For example, if one were using a mouse model to assess the potential in-human efficacy of an antibody that has enhanced affinity for human FcγRIIIa, an appropriate proxy variant would have enhanced affinity for mouse FcγRIII-2 (mouse CD16-2). Alternatively if one were using a mouse model to assess the potential in-human efficacy of an antibody that has reduced affinity for the inhibitory human FcγRIIb, an appropriate proxy variant would have reduced affinity for mouse FcγRII. It should also be noted that the proxy antibodies could be created in the context of a human antibody, an animal antibody, or both.

In a preferred embodiment, the testing of antibodies may include study of efficacy in primates (e.g. cynomolgus monkey model) to facilitate the evaluation of depletion of specific target cells harboring target antigen. Additional primate models include but not limited to that of the rhesus monkey and Fc polypetides in therapeutic studies of autoimmune, transplantation and cancer.

Toxicity studies are performed to determine the antibody or Fc-fusion related-effects that cannot be evaluated in standard pharmacology profile or occur only after repeated administration of the agent. Most toxicity tests are performed in two species—a rodent and a non-rodent—to ensure that any unexpected adverse effects are not overlooked before new therapeutic entities are introduced into man. In general, these models may measure a variety of toxicities including genotoxicity, chronic toxicity, immunogenicity, reproductive/developmental toxicity and carcinogenicity. Included within the aforementioned parameters are standard measurement of food consumption, bodyweight, antibody formation, clinical chemistry, and macro- and microscopic examination of standard organs/tissues (e.g. cardiotoxicity). Additional parameters of measurement are injection site trauma and the measurement of neutralizing antibodies, if any. Traditionally, monoclonal antibody therepeutics, naked or conjugated are evaluated for cross-reactivity with normal tissues, immunogenicity/antibody production, conjugate or linker toxicity and "bystander" toxicity of radiolabeled species. Nonetheless, such studies may have to be individualized to address specific concerns and following the guidance set by ICH S6 (Safety studies for biotechnological products also noted above). As such, the general principles are that the products are sufficiently well characterized and for which impurities/contaminants have been removed, that the test material is comparable throughout development, and GLP compliance.

The pharmacokinetics (PK) of the antibodies of the invention can be studied in a variety of animal systems, with the most relevant being non-human primates such as the cynomolgus, rhesus monkeys. Single or repeated i.v./s.c. administrations over a dose range of 6000-fold (0.05-300 mg/kg) can be evaluated for the half-life (days to weeks) using plasma concentration and clearance as well as volume of distribution at a steady state and level of systemic absorbance can be measured. Examples of such parameters of measurement generally include maximum observed plasma concentration (Cmax), the time to reach Cmax (Tmax), the area under the plasma concentration-time curve from time 0 to infinity [AUC(0-inf] and apparent elimination half-life (T1/2). Additional measured parameters could include compartmental analysis of concentration-time data obtained following i.v. administration and bioavailability. Examples of pharmacological/toxicological studies using cynomolgus have been established for Rituxan and Zevalin in which monoclonal antibodies to CD20 are cross-reactive. Biodistribution, dosimetry (for radiolabled antibodies), and PK studies can also be done in rodent models. Such studies would evaluate tolerance at all doses administered, toxicity to local tissues, preferential localization to rodent xenograft animal models, depletion of target cells (e.g. CD20 positive cells).

The antibodies of the present invention may confer superior pharmacokinetics on Fc-containing therapeutics in animal systems or in humans. For example, increased binding to FcRn may increase the half-life and exposure of the Fc-containing drug. Alternatively, decreased binding to FcRn may decrease the half-life and exposure of the Fc-containing drug in cases where reduced exposure is favorable such as when such drug has side-effects.

It is known in the art that the array of Fc receptors is differentially expressed on various immune cell types, as well as in different tissues. Differential tissue distribution of Fc receptors may ultimately have an impact on the pharmacodynamic (PD) and pharmacokinetic (PK) properties of antibodies of the present invention. Because antibodies of the presentation have varying affinities for the array of Fc receptors, further screening of the polypeptides for PD and/or PK properties may be extremely useful for defining the optimal balance of PD, PK, and therapeutic efficacy conferred by each candidate polypeptide.

Pharmacodynamic studies may include, but are not limited to, targeting specific tumor cells or blocking signaling mechanisms, measuring depletion of target antigen expressing cells or signals, etc. The antibodies of the present invention may target particular effector cell populations and thereby direct Fc-containing drugs to recruit certain activities to improve potency or to increase penetration into a particularly favorable physiological compartment. For example, neutrophil activity and localization can be targeted by an antibody that preferentially targets FcγRIIIb. Such pharmacodynamic effects may be demonstrated in animal models or in humans.

Clinical Use

The antibodies of the present invention may be used for various therapeutic purposes. As will be appreciated by those in the art, the antibodies of the present invention may be used for any therapeutic purpose that uses antibodies and the like. In a preferred embodiment, the antibodies are administered to a patient to treat disorders including but not limited to cancer, autoimmune and inflammatory diseases, and infectious diseases.

A "patient" for the purposes of the present invention includes both humans and other animals, preferably mammals and most preferably humans. Thus the antibodies of the present invention have both human therapy and veterinary applications. The term "treatment" or "treating" in the present invention is meant to include therapeutic treatment, as well as prophylactic, or suppressive measures for a disease or disorder. Thus, for example, successful administration of an antibody prior to onset of the disease results in treatment of the disease. As another example, successful administration of an optimized antibody after clinical manifestation of the disease to combat the symptoms of the disease comprises treatment of the disease. "Treatment" and "treating" also encompasses administration of an optimized antibody after the appearance of the disease in order to eradicate the disease. Successful administration of an agent after onset and after clinical symptoms have developed, with possible abatement of clinical symptoms and perhaps amelioration of the disease, comprises treatment of the disease. Those "in need of treatment" include mammals already having the disease or disorder, as well as those prone to having the disease or disorder, including those in which the disease or disorder is to be prevented.

In one embodiment, an antibody of the present invention is administered to a patient having a disease involving inappropriate expression of a protein or other molecule. Within the scope of the present invention this is meant to include diseases and disorders characterized by aberrant proteins, due for example to alterations in the amount of a protein present, protein localization, posttranslational modification, conformational state, the presence of a mutant or pathogen protein, etc. Similarly, the disease or disorder may be characterized by alterations molecules including but not limited to polysaccharides and gangliosides. An overabundance may be due to any cause, including but not limited to overexpression at the molecular level, prolonged or accumulated appearance at the site of action, or increased activity of a protein relative to normal. Included within this definition are diseases and disorders characterized by a reduction of a protein. This reduction may be due to any cause, including but not limited to reduced expression at the molecular level, shortened or reduced appearance at the site of action, mutant forms of a protein, or decreased activity of a protein relative to normal. Such an overabundance or reduction of a protein can be measured relative to normal expression, appearance, or activity of a protein, and said measurement may play an important role in the development and/or clinical testing of the antibodies of the present invention.

By "cancer" and "cancerous" herein refer to or describe the physiological condition in mammals that is typically characterized by unregulated cell growth. Examples of cancer include but are not limited to carcinoma, lymphoma, blastoma, sarcoma (including liposarcoma), neuroendocrine tumors, mesothelioma, schwanoma, meningioma, adenocarcinoma, melanoma, and leukemia or lymphoid malignancies.

More particular examples of such cancers include hematologic malignancies, such as non-Hodgkin's lymphomas (NHL). NHL cancers include but are not limited to Burkitt's lymphoma (BL), small lymphocytic lymphoma/chronic lymphocytic leukemia (SLL/CLL), mantle cell lymphoma (MCL), follicular lymphoma (FL), diffuse large B-cell lymphoma (DLCL), marginal zone lymphoma (MZL), hairy cell leukemia (HCL) and lymphoplasmacytic leukemia (LPL), extranodal marginal zone B-cell lymphoma of mucosa-associated lymphoid tissue (MALT), nodal marginal zone B cell lymphoma, mediastinal large cell lymphoma, intravascular large cell lymphoma, primary effusion lymphoma, precursor B-lymphoblastic leukemia/lymphoma, precursor T- and NK-cells lymphoma (precursor T lymphoblastic lymphoma, blastic NK cell lymphoma), tumors of the mature T and NK cells, including peripheral T-cell lymphoma and leukemia (PTL), adult T-cell leukemia/T-cell lymphomas and large granular lymphocytic leukemia, T-cell chronic lymphocytic leukemia/prolymphocytic leukemia, T-cell large granular lymphocytic leukemia, aggressive NK-cell leukemia, extranodal T-/NK cell lymphoma, enteropathy-type T-cell lymphoma, hepatosplenic T-cell lymphoma, anaplastic large cell lymphoma (ALCL), angiocetric and angioimmunoblastic T-cell lymphoma, mycosis fungoides/Sezary syndrome, and cutaneous T-cell lymphoma (CTCL). Other cancers that may be treatable by the antibodies of the invention include but are not limited to Hodgkin's lymphoma, tumors of lymphocyte precursor cells, including B-cell acute lymphoblastic leukemia/lymphoma (B-ALL), and T-cell acute lymphoblastic leukemia/lymphoma (T-ALL), thymoma, Langerhans cell histocytosis, multiple myeloma, myeloid neoplasias such as acute myelogenous leukemias (AML), including AML with maturation, AML without differentiation, acute promyelocytic leukemia, acute myelomonocytic leukemia, and acute monocytic leukemias, myelodysplastic syndromes, and chronic myeloproliferative disorders (MDS), including chronic myelogenous leukemia (CML). Other cancers that may be treatable by the antibodies of the invenntion include but are not limited to tumors of the central nervous system such as glioma, glioblastoma, neuroblastoma, astrocytoma, medulloblastoma, ependymoma, and retinoblastoma; solid tumors of the head and neck (eg. nasopharyngeal cancer, salivary gland carcinoma, and esophagael cancer), lung (eg. small-cell lung cancer, non-small cell lung cancer, adenocarcinoma of the lung and squamous carcinoma of the lung), digestive system (eg. gastric or stomach cancer including gastrointestinal cancer, cancer of the bile duct or biliary tract, colon cancer, rectal cancer, colorectal cancer, and anal carcinoma), reproductive system (eg. testicular, penile, or prostate cancer, uterine, vaginal, vulval, cervical, ovarian, and endometrial cancer), skin (eg. melanoma, basal cell carcinoma, squamous cell cancer, actinic keratosis), liver (eg. liver cancer, hepatic carcinoma, hepatocellular cancer, and hepatoma), bone (eg. osteoclastoma, and osteolytic bone cancers) additional tissues and organs (eg. pancreatic cancer, bladder cancer, kidney or renal cancer, thyroid cancer, breast cancer, cancer of the peritoneum, and Kaposi's sarcoma), and tumors of the vascular system (eg. angiosarcoma and hemagiopericytoma).

Preferred oncology indications that may be treated by anti-CD19 antibodies of the invention include but are not limited to all non-Hodgkin's lymphomas (NHL), especially refractory/resistant NHL, chronic lymphocytic leukemia (CLL), B-cell acute lymphoblastic leukemia/lymphoma (B-ALL), and mantle cell lymphoma (MCL).

Autoimmunity results from a breakdown of self-tolerance involving humoral and/or cell-mediated immune mechanisms in. Among of the consequences of failure in central and/or peripheral tolerance, are survival and activation of self-reactive B cells and T cells. Several autoimmune diseases are defined by excessive activation of both B and/or T lymphocytes. Activation of these cells requires in cooperation, antigen engagement and co-stimulatory signals from interacting lymphocytes. Antibody-mediated depletion, inhibition, anti-proliferation, and/or blockade of B cells are therapeutic approaches for the treatment of autoimmune disease.

By "autoimmune diseases" herein include allogenic islet graft rejection, alopecia areata, ankylosing spondylitis, antiphospholipid syndrome, autoimmune Addison's disease, antineutrophil cytoplasmic autoantibodies (ANCA), autoimmune diseases of the adrenal gland, autoimmune hemolytic anemia, autoimmune hepatitis, autoimmune myocarditis, autoimmune neutropenia, autoimmune oophoritis and orchitis, autoimmune thrombocytopenia, autoimmune urticaria, Behcet's disease, bullous pemphigoid, cardiomyopathy, Castleman's syndrome, celiac spruce-dermatitis, chronic fatigue immune disfunction syndrome, chronic inflammatory demyelinating polyneuropathy, Churg-Strauss syndrome, cicatrical pemphigoid, CREST syndrome, cold agglutinin disease, Crohn's disease, dermatomyositis, discoid lupus, essential mixed cryoglobulinemia, factor VIII deficiency, fibromyalgia-fibromyositis, glomerulonephritis, Grave's disease, Guillain-Barre, Goodpasture's syndrome, graft-versus-host disease (GVHD), Hashimoto's thyroiditis, hemophilia A, idiopathic pulmonary fibrosis, idiopathic thrombocytopenia purpura (ITP), IgA neuropathy, IgM polyneuropathies, immune mediated thrombocytopenia, juvenile arthritis, Kawasaki's disease, lichen plantus, lupus erthematosis, Meniere's disease, mixed connective tissue disease, multiple sclerosis (MS), type 1 diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobinulinemia, primary biliary cirrhosis, psoriasis, psoriatic arthritis, Reynauld's phenomenon, Reiter's syndrome, rheumatoid arthritis (RA), sarcoidosis, scleroderma, Sjogren's syndrome, solid organ transplant rejection, stiff-man syndrome, systemic lupus erythematosus (SLE), takayasu arteritis, temporal arteristis/giant cell arteritis, thrombotic thrombocytopenia purpura, ulcerative colitis, uveitis, vasculitides such as dermatitis herpetiformis vasculitis, vitiligo, and Wegner's granulomatosis.

Preferred autoimmune indications that may be treated by anti-CD19 antibodies of the invention include but are not limited to rheumatoid arthritis (RA), systemic lupus erythematosus (SLE or lupus), multiple sclerosis, Sjogren's syndrome, and idiopathic thrombocytopenia purpura (ITP).

By "inflammatory disorders" herein include acute respiratory distress syndrome (ARDS), acute septic arthritis, adjuvant arthritis, juvenile idiopathic arthritis, allergic encephalomyelitis, allergic rhinitis, allergic vasculitis, allergy, asthma, atherosclerosis, chronic inflammation due to chronic bacterial or viral infectionis, chronic obstructive pulmonary disease (COPD), coronary artery disease, encephalitis, inflammatory bowel disease, inflammatory osteolysis, inflammation associated with acute and delayed hypersensitivity reactions, inflammation associated with tumors, peripheral nerve injury or demyelinating diseases, inflammation associated with tissue trauma such as burns and ischemia, inflammation due to meningitis, multiple organ injury syndrome, pulmonary fibrosis, sepsis and septic shock, Stevens-Johnson syndrome, undifferentiated arthropy, and undifferentiated spondyloarthropathy.

By "infectious diseases" herein include diseases caused by pathogens such as viruses, bacteria, fungi, protozoa, and parasites. Infectious diseases may be caused by viruses including adenovirus, cytomegalovirus, dengue, Epstein-Barr, hanta, hepatitis A, hepatitis B, hepatitis C, herpes simplex type I, herpes simplex type II, human immunodeficiency virus, (HIV), human papilloma virus (HPV), influenza, measles, mumps, papova virus, polio, respiratory syncytial virus, rinderpest, rhinovirus, rotavirus, rubella, SARS virus, smallpox, viral meningitis, and the like. Infections diseases may also be caused by bacteria including *Bacillus antracis, Borrelia burgdorferi, Campylobacter jejuni, Chlamydia trachomatis, Clostridium botulinum, Clostridium tetani, Diptheria, E. coli, Legionella, Helicobacter pylori, Mycobacterium rickettsia, Mycoplasma nesisseria, Pertussis, Pseudomonas aeruginosa, S. pneumonia, Streptococcus, Staphylococcus, Vibria cholerae, Yersinia pestis*, and the like. Infectious diseases may also be caused by fungi such as *Aspergillus fumigatus, Blastomyces dermatitidis, Candida albicans, Coccidioides immitis, Cryptococcus neoformans, Histoplasma capsulatum, Penicillium marneffei*, and the like. Infectious diseases may also be caused by protozoa and parasites such as chlamydia, kokzidioia, leishmania, malaria, rickettsia, trypanosoma, and the like.

Furthermore, antibodies of the present invention may be used to prevent or treat additional conditions including but not limited to heart conditions such as congestive heart failure (CHF), myocarditis and other conditions of the myocardium; skin conditions such as rosecea, acne, and eczema; bone and tooth conditions such as bone loss, osteoporosis, Paget's disease, Langerhans' cell histiocytosis, periodontal disease, disuse osteopenia, osteomalacia, monostotic fibrous dysplasia, polyostotic fibrous dysplasia, bone metastasis, bone pain management, humoral malignant hypercalcemia, periodontal reconstruction, spinal cord injury, and bone fractures; metabolic conditions such as Gaucher's disease; endocrine conditions such as Cushing's syndrome; and neurological conditions.

A number of the receptors that may interact with the antibodies of the present invention are polymorphic in the human population. For a given patient or population of patients, the efficacy of the antibodies of the present invention may be affected by the presence or absence of specific polymorphisms in proteins. For example, FcγRIIIA is polymorphic at position 158, which is commonly either V (high affinity) or F (low affinity). Patients with the V/V homozygous genotype are observed to have a better clinical response to treatment with the anti-CD20 antibody Rituxan® (rituximab), likely because these patients mount a stronger NK response (Dall'Ozzo et al. (2004) Cancer Res. 64:4664-9, incorporated entirely by reference). Additional polymorphisms include but are not limited to FcγRIIA R131 or H131, and such polymorphisms are known to either increase or decrease Fc binding and subsequent biological activity, depending on the polymorphism. antibodies of the present invention may bind preferentially to a particular polymorphic form of a receptor, for example FcγRIIIA 158 V, or to bind with equivalent affinity to all of the polymorphisms at a particular position in the receptor, for example both the 158V and 158F polymorphisms of FcγRIIIA In a preferred embodiment, antibodies of the present invention may have equivalent binding to polymorphisms may be used in an antibody to eliminate the differential efficacy seen in patients with different polymorphisms. Such a property may give greater consistency in therapeutic response and reduce non-responding patient populations. Such variant Fc with indentical binding to receptor polymorphisms may have increased biological activity, such as ADCC, CDC or circulating half-life, or alternatively decreased activity, via modulation of the binding to the relevant Fc receptors. In a preferred embodiment, antibodies of the present invention may bind with higher or lower affinity to one of the polymorphisms of a receptor, either accentuating the existing difference in binding or reversing the difference. Such a property may allow creation of therapeutics particularly tailored for efficacy with a patient population possessing such polymorphism. For example, a patient population possessing a polymorphism with a higher affinity for an inhibitory receptor such as FcγRIIB could receive a drug containing an antibody with reduced binding to such polymorphic form of the receptor, creating a more efficacious drug.

In a preferred embodiment, patients are screened for one or more polymorphisms in order to predict the efficacy of the antibodies of the present invention. This information may be used, for example, to select patients to include or exclude from clinical trials or, post-approval, to provide guidance to physicians and patients regarding appropriate dosages and treatment options. For example, in patients that are homozygous or heterozygous for FcγRIIIA 158F antibody drugs such as the anti-CD20 mAb, Rituximab are minimally effective (Carton 2002 Blood 99: 754-758; Weng 2003 J. Clin. Oncol. 21:3940-3947, both incorporated entirely by reference); such patients may show a much better clinical response to the antibodies of the present invention. In one embodiment, patients are selected for inclusion in clinical trials for an antibody of the present invention if their genotype indicates that they are likely to respond significantly better to an antibody of the present invention as compared to one or more currently used antibody therapeutics. In another embodiment, appropriate dosages and treatment regimens are determined using such genotype information. In another embodiment, patients are selected for inclusion in a clinical trial or for receipt of therapy post-approval based on their polymorphism genotype, where such therapy contains an antibody engineered to be specifically efficacious for such population, or alternatively where such therapy contains an antibody that does not show differential activity to the different forms of the polymorphism.

Included in the present invention are diagnostic tests to identify patients who are likely to show a favorable clinical response to an antibody of the present invention, or who are likely to exhibit a significantly better response when treated with an antibody of the present invention versus one or more currently used antibody therapeutics. Any of a number of methods for determining FcγR polymorphisms in humans known in the art may be used.

Furthermore, the present invention comprises prognostic tests performed on clinical samples such as blood and tissue samples. Such tests may assay for effector function activity, including but not limited to ADCC, CDC, phagocytosis, and opsonization, or for killing, regardless of mechanism, of cancerous or otherwise pathogenic cells. In a preferred embodiment, ADCC assays, such as those described previously, are used to predict, for a specific patient, the efficacy of a given antibody of the present invention. Such information may be used to identify patients for inclusion or exclusion in clinical trials, or to inform decisions regarding appropriate dosages and treatment regemins. Such information may also be used to select a drug that contains a particular antibody that shows superior activity in such assay.

Formulation

Pharmaceutical compositions are contemplated wherein an antibody of the present invention and and one or more therapeutically active agents are formulated. Formulations of the antibodies of the present invention are prepared for storage by mixing said antibody having the desired degree of purity with optional pharmaceutically acceptable carriers, excipients or stabilizers (Remington's Pharmaceutical Sciences 16th edition, Osol, A. Ed., 1980, incorporated entirely by reference), in the form of lyophilized formulations or aqueous solutions. Acceptable carriers, excipients, or stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl orbenzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g. Zn-protein complexes); and/or non-ionic surfactants such as TWEEN™, PLURONICS™ or polyethylene glycol (PEG). In a preferred embodiment, the pharmaceutical composition that comprises the antibody of the present invention may be in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration are preferably sterile. This is readily accomplished by filtration through sterile filtration membranes or other methods.

The antibodies disclosed herein may also be formulated as immunoliposomes. A liposome is a small vesicle comprising various types of lipids, phospholipids and/or surfactant that is useful for delivery of a therapeutic agent to a mammal. Liposomes containing the antibody are prepared by methods known in the art, such as described in Epstein et al., 1985, *Proc Natl Acad Sci USA*, 82:3688; Hwang et al., 1980, *Proc Natl Acad Sci USA*, 77:4030; U.S. Pat. Nos. 4,485,045; 4,544,545; and PCT WO 97/38731, all incorporated entirely by reference. Liposomes with enhanced circulation time are disclosed in U.S. Pat. No. 5,013,556, incorporated entirely by reference. The components of the liposome are commonly arranged in a bilayer formation, similar to the lipid arrangement of biological membranes. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. A chemotherapeutic agent or other therapeutically active agent is optionally contained within the liposome (Gabizon et al., 1989, *J National Cancer Inst* 81:1484, incorporated entirely by reference).

The antibody and other therapeutically active agents may also be entrapped in microcapsules prepared by methods including but not limited to coacervation techniques, interfacial polymerization (for example using hydroxymethylcellulose or gelatin-microcapsules, or poly-(methylmethacylate) microcapsules), colloidal drug delivery systems (for example, liposomes, albumin microspheres, microemulsions, nano-particles and nanocapsules), and macroemulsions. Such techniques are disclosed in Remington's Pharmaceutical Sciences 16th edition, Osol, A. Ed., 1980, incorporated entirely by reference. Sustained-release preparations may be prepared. Suitable examples of sustained-release preparations include semipermeable matrices of solid hydrophobic polymer, which matrices are in the form of shaped articles, e.g. films, or microcapsules. Examples of sustained-release matrices include polyesters, hydrogels (for example poly(2-hydroxyethyl-methacrylate), or poly(vinylalcohol)), polylactides (U.S. Pat. No. 3,773,919, incorporated entirely by reference), copolymers of L-glutamic acid and gamma ethyl-L-glutamate, non-degradable ethylene-vinyl acetate, degradable lactic acid-glycolic acid copolymers such as the Lupron Depot® (which are injectable microspheres composed of lactic acid-glycolic acid copolymer and leuprolide acetate), poly-D-(–)-3-hydroxybutyric acid, and ProLease® (commercially available from Alkermes), which is a microsphere-based delivery system composed of the desired bioactive molecule incorporated into a matrix of poly-DL-lactide-co-glycolide (PLG).

Administration

Administration of the pharmaceutical composition comprising an antibody of the present invention, preferably in the form of a sterile aqueous solution, may be done in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary, vaginally, parenterally, rectally, or intraocularly. In some instances, for example for the treatment of wounds, inflammation, etc., the antibody may be directly applied as a solution or spray. As is known in the art, the pharmaceutical composition may be formulated accordingly depending upon the manner of introduction.

Subcutaneous administration may be preferable in some circumstances because the patient may self-administer the pharmaceutical composition. Many protein therapeutics are not sufficiently potent to allow for formulation of a therapeutically effective dose in the maximum acceptable volume for subcutaneous administration. This problem may be addressed in part by the use of protein formulations comprising arginine-HCl, histidine, and polysorbate (see WO 04091658, incorporated entirely by reference). Antibodies of the present invention may be more amenable to subcutaneous administration due to, for example, increased potency, improved serum half-life, or enhanced solubility.

As is known in the art, protein therapeutics are often delivered by IV infusion or bolus. The antibodies of the present invention may also be delivered using such methods. For example, administration may venious be by intravenous infusion with 0.9% sodium chloride as an infusion vehicle.

Pulmonary delivery may be accomplished using an inhaler or nebulizer and a formulation comprising an aerosolizing agent. For example, AERx® inhalable technology commercially available from Aradigm, or Inhance™ pulmonary delivery system commercially available from Nektar Therapeutics may be used. Antibodies of the present invention may be more amenable to intrapulmonary delivery. FcRn is present in the lung, and may promote transport from the lung to the bloodstream (e.g. Syntonix WO 04004798, Bitonti et al. (2004) Proc. Nat. Acad. Sci. 101: 9763-8, both incorporated entirely by reference). Accordingly, antibodies that bind FcRn more effectively in the lung or that are released more efficiently in the bloodstream may have improved bioavailability following intrapulmonary administration. Antibodies of the present invention may also be more amenable to intrapulmonary administration due to, for example, improved solubility or altered isoelectric point.

Furthermore, antibodies of the present invention may be more amenable to oral delivery due to, for example, improved stability at gastric pH and increased resistance to proteolysis. Furthermore, FcRn appears to be expressed in the intestinal epithelia of adults (Dickinson et al. (1999) J. Clin. Invest. 104:903-11, incorporated entirely by reference), so antibodies of the present invention with improved FcRn interaction profiles may show enhanced bioavailability following oral administration. FcRn mediated transport of antibodies may also occur at other mucus membranes such as those in the gastrointestinal, respiratory, and genital tracts (Yoshida et al. (2004) Immunity 20:769-83, incorporated entirely by reference).

In addition, any of a number of delivery systems are known in the art and may be used to administer the antibodies of the present invention. Examples include, but are not limited to, encapsulation in liposomes, microparticles, microspheres (eg. PLA/PGA microspheres), and the like. Alternatively, an implant of a porous, non-porous, or gelatinous material, including membranes or fibers, may be used. Sustained release systems may comprise a polymeric material or matrix such as polyesters, hydrogels, poly(vinylalcohol),polylactides, copolymers of L-glutamic acid and ethyl-L-gutamate, ethylene-vinyl acetate, lactic acid-glycolic acid copolymers such as the Lupron Depot®, and poly-D-(–)-3-hydroxyburyric acid. It is also possible to administer a nucleic acid encoding the antibody of the current invention, for example by retroviral infection, direct injection, or coating with lipids, cell surface receptors, or other transfection agents. In all cases, controlled release systems may be used to release the antibody at or close to the desired location of action.

Dosing

The dosing amounts and frequencies of administration are, in a preferred embodiment, selected to be therapeutically or prophylactically effective. As is known in the art, adjustments for protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

The concentration of the therapeutically active antibody in the formulation may vary from about 0.1 to 100 weight %. In a preferred embodiment, the concentration of the antibody is in the range of 0.003 to 1.0 molar. In order to treat a patient, a therapeutically effective dose of the antibody of the present invention may be administered. By "therapeutically effective dose" herein is meant a dose that produces the effects for which it is administered. The exact dose will depend on the purpose of the treatment, and will be ascertainable by one skilled in the art using known techniques. Dosages may range from 0.0001 to 100 mg/kg of body weight or greater, for example 0.1, 1, 10, or 50 mg/kg of body weight, with 1 to 10 mg/kg being preferred.

In some embodiments, only a single dose of the antibody is used. In other embodiments, multiple doses of the antibody are administered. The elapsed time between administrations may be less than 1 hour, about 1 hour, about 1-2 hours, about 2-3 hours, about 3-4 hours, about 6 hours, about 12 hours, about 24 hours, about 48 hours, about 2-4 days, about 4-6 days, about 1 week, about 2 weeks, or more than 2 weeks.

In other embodiments the antibodies of the present invention are administered in metronomic dosing regimes, either by continuous infusion or frequent administration without extended rest periods. Such metronomic administration may involve dosing at constant intervals without rest periods. Typically such regimens encompass chronic low-dose or continuous infusion for an extended period of time, for example 1-2 days, 1-2 weeks, 1-2 months, or up to 6 months or more. The use of lower doses may minimize side effects and the need for rest periods.

In certain embodiments the antibody of the present invention and one or more other prophylactic or therapeutic agents are cyclically administered to the patient. Cycling therapy involves administration of a first agent at one time, a second agent at a second time, optionally additional agents at additional times, optionally a rest period, and then repeating this sequence of administration one or more times. The number of cycles is typically from 2-10. Cycling therapy may reduce the development of resistance to one or more agents, may minimize side effects, or may improve treatment efficacy.

Combination Therapies

The antibodies of the present invention may be administered concomitantly with one or more other therapeutic regimens or agents. The additional therapeutic regimes or agents may be used to improve the efficacy or safety of the antibody. Also, the additional therapeutic regimes or agents may be used to treat the same disease or a comorbidity rather than to alter the action of the antibody. For example, an antibody of the present invention may be administered to the patient along with chemotherapy, radiation therapy, or both chemotherapy and radiation therapy. The antibody of the present invention may be administered in combination with one or more other prophylactic or therapeutic agents, including but not limited to cytotoxic agents, chemotherapeutic agents, cytokines, growth inhibitory agents, anti-hormonal agents, kinase inhibitors, anti-angiogenic agents, cardioprotectants, immunostimulatory agents, immunosuppressive agents, agents that promote proliferation of hematological cells, angiogenesis inhibitors, protein tyrosine kinase (PTK) inhibitors, additional antibodies, FcγRIIb or other Fc receptor inhibitors, or other therapeutic agents.

The terms "in combination with" and "co-administration" are not limited to the administration of said prophylactic or therapeutic agents at exactly the same time. Instead, it is meant that the antibody of the present invention and the other agent or agents are administered in a sequence and within a time interval such that they may act together to provide a benefit that is increased versus treatment with only either the antibody of the present invention or the other agent or agents. It is preferred that the antibody and the other agent or agents act additively, and especially preferred that they act synergistically. Such molecules are suitably present in combination in amounts that are effective for the purpose intended. The skilled medical practitioner can determine empirically, or by considering the pharmacokinetics and modes of action of the agents, the appropriate dose or doses of each therapeutic agent, as well as the appropriate timings and methods of administration.

In one embodiment, the antibodies of the present invention are administered with one or more additional molecules comprising antibodies or Fc. The antibodies of the present invention may be co-administered with one or more other antibodies that have efficacy in treating the same disease or an additional comorbidity; for example two antibodies may be administered that recognize two antigens that are overexpressed in a given type of cancer, or two antigens that mediate pathogenesis of an autoimmune or infectious disease.

Examples of anti-cancer antibodies that may be co-administered include, but are not limited to, anti-17-1A cell surface antigen antibodies such as Panorex™ (edrecolomab); anti-4-1BB antibodies; anti-4Dc antibodies; anti-A33 antibodies such as A33 and CDP-833; anti-α4β1 integrin antibodies such as natalizumab; anti-α4β7 integrin antibodies such as LDP-02; anti-αVβ1 integrin antibodies such as F-200, M-200, and SJ-749; anti-αVβ3 integrin antibodies such as abciximab, CNTO-95, Mab-17E6, and Vitaxin™; anti-complement factor 5 (C5) antibodies such as 5G1.1; anti-CA125 antibodies such as OvaRex® (oregovomab); anti-CD3 antibodies such as Nuvion® (visilizumab) and Rexomab; anti-CD4 antibodies such as IDEC-151, MDX-CD4, OKT4A; anti-CD6 antibodies such as Oncolysin B and Oncolysin CD6; anti-CD7 antibodies such as HB2; anti-CD19 antibodies such as B43, MT-103, and Oncolysin B; anti-CD20 antibodies such as 2H7, 2H7.v16, 2H7.v114, 2H7.v115, Bexxar® (tositumomab, I-131 labeled anti-CD20), Rituxan® (rituximab), and Zevalin® (Ibritumomab tiuxetan, Y-90 labeled anti-CD20); anti-CD22 antibodies such as Lymphocide™ (epratuzumab, Y-90 labeled anti-CD22); anti-CD23 antibodies such as IDEC-152; anti-CD25 antibodies such as basiliximab and Zenapax® (daclizumab); anti-CD30 antibodies such as AC10, MDX-060, and SGN-30; anti-CD33 antibodies such as Mylotarg® (gemtuzumab ozogamicin), Oncolysin M, and Smart M195; anti-CD38 antibodies; anti-CD40 antibodies such as SGN-40 and toralizumab; anti-CD40L antibodies such as 5c8, Antova™, and IDEC-131; anti-CD44 antibodies such as bivatuzumab; anti-CD46 antibodies; anti-CD52 antibodies such as Campath® (alemtuzumab); anti-CD55 antibodies such as SC-1; anti-CD56 antibodies such as huN901-DM1; anti-CD64 antibodies such as MDX-33; anti-CD66e antibodies such as)CR-303; anti-CD74 antibodies such as IMMU-110; anti-CD80 antibodies such as galiximab and IDEC-114; anti-CD89 antibodies such as MDX-214; anti-CD123 antibodies; anti-CD138 antibodies such as B-B4-DM1; anti-CD146 antibodies such as AA-98; anti-CD148 antibodies; anti-CEA antibodies such as cT84.66, labetuzumab, and Pentacea™; anti-CTLA-4 antibodies such as MDX-101; anti-CXCR4 antibodies; anti-EGFR antibodies such as ABX-EGF, Erbitux® (cetuximab), IMC-C225, and Merck Mab 425; anti-EpCAM antibodies such as Crucell's anti-EpCAM, ING-1, and IS-IL-2; anti-ephrin B2/EphB4 antibodies; anti-Her2 antibodies such as Herceptin®, MDX-210; anti-FAP (fibroblast activation protein) antibodies such as sibrotuzumab; anti-ferritin antibodies such as NXT-211; anti-FGF-1 antibodies; anti-FGF-3 antibodies; anti-FGF-8 antibodies; anti-FGFR antibodies, anti-fibrin antibodies; anti-G250 antibodies such as WX-G250 and Rencarex®; anti-GD2 ganglioside antibodies such as EMD-273063 and TriGem; anti-GD3 ganglioside antibodies such as BEC2, KW-2871, and mitumomab; anti-gpIIb/IIIa antibodies such as ReoPro; anti-heparinase antibodies; anti-Her2/ErbB2 antibodies such as Herceptin® (trastuzumab), MDX-210, and pertuzumab; anti-HLA antibodies such as Oncolym®, Smart 1D10; anti-HM1.24 antibodies; anti-ICAM antibodies such as ICM3; anti-IgA receptor antibodies; anti-IGF-1 antibodies such as CP-751871 and EM-164; anti-IGF-1R antibodies such as IMC-A12; anti-IL-6 antibodies such as CNTO-328 and elsilimomab; anti-IL-15 antibodies such as HuMax™-IL15; anti-KDR antibodies; anti-laminin 5 antibodies; anti-Lewis Y antigen antibodies such as Hu3S193 and IGN-311; anti-MCAM antibodies; anti-Muc1 antibodies such as BravaRex and TriAb; anti-NCAM antibodies such as ERIC-1 and ICRT; anti-PEM antigen antibodies such as Theragyn and Therex; anti-PSA antibodies; anti-PSCA antibodies such as IG8; anti-Ptk antbodies; anti-PTN antibodies; anti-RANKL antibodies such as AMG-162; anti-RLIP76 antibodies; anti-SK-1 antigen antibodies such as Monopharm C; anti-STEAP antibodies; anti-TAG72 antibodies such as CC49-SCA and MDX-220; anti-TGF-β antibodies such as CAT-152; anti-TNF-α antibodies such as CDP571, CDP870, D2E7, Humira® (adalimumab), and Remicade® (infliximab); anti-TRAIL-R1 and TRAIL-R2 antibodies; anti-VE-cadherin-2 antibodies; and anti-VLA-4 antibodies such as Antegren™. Furthermore, anti-idiotype antibodies including but not limited to the GD3 epitope antibody BEC2 and the gp72 epitope antibody 105AD7, may be used. In addition, bispecific antibodies including but not limited to the anti-CD3/CD20 antibody Bi20 may be used.

Examples of antibodies that may be co-administered to treat autoimmune or inflammatory disease, transplant rejection, GVHD, and the like include, but are not limited to, anti-α4β7 integrin antibodies such as LDP-02, anti-beta2 integrin antibodies such as LDP-01, anti-complement (C5) antibodies such as 5G1.1, anti-CD2 antibodies such as BTI-322, MEDI-507, anti-CD3 antibodies such as OKT3, SMART anti-CD3, anti-CD4 antibodies such as IDEC-151, MDX-CD4, OKT4A, anti-CD11a antibodies, anti-CD14 antibodies such as IC14, anti-CD18 antibodies, anti-CD23 antibodies such as DEC 152, anti-CD25 antibodies such as Zenapax, anti-CD40L antibodies such as 5c8, Antova, IDEC-131, anti-CD64 antibodies such as MDX-33, anti-CD80 antibodies such as IDEC-114, anti-CD147 antibodies such as ABX-CBL, anti-E-selectin antibodies such as CDP850, anti-gpIIb/IIIa antibodies such as ReoPro/Abcixima, anti-ICAM-3 antibodies such as ICM3, anti-ICE antibodies such as VX-740, anti-FcγR1 antibodies such as MDX-33, anti-IgE antibodies such as rhuMab-E25, anti-IL-4 antibodies such as SB-240683, anti-IL-5 antibodies such as SB-240563, SCH55700, anti-IL-8 antibodies such as ABX-IL8, anti-interferon gamma antibodies, and anti-TNFα antibodies such as CDP571, CDP870, D2E7, Infliximab, MAK-195F, anti-VLA-4 antibodies such as Antegren. Examples of other Fc-containing molecules that may be co-administered to treat autoimmune or inflammatory disease, transplant rejection, GVHD, and the like include, but are not limited to, the p75 TNF receptor/Fc fusion Enbrel® (etanercept) and Regeneron's IL-1 trap.

Examples of antibodies that may be co-administered to treat infectious diseases include, but are not limited to, anti-anthrax antibodies such as ABthrax, anti-CMV antibodies such as CytoGam and sevirumab, anti-cryptosporidium antibodies such as CryptoGAM, Sporidin-G, anti-helicobacter antibodies such as Pyloran, anti-hepatitis B antibodies such as HepeX-B, Nabi-HB, anti-HIV antibodies such as HRG-214, anti-RSV antibodies such as felvizumab, HNK-20, palivizumab, RespiGam, and anti-staphylococcus antibodies such as Aurexis, Aurograb, BSYX-A110, and SE-Mab.

Alternatively, the antibodies of the present invention may be co-administered or with one or more other molecules that compete for binding to one or more Fc receptors. For example, co-administering inhibitors of the inhibitory receptor FcγRIIb may result in increased effector function. Similarly, co-administering inhibitors of the activating receptors such as FcγRIIIa may minimize unwanted effector function. Fc receptor inhibitors include, but are not limited to, Fc molecules that are engineered to act as competitive inhibitors for binding to FcγRIIb FcγRIIIa, or other Fc receptors, as well as other immunoglobulins and specifically the treatment called IVIg (intravenous immunoglobulin). In one embodiment, the inhibitor is administered and allowed to act before the antibody is administered. An alternative way of achieving the effect of sequential dosing would be to provide an immediate release dosage form of the Fc receptor inhibitor and then a sustained release formulation of the antibody of the invention. The immediate release and controlled release formulations could be administered separately or be combined into one unit dosage form. Administration of an FcγRIIb inhibitor may also be used to limit unwanted immune responses, for example anti-Factor VIII antibody response following Factor VIII administration to hemophiliacs.

In one embodiment, the antibodies of the present invention are administered with a chemotherapeutic agent. By "chemotherapeutic agent" as used herein is meant a chemical compound useful in the treatment of cancer. Examples of chemotherapeutic agents include but are not limited to alkylating agents such as thiotepa and cyclosphosphamide (CYTOXAN™); alkyl sulfonates such as busulfan, improsulfan and piposulfan; androgens such as calusterone, dromostanolone propionate, epitiostanol, mepitiostane, testolactone; anti-adrenals such as aminoglutethimide, mitotane, trilostane; anti-androgens such as flutamide, nilutamide, bicalutamide, leuprolide, and goserelin; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti estrogens including for example tamoxifen, raloxifene, aromatase inhibiting 4(5)-imidazoles, 4-hydroxytamoxifen, trioxifene, keoxifene, LY 117018, onapristone, and toremifene (Fareston); anti-metabolites such as methotrexate and 5-fluorouracil (5-FU); folic acid analogues such as denopterin, methotrexate, pteropterin, trimetrexate; aziridines such as benzodopa, carboquone, meturedopa, and uredopa; ethylenimines and methylamelamines including altretamine, triethylenemelamine, trietylenephosphoramide, triethyl nethiophosphaoramide and trimethylolomelamine; folic acid replenisher such as frolinic acid; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; platinum analogs such as cisplatin and carboplatin; vinblastine; platinum; proteins such as arginine deiminase and asparaginase; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; taxanes, e.g. paclitaxel (TAXOL®, Bristol-Myers Squibb Oncology, Princeton, N.J.) and docetaxel (TAXOTERE®, Rhne-Poulenc Rorer, Antony, France); topoisomerase inhibitor RFS 2000; thymidylate synthase inhibitor (such as Tomudex); additional chemotherapeutics including aceglatone; aldophosphamide glycoside; aminolevulinic acid; amsacrine; bestrabucil; bisantrene; edatraxate; defofamine; demecolcine; diaziquone; difluoromethylornithine (DMFO); elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2''-trichlorotriethyl amine; urethan; vindesine; dacarb azine; mannomustine; mitobronitol; mitolactol; pipobroman; gacytosine; arabinoside ("Ara-C"); cyclophosphamide; thiotepa; chlorambucil; gemcitabine; 6-thioguanine; mercaptopurine; methotrexate; etoposide (VP-16); ifosfamide; mitomycin C; mitoxantrone; vincristine; vinorelbine; navelbine; novantrone; teniposide; daunomycin; aminopterin; xeloda; ibandronate; CPT-11; retinoic acid; esperamicins; capecitabine. Pharmaceutically acceptable salts, acids or derivatives of any of the above may also be used.

A chemotherapeutic or other cytotoxic agent may be administered as a prodrug. By "prodrug" as used herein is meant a precursor or derivative form of a pharmaceutically active substance that is less cytotoxic to tumor cells compared to the parent drug and is capable of being enzymatically activated or converted into the more active parent form. See, for example Wilman, 1986, Biochemical Society Transactions, 615th Meeting Belfast, 14:375-382; Stella et al., "Prodrugs: A Chemical Approach to Targeted Drug Delivery," Directed Drug Delivery; and Borchardt et al., (ed.): 247-267, Humana Press, 1985, all incorporated entirely by reference. The prodrugs that may find use with the present invention include but are not limited to phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use with the antibodies of the present invention include but are not limited to any of the aforementioned chemotherapeutic agents.

A variety of other therapeutic agents may find use for administration with the antibodies of the present invention. In one embodiment, the antibody is administered with an anti-angiogenic agent. By "anti-angiogenic agent" as used herein is meant a compound that blocks, or interferes to some degree, the development of blood vessels. The anti-angiogenic factor may, for instance, be a small molecule or a protein, for example an antibody, Fc fusion, or cytokine, that binds to a growth factor or growth factor receptor involved in promoting angiogenesis. The preferred anti-angiogenic factor herein is an antibody that binds to Vascular Endothelial Growth Factor (VEGF). Other agents that inhibit signaling through VEGF may also be used, for example RNA-based therapeutics that reduce levels of VEGF or VEGF-R expression, VEGF-toxin fusions, Regeneron's VEGF-trap, and antibodies that bind VEGF-R. In an alternate embodiment, the antibody is administered with a therapeutic agent that induces or enhances adaptive immune response, for example an antibody that targets CTLA-4. Additional anti-angiogenesis agents include, but are not limited to, angiostatin (plasminogen fragment), antithrombin III, angiozyme, ABT-627, Bay 12-9566, benefin, bevacizumab, bisphosphonates, BMS-275291, cartilage-derived inhibitor (CDI), CAI, CD59 complement fragment, CEP-7055, Col 3, combretastatin A-4, endostatin (collagen XVIII fragment), farnesyl transferase inhibitors, fibronectin fragment, gro-beta, halofuginone, heparinases, heparin hexasaccharide fragment, HMV833, human chorionic gonadotropin (hCG), IM-862, interferon alpha, interferon beta, interferon gamma, interferon inducible protein 10 (IP-10), interleukin- 12, kringle 5 (plasminogen fragment), marimastat, metalloproteinase inhibitors (eg. TIMPs), 2-methodyestradiol, MMI 270 (CGS 27023A), plasminogen activiator inhibitor (PAI), platelet factor-4 (PF4), prinomastat, prolactin 16 kDa fragment, proliferin-related protein (PRP), PTK 787/ZK 222594, retinoids, solimastat, squalamine, SS3304, SU5416, SU6668, SU11248, tetrahydrocortisol-S, tetrathiomolybdate, thalidomide, thrombospondin-1 (TSP-1), TNP-470, transforming growth factor beta (TGF-β), vasculostatin, vasostatin (calreticulin fragment), ZS6126, and ZD6474.

In a preferred embodiment, the antibody is administered with a tyrosine kinase inhibitor. By "tyrosine kinase inhibitor" as used herein is meant a molecule that inhibits to some extent tyrosine kinase activity of a tyrosine kinase. Examples of such inhibitors include but are not limited to quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo (2,3-d) pyrimidines; curcumin (diferuloyl methane, 4,5-bis (4-fluoroanilino)phthalimide); tyrphostines containing nitrothiophene moieties; PD-0183805 (Warner-Lambert); antisense molecules (e.g. those that bind to ErbB-encoding nucleic acid); quinoxalines (U.S. Pat. No. 5,804,396); tryphostins (U.S. Pat. No. 5,804,396); ZD6474 (Astra Zeneca); PTK-787 (Novartis/Schering A G); pan-ErbB inhibitors such as C1-1033 (Pfizer); Affinitac (ISIS 3521; Isis/Lilly); Imatinib mesylate (STI571, Gleevec®; Novartis); PKI 166 (Novartis); GW2016 (Glaxo SmithKline); C1-1033 (Pfizer); EKB-569 (Wyeth); Semaxinib (Sugen); ZD6474 (AstraZeneca); PTK-787 (Novartis/Schering AG); INC-1C11 (Imclone); or as described in any of the following patent publications: U.S. Pat. No. 5,804,396; PCT WO 99/09016 (American Cyanimid); PCT WO 98/43960 (American Cyanamid); PCT WO 97/38983 (Warner-Lambert); PCT WO 99/06378 (Warner-Lambert); PCT WO 99/06396 (Warner-Lambert); PCT WO 96/30347 (Pfizer, Inc); PCT WO 96/33978 (AstraZeneca); PCT WO96/3397 (AstraZeneca); PCT WO 96/33980 (AstraZeneca), gefitinib (IRESSA™, ZD1839, AstraZeneca), and OSI-774 (Tarceva™, OSI Pharmaceuticals/Genentech), all patent publications incorporated entirely by reference.

In another embodiment, the antibody is administered with one or more immunomodulatory agents. Such agents may increase or decrease production of one or more cytokines, up- or down-regulate self-antigen presentation, mask MHC antigens, or promote the proliferation, differentiation, migration, or activation state of one or more types of immune cells. Immunomodulatory agents include but not limited to: non-steroidal anti-inflammatory drugs (NSAIDs) such as asprin, ibuprofed, celecoxib, diclofenac, etodolac, fenoprofen, indomethacin, ketorolac, oxaprozin, nabumentone, sulindac, tolmentin, rofecoxib, naproxen, ketoprofen, and nabumetone; steroids (eg. glucocorticoids, dexamethasone, cortisone, hydrocortisone, methylprednisolone, prednisone, prednisolone, trimcinolone, azulfidineicosanoids such as prostaglandins, thromboxanes, and leukotrienes; as well as topical steroids such as anthralin, calcipotriene, clobetasol, and tazarotene); cytokines such as TGFb, IFNa, IFNb, IFNg, IL-2, IL-4, IL-10; cytokine, chemokine, or receptor antagonists including antibodies, soluble receptors, and receptor-Fc fusions against BAFF, B7, CCR2, CCR5, CD2, CD3, CD4, CD6, CD7, CD8, CD11, CD14, CD15, CD17, CD18, CD20, CD23, CD28, CD40, CD40L, CD44, CD45, CD52, CD64, CD80, CD86, CD147, CD152, complement factors (C5, D) CTLA4, eotaxin, Fas, ICAM, ICOS, IFNα, IFβ, IFNγ, IFNAR, IgE, IL-1, IL-2, IL-2R, IL-4, IL-5R, IL-6, IL-8, IL-9 IL-12, IL-13, IL-13R1, IL-15, IL-18R, IL-23, integrins, LFA-1, LFA-3, MHC, selectins, TGFβ, TNFα, TNFβ, TNF-R1, T-cell receptor, including Enbrel® (etanercept), Humira® (adalimumab), and Remicade® (infliximab); heterologous anti-lymphocyte globulin; other immunomodulatory molecules such as 2-amino-6-aryl-5 substituted pyrimidines, anti-idiotypic antibodies for MHC binding peptides and MHC fragments, azathioprine, brequinar, bromocryptine, cyclophosphamide, cyclosporine A, D-penicillamine, deoxyspergualin, FK506, glutaraldehyde, gold, hydroxychloroquine, leflunomide, malononitriloamides (eg. leflunomide), methotrexate, minocycline, mizoribine, mycophenolate mofetil, rapamycin, and sulfasasazine.

In an alternate embodiment, antibody of the present invention are administered with a cytokine. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

In a preferred embodiment, cytokines or other agents that stimulate cells of the immune system are co-administered with the antibody of the present invention. Such a mode of treatment may enhance desired effector function. For examle, agents that stimulate NK cells, including but not limited to IL-2 may be co-administered. In another embodiment, agents that stimulate macrophages, including but not limited to C5a, formyl peptides such as N-formyl-methionyl-leucyl-phenylalanine (Beigier-Bompadre et al. (2003) Scand. J. Immunol. 57: 221-8, incorporated entirely by reference), may be co-administered. Also, agents that stimulate neutrophils, including but not limited to G-CSF, GM-CSF, and the like may be administered. Furthermore, agents that promote migration of such immunostimulatory cytokines may be used. Also additional agents including but not limited to interferon gamma, IL-3 and IL-7 may promote one or more effector functions.

In an alternate embodiment, cytokines or other agents that inhibit effector cell function are co-administered with the antibody of the present invention. Such a mode of treatment may limit unwanted effector function.

In an additional embodiment, the antibody is administered with one or more antibiotics, including but not limited to: aminoglycoside antibiotics (eg. apramycin, arbekacin, bambermycins, butirosin, dibekacin, gentamicin, kanamycin, neomycin, netilmicin, paromomycin, ribostamycin, sisomycin, spectrinomycin), aminocyclitols (eg. sprctinomycin), amphenicol antibiotics (eg. azidamfenicol, chloramphenicol, florfrnicol, and thiamphemicol), ansamycin antibiotics (eg. rifamide and rifampin), carbapenems (eg. imipenem, meropenem, panipenem); cephalosporins (eg. cefaclor, cefadroxil, cefamandole, cefatrizine, cefazedone, cefozopran, cefpimizole, cefpiramide, cefpirome, cefprozil, cefuroxine, cefixime, cephalexin, cephradine), cephamycins (cefbuperazone, cefoxitin, cefminox, cefmetazole, and cefotetan); lincosamides (eg. clindamycin, lincomycin); macrolide (eg. azithromycin, brefeldin A, clarithromycin, erythromycin, roxithromycin, tobramycin), monobactams (eg. aztreonam, carumonam, and tigernonam); mupirocin; oxacephems (eg. flomoxef, latamoxef, and moxalactam); penicillins (eg. amdinocillin, amdinocillin pivoxil, amoxicillin, bacampicillin, bexzylpenicillinic acid, benzylpenicillin sodium, epicillin, fenbenicillin, floxacillin, penamecillin, penethamate hydriodide, penicillin o-benethamine, penicillin O, penicillin V, penicillin V benzoate, penicillin V hydrabamine, penimepicycline, and phencihicillin potassium); polypeptides (eg. bacitracin, colistin, polymixin B, teicoplanin, vancomycin); quinolones (amifloxacin, cinoxacin, ciprofloxacin, enoxacin, enrofloxacin, feroxacin, flumequine, gatifloxacin, gemifloxacin, grepafloxacin, lomefloxacin, moxifloxacin, nalidixic acid, norfloxacin, ofloxacin, oxolinic acid, pefloxacin, pipemidic acid, rosoxacin, rufloxacin, sparfloxacin, temafloxacin, tosufloxacin, trovafloxacin); rifampin; streptogramins (eg. quinupristin, dalfopristin); sulfonamides (sulfanilamide, sulfamethoxazole); tetracyclenes (chlortetracycline, demeclocycline hydrochloride, demethylchlortetracycline, doxycycline, duramycin, minocycline, neomycin, oxytetracycline, streptomycin, tetracycline, vancomycin).

Anti-fungal agents such as amphotericin B, ciclopirox, clotrimazole, econazole, fluconazole, flucytosine, itraconazole, ketoconazole, niconazole, nystatin, terbinafine, terconazole, and tioconazole may also be used.

Antiviral agents including protease inhibitors, reverse transcriptase inhibitors, and others, including type I interferons, viral fusion inhibitors, and neuramidase inhibitors, may also be used. Examples of antiviral agents include, but are not limited to, acyclovir, adefovir, amantadine, amprenavir, clevadine, enfuvirtide, entecavir, foscarnet, gangcyclovir, idoxuridine, indinavir, lopinavir, pleconaril, ribavirin, rimantadine, ritonavir, saquinavir, trifluridine, vidarabine, and zidovudine, may be used.

The antibodies of the present invention may be combined with other therapeutic regimens. For example, in one embodiment, the patient to be treated with an antibody of the present invention may also receive radiation therapy. Radiation therapy can be administered according to protocols commonly employed in the art and known to the skilled artisan. Such therapy includes but is not limited to cesium, iridium, iodine, or cobalt radiation. The radiation therapy may be whole body irradiation, or may be directed locally to a specific site or tissue in or on the body, such as the lung, bladder, or prostate. Typically, radiation therapy is administered in pulses over a period of time from about 1 to 2 weeks. The radiation therapy may, however, be administered over longer periods of time. For instance, radiation therapy may be administered to patients having head and neck cancer for about 6 to about 7 weeks. Optionally, the radiation therapy may be administered as a single dose or as multiple, sequential doses. The skilled medical practitioner can determine empirically the appropriate dose or doses of radiation therapy useful herein. In accordance with another embodiment of the invention, the antibody of the present invention and one or more other anti-cancer therapies are employed to treat cancer cells ex vivo. It is contemplated that such ex vivo treatment may be useful in bone marrow transplantation and particularly, autologous bone marrow transplantation. For instance, treatment of cells or tissue(s) containing cancer cells with antibody and one or more other anti-cancer therapies, such as described above, can be employed to deplete or substantially deplete the cancer cells prior to transplantation in a recipient patient.

It is of course contemplated that the antibodies of the invention may employ in combination with still other therapeutic techniques such as surgery or phototherapy.

EXAMPLES

Examples are provided below to illustrate the present invention. These examples are not meant to constrain the present invention to any particular application or theory of operation.

For reference to immunoglobulin variable regions, positions are numbered according to the Kabat numbering scheme. For reference to immunoglobulin constant regions, positions are numbered according to the EU index as in Kabat (Kabat et al., 1991, *Sequences of Proteins of Immunological Interest*, 5th Ed., United States Public Health Service, National Institutes of Health, Bethesda).

Example 1. Anti-CD19 Antibodies with Amino Acid Modifications that Enhance Effector Function The anti-CD19 antibodies of the invention are intended as clinical candidates for anti-cancer therapeutics. To investigate the possibility of improving the effector function of an antibody that targets CD19, variant versions of anti-CD19 antibodies were engineered.

FIG. 6 provides some heavy and light chain variable region sequences of the anti-CD19 antibodies 4G7 (Meeker, T. C. et al. 1984. Hybridoma. 3: 305-320) and HD37 (Pezzuto, A. et al. 1987. J. Immunol. 138: 2793-2799) used in the present study. The mouse, parent chimeric heavy and light chains are labeled H0 4G7, H0 HD37, L0 4G7, and L0 HD37 respectively. Variants of the present invention could also be made in the context of the anti-CD19 antibody B43 (Uckun, F. M. et al. 1998. Blood. 71: 13-29) which has similar properties to HD37 and shares identical CDRs and an overall 97% sequence identity relative to the HD37 H0 and L0 sequences shown in FIG. 6. The genes for murine WT 4G7 and HD37 VH and VL, designated H0 and L0 respectively, were constructed using gene synthesis techniques and subcloned into the mammalian expression vector pcDNA3.1Zeo (Invitrogen) comprising the full length light kappa (Cκ) and heavy chain IgG1 constant regions. Variant S239D/I332E (effector function enhanced anti-CD19) was constructed in the Fc region of a hybrid IgG1/IgG2 (referred to as "Hybrid", FIG. 2) antibody in the pcDNA3.1Zeo vector using QuikChange mutagenesis techniques (Stratagene). All sequences were sequenced to confirm the fidelity of the sequence. Plasmids containing heavy chain gene (VH-CH1-CH2-CH3) (wild-type or variants) were co-transfected with plasmid containing light chain gene (VL-CLκ) into 293T cells. Media were harvested 5 days after transfection, and antibodies were purified from the supernatant using protein A affinity chromatography (Pierce, Catalog #20334)

The relative binding affinities of 4G7 Hybrid S239D/I332E and 4G7 IgG1 antibody were calculated by determining binding parameters on Biacore™ using a panel of Fc receptors (FIG. 7). Briefly, protein A/G was coupled to a flow cell of a CM5 chip. IgG was first diluted to 25 nM and immobilized to protein A/G channel to ~1000 RUs. FcγR-His was serially diluted and injected at 30 mL/min for 2 min followed by dissociation for 3 min. To determine KD the resulting sensorgrams are "group-fitted" using the 1:1 interaction model available in BIAevaluation software. Values of $K_D$ that were higher than $5 \times 10^{-6}$ M are labeled as ND (not determined) in FIG. 7. The data indicate that WT IgG1 antibody binds V158 FcγRIIIa with an affinity of approximately 240 nM, consistent with the literature (Okazaki et al, 2004, J Mol Bio 336:1239-49; Lazar et al, Proc Natl Acad Sci USA 103(11):4005-4010). The Fc variant version binds with an affinity to V158 FcγRIIIa of about 4.7 nM, indicating an affinity enhancement of about 50-fold relative to WT. Binding of variant anti-CD19 to F158 FcγRIIIa is about 16.7 nM.

Figure 8A:
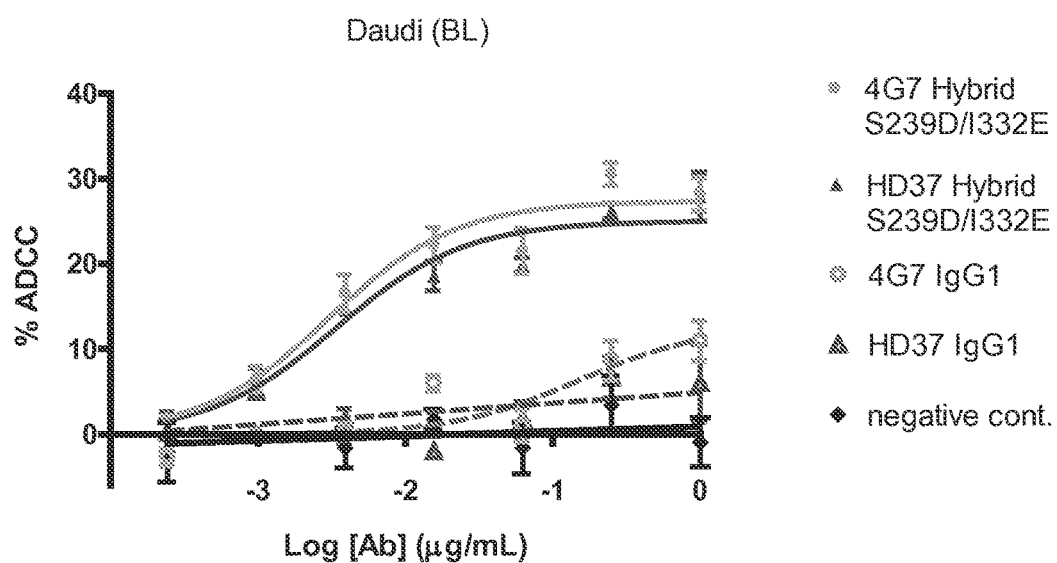
FIGS. 8A and 8B. ADCC of 4G7 Hybrid S239D/I332E, HD37 Hybrid S239D/I332E, 4G7 IgG1, HD37 IgG1, and a negative control antibody on the Daudi cell line (FIG. 8A) and ADCC of 4G7 Hybrid S239D/I332E, 4G7 IgG1, rituximab, and a negative control antibody on the SUP-B15 and Raji cell lines (FIG. 8B).
Figure 8B:
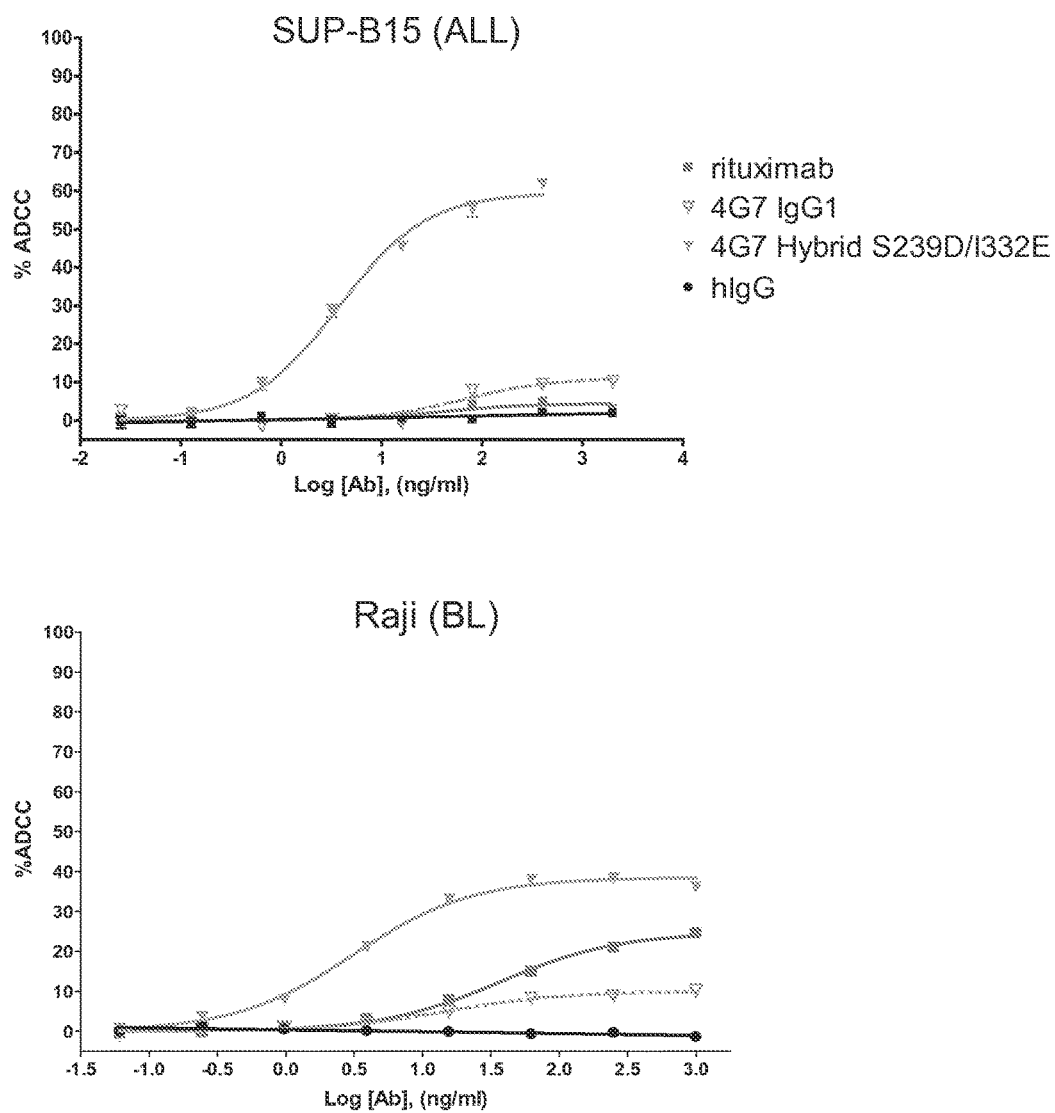

To assess the capacity of the antibody variants to mediate effector function against CD19 expressing cells, effector function enhanced anti-CD19 was tested in a cell-based ADCC assay. Human peripheral blood monocytes (PBMCs) were isolated from leukopaks and used as effector cells, and CD19 positive cancer cells were used as target cells. Target cells were seeded at 10,000 (Raji and MEC-1) and 20,000 (SUP-B15) cells/well in 96-well plates and treated with designated antibodies in triplicates. PBMCs isolated using a Ficoll gradient were added in excess to target cells and co-cultured for 4 hrs before processing for LDH activity using the Cytotoxicity Detection Kit according to the manufacturer's instructions. FIG. 8a shows the results of the ADCC assay comparing 4G7 IgG1 and 4G7 Hybrid S239D/I332E antibodies, and HD37 IgG1 and HD37 Hybrid S239D/I332E on the cell line Daudi (BL). FIG. 8b shows the results of the ADCC assay comparing 4G7 IgG1 and 4G7 Hybrid S239D/I332E antibodies, and anti-CD20 rituximab on the cell lines SUP-B15 (ALL) and Raji (Burkitt's Lymphoma). The graphs show that the antibodies differ not only in their EC50, reflecting their relative potency, but also in the maximal level of ADCC attainable by the antibodies at saturating concentrations, reflecting their relative efficacy. Considerable enhancements in potency and efficacy are observed for the Fc variant antibodies as compared to the antibody with WT Fc region. The chimeric IgG1 antibody has very little efficacy or potency.

EC50 of a dose response curve such as that in FIG. 8 represents the concentration of a compound where 50% of its maximal effect is observed. In a clinical setting, potency reflects the concentration of antibody needed to carry out its therapeutic effect. Thus the data in FIG. 8 show that the Fc optimized anti-CD19 antibodies act in vivo at a concentration or dose lower than that of a WT anti-CD19 or anti-CD20 antibody. In FIG. 8b, whereas WT IgG1 anti-CD19 at saturating concentration mediates approximately 10% maximal ADCC, Fc variant anti-CD19 lyses approximately 60% of the target cells. In a clinical setting, efficacy reflects the maximal therapeutic benefit from the administered drug.

Figure 9:
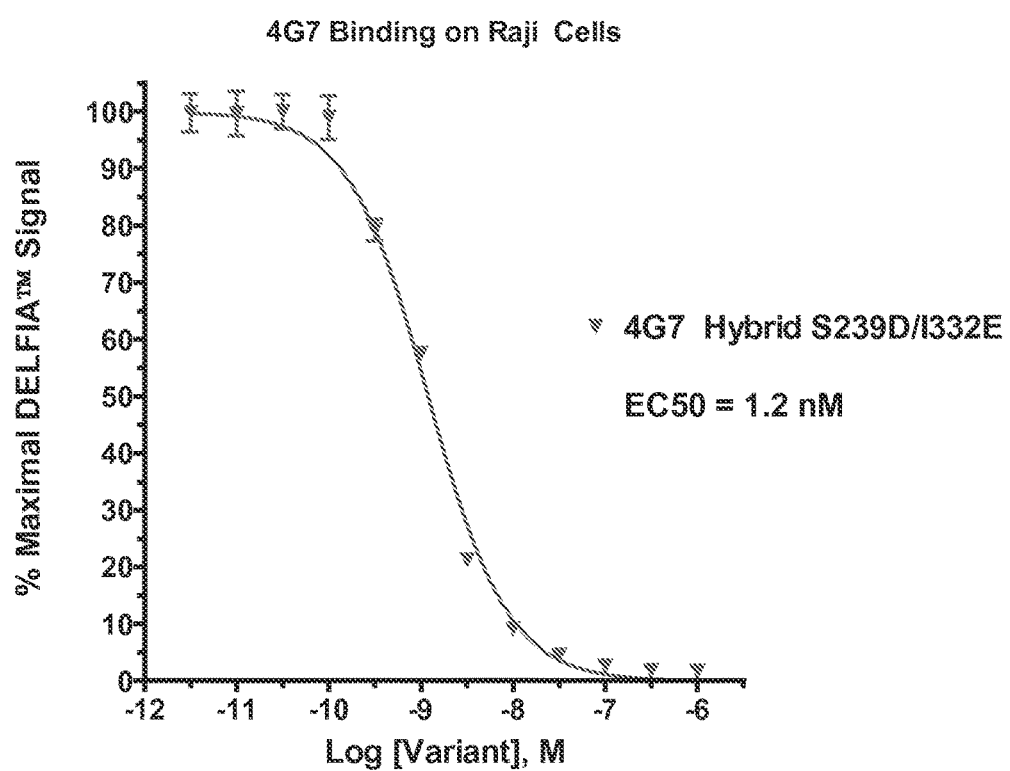
FIG. 9. A cell-surface binding assay of 4G7 Hybrid S239D/I332E to Raji cells.

Example 2. Binding of an Effector Function Enhanced Anti-CD19 Antibody to a B-Cell Derived Tumor Cell Line The relative binding of 4G7 Hybrid S239D/I332E to the Raji cell line was measured. Affinities of enhanced effector function anti-CD19 variants were determined by using the DELFIA® system (PerkinElmer Life Sciences) which is based on Time-Resolved Fluorometry (TRF). Anti-CD19 (H0L0) is labeled with Europium using the Eu-Labeling kit available from PerkinElmer Biosciences. Unlabeled wild-type (WT) or variants (cold) are serially diluted (typically starting from 1 uM) in ½ log steps and mixed with a fixed concentration of labeled (or hot) anti-CD19. The mix of "hot" and "cold" antibodies are then added to 100,000 Raji Cells (that have a high density of surface expressed CD-19 antigen) and incubated on ice for 30 min. The assay is essentially applied as a competition assay for screening anti-CD19 antibodies of different affinities. In the absence of competing affinity variants, Eu-anti-CD19 and surface CD19 interact and produce a signal at 613 nm when the Europium is excited at 340 nm. Addition of wild type or variant competes with Eu-anti-CD19-CD19 interaction, reducing fluorescence quantitatively to enable determination of relative binding affinities. FIG. 9 shows results of a cell-surface binding assay of enhanced effector function anti-CD19 to Raji cells. As can be seen, the calculated EC50 value is 1.2 nM.

Example 3. ADCC of an Anti-CD19 Antibody with Enhanced Cytotoxicity Against Multiple Lymphoma Cell Lines In order to evaluate cytotoxic properties of effector function enhanced anti-CD19, ADCC assays were performed on a panel of 14 cell lines representing various lymphomas and leukemias (FIG. 10a). Cell lines tested were the Follicular Lymphoma (FL) cell lines DoHH-2 and SC1; Mantle Cell Lymphoma (MCL) cell line Jeko-1; Burkitt's Lymphoma (BL) cell lines Daudi and Raji; Chronic Lymphocytic Leukemia (CLL) cell lines MEC1 and WaC3CD5; Hairy Cell Leukemia (HCL) cell line Bonna-12; Chronic Myelogenous Leukemia (CML) cell line BV-173; and Acute Lymphoblastic Leukemia (ALL) cell lines VAL, SUP-B15, NALM-6, RS4; 11, and 697. Human peripheral blood monocytes (PBMCs) were isolated from leukopaks and used as effector cells, and CD19 positive cancer cells were used as target cells. Target cells were seeded in 96-well plates and treated with designated antibodies in triplicate. PBMCs isolated using a Ficoll gradient were added in excess to target cells and co-cultured for 4 hrs before processing for LDH activity using the Cytotoxicity Detection Kit according to the manufacturer's instructions. Both parameters, potency (EC50) and efficacy (% ADCC) were normalized to that of rituximab (anti-CD20). This screen has demonstrated the cytotoxic superiority in vitro of effector function enhanced anti-CD19 over a broad range of cell lines, especially representing the lympho-proliferative disease that originates in early stages of B cell development. FIG. 10b lists cell lines used and their corresponding cancer type.

Example 4. Anti-CD19 Antibodies with Reduced Potential for Immunogenicity

Due to the wide use of hybridoma technology, a substantial number of antibodies are derived from nonhuman sources. However, nonhuman proteins are often immunogenic when administered to humans, thereby greatly reducing their therapeutic utility. Immunogenicity is the result of a complex series of responses to a substance that is perceived as foreign, and may include production of neutralizing and non-neutralizing antibodies, formation of immune complexes, complement activation, mast cell activation, inflammation, hypersensitivity responses, and anaphylaxis. Several factors can contribute to protein immunogenicity, including but not limited to protein sequence, route and frequency of administration, and patient population. Immunogenicity may limit the efficacy and safety of a protein therapeutic in multiple ways. Efficacy can be reduced directly by the formation of neutralizing antibodies. Efficacy may also be reduced indirectly, as binding to either neutralizing or non-neutralizing antibodies typically leads to rapid clearance from serum. Severe side effects and even death may occur when an immune reaction is raised. Thus in a preferred embodiment, protein engineering is used to reduce the immunogenicity of the CD19 targeting proteins of the present invention.

Figure 15B:
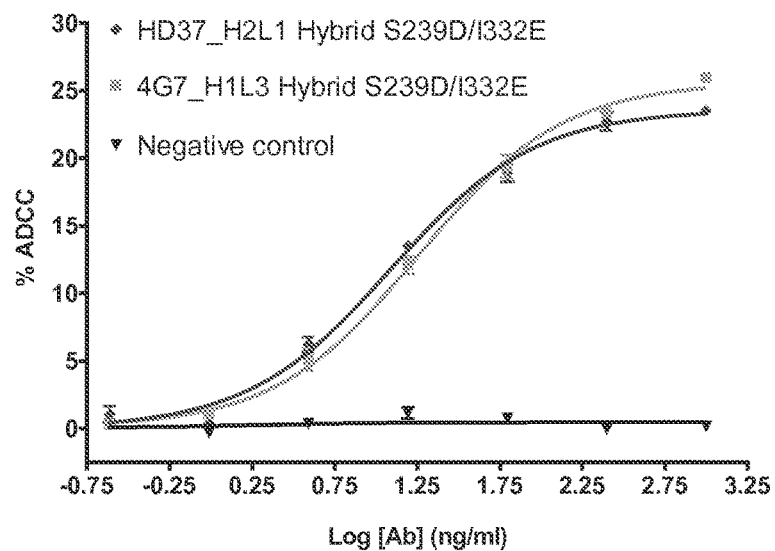

In order to reduce the potential for immunogenicity of the anti-CD19 proteins of the present invention, the immunogenicity of the anti-CD19 antibodies 4G7 and HD37 were reduced using a method described in U.S. Ser. No. 60/619,483, filed Oct. 14, 2004 and U.S. Ser. No. 11/004,590, entitled "Methods of Generating Variant Proteins with Increased Host String Content and Compositions Thereof", filed on Dec. 6, 2004. The methods reduce the potential for immunogenicity by increasing the human string content of the antibody through mutations. The heavy and light chains with reduced potential for immunogenicity are named H1, H2, H3, H4, etc and L1, L2, L3, etc. and are shown in FIGS. 11 thru 14. The heavy and light chains of the original antibodies, 4G7 and HD37, are referred to as H0 and L0, respectively. Combinations of the different heavy and light chains were expressed and the resulting antibodies, with names such as H3L3, H3/L3 or H3 L3, were purified and examined. Anti-CD19 antibodies were expressed by transient transfection of vectors encoding the heavy and light chains into 293T cells grown in 10% ultra low IgG fetal bovine serum with 1 mM sodium pyruvate and 1× non-essential amino acids (Gibco®, Invitrogen Hayward Calif.). Five days after transfection, the culture media was removed and passed through a protein A column (Pierce Biotechnology Inc, Rockford Md.) The heavy chains may be made with any type of constant domain including, in humans, IgG1, IgG2 and hybrids comprising IgG1 and IgG2 as well as mouse constant domains such as IgG1 and IgG2a, which may be reffered to as mIgG1 and mIgG2a. The sequences of human heavy chains may be found in FIG. 2. The relative binding of anti-CD19 variants with reduced immunogenicity to the Raji cell line was measured. Affinities of reduced immunogenicity anti-CD19 variants were determined by using the DELFIA® system (PerkinElmer Life Sciences) which is based on Time-Resolved Fluorometry (TRF). Anti-CD19 is labeled with Europium using the Eu-Labeling kit available from PerkinElmer Biosciences. Unlabeled wild-type (WT) or variants (cold) are serially diluted (typically starting from 1 uM) in ½ log steps and mixed with a fixed concentration of labeled (or hot) anti-CD19. The mix of "hot" and "cold" antibodies are then added to 100,000 Raji Cells (that have a high density of surface expressed CD-19 antigen) and incubated on ice for 30 min. The assay is essentially applied as a competition assay for screening anti-CD19 antibodies of different affinities. In the absence of competing affinity variants, Eu-anti-CD19 and surface CD19 interact and produce a signal at 613 nm when the Europium is excited at 340 nm. Addition of wild type or variant competes with Eu-anti-CD19-CD19 interaction, reducing fluorescence quantitatively to enable determination of relative binding affinities. FIG. 15a shows results of a cell-surface binding assay of reduced immunogenicity 4G7 variants to Raji cells. Based on binding affinity and stability, the variable region 4G7 H1L1 was chosen for further development. FIG. 15b shows results of an ADCC assay on reduced immunogenicity templates HD37_H2L1 Hybrid S239D/I332E and 4G7_H1L3 Hybrid S239D/I332E on the cell line MEC-1 (CLL). This ADCC assay was performed as in the previous assays. Both antibodies are active on this cell line and therefore may be potential treatments for CLL.

Example 5. Affinity and Stability Enhancement of Effector Function Enhanced Anti-CD19

Affinity maturation of 4G7 mAb H1L1 was carried out in order to further increase CD19 binding affinity as well as ADCC potency. The affinity maturation was performed in three stages using a computational/protein engineering approach. First, operating under the hypothesis that the specificity determining residues (SDRs) (Padlan, E. A. et al. 1995. FASEB J. 9: 133-139) in the CDRs of an antibody have already been optimized by B-cells in the process of in vivo somatic hypermutation, a library of 94 variants was designed to determine those residues in the CDRs that were critical for antigen binding, and thus should not be changed during the engineering process. This library consisted of one or two "probing" mutations made at positions in the CDRs with sites chosen using structural modeling as well as the likelihood that a position is often an SDR, which was compiled from analysis of available antigen-antibody complex structures in the Protein Data Bank (PDB) (MacCallum, R. M. et al. 1996. JMB 262: 732-745; Almagro, J. C. 2004. J. Mol. Recognit. 17:132-143).

Variant mutations were introduced using the QuikChange mutagenesis kit in the Fab format of the H1L1 template and contained a 6×-His tag. Variant Fabs were expressed in 293T cells using 24-well plates and were analyzed by AlphaScreen or flow cytometry using Raji or RS4; 11 cells, and with the concentration of each variant determined using a His-binding chip by Biacore™. Out of 50 positions, 17 positions were identified that were critical to antigen binding, enabling us to reduce the library size in the next round of affinity maturation and giving us valuable structural information as to which positions lie close to the antigen interface and would make good targets for finding increased affinity variants. The 17 SDRs identified in our analysis are in excellent agreement with the average number of SDRs present in antibodies whose antigen-antibody complexes have been solved (Almagro, J. C. 2004. J. Mol. Recognit. 17:132-143). In addition to the valuable structural information gained from this library, some variants were obtained that had an increased affinity.

The remaining 33 CDR positions were ranked in order of importance based on analysis of the first library results and by mapping the SDRs onto a structural model of the H1L1 template. Through this analysis it was determined that nearly the entire antigen-antibody binding interface could be explored with a total frequency of 12.2 amino acids per position (~9.3 new variants per position) with a second round library size of 279 variants. Library Design Automation (LDA™) (U.S. Ser. No. 11/367,184, filed Mar. 3, 2006) was used to design an optimized library of variants that was tuned for both fitness and coverage based on the number of variants desired. The final second round library when adjusted for high-throughput format contained 265 variants at 30 positions. This library yielded several variants displaying increased binding affinity. Anti-CD19 Fab variants were screened by flow cytometry to determine the affinity. The cell line RS4; 11, known to express CD19, were suspended in PBS and plated at 200,000 cells/well in a 96-well round bottom plate. A serial dilution of CD19 antibodies were added to the RS4; 11 cells at an unknown concentration. The cells were incubated on ice for 30 minutes and then washed 4 times in PBS. An anti-Fab PE-labeled F(ab')$_2$ was diluted 1/50 in PBS, which was then used to resuspend the anti-CD19 Fab coated RS4; 11. Cells were incubated for 30 minutes and washed two times. The cells were then fixed and the binding assay was evaluated on a FACS Canto II flow cytometer. The MFI was used to measure the tightness of binding. From both libraries one and two, a total of 30 increased affinity single variants were obtained at 11 positions.

Figure 16:
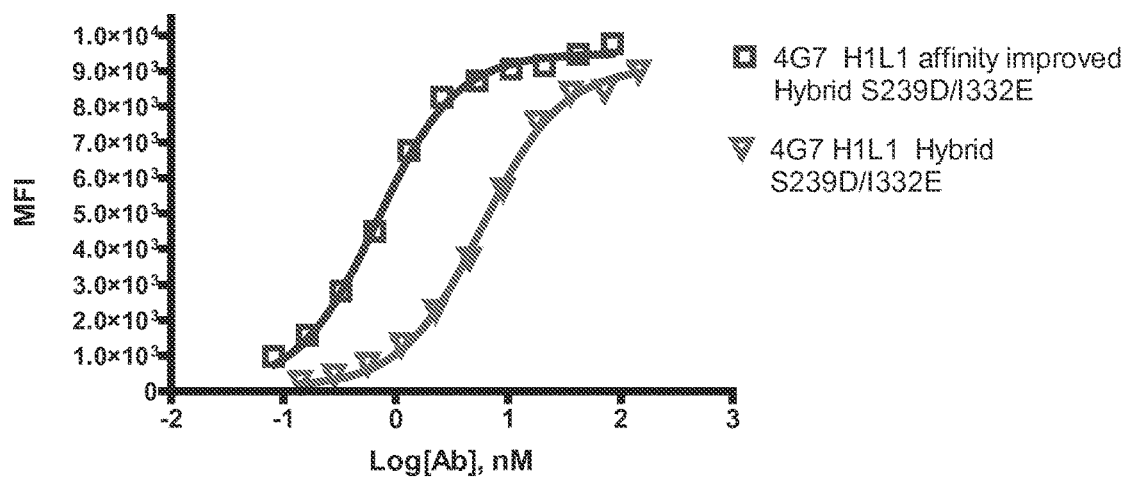
FIG. 16. Cell-binding affinity on RS4; 11 cells of affinity matured 4G7 relative to the H1L1 mAb.
Figure 17:
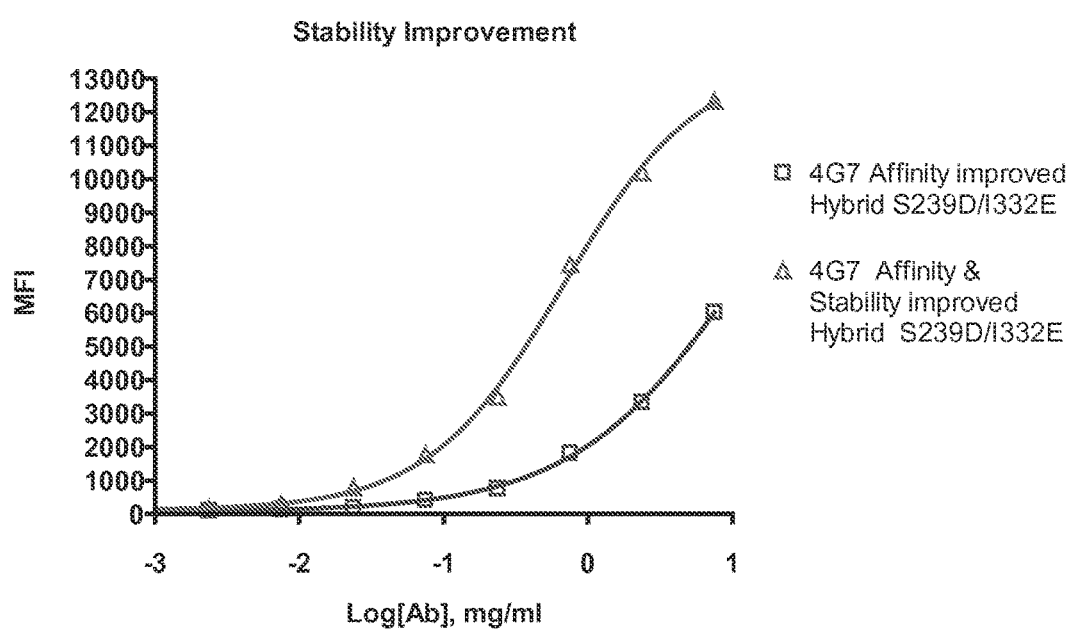
FIG. 17. Cell-binding data to RS4; 11 cells of 4G7 variants incubated for 5 days at 37° C., pH 9.0 in 200 mM Tris-HCL showing the improvement in stability obtained.

Analysis of the binding data from the first two libraries as well as further structural analysis enabled us to design a third and final library containing combinations of 2-8 single variants. This library consisted of 149 variants at 8 positions. From these, 20 variants showed a significant increase in affinity and were selected for conversion to full length format for simultaneous measurement of binding affinity and ADCC. To assess solution properties, stability assays on these variants were performed. The final set of mutations included in the final 20 were heavy chain variants T57P, K58E, S100cT, R100dS, and light chain variants L27cQ, S27eV, A55N, F96I, and F96N. Accelerated stability studies revealed that at least one of the affinity enhancing mutations created instability in the protein and caused these variants to lose all potency after only 8 hrs at 37° C. Taking the binding and stability data into account, a final affinity matured candidate mAb was able to be selected which displayed an ~10-fold increase in binding affinity on RS4; 11 cells relative to the H1L1 mAb (FIG. 16). Variants designed to increase the long-term stability of the anti-CD19 molecule were also designed and screened. FIG. 17 shows binding data for variants incubated for 5 days at 37° C., pH 9.0 in 200 mM Tris-HCl, demonstrating the improvement in stability obtained from an anti-CD19 variant.

Figure 27:
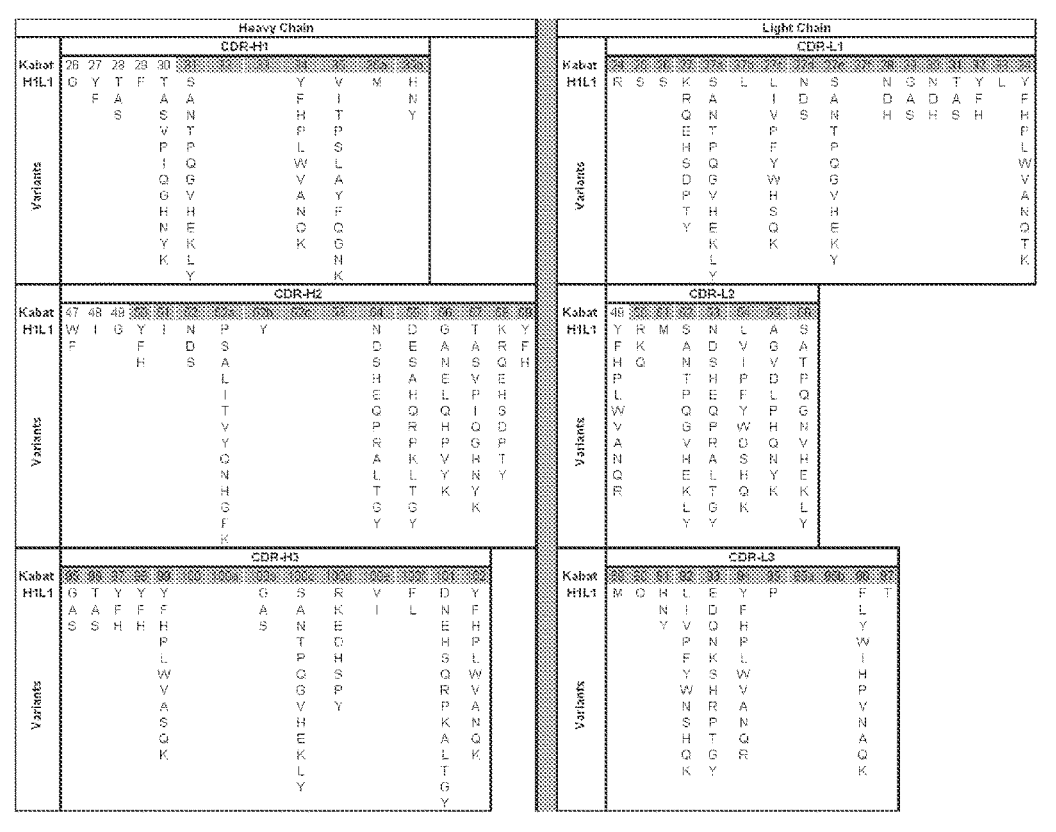

All single subsitutions made for enhanced stability and/or affinity are shown in FIG. 27. FIG. 28 lists all anti-CD19 variable region variants constructed to optimize affinity and stability. FIG. 29 lists preferred variants and relative increase in binding affinity versus the parent H1L1 mAb. Sequences for the preferred affinity and/or stability enhanced heavy chain variants are shown in FIG. 18. Sequences for the preferred affinity and/or stability enhanced light chain variants are shown in FIG. 19. Amino acid sequences of full length hybrid S239D/I332E variants containing the affinity and stability improved variable regions are provided as SEQ ID NOs: 86-110. Affinity and stability improved CDR's are provided as SEQ ID NOs: 111-131.

Example 6. Anti-Proliferative Properties of 4G7 Hybrid S239D/I332 on Raji Cells

Figure 20:
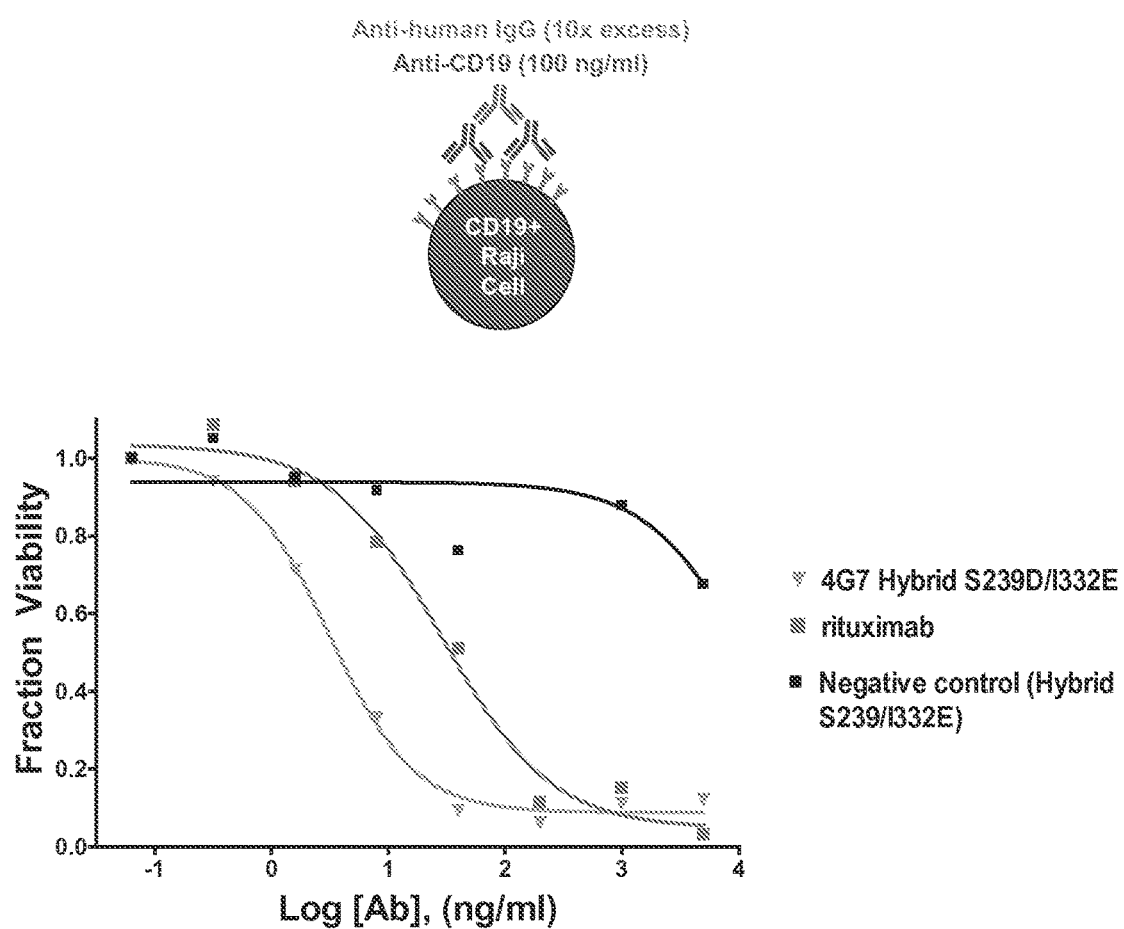
FIG. 20. Anti-proliferative properties of 4G7 Hybrid S239D/I332E on Raji cells.

To observe an anti-proliferative effect in vitro, many antibodies require cross-linking, usually accomplished by a secondary antibody. It has been proposed that corresponding in vivo effects for these antibodies may be dependent on cross-linking mediated by Fc receptors expressed on the surface of effector cells. In this experiment Raji cells were grown for 3 days in the presence of 100 ng/mL 4G7 Hybrid S239D/I332E, 4G7 IgG1, or anti-CD20 (rituximab) or control antibodies (non-CD19 binding variable region with Hybrid S239D/I332E variants Fc) at varying concentrations with 10× molar excess of cross-linking antibody. Cell growth was measured using an ATP-dependent luminescence assay. Results for the anti-proliferation assay are shown in FIG. 20. Both 4G7 Hybrid S239D/I332E and 4G7 IgG1 show stronger anti-proliferation effects than rituximab.

Example 7. Anti-Proliferative Properties of 4G7 Stability and Affinity Improved Hybrid S239D/I332E on SU-DHL-6 Cells In this experiment SU-DHL-6 cells were either grown for 3 days in the presence of humanized 4G7 stability and affinity improved Hybrid S239D/I332E and control antibodies at varying concentrations with 10× molar excess of cross-linking antibody and 6000 cells/well or were grown in the presence of a fixed concentration of antibody at 3000 cells/well and viability at specific time points measured for a total of 72 hours. Results for the anti-proliferation assay are shown in FIG. 21. 4G7 stability and affinity improved Hybrid S239D/I332E shows stronger anti-proliferation effects than rituximab. 4G7 stability and affinity improved Hybrid S239D/I332E also shows anti-proliferative effects even in the absence of cross-linking antibody.

Example 8. Phagocytosis of Raji and RS4,11 Cells with 4G7 Stability and Affinity Improved Hybrid S239D/I332E Unlike NK cells which only express FcγRIIIa and sometimes FcγRIIc, monocytes and monocyte-derived effector cells express the range of FcγRs, including FcγRI, FcγRIIa, FcγRIIb, and FcγRIIIa. Thus the activation and function of monocyte-derived effector cells, including for example macrophages, may be dependent on engagement of antibody immune complexes with receptors other than only FcγRIIIa. Indeed as described in PCT/US2006/038842, Desjarlais J. R. et al., filed Oct. 3, 2006, phagocytosis by macrophages is mediated in part by engagement of antibody with FcγRIIa.

Figure 22:
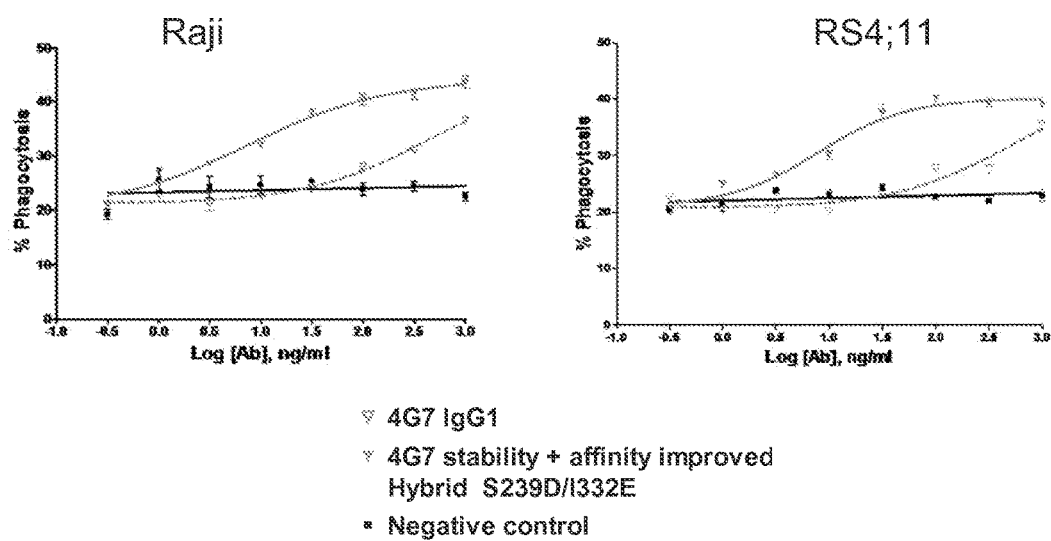
FIG. 22. Phagocytosis of Raji and RS4; 11 cells with 4G7 stability and affinity improved Hybrid S239D/I332E.

To assess the ability of 4G7 stability and affinity improved Hybrid S239D/I332E to mediate phagocytosis a flow cytometry based phagocytosis assay was performed. Purified CD14$^+$ monocytes were cultured in macrophage colony stimulating factor (50 ng/ml) for 5 days in a humidified incubator to differentiate macrophages. RS4; 11 or Raji cells were used as targets. The target cells were labeled with PKH67 (Sigma) according to the manufacture's instructions. Cells were added to a 96 well plate after which a serial dilution of WT and Fc modified anti-CD19 antibodies were added. Monocyte-derived macrophages were then added to the wells at an effector to target ratio of 4:1. These assays were performed in the presence of human serum. The co-culture of cells were briefly spun down and then incubated in a humidified incubator for 4 hours. The cells were harvested, and macrophages were stained with a second fluorescent color to distinguish them from the target. The cells were fixed in 1% PFA and phagocytosis was evaluated on a FACS Canto II flow cytometer. The read out of phagocytosis was determined by the number of double positive cells divided by the total number of tumor cells. Results of the phagocytosis assay are shown in FIG. 22. 4G7 stability and affinity improved Hybrid S239D/I332E shows an increased level of phagocytosis on both cell lines compared to the IgG1 anti-CD19 antibody.

Macrophages are phagocytes that act as scavengers to engulf dead cells, foreign substances, and other debris. Importantly, macrophages are professional antigen presenting cells (APCs), taking up pathogens and foreign structures in peripheral tissues, then migrating to secondary lymphoid organs to initiate adaptive immune responses by activating naive T-cells. Thus the results of the previous experiment suggest that modification of anti-CD19 antibodies may enable mechanisms of action that include both innate cytotoxic effector functions, as well as effector functions that can potentially lead to long-term adaptive immune response.

Figure 23:
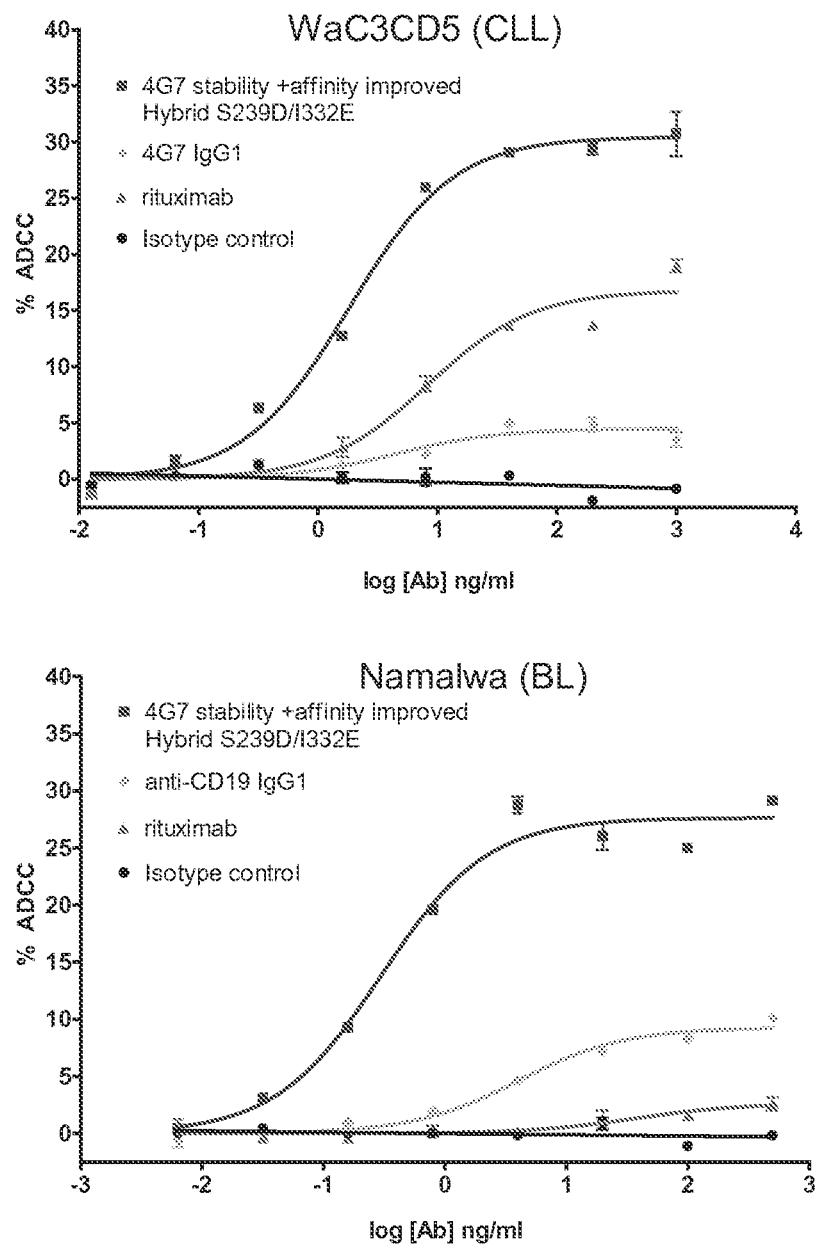
FIG. 23. ADCC of 4G7 stability and affinity improved Hybrid S239D/I332E against multiple lymphoma cell lines using purified natural killer (NK) cells.

Example 9. ADCC of 4G7 Stability and Affinity Improved Hybrid S239D/I332E Against Multiple Lymphoma Cell Lines Using Purified Natural Killer (NK) Cells In order to evaluate cytotoxic properties of 4G7 stability and affinity improved Hybrid S239D/I332E, ADCC assays were performed with purified NK cells on a panel of 6 cell lines representing various lymphomas and leukemias (FIG. 23). ADCC with purified NK cells is done in 96-well microtiter plates. The NK cells were purified from human PBMC using the kit from Miltenyi Biotec (Cat #130-091-152) and incubated in 10% FBS/RPMI1640 overnight with 10 ng/ml IL-2. The following day, 10,000 (WaC3CD5, Namalwa, Bonna-12, Ramos) or 20,000 (RS4; 11, BV-173) cancer target cells are opsonized with varying concentrations of antibody and 50 k NK cells are used for each antibody concentration in triplicates. The target cells are washed three times while NK cells are washed twice with RPMI1640 and both resuspended in 1% FBS/RPMI1640 and added to the antibody solutions. After 4 hours of incubation at 37° C. in a humidified incubator with 5% $CO_2$, the assay was quantified using LDH dependent CytoTox-One fluorescence dependent detection system from Promega (# PAG7891). Total LDH signal is determined from the Triton-X100 lysed target cells (Total Target LDH) and used to normalize against the spontaneous LDH background (Spontaneous Background) adjusted experimental values. Thus % ADCC=((Experimental Value−Spontaneous Background)/(Total Target LDH−Target LDH))*100. Spontaneous background is the value obtained from the Target and NK cells co-incubated in the absence of antibody. Target LDH is the value from the target cancer cells alone spontaneously releasing LDH during the incubation. FIG. 23 shows results of the ADCC assay for 6 cell lines using 4G7 stability and affinity improved Hybrid S239D/I332E, 4G7 IgG1 (with affinity/stability optimized variable region), rituximab (anti-CD20), and an isotype control antibody. For all cell lines tested, 4G7 stability and affinity improved Hybrid S239D/I332E performs better in both potency and efficacy when compared to 4G7 IgG1 and rituximab.

Figure 24:
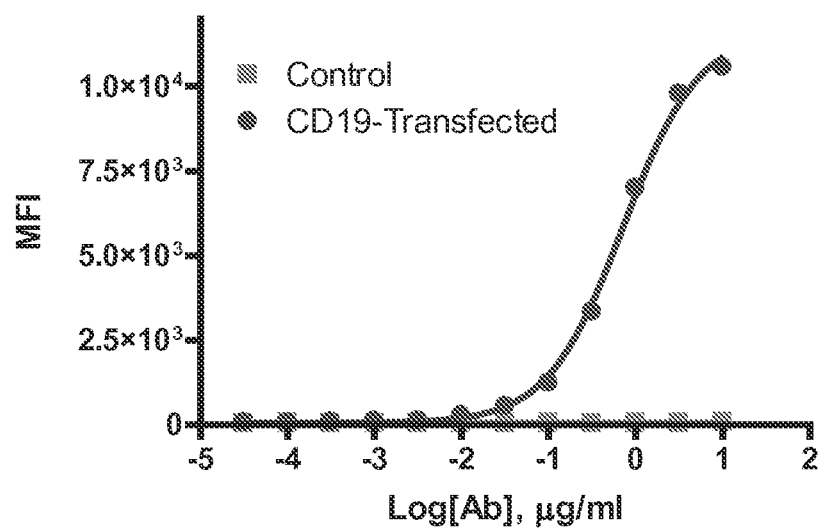
FIG. 24. 4G7 stability and affinity improved Hybrid S239D/I332E binding to 293T cells transfected with human CD19.

Example 10. 4G7 Stability and Affinity Improved Hybrid S239D/I332E Binding to CD19 Transfected 293T Cells A human CD19 clone was ordered from Origene (catalog No. SC127938) and transfected into 293T cells. Cells were suspended in PBS and plated at 100 000 cells/well. A serial dilution of 4G7 stability and affinity improved Hybrid S239D/I332E was added to the cells and then the cells were incubated on ice for 30 minutes and then washed 4 times in PBS. An anti-Fab PE-labeled F(ab')$_2$ was diluted 1/50 in PBS, which was then used to resuspend the 4G7 stability and affinity improved Hybrid S239D/I332E anti-CD19 coated 293T cells. Cells were incubated for 30 minutes and washed two times. The cells were then fixed and the binding was evaluated on a FACS Canto II flow cytometer. FIG. 24 displays results for this assay. The results show that 4G7 stability and affinity improved Hybrid S239D/I332E binds to 293T cells transfected with CD19 and does not bind to the control cells (normal 293T cells).

Figure 25A:
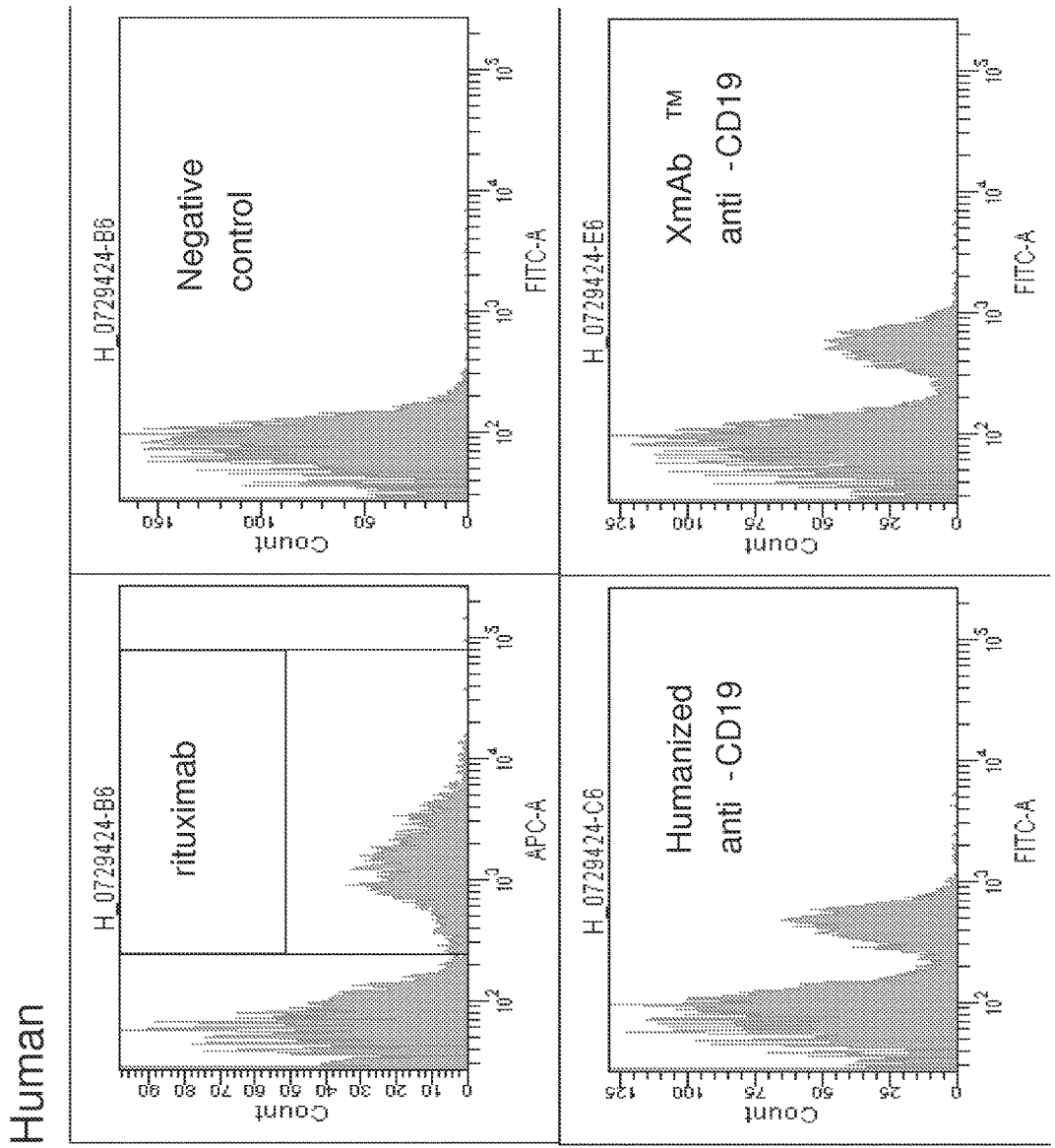
FIGS. 25A, 25B, and 25C. Cross-reactivity of 4G7 stability and affinity improved Hybrid S239D/I332E to both cynomolgus and rhesus CD19.
Figure 25B:
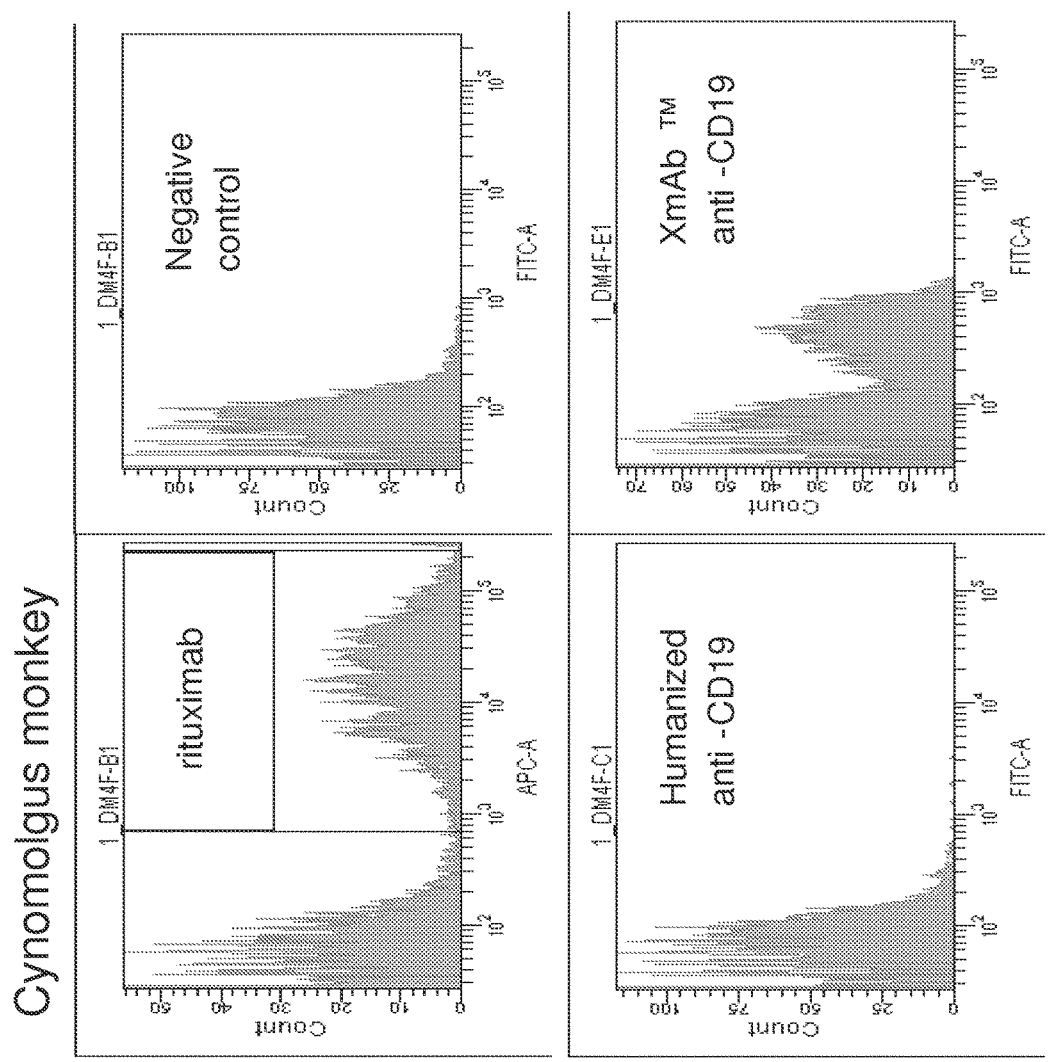
Figure 25C:
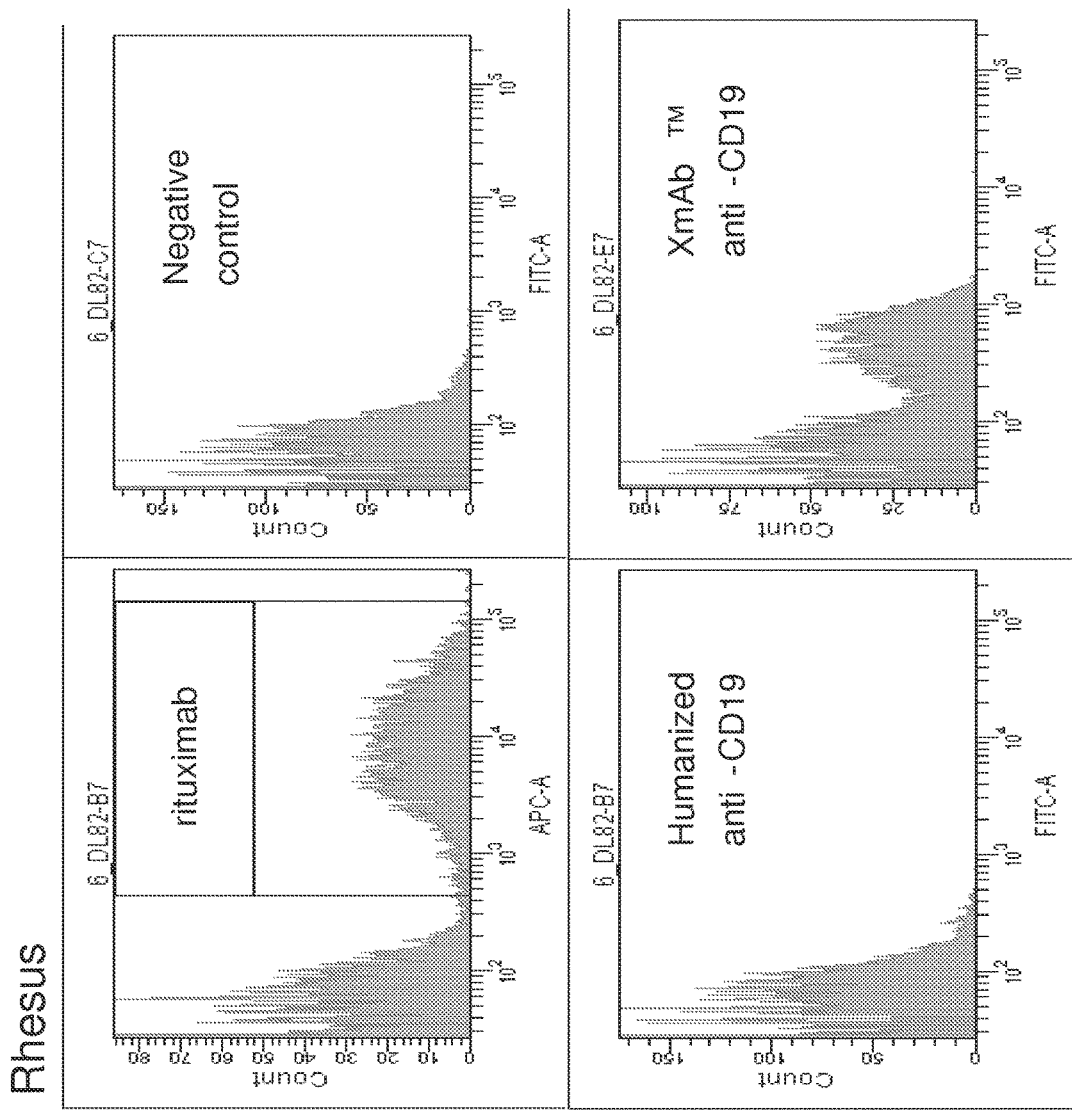

Example 11. 4G7 Stability and Affinity Improved Hybrid S239D/I332E is Cross-Reactive with CD19 from Cynomolgus and Rhesus Monkeys Pre-clinical testing of drugs in monkeys is typically an important step in drug discovery in order to assess potential toxicity. Blood samples from five cynomolgus (*Macaca fascicularis*; genus=*Macaca* (Latin) or Macaque (English); species=*fascicularis*) and five rhesus (*Macaca mulatta*) monkeys were obtained. 4G7 stability+affinity improved Hybrid S239D/I332E anti-CD19, anti-CD19 IgG1 (reduced immunogenicity, but without affinity/stability optimized variable region), rituximab (anti-CD20), and negative control (enhanced Fc, non-binding variable region) were directly labeled with FITC. Rituximab was also labeled with APC to identify the B-cell fraction of cells. Human PBMCs were used as positive controls throughout. Blood samples and PBMCs were pre-incubated with 2 mg/mL of an isotype control antibody with enhanced Fc to block any potential FcγR binding. In each experiment, rituximab-APC and one of the test variants were included in the assay. Detection is made using a FACS Canto II flow cytometer with gate lymphocyte fractions based on the forward and side scattering. Results are shown in FIG. 25. Non-affinity/stability matured anti-CD19 (as well as its parental murine antibody) does not cross-react with cynomolgus or rhesus CD19. Variants that increased binding and stability of the anti-CD19 molecule enabled cross-reactivity of 4G7 stability and affinity improved Hybrid S239D/I332E to both cynomolgus and rhesus CD19.

Example 12. ADCC of an Enhanced Effector Function Anti-CD19 Antibody with Reduced Fucose Content Anti-CD19 antibodies with enhanced effector function (4G7 H1L1 Hybrid S239D/I332E) were evaluated with reduced fucose content. The Lec13 cell line (Ripka et al. Arch. Biochem. Biophys. 49:533-545 (1986)) was utilized to express anti-CD19 antibodies with reduced fucose content. Lec13 refers to the lectin-resistant Chinese Hamster Ovary (CHO) mutant cell line which displays a defective fucose metabolism and therefore has a diminished ability to add fucose to complex carbohydrates. That cell line is described in Ripka & Stanley, 1986, Somatic Cell & Molec. Gen. 12(1):51-62; and Ripka et al., 1986, Arch. Biochem. Biophys. 249(2):533-545. Lec13 cells are believed to lack the transcript for GDP-D-mannose-4,6-dehydratase, a key enzyme for fucose metabolism. Ohyama et al., 1988, J. Biol. Chem. 273(23):14582-14587. GDP-D-mannose-4,6-dehydratase generates GDP-mannose-4-keto-6-D-deoxymannose from GDP-mannose, which is then converted by the FX protein to GDP-L-fucose. Expression of fucosylated oligosaccharides is dependent on the GDP-L-fucose donor substrates and fucosyltransferase(s). The Lec13 CHO cell line is deficient in its ability to add fucose, but provides IgG with oligosaccharide which is otherwise similar to that found in normal CHO cell lines and from human serum (Jefferis, R. et al., 1990, Biochem. J. 268, 529-537; Raju, S. et al., 2000, Glycobiology 10, 477-486; Routier, F. H., et al., 1997, Glycoconj. J. 14, 201-207). Normal CHO and HEK293 cells add fucose to IgG oligosaccharide to a high degree, typically from 80-98%, and IgGs from sera are also highly fucosylated (Jefferis, R. et al., 1990, Biochem. J. 268, 529-537; Raju, S. et al., 2000, Glycobiology 10, 477-486; Routier, F. H., et al., 1997, Glycoconj. J. 14, 201-207; Shields et al., 2002, J Biol Chem 277(90):26733-26740). It is well established that antibodies expressed in transfected Lec13 cells consistently produce about 10% fucosylated carbohydrate (Shields et al., 2002, J Biol Chem 277(90): 26733-26740).

ADCC assays were performed on RS4; 11 and MEC-1 cells using anti-CD19 antibodies with and without enhanced effector function variants and with and without reduced fucosylation. FIG. 26 shows the results of these ADCC assays. Both ADCC potency and efficacy are similar for anti-CD19 antibody with amino acid modifications (4G7_H1L1_Hybrid 239D/I332E +fucose) and anti-CD19 IgG1 with reduced fucose content (4G7_H1L1_IgG1_WT—fucose). ADCC potency is further increased by combining amino acid modification with reduced fucose content (4G7_H1L1_Hybrid_239D/332E—fucose). (FIG. 26). This experiment thus illustrates that combinations of amino acid modifications and modified glycoforms may be used to optimize anti-CD19 antibodies for effector function properties.

The use of the Lec13 cell line is not meant to limit the present invention to that particular mode of reducing fucose content. A variety of other methods are known in the art for controlling the level of fucosylated and/or bisecting oligosaccharides that are covalently attached to the Fc region, including but not limited to expression in various organisms or cell lines, engineered or otherwise (for example Lec13 CHO cells or rat hybridoma YB2/0 cells), regulation of enzymes involved in the glycosylation pathway (for example FUT8 [α1,6-fucosyltransferase] and/or β1-4-N-acetylglucosaminyltransferase III [GnTIII]), and modification of modifying carbohydrate(s) after the IgG has been expressed (Umaña et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473; Yamane-Ohnuki et al., 2004, Biotechnology and Bioengineering 87(5):614-621); (U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1).

The use of particular modifications to enhance effector function, for example the substitutions 239D and 332E and the reduced level of fucose, are not meant to constrain the anti-CD19 antibodies to these particular modifications. As described above in the section entitled "Modifications for optimizing effector function", a large number of modifications, including amino acid modifications and modified glycoforms, are contemplated for anti-CD19 antibodies to improve their effector function properties.

Example 13. Anti-CD19 Antibodies Inhibit Proliferation of Primary B Cells—Applications of Anti-CD19 Antibodies to Treat Autoimmune Diseases The ability of the anti-CD19 antibodies of this invention to deplete B cells through ADCC effector function is exemplified by their ability to lyse a variety of cell lines representative of a range of B cell lineages, as shown in the preceding examples. This function is mediated by effector cells such as NK cells and macrophages that express FcγRs, triggering of which induces lysis of the CD19-coated target cells. An additional mechanism of action may also be mediated against antigen-activated B cells. Antigen activation of B cells can be mimicked by the use of antibodies to the B-cell receptor (BCR). This leads to their proliferation in culture, a generic measure of activation.

Figure 30A:
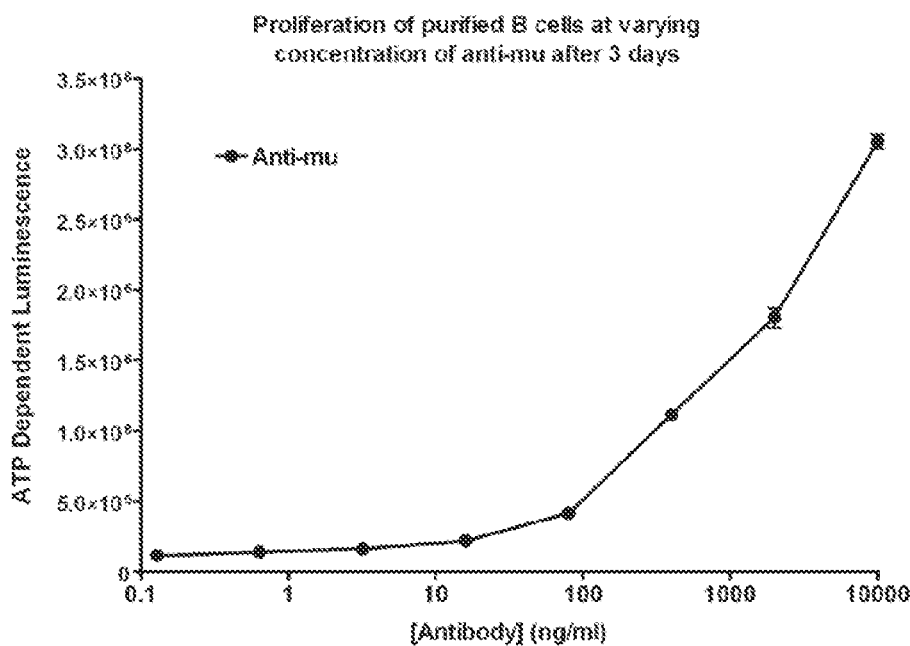
FIGS. 30A and 30B. B cell proliferation assay, showing capacity of variant anti-CD19 antibodies to inhibit viability of primary B cells.

Antigen binding can be mimicked in vitro by cross-linking BCR (mu or IgM) with anti-mu (anti-μ, anti-IgM) antibody. In order to demonstrate this activity, Peripheral Blood Mononuclear Cells (PBMCs) were prepared from Leukophoresis Pack by Ficoll density gradient, and primary human B cells were purified from PBMCs using magnetic negative selection kit purchased from Miltenyi Biotec. The proliferation assay was performed in 10% FBS/RPMI1640 medium in total of 100 ul volume in 96 well micro-titer plates in triplicates. B cell activation was induced using F(ab')2 fragment of goat anti-mu antibody (Jackson Immunoresearch, Inc.). In 50 ul of medium, serial dilutions of the anti-mu antibody was aliquoted in 96 well micro-titer plate, to which 83,000 purified B cells were added in 50 ul volume. Then the micro-titer plate was incubated at 37° C. for 3 days after which, ATP luminescence assay format (Cell TiterGlo Kit from Promega) was used to detect the live cells using luminometer. FIG. 30a shows that there is a dose-dependence of B cell proliferation on anti-mu antibody concentration.

In order to evaluate the capacity of the WT (4G7_H3_L1 IgG1_WT) and variant (4G7_H3_L1_Hybrid_239D/332E) anti-CD19 antibodies to modulate B-cell proliferation, an assay was carried out to monitor viability of primary human B cells in the presence of anti-CD19 and co-stimular anti-mu antibody. As described above, PBMCs were prepared from Leukophoresis Pack by Ficoll density gradient, and primary human B cells were purified from PBMCs using magnetic negative selection. The proliferation assay was performed in 10% FBS/RPMI1640 medium in total of 100 ul volume in 96 well micro-titer plates in triplicates. To induce activation of B cells, the F(ab')2 fragment of goat anti-mu antibody was used. In 50 ul of medium, a fixed concentration (2 mg/ml) of anti-mu with five fold serial dilutions of the antibodies were performed in 96 well micro-titer plate, to which 100,000 purified B cells were added in 50 ul volume. Then the micro-titer plate was incubated at 37° C. for 3 days after which, ATP luminescence assay format was used to detect the live cells using luminometer.

Figure 30B:
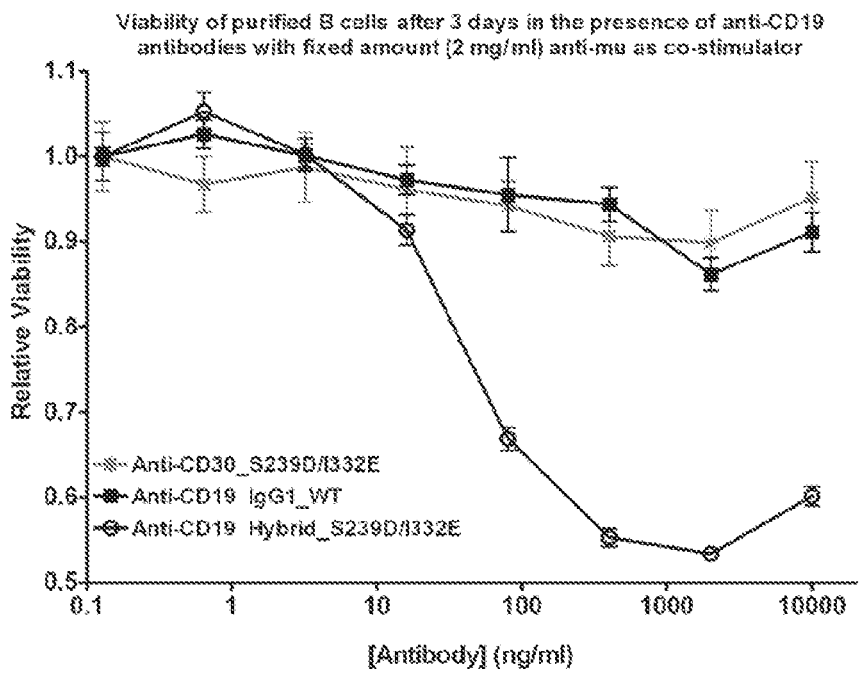

The results, provided in FIG. 30b, show that WT anti-CD19 antibody has no effect on primary B-cell proliferation, similar to negative control with anti-CD30 antibody (CD30 is not expressed on B cells). In contrast, the anti-CD19 antibody comprising Fc modifications has significant inhibitory activity against B-cell viability. Notably, in vitro signaling as a result of anti-mu antibody cross-linking mimicks antigen engagement of BCR, and is a proxy for BCR engagement by autoantigen in a clinical autoimmune setting.

The pathogenesis of most autoimmune diseases is coupled to the production of autoantibodies against self antigens, leading to a variety of associated pathologies. For example, SLE is characterized by production of auto- or self-antibodies to double stranded DNA. Accordingly, in the aforedescribed experiment BCR engagement in vitro by anti-mu antibody mimicks stimulation of B cells in lupus patients in vivo by anti-double-stranded DNA antibodies. Autoantibodies are produced by terminally differentiated plasma cells that are derived from naïve or memory B cells. Furthermore, B cells can have other effects on autoimmune pathology, as antigen-presenting cells (APCs) that can interact with and stimulate helper T cells, further stimulating the cycle of anti-self immune response. Given the expression of CD19 on most of the B-cell lineage, ranging from pre-B to plasma cells, the antibodies of this invention may have broad utility for the treatment of autoimmune diseases. Examples of such autoimmune diseases include, but are not limited to, rheumatoid arthritis (RA), systemic lupus erythematosus (SLE or lupus), multiple sclerosis, Sjogren's syndrome, and idiopathic thrombocytopenia purpura (ITP).

The current example demonstrates that anti-CD19 antibodies of the invention can substantially inhibit B cell proliferation in a dose-dependent manner, indicating that they can inhibit antigen-stimulated activation of B cells. B-cell activation by antigen can also initiate the process of class-switching and ultimately terminal differentiation into antibody-secreting plasma cells. The antibodies of this invention are thus capable of inhibiting these processes via an additional mechanism of action that does not require effector cells. This inhibition is expected to have beneficial impact on autoimmune disease by preventing the terminal differentiation of naïve and memory B cell populations, thus preventing the differentiation of autoantibody-secreting plasma cells. It is also possible that additional aspects of B-cell biology such as antigen presentation will be affected by the anti-CD19 antibodies.

```
IgG1 G1m(a,z) allotype (SEQ ID NO: 80)
ASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCDKTHTCPPCPAP

ELLGGPSVFLFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLDSDGSFFLYSK

LTVDKSRWQQGNVFSCSVMHEALHNHYTQKSLSLSPGK

IgG1 G1m(a,x,z) allotype (SEQ ID NO: 81)
ASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCDKTHTCPPCPAP

ELLGGPSVFLFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLDSDGSFFLYSK

LTVDKSRWQQGNVFSCSVMHEGLHNHYTQKSLSLSPGK

IgG1 G1m(f) allotype (SEQ ID NO: 82)
ASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKRVEPKSCDKTHTCPPCPAP

ELLGGPSVFLFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLDSDGSFFLYSK

LTVDKSRWQQGNVFSCSVMHEALHNHYTQKSLSLSPGK

IgG1 G1m(a,f) allotype (SEQ ID NO: 83)
ASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKRVEPKSCDKTHTCPPCPAP

ELLGGPSVFLFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLDSDGSFFLYSK

LTVDKSRWQQGNVFSCSVMHEALHNHYTQKSLSLSPGK

IgG2 G2m(n+) allotype (SEQ ID NO: 84)
ASTKGPSVFPLAPCSRSTSESTAALGCLVKDYFPEPVTVSWNSGALTSGVHTFPA

VLQSSGLYSLSSVVTVPSSNFGTQTYTCNVDHKPSNTKVDKTVERKCCVECPPCPAPPV

AGPSVFLFPPKPKDTLMISRTPEVTCVVVDVSHEDPEVQFNWYVDGVEVHNAKTKPREE

QFNSTFRVVSVLTVVHQDWLNGKEYKCKVSNKGLPAPIEKTISKTKGQPREPQVYTLPP

SREEMTKNQVSLTCLVKGFYPSDIAVEWESNGQPENNYKTTPPMLDSDGSFFLYSKLTV

DKSRWQQGNVFSCSVMHEALHNHYTQKSLSLSPGK

IgG2 G2m(n-) allotype (SEQ ID NO: 85)
ASTKGPSVFPLAPCSRSTSESTAALGCLVKDYFPEPVTVSWNSGALTSGVHTFPA
```

-continued

VLQSSGLYSLSSVVTVPSSNFGTQTYTCNVDHKPSNTKVDKTVERKCCVECPPCPAPPV

AGPSVFLFPPKPKDTLMISRTPEVTCVVVDVSHEDPEVQFNWYVDGMEVHNAKTKPRE

EQFNSTFRVVSVLTVVHQDWLNGKEYKCKVSNKGLPAPIEKTISKTKGQPREPQVYTLP

PSREEMTKNQVSLTCLVKGFYPSDIAVEWESNGQPENNYKTTPPMLDSDGSFFLYSKLT

VDKSRWQQGNVFSCSVMHEALHNHYTQKSLSLSPGK

4G7 H1 Hybrid S239D/I332E (SEQ ID NO: 86)
EVQLVESGGGLVKPGGSLKLSCAASGYTFTSYVMHWVRQAPGKGLEWIGYINPY

NDGTKYNEKFQGRVTISSDKSISTAYMELSSLRSEDTAMYYCARGTYYYGSRVFDYWG

QGTLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCP

PCPAPELLGGPDVFLFPPKPKDTLMISRTPEVTCVVVDVSHEDPEVQFNWYVDGVEVHN

AKTKPREEQFNSTFRVVSVLTVVHQDWLNGKEYKCKVSNKALPAPEEKTISKTKGQPR

EPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPGK

4G7 H1.52 Hybrid S239D/I332E (SEQ ID NO: 87)
EVQLVESGGGLVKPGGSLKLSCAASGYTFTSYVMHWVRQAPGKGLEWIGYINPY

NDGTKYNEKFQGRVTISSDKSISTAYMELSSLRSEDTAMYYCARGTYYYGTRVFDYWG

QGTLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCP

PCPAPELLGGPDVFLFPPKPKDTLMISRTPEVTCVVVDVSHEDPEVQFNWYVDGVEVHN

AKTKPREEQFNSTFRVVSVLTVVHQDWLNGKEYKCKVSNKALPAPEEKTISKTKGQPR

EPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPGK

4G7 H1.78 Hybrid S239D/I332E (SEQ ID NO: 88)
EVQLVESGGGLVKPGGSLKLSCAASGYTFTSYVMHWVRQAPGKGLEWIGYINPY

NAGTKYNEKFQGRVTISSDKSISTAYMELSSLRSEDTAMYYCARGTYYYGSRVFDYWG

QGTLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCP

PCPAPELLGGPDVFLFPPKPKDTLMISRTPEVTCVVVDVSHEDPEVQFNWYVDGVEVHN

AKTKPREEQFNSTFRVVSVLTVVHQDWLNGKEYKCKVSNKALPAPEEKTISKTKGQPR

EPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPGK

4G7 H1.191 Hybrid S239D/I332E (SEQ ID NO: 89)
EVQLVESGGGLVKPGGSLKLSCAASGYTFTSYVMHWVRQAPGKGLEWIGYINPY

NDGTEYNEKFQGRVTISSDKSISTAYMELSSLRSEDTAMYYCARGTYYYGTRVFDYWG

QGTLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCP

PCPAPELLGGPDVFLFPPKPKDTLMISRTPEVTCVVVDVSHEDPEVQFNWYVDGVEVHN

AKTKPREEQFNSTFRVVSVLTVVHQDWLNGKEYKCKVSNKALPAPEEKTISKTKGQPR

EPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPGK

4G7 H1.192 Hybrid S239D/I332E (SEQ ID NO: 90)
EVQLVESGGGLVKPGGSLKLSCAASGYTFTSYVMHWVRQAPGKGLEWIGYINPY -continued

NDGPKYNEKFQGRVTISSDKSISTAYMELSSLRSEDTAMYYCARGTYYYGTRVEDYWG

QGTLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCP

PCPAPELLGGPDVFLFPPKPKDTLMISRTPEVTCVVVDVSHEDPEVQFNWYVDGVEVHN

AKTKPREEQFNSTFRVVSVLTVVHQDWLNGKEYKCKVSNKALPAPEEKTISKTKGQPR

EPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPGK

4G7 H1.196 Hybrid S239D/I332E (SEQ ID NO: 91)
EVQLVESGGGLVKPGGSLKLSCAASGYTFTSYVMHW VRQAPGKGLEWIGYINPY

NDGPKYNEKFQGRVTISSDKSISTAYMELSSLRSEDTAMYYCARGTYYYGTSVFDYWG

QGTLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCP

PCPAPELLGGPDVFLFPPKPKDTLMISRTPEVTCVVVDVSHEDPEVQFNWYVDGVEVHN

AKTKPREEQFNSTFRVVSVLTVVHQDWLNGKEYKCKVSNKALPAPEEKTISKTKGQPR

EPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPGK

4G7 H1.201 Hybrid S239D/I332E (SEQ ID NO: 92)
EVQLVESGGGLVKPGGSLKLSCAASGYTFTSYVMHWVRQAPGKGLEWIGYINPY

NSGTKYNEKFQGRVTISSDKSISTAYMELSSLRSEDTAMYYCARGTYYYGTRVFDYWG

QGTLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCP

PCPAPELLGGPDVFLFPPKPKDTLMISRTPEVTCVVVDVSHEDPEVQFNWYVDGVEVHN

AKTKPREEQFNSTFRVVSVLTVVHQDWLNGKEYKCKVSNKALPAPEEKTISKTKGQPR

EPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPGK

4G7 H1.202 Hybrid S239D/I332E (SEQ ID NO: 93)
EVQLVESGGGLVKPGGSLKLSCAASGYTFTSYVMHWVRQAPGKGLEWIGYINPY

NEGTKYNEKFQGRVTISSDKSISTAYMELSSLRSEDTAMYYCARGTYYYGTRVFDYWG

QGTLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCP

PCPAPELLGGPDVFLFPPKPKDTLMISRTPEVTCVVVDVSHEDPEVQFNWYVDGVEVHN

AKTKPREEQFNSTFRVVSVLTVVHQDWLNGKEYKCKVSNKALPAPEEKTISKTKGQPR

EPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPGK

4G7 H1.203 Hybrid S239D/I332E (SEQ ID NO: 94)
EVQLVESGGGLVKPGGSLKLSCAASGYTFTSYVMHWVRQAPGKGLEWIGYINPY

NSGTEYNEKFQGRVTISSDKSISTAYMELSSLRSEDTAMYYCARGTYYYGTRVEDYWG

QGTLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCP

PCPAPELLGGPDVFLFPPKPKDTLMISRTPEVTCVVVDVSHEDPEVQFNWYVDGVEVHN

AKTKPREEQFNSTFRVVSVLTVVHQDWLNGKEYKCKVSNKALPAPEEKTISKTKGQPR

EPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPGK

4G7 H1.204 Hybrid S239D/I332E (SEQ ID NO: 95)
EVQLVESGGGLVKPGGSLKLSCAASGYTFTSYVMHWVRQAPGKGLEWIGYINPY

NEGTEYNEKFQGRVTISSDKSISTAYMELSSLRSEDTAMYYCARGTYYYGTRVEDYWG

QGTLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCP

PCPAPELLGGPDVFLFPPKPKDTLMISRTPEVTCVVVDVSHEDPEVQFNWYVDGVEVHN

AKTKPREEQFNSTFRVVSVLTVVHQDWLNGKEYKCKVSNKALPAPEEKTISKTKGQPR

EPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPGK

4G7 L1 (SEQ ID NO: 96)
DIVMTQSPATLSLSPGERATLSCRSSKSLLNSNGNTYLYWFQQKPGQSPQLLIYR

MSNLASGVPDRFSGSGSGTEFTLTISSLEPEDFAVYYCMQHLEYPFTFGAGTKLEIKRTV

AAPSVFIFPPSDEQLKSGTASVVCLLNNFYPREAKVQWKVDNALQSGNSQESVTEQDSK

DSTYSLSSTLTLSKADYEKHKVYACEVTHQGLSSPVTKSFNRGEC

4G7 L1.26 (SEQ ID NO: 97)
DIVMTQSPATLSLSPGERATLSCRSSKSLQNSNGNTYLYWFQQKPGQSPQLLIYR

MSNLASGVPDRFSGSGSGTEFTLTISSLEPEDFAVYYCMQHLEYPFTFGAGTKLEIKRTV

AAPSVFIFPPSDEQLKSGTASVVCLLNNFYPREAKVQWKVDNALQSGNSQESVTEQDSK

DSTYSLSSTLTLSKADYEKHKVYACEVTHQGLSSPVTKSFNRGEC

4G7 L1.32 (SEQ ID NO: 98)
DIVMTQSPATLSLSPGERATLSCRSSKSLLNVNGNTYLYWFQQKPGQSPQLLIYR

MSNLASGVPDRFSGSGSGTEFTLTISSLEPEDFAVYYCMQHLEYPFTFGAGTKLEIKRTV

AAPSVFIFPPSDEQLKSGTASVVCLLNNFYPREAKVQWKVDNALQSGNSQESVTEQDSK

DSTYSLSSTLTLSKADYEKHKVYACEVTHQGLSSPVTKSFNRGEC

4G7 L1.64 (SEQ ID NO: 99)
DIVMTQSPATLSLSPGERATLSCRSSKSLLNSNGNTYLYWFQQKPGQSPQLLIYR

MSNLASGVPDRFSGSGSGTEFTLTISSLEPEDFAVYYCMQHLEYPITFGAGTKLEIKRTVA

APSVFIFPPSDEQLKSGTASVVCLLNNFYPREAKVQWKVDNALQSGNSQESVTEQDSKD

STYSLSSTLTLSKADYEKHKVYACEVTHQGLSSPVTKSFNRGEC

4G7 L1.68 (SEQ ID NO: 100)
DIVMTQSPATLSLSPGERATLSCRSSKSLLNSNGNTYLYWFQQKPGQSPQLLIYR

MSNLASGVPDRFSGSGSGTEFTLTISSLEPEDFAVYYCMQHLEYPNTFGAGTKLEIKRTV

AAPSVFIFPPSDEQLKSGTASVVCLLNNFYPREAKVQWKVDNALQSGNSQESVTEQDSK

DSTYSLSSTLTLSKADYEKHKVYACEVTHQGLSSPVTKSFNRGEC

4G7 L1.96 (SEQ ID NO: 101)
DIVMTQSPATLSLSPGERATLSCRSSKSLLNSNGNTYLYWFQQKPGQSPQLLIYR

MSNLNSGVPDRFSGSGSGTEFTLTISSLEPEDFAVYYCMQHLEYPFTFGAGTKLEIKRTV

AAPSVFIFPPSDEQLKSGTASVVCLLNNFYPREAKVQWKVDNALQSGNSQESVTEQDSK

DSTYSLSSTLTLSKADYEKHKVYACEVTHQGLSSPVTKSFNRGEC

4G7 L1.145 (SEQ ID NO: 102)
DIVMTQSPATLSLSPGERATLSCRSSKSLQNSNGNTYLYWFQQKPGQSPQLLIYR

MSNLASGVPDRFSGSGSGTEFTLTISSLEPEDFAVYYCMQHLEYPITFGAGTKLEIKRTVA

APSVFIFPPSDEQLKSGTASVVCLLNNFYPREAKVQWKVDNALQSGNSQESVTEQDSKD

STYSLSSTLTLSKADYEKHKVYACEVTHQGLSSPVTKSFNRGEC

-continued

4G7 L1.148 (SEQ ID NO: 103)
DIVMTQSPATLSLSPGERATLSCRSSKSLQNSNGNTYLYWFQQKPGQSPQLLIYR

MSNLNSGVPDRFSGSGSGTEFTLTISSLEPEDFAVYYCMQHLEYPNTFGAGTKLEIKRTV

AAPSVFIFPPSDEQLKSGTASVVCLLNNFYPREAKVQWKVDNALQSGNSQESVTEQDSK

DSTYSLSSTLTLSKADYEKHKVYACEVTHQGLSSPVTKSFNRGEC

4G7 L1.149 (SEQ ID NO: 104)
DIVMTQSPATLSLSPGERATLSCRSSKSLQNSNGNTYLYWFQQKPGQSPQLLIYR

MSNLNSGVPDRFSGSGSGTEFTLTISSLEPEDFAVYYCMQHLEYPITFGAGTKLEIKRTVA

APSVFIFPPSDEQLKSGTASVVCLLNNFYPREAKVQWKVDNALQSGNSQESVTEQDSKD

STYSLSSTLTLSKADYEKHKVYACEVTHQGLSSPVTKSFNRGEC

4G7 L1.154 (SEQ ID NO: 105)
DIVMTQSPATLSLSPGERATLSCRSSKSLQNVNGNTYLYWFQQKPGQSPQLLIYR

MSNLNSGVPDRFSGSGSGTEFTLTISSLEPEDFAVYYCMQHLEYPNTFGAGTKLEIKRTV

AAPSVFIFPPSDEQLKSGTASVVCLLNNFYPREAKVQWKVDNALQSGNSQESVTEQDSK

DSTYSLSSTLTLSKADYEKHKVYACEVTHQGLSSPVTKSFNRGEC

4G7 L1.155 (SEQ ID NO: 106)
DIVMTQSPATLSLSPGERATLSCRSSKSLQNVNGNTYLYWFQQKPGQSPQLLIYR

MSNLNSGVPDRFSGSGSGTEFTLTISSLEPEDFAVYYCMQHLEYPITFGAGTKLEIKRTVA

APSVFIFPPSDEQLKSGTASVVCLLNNFYPREAKVQWKVDNALQSGNSQESVTEQDSKD

STYSLSSTLTLSKADYEKHKVYACEVTHQGLSSPVTKSFNRGEC

4G7 L1.160 (SEQ ID NO: 107)
DIVMTQSPATLSLSPGERATLSCRSSKSLQNVNANTYLYWFQQKPGQSPQLLIYR

MSNLNSGVPDRFSGSGSGTEFTLTISSLEPEDFAVYYCMQHLEYPITFGAGTKLEIKRTVA

APSVFIFPPSDEQLKSGTASVVCLLNNFYPREAKVQWKVDNALQSGNSQESVTEQDSKD

STYSLSSTLTLSKADYEKHKVYACEVTHQGLSSPVTKSFNRGEC

4G7 L1.162 (SEQ ID NO: 108)
DIVMTQSPATLSLSPGERATLSCRSSKSLQNANANTYLYWFQQKPGQSPQLLIYR

MSNLNSGVPDRFSGSGSGTEFTLTISSLEPEDFAVYYCMQHLEYPITFGAGTKLEIKRTVA

APSVFIFPPSDEQLKSGTASVVCLLNNFYPREAKVQWKVDNALQSGNSQESVTEQDSKD

STYSLSSTLTLSKADYEKHKVYACEVTHQGLSSPVTKSFNRGEC

4G7 L1.163 (SEQ ID NO: 109)
DIVMTQSPATLSLSPGERATLSCRSSKSLQNANSNTYLYWFQQKPGQSPQLLIYR

MSNLNSGVPDRFSGSGSGTEFTLTISSLEPEDFAVYYCMQHLEYPITFGAGTKLEIKRTVA

APSVFIFPPSDEQLKSGTASVVCLLNNFYPREAKVQWKVDNALQSGNSQESVTEQDSKD

STYSLSSTLTLSKADYEKHKVYACEVTHQGLSSPVTKSFNRGEC

4G7 L1.164 (SEQ ID NO: 110)
DIVMTQSPATLSLSPGERATLSCRSSKSLQNANGNTYLYWFQQKPGQSPQLLIYR

MSNLNSGVPDRFSGSGSGTEFTLTISSLEPEDFAVYYCMQHLEYPITFGAGTKLEIKRTVA

APSVFIFPPSDEQLKSGTASVVCLLNNFYPREAKVQWKVDNALQSGNSQESVTEQDSKD

STYSLSSTLTLSKADYEKHKVYACEVTHQGLSSPVTKSFNRGEC

4G7 VH CDR2 D55A (SEQ ID NO: 111)
YINPYNAGTKYNEKFKG

4G7 VH CDR2 T57P (SEQ ID NO: 112)
YINPYNDGPKYNEKFKG

4G7 VH CDR2 K58E (SEQ ID NO: 113)
YINPYNDGTEYNEKFKG

-continued

4G7 VH CDR2 D55S (SEQ ID NO: 114)
YINPYNSGTKYNEKFKG

4G7 VH CDR2 D55E (SEQ ID NO: 115)
YINPYNEGTKYNEKFKG

4G7 VH CDR3 S100T (SEQ ID NO: 116)
GTYYYGTRVFDY

4G7 VH CDR3 R100dS (SEQ ID NO: 117)
GTYYYGSSVFDY

4G7 VH CDR3 S100cT/R100dS (SEQ ID NO: 118)
GTYYYGTSVFDY

4G7 VL CDR1 L27cQ (SEQ ID NO: 119)
RSSKSLQNSNGNTYLY

4G7 VL CDR1 L27cQ/S27eV (SEQ ID NO: 120)
RSSKSLQNVNGNTYLY

4G7 VL CDR1 S27eV (SEQ ID NO: 121)
RSSKSLLNVNGNTYLY

4G7 VL CDR1 G29A (SEQ ID NO: 122)
RSSKSLLNSNANTYLY

4G7 VL CDR1 L27cQ/S27eV/G29A (SEQ ID NO: 123)
RSSKSLQNVNANTYLY

4G7 VL CDR1 S27eA (SEQ ID NO: 124)
RSSKSLLNANGNTYLY

4G7 VL CDR1 L27cQ/S27eA/G29A (SEQ ID NO: 125)
RSSKSLQNANANTYLY

4G7 VL CDR1 G29S (SEQ ID NO: 126)
RSSKSLLNSNSNTYLY

4G7 VL CDR1 L27cQ/S27eA/G29S (SEQ ID NO: 127)
RSSKSLQNANSNTYLY

4G7 VL CDR1 L27cQ/S27eA (SEQ ID NO: 128)
RSSKSLQNANGNTYLY

4G7 VL CDR2 A55N (SEQ ID NO: 129)
RMSNLNS

4G7 VL CDR3 F96I (SEQ ID NO: 130)
MQHLEYPIT

4G7 VL CDR3 F96N (SEQ ID NO: 131)
MQHLEYPNT

4G7 VH CDR1 (SEQ ID NO: 132): SYVMH

4G7 VH CDR2 (SEQ ID NO: 133): YINPYNDGTKYNEKFKG

4G7 VH CDR3 (SEQ ID NO: 134): GTYYYGSRVFDY

4G7 VL CDR1 (SEQ ID NO: 135): RSSKSLLNSNGNTYLY

4G7 VL CDR2 (SEQ ID NO: 136): RMSNLAS

4G7 VL CDR3 (SEQ ID NO: 137): MQHLEYPFT

HD37 VH CDR1 (SEQ ID NO: 138): SYWMN

HD37 VH CDR2 (SEQ ID NO: 139): QIWPGDGDTNYNGKFKG

HD37 VH CDR3 (SEQ ID NO: 140): RETTTVGRYYYAMDY

HD37 VL CDR1 (SEQ ID NO: 141): KASQSVDYDGDSYLN

HD37 VL CDR2 (SEQ ID NO: 142): DASNLVS

HD37 VL CDR3 (SEQ ID NO: 143): QQSTEDPWT

All cited references are herein expressly incorporated by reference in their entirety.

Whereas particular embodiments of the invention have been described above for purposes of illustration, it will be appreciated by those skilled in the art that numerous variations of the details may be made without departing from the invention as described in the appended claims.

---

What is claimed is:

1. A nucleic acid encoding a heavy chain sequence and light chain sequence of an antibody that binds CD19, said antibody comprising a heavy chain and a light chain, said heavy chain comprising a variable region having a CDR1 comprising SEQ ID NO:132, a CDR2 comprising SEQ ID NO:147, and a CDR3 comprising SEQ ID NO:116; and said light chain comprising a variable region having a CDR1 comprising SEQ ID NO:120, a CDR2 comprising SEQ ID NO:129, and a CDR3 comprising SEQ ID NO:130, wherein the Fc domain comprises an amino acid substitution at position S239 and/or I332, and wherein the Fc numbering is according to the EU index as in Kabat.

2. The nucleic acid according to claim 1, wherein said heavy chain variable region comprises SEQ ID NO:40.

3. The nucleic acid according to claim 1, wherein said light chain variable region comprises SEQ ID NO:58.

4. The nucleic acid according to claim 1, wherein said heavy chain comprises SEQ ID NO:40 and said light chain sequence comprises SEQ ID NO:58.

5. The nucleic acid according to claim 1, wherein the amino acid substitution is at position S239.

6. The nucleic acid according to claim 2, wherein the amino acid substitution is at position S239.

7. The nucleic acid according to claim 3, wherein the amino acid substitution is at position S239.

8. The nucleic acid according to claim 4, wherein the amino acid substitution is at position S239.

9. The nucleic acid according to claim 5, wherein the substitution is S239D.

10. The nucleic acid according to claim 6, wherein the substitution is S239D.

11. The nucleic acid according to claim 7, wherein the substitution is S239D.

12. The nucleic acid according to claim 8, wherein the substitution is S239D.

13. The nucleic acid according to claim 1, wherein the amino acid substitution is at position I332.

14. The nucleic acid according to claim 2, wherein the acid substitution is at position I332.

15. The nucleic acid according to claim 3, wherein the amino acid substitution is amino acid substitution at position I332.

16. The nucleic acid according to claim 4, wherein the amino acid substitution is amino acid substitution at position I332.

17. The nucleic acid according to claim 13, wherein the amino acid substitution is at position I332E.

18. The nucleic acid according to claim 14, wherein the substitution is I332E.

19. The nucleic acid according to claim 15, wherein the substitution is I332E.

20. The nucleic acid according to claim 16, wherein the substitution is I332E.

21. The nucleic acid according to claim 1, wherein the amino acid substitutions are S239D and I332E.

22. The nucleic acid according to claim 2, wherein the amino acid substitutions are S239D and I332E.

23. The nucleic acid according to claim 3, wherein the amino acid substitutions are S239D and I332E.

24. The nucleic acid according to claim 4, wherein the amino acid substitutions are S239D and I332E.

25. The nucleic acid according to claim 1, wherein said heavy chain variable region comprises SEQ ID NO: 87.

26. The nucleic acid according to claim 1, wherein said light chain variable region comprises SEQ ID NO: 106.

27. The nucleic acid according to claim 1, wherein said heavy chain variable region comprises SEQ ID NO: 87 and said light chain variable region comprises SEQ ID NO: 106.

* * * * *